US010407691B2

(12) United States Patent
Ronald et al.

(10) Patent No.: US 10,407,691 B2
(45) Date of Patent: Sep. 10, 2019

(54) ENGINEERING PATHOGEN RESISTANCE IN PLANTS

(71) Applicant: The Regents of the University of California, Oakland, CA (US)

(72) Inventors: Pamela Ronald, Davis, CA (US); Benjamin Schwessinger, Canberra (AU); Rory Pruitt, Davis, CA (US); Anna Joe, Davis, CA (US); Weiguo Zhang, Zurich (CH)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/382,461

(22) Filed: Dec. 16, 2016

(65) Prior Publication Data

US 2018/0002717 A1 Jan. 4, 2018

Related U.S. Application Data

(63) Continuation of application No. PCT/US2015/036439, filed on Jun. 18, 2015.

(60) Provisional application No. 62/013,709, filed on Jun. 18, 2014.

(51) Int. Cl.

| | |
|---|---|
| ***C12N 15/82*** | (2006.01) |
| ***C07K 14/195*** | (2006.01) |
| ***A01N 63/02*** | (2006.01) |
| ***C07K 14/415*** | (2006.01) |
| ***C12P 21/02*** | (2006.01) |

(52) U.S. Cl.

CPC ......... *C12N 15/8279* (2013.01); *A01N 63/02* (2013.01); *C07K 14/195* (2013.01); *C07K 14/415* (2013.01); *C12N 15/8281* (2013.01); *C12P 21/02* (2013.01)

(58) Field of Classification Search

CPC ............ C12N 15/8279; C12N 15/8281; C12N 15/8282

See application file for complete search history.

(56) References Cited

U.S. PATENT DOCUMENTS

| | | | |
|---|---|---|---|
| 6,252,138 B1 | 6/2001 | Karimi et al. | |
| 6,624,139 B1 | 9/2003 | Wei et al. | |
| 2010/0122376 A1 | 5/2010 | Zipfel et al. | |
| 2012/0115728 A1 | 5/2012 | Su et al. | |
| 2012/0151636 A1* | 6/2012 | Ronald ................ | C07K 14/195 800/320.2 |
| 2013/0172185 A1 | 7/2013 | Wei | |

FOREIGN PATENT DOCUMENTS

| | | |
|---|---|---|
| WO | 2010/117978 A1 | 10/2010 |
| WO | 2015/195921 A2 | 12/2015 |

OTHER PUBLICATIONS

Guo, Haiwei H., Juno Choe, and Lawrence A. Loeb. "Protein tolerance to random amino acid change." Proceedings of the National Academy of Sciences 101.25 (2004): 9205-9210 (Year: 2004).*

Lee SW, Han SW, Sririyanum M, Park CJ, Seo YS, Ronald PC. 2009. A type I-secreted, sulfated peptide triggers XA21-mediated innate immunity. Science. 326(5954):850-3. doi: 10.1126/science.1173438. (Year: 2009).*

Niño-Liu, D. O., et al., "Xanthomonas oryzae pathovars: model pathogens of a model crop." Molecular plant pathology 7.5 (2006): 303-324 (Year: 2006).*

International Search Report and Written Opinion from PCT/US2015/036439, dated Sep. 29, 2015, 6 pages.

Xanthomonas axonopodis pv. citrumelo F1, complete genome; NCBI Reference Sequence: NC_016010.1.

* cited by examiner

*Primary Examiner* — Weihua Fan

(74) *Attorney, Agent, or Firm* — Kilpatrick Townsend & Stockton LLP

(57) ABSTRACT

Provided herein are compounds and methods for increasing disease resistance and/or root length in plants.

11 Claims, 55 Drawing Sheets

Specification includes a Sequence Listing.

GluC cut: KGRPE|PLDQRLWKHVGGGDYPPPGANPKHDPPPRNPGHH

Trypsin cut: KGRPEPLDQR|LWK|HVGGGDYPPPGANPK|HDPPPR|NPGHH

ArgC cut: KGRPEPLDQR|LWKHVGGGDYPPPGANPKHDPPPR|NPGHH

LysC cut: KGRPEPLDQRLWK|HVGGGDYPPPGANPK|HDPPPRNPGHH

AspN cut: KGRPEPL|DQRLWKHVGGG|DYPPPGANPKH|DPPPRNPGHH

FIG. 8

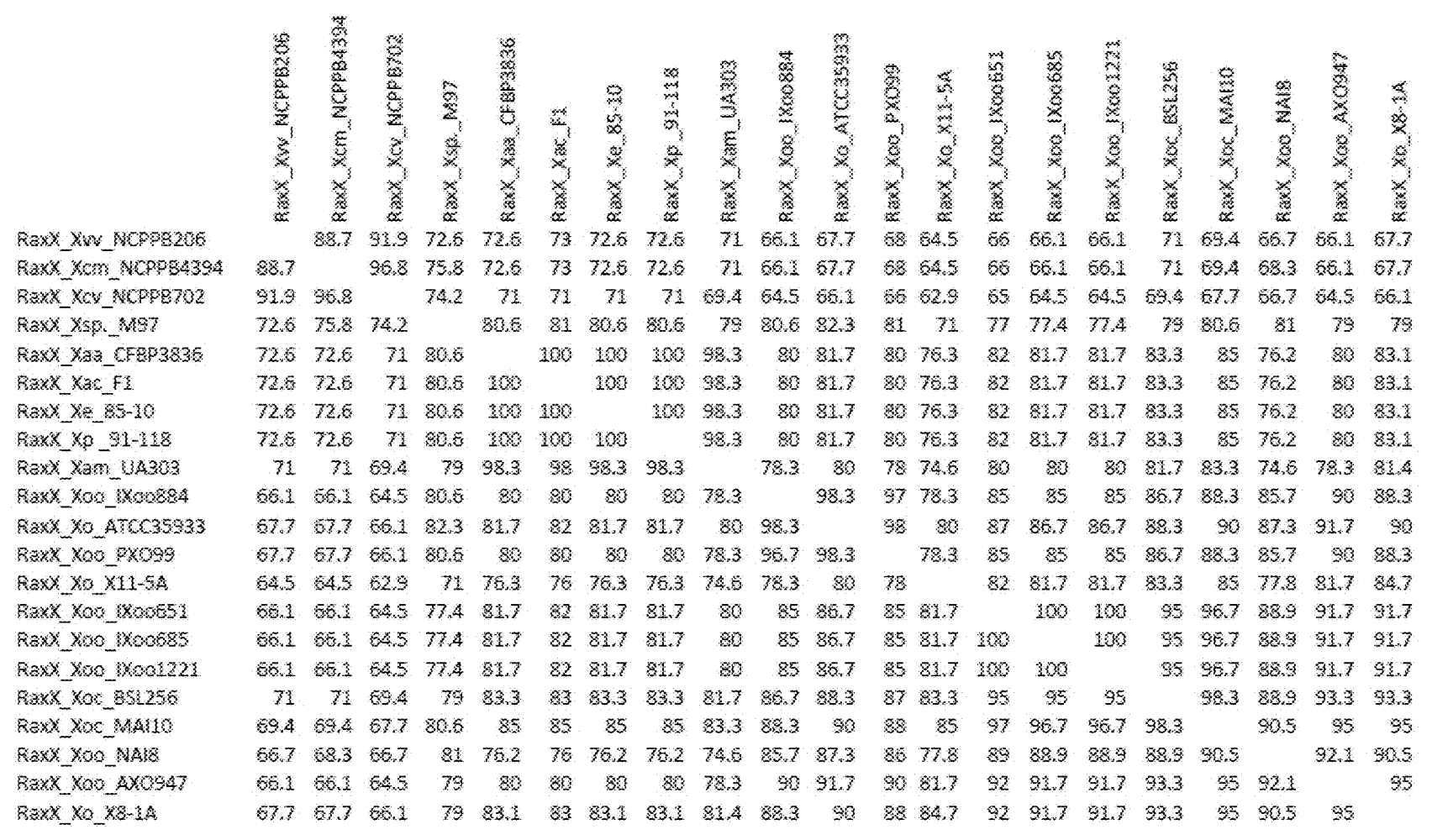

| | RaxX_Xvv_NCPPB206 | RaxX_Xcm_NCPPB4394 | RaxX_Xcv_NCPPB702 | RaxX_Xsp._M97 | RaxX_Xaa_CFBP3836 | RaxX_Xac_F1 | RaxX_Xe_85-10 | RaxX_Xp_91-118 | RaxX_Xam_UA303 | RaxX_Xoo_IXoo884 | RaxX_Xo_ATCC35933 | RaxX_Xoo_PXO99 | RaxX_Xo_X11-5A | RaxX_Xoo_IXoo651 | RaxX_Xoo_IXoo685 | RaxX_Xoo_IXoo1221 | RaxX_Xoc_BSL256 | RaxX_Xoc_MAI10 | RaxX_Xoo_NAI8 | RaxX_Xoo_AXO947 | RaxX_Xo_X8-1A |
|---|---|---|---|---|---|---|---|---|---|---|---|---|---|---|---|---|---|---|---|---|---|
| RaxX_Xvv_NCPPB206 | | 88.7 | 91.9 | 72.6 | 72.6 | 73 | 72.6 | 72.6 | 71 | 66.1 | 67.7 | 68 | 64.5 | 66 | 66.1 | 66.1 | 71 | 69.4 | 66.7 | 66.1 | 67.7 |
| RaxX_Xcm_NCPPB4394 | 88.7 | | 96.8 | 75.8 | 72.6 | 73 | 72.6 | 72.6 | 71 | 66.1 | 67.7 | 68 | 64.5 | 66 | 66.1 | 66.1 | 71 | 69.4 | 68.3 | 66.1 | 67.7 |
| RaxX_Xcv_NCPPB702 | 91.9 | 96.8 | | 74.2 | 71 | 71 | 71 | 71 | 69.4 | 64.5 | 66.1 | 66 | 62.9 | 65 | 64.5 | 64.5 | 69.4 | 67.7 | 66.7 | 64.5 | 66.1 |
| RaxX_Xsp._M97 | 72.6 | 75.8 | 74.2 | | 80.6 | 81 | 80.6 | 80.6 | 79 | 80.6 | 82.3 | 81 | 71 | 77 | 77.4 | 77.4 | 79 | 80.6 | 81 | 79 | 79 |
| RaxX_Xaa_CFBP3836 | 72.6 | 72.6 | 71 | 80.6 | | 100 | 100 | 100 | 98.3 | 80 | 81.7 | 80 | 76.3 | 82 | 81.7 | 81.7 | 83.3 | 85 | 76.2 | 80 | 83.1 |
| RaxX_Xac_F1 | 72.6 | 72.6 | 71 | 80.6 | 100 | | 100 | 100 | 98.3 | 80 | 81.7 | 80 | 76.3 | 82 | 81.7 | 81.7 | 83.3 | 85 | 76.2 | 80 | 83.1 |
| RaxX_Xe_85-10 | 72.6 | 72.6 | 71 | 80.6 | 100 | 100 | | 100 | 98.3 | 80 | 81.7 | 80 | 76.3 | 82 | 81.7 | 81.7 | 83.3 | 85 | 76.2 | 80 | 83.1 |
| RaxX_Xp _91-118 | 72.6 | 72.6 | 71 | 80.6 | 100 | 100 | 100 | | 98.3 | 80 | 81.7 | 80 | 76.3 | 82 | 81.7 | 81.7 | 83.3 | 85 | 76.2 | 80 | 83.1 |
| RaxX_Xam_UA303 | 71 | 71 | 69.4 | 79 | 98.3 | 98 | 98.3 | 98.3 | | 78.3 | 80 | 78 | 74.6 | 80 | 80 | 80 | 81.7 | 83.3 | 74.6 | 78.3 | 81.4 |
| RaxX_Xoo_IXoo884 | 66.1 | 66.1 | 64.5 | 80.6 | 80 | 80 | 80 | 80 | 78.3 | | 98.3 | 97 | 78.3 | 85 | 85 | 85 | 86.7 | 88.3 | 85.7 | 90 | 88.3 |
| RaxX_Xo_ATCC35933 | 67.7 | 67.7 | 66.1 | 82.3 | 81.7 | 82 | 81.7 | 81.7 | 80 | 98.3 | | 98 | 80 | 87 | 86.7 | 86.7 | 88.3 | 90 | 87.3 | 91.7 | 90 |
| RaxX_Xoo_PXO99 | 67.7 | 67.7 | 66.1 | 80.6 | 80 | 80 | 80 | 80 | 78.3 | 96.7 | 98.3 | | 78.3 | 85 | 85 | 85 | 86.7 | 88.3 | 85.7 | 90 | 88.3 |
| RaxX_Xo_X11-5A | 64.5 | 64.5 | 62.9 | 71 | 76.3 | 76 | 76.3 | 76.3 | 74.6 | 78.3 | 80 | 78 | | 82 | 81.7 | 81.7 | 83.3 | 85 | 77.8 | 81.7 | 84.7 |
| RaxX_Xoo_IXoo651 | 66.1 | 66.1 | 64.5 | 77.4 | 81.7 | 82 | 81.7 | 81.7 | 80 | 85 | 86.7 | 85 | 81.7 | | 100 | 100 | 95 | 96.7 | 88.9 | 91.7 | 91.7 |
| RaxX_Xoo_IXoo685 | 66.1 | 66.1 | 64.5 | 77.4 | 81.7 | 82 | 81.7 | 81.7 | 80 | 85 | 86.7 | 85 | 81.7 | 100 | | 100 | 95 | 96.7 | 88.9 | 91.7 | 91.7 |
| RaxX_Xoo_IXoo1221 | 66.1 | 66.1 | 64.5 | 77.4 | 81.7 | 82 | 81.7 | 81.7 | 80 | 85 | 86.7 | 85 | 81.7 | 100 | 100 | | 95 | 96.7 | 88.9 | 91.7 | 91.7 |
| RaxX_Xoc_BSL256 | 71 | 71 | 69.4 | 79 | 83.3 | 83 | 83.3 | 83.3 | 81.7 | 86.7 | 88.3 | 87 | 83.3 | 95 | 95 | 95 | | 98.3 | 88.9 | 93.3 | 93.3 |
| RaxX_Xoc_MAI10 | 69.4 | 69.4 | 67.7 | 80.6 | 85 | 85 | 85 | 85 | 83.3 | 88.3 | 90 | 88 | 85 | 97 | 96.7 | 96.7 | 98.3 | | 90.5 | 95 | 95 |
| RaxX_Xoo_NAI8 | 66.7 | 68.3 | 66.7 | 81 | 76.2 | 76 | 76.2 | 76.2 | 74.6 | 85.7 | 87.3 | 86 | 77.8 | 89 | 88.9 | 88.9 | 88.9 | 90.5 | | 92.1 | 90.5 |
| RaxX_Xoo_AXO947 | 66.1 | 66.1 | 64.5 | 79 | 80 | 80 | 80 | 80 | 78.3 | 90 | 91.7 | 90 | 81.7 | 92 | 91.7 | 91.7 | 93.3 | 95 | 92.1 | | 95 |
| RaxX_Xo_X8-1A | 67.7 | 67.7 | 66.1 | 79 | 83.1 | 83 | 83.1 | 83.1 | 81.4 | 88.3 | 90 | 88 | 84.7 | 92 | 91.7 | 91.7 | 93.3 | 95 | 90.5 | 95 | |

FIG. 9

| | RaxX_Xvv_NCPPB206 | RaxX_Xcm_NCPPB4394 | RaxX_Xcv_NCPPB702 | RaxX_Xsp._M97 | RaxX_Xam_UA303 | RaxX_Xaa_CFBP3836 | RaxX_Xe_85-10 | RaxX_Xp_91-118 | RaxX_Xac_F1 | RaxX_Xoo_IXoo884 | RaxX_Xoo_PXO99 | RaxX_Xo_ATCC35933 | RaxX_Xo_X8-1A | RaxX_Xo_X11-5A | RaxX_Xoo_AXO947 | RaxX_Xoo_NAI8 | RaxX_Xoo_IXoo651 | RaxX_Xoo_IXoo685 | RaxX_Xoo_IXoo1221 | RaxX_Xoc_BSL256 | RaxX_Xoc_MAI10 |
|---|---|---|---|---|---|---|---|---|---|---|---|---|---|---|---|---|---|---|---|---|---|
| RaxX_Xvv_NCPPB206 | | 95.2 | 96.3 | 81 | 76.7 | 77 | 77.2 | 77 | 77 | 76 | 76.2 | 76.2 | 77.2 | 72.5 | 76.7 | 78.6 | 76.7 | 76.7 | 76.7 | 78.3 | 77.8 |
| RaxX_Xcm_NCPPB4394 | 95.2 | | 98.9 | 83.6 | 77.2 | 78 | 77.8 | 78 | 77 | 77 | 77.2 | 77.2 | 78.3 | 73.5 | 77.8 | 79.7 | 77.2 | 77.2 | 77.2 | 78.8 | 78.3 |
| RaxX_Xcv_NCPPB702 | 96.3 | 98.9 | | 82.5 | 76.2 | 77 | 76.7 | 77 | 76 | 76 | 76.2 | 76.2 | 77.2 | 72.5 | 76.7 | 78.6 | 76.2 | 76.2 | 76.2 | 77.8 | 77.2 |
| RaxX_Xsp._M97 | 81 | 83.6 | 82.5 | | 84.7 | 85 | 84.7 | 85 | 84 | 82 | 82 | 82.5 | 82 | 75.1 | 81.5 | 82.8 | 81 | 81 | 81 | 81.5 | 82 |
| RaxX_Xam_UA303 | 76.7 | 77.2 | 76.2 | 84.7 | | 99 | 98.9 | 99 | 98 | 87 | 86.9 | 87.4 | 90 | 83.3 | 87.4 | 83.3 | 87.4 | 87.4 | 87.4 | 87.4 | 88 |
| RaxX_Xaa_CFBP3836 | 77.2 | 77.8 | 76.7 | 84.7 | 98.9 | | 100 | 100 | 99 | 87 | 86.9 | 87.4 | 90 | 83.3 | 87.4 | 83.3 | 87.4 | 87.4 | 87.4 | 87.4 | 88 |
| RaxX_Xe_85-10 | 77.2 | 77.8 | 76.7 | 84.7 | 98.9 | 100 | | 100 | 99 | 87 | 86.9 | 87.4 | 90 | 83.3 | 87.4 | 83.3 | 87.4 | 87.4 | 87.4 | 87.4 | 88 |
| RaxX_Xp_91-118 | 77.2 | 77.8 | 76.7 | 84.7 | 98.9 | 100 | 100 | | 99 | 87 | 86.9 | 87.4 | 90 | 83.3 | 87.4 | 83.3 | 87.4 | 87.4 | 87.4 | 87.4 | 88 |
| RaxX_Xac_F1 | 76.7 | 77.2 | 76.2 | 84.1 | 98.3 | 99 | 99.4 | 99 | | 86 | 86.3 | 86.9 | 89.4 | 82.8 | 86.9 | 82.8 | 87.4 | 87.4 | 87.4 | 86.9 | 87.4 |
| RaxX_Xoo_IXoo884 | 75.7 | 76.7 | 75.7 | 82 | 86.9 | 87 | 86.9 | 87 | 86 | | 98.9 | 99.5 | 92.3 | 84.7 | 95.1 | 90.6 | 92.9 | 92.9 | 92.9 | 92.9 | 93.4 |
| RaxX_Xoo_PXO99 | 76.2 | 77.2 | 76.2 | 82 | 86.9 | 87 | 86.9 | 87 | 86 | 99 | | 99.5 | 92.3 | 84.7 | 95.1 | 90.6 | 92.9 | 92.9 | 92.9 | 92.9 | 93.4 |
| RaxX_Xo_ATCC35933 | 76.2 | 77.2 | 76.2 | 82.5 | 87.4 | 87 | 87.4 | 87 | 87 | 100 | 99.5 | | 92.9 | 85.2 | 95.6 | 91.1 | 93.4 | 93.4 | 93.4 | 93.4 | 94 |
| RaxX_Xo_X8-1A | 77.2 | 78.3 | 77.2 | 82 | 90 | 90 | 90 | 90 | 89 | 92 | 92.3 | 92.9 | | 89.4 | 95.1 | 90.6 | 92.9 | 92.9 | 92.9 | 92.9 | 93.4 |
| RaxX_Xo_X11-5A | 72.5 | 73.5 | 72.5 | 75.1 | 83.3 | 83 | 83.3 | 83 | 83 | 85 | 84.7 | 85.2 | 89.4 | | 85.8 | 81.8 | 85.2 | 85.2 | 85.2 | 85.2 | 85.8 |
| RaxX_Xoo_AXO947 | 76.7 | 77.8 | 76.7 | 81.5 | 87.4 | 87 | 87.4 | 87 | 87 | 95 | 95.1 | 95.6 | 95.1 | 85.8 | | 94.3 | 96.7 | 96.7 | 96.7 | 96.7 | 97.3 |
| RaxX_Xoo_NAI8 | 78.6 | 79.7 | 78.6 | 82.8 | 83.3 | 83 | 83.3 | 83 | 83 | 91 | 90.6 | 91.1 | 90.6 | 81.8 | 94.3 | | 92.2 | 92.2 | 92.2 | 92.2 | 92.7 |
| RaxX_Xoo_IXoo651 | 76.7 | 77.2 | 76.2 | 81 | 87.4 | 87 | 87.4 | 87 | 87 | 93 | 92.9 | 93.4 | 92.9 | 85.2 | 96.7 | 92.2 | | 100 | 100 | 96.7 | 97.3 |
| RaxX_Xoo_IXoo685 | 76.7 | 77.2 | 76.2 | 81 | 87.4 | 87 | 87.4 | 87 | 87 | 93 | 92.9 | 93.4 | 92.9 | 85.2 | 96.7 | 92.2 | 100 | | 100 | 96.7 | 97.3 |
| RaxX_Xoo_IXoo1221 | 76.7 | 77.2 | 76.2 | 81 | 87.4 | 87 | 87.4 | 87 | 87 | 93 | 92.9 | 93.4 | 92.9 | 85.2 | 96.7 | 92.2 | 100 | 100 | | 96.7 | 97.3 |
| RaxX_Xoc_BSL256 | 78.3 | 78.8 | 77.8 | 81.5 | 87.4 | 87 | 87.4 | 87 | 87 | 93 | 92.9 | 93.4 | 92.9 | 85.2 | 96.7 | 92.2 | 96.7 | 96.7 | 96.7 | | 99.5 |
| RaxX_Xoc_MAI10 | 77.8 | 78.3 | 77.2 | 82 | 88 | 88 | 88 | 88 | 87 | 93 | 93.4 | 94 | 93.4 | 85.8 | 97.3 | 92.7 | 97.3 | 97.3 | 97.3 | 99.5 | |

FIGS. 25A, 25B, 25C and 25D
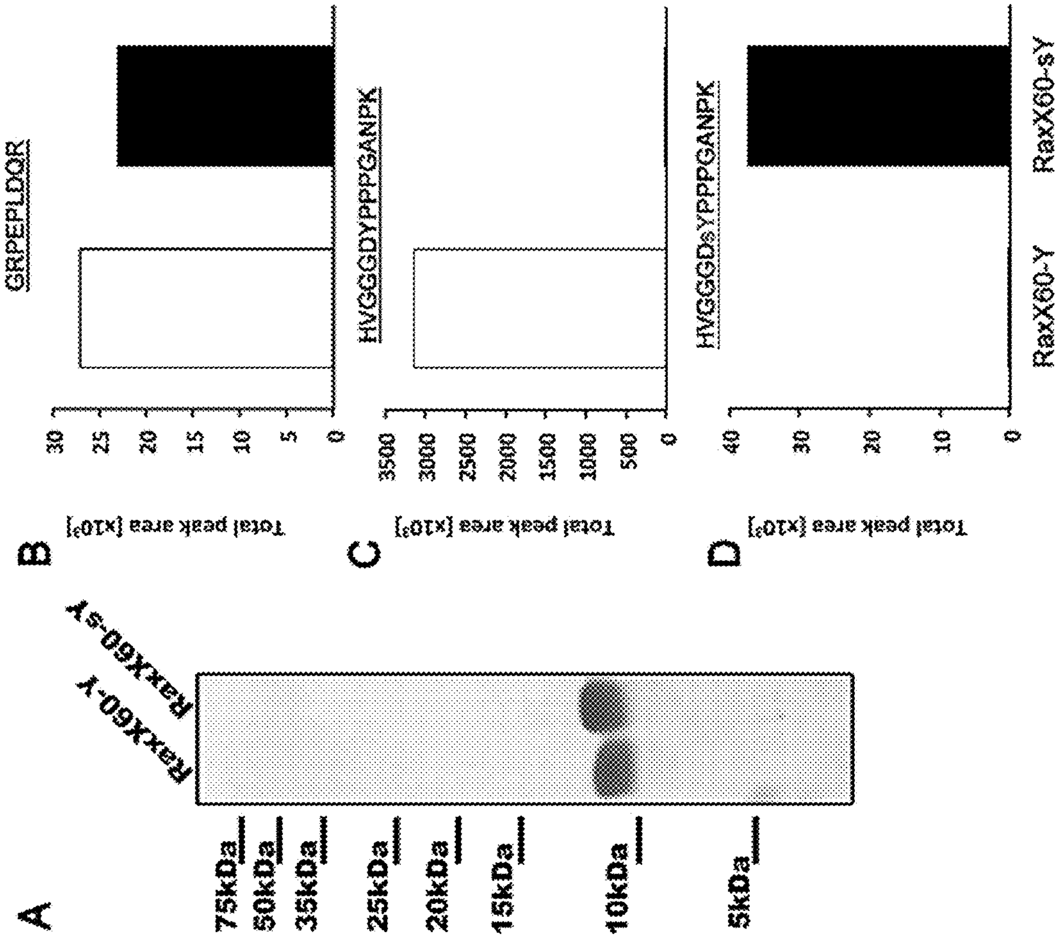
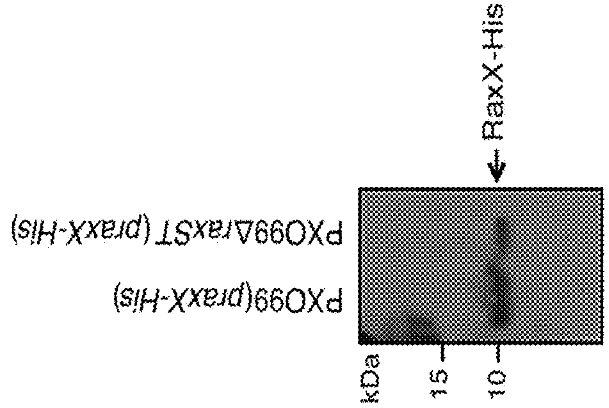
FIG. 24

C

R.LWKHVGGGDsYPPPGANPKHDPPPR.N
514.8929+++

D

G.DsYPPPGANPKH.D
636.7693++

FIGS. 35A and 35B
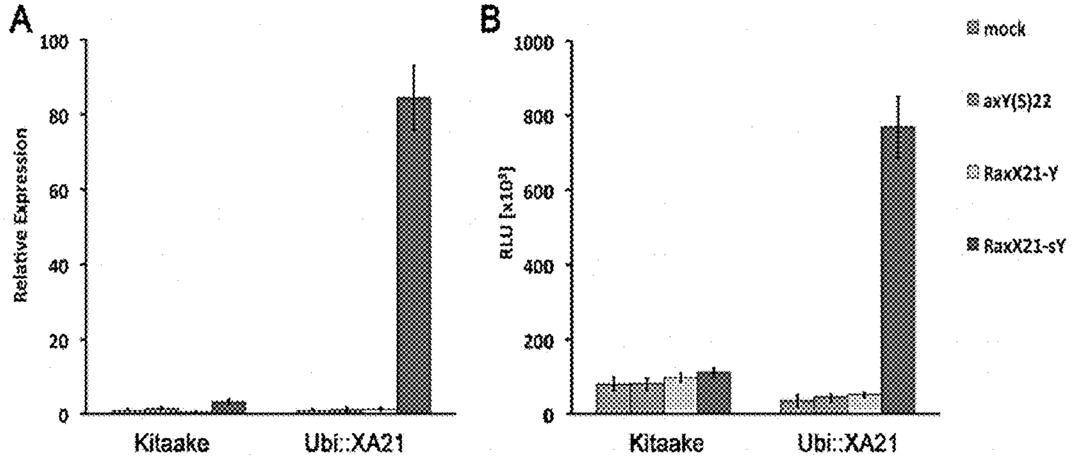
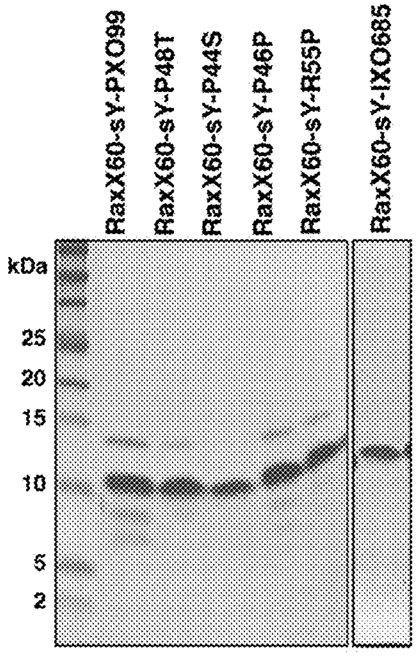
FIG. 36

FIG. 40a-f
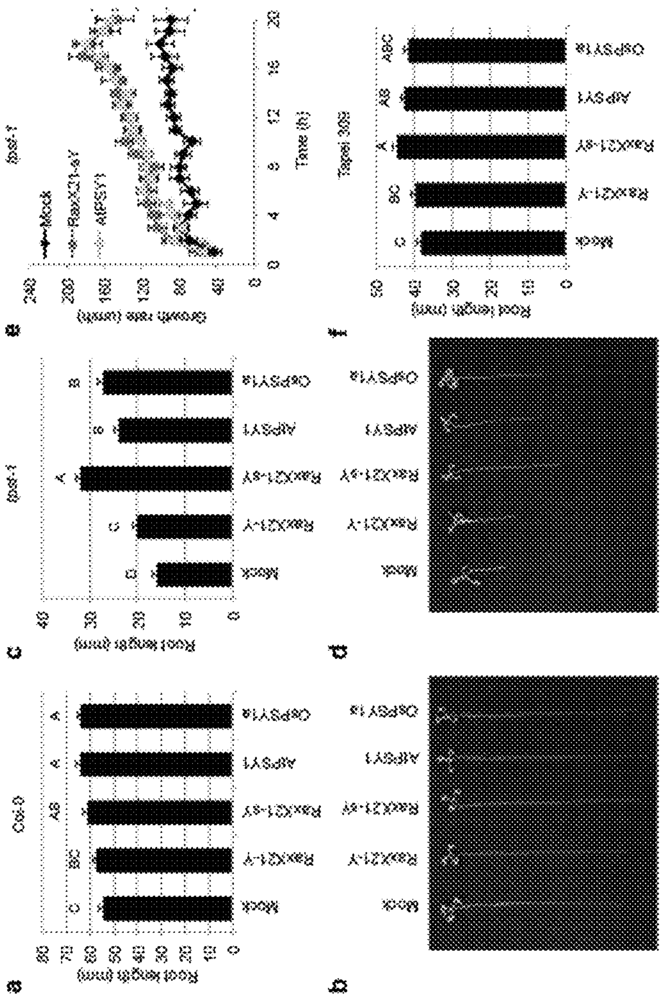

FIG. 41a-b
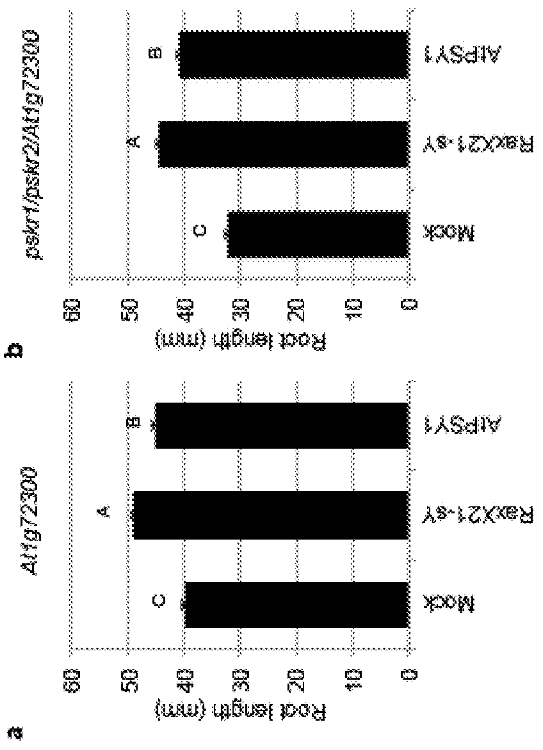

FIG. 42a-d
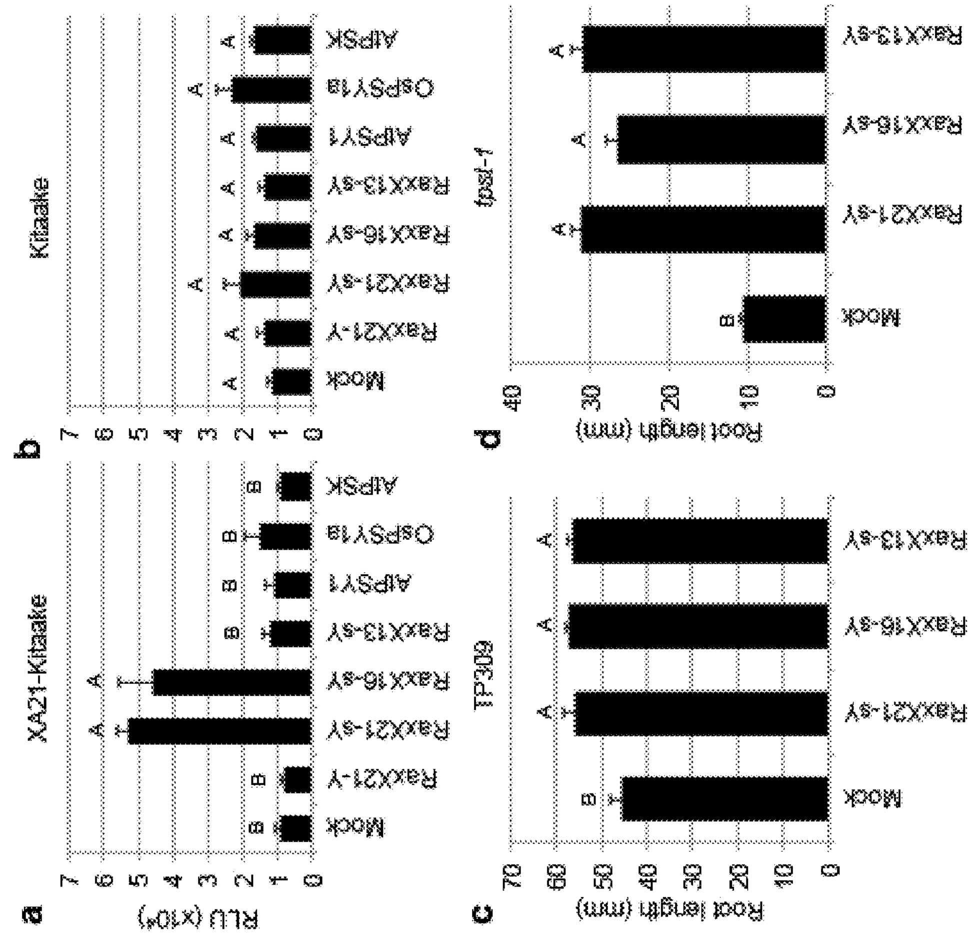

*tpst-1*

| | | |
|---|---|---|
| TaPSY3 | MGRANCSVPLLLVLLAFLSCFFLAHGLYGLTELFGSPDLSPEAILLIFALSFLVLAAAVAGASGNRKMFLPREGAAAAAG... | 80 |
| MaPSY5 | MSICIDTGCLSSSFLTFLSPKGGKVGDOTESASGREHSLKGDHFGFVLGEMERVSLHLLVILLALSHLLVSSQ... | 73 |
| OsPSY3 | MRTAAAKARCSVPFILAALAALSCVFLVHAAAAAAAAAVTTTTTSVVGYRRALLPREAAAVVMP... | 64 |
| OsPSY8 | MAQQQRRRRRGGSLAVLLLLLLLAALLLSLSLLARVDAAATVSS... | 44 |
| AtPSY5 | MPLRIEPLSLLFLILIICSSSLGMTINLASQHIHLSPRSAFA... | 42 |
| TaPSY2 | MECRKMKPVLALVLLLSCHLLLPLVSSVPVSRSVSLENHQ... | 40 |
| OsPSY2 | MRRAMERRPRDLVAVLALSCLLLLLPLLVSSVPMSRSLH... | 39 |
| OsPSY4 | MKMEQVSQRKAPLLVLVILCGLLLLLPLVSSVPLSRS... | 37 |
| OsPSY6 | MARSASGRSLLVILLAVSLLLVASSDAARFTRSNRM... | 36 |
| OsPSY5 | MERVPAVHLAVVLLAFCCLIHASSSAETPLPPAL... | 34 |
| MaPSY2 | MEQKKPLSHLLALLLLSCLLSVDAAPLS... | 28 |
| MaPSY3 | MDQRKPAICLCTLLCFSWILSLVAVPLP... | 28 |
| S1PSY3 | MAAPFFRLFISFLCFSYTINSFINAVP... | 27 |
| MaPSY4 | MVDTKGMTSLRLLLISLALAHLIAAS... | 26 |
| OsPSY1a | MRRVMEMRSRDLVAVLAMSSLLLLPL... | 26 |
| OsPSY1b | | |
| OsPSY1c | | |
| OsPSY1d | | |
| S1PSY2 | MATTLFLAFLCFSQVIYLNTIPIT... | 24 |
| OsPSY7 | MPSVSVASSMSKLKFLVTVVLVI... | 23 |
| S1PSY4 | MEKKVSFLSLLLLIFVGFSLLI... | 22 |
| S1PSY5 | MVQKIGFHLLLLFIFATIISTA... | 22 |
| S1PSY1 | MAAGFGIRHYLC... | 12 |
| MaPSY1 | MPRVKTFLIF... | 10 |
| AtPSY8x | MFSKMQLVVL... | 10 |
| AtPSY8a | | |
| AtPSY8b | | |
| AtPSY8c | | |
| TaPSY1 | MPKPTFVLA... | 9 |
| AtPSY6 | MLSKIKPV... | 8 |
| AtPSY7 | MLSKMKLV... | 8 |
| AtPSY3 | MGYSSSSR... | 8 |
| AtPSY1 | MTFVVR... | 6 |
| AtPSY4 | MVFCYA... | 6 |
| AtPSY2 | MSFGT... | 5 |
| RaxX A1 Xoo | | 0 |
| RaxX K1 Xt | | 0 |

FIG. 45A

*tpst-1*

SEQUENCE LISTING

<160> NUMBER OF SEQ ID NOS: 235

<210> SEQ ID NO 1
<211> LENGTH: 24
<212> TYPE: PRT
<213> ORGANISM: Artificial Sequence
<220> FEATURE:
<223> OTHER INFORMATION: Synthetic construct

<400> SEQUENCE: 1

```
Leu Trp Lys His Val Gly Gly Gly Asp Tyr Pro Pro Pro Gly Ala Asn
1               5                   10                  15

Pro Lys His Asp Pro Pro Pro Arg
            20
```

<210> SEQ ID NO 2
<211> LENGTH: 34
<212> TYPE: PRT
<213> ORGANISM: Artificial Sequence
<220> FEATURE:
<223> OTHER INFORMATION: Synthetic construct

<400> SEQUENCE: 2

```
Pro Leu Asp Gln Arg Leu Trp Lys His Val Gly Gly Gly Asp Tyr Pro
1               5                   10                  15

Pro Pro Gly Ala Asn Pro Lys His Asp Pro Pro Pro Arg Asn Pro Gly
            20                  25                  30

His His
```

<210> SEQ ID NO 3
<211> LENGTH: 39
<212> TYPE: PRT
<213> ORGANISM: Artificial Sequence
<220> FEATURE:
<223> OTHER INFORMATION: Synthetic construct

<400> SEQUENCE: 3

```
Lys Gly Arg Pro Glu Pro Leu Asp Gln Arg Leu Trp Lys His Val Gly
1               5                   10                  15

Gly Gly Asp Tyr Pro Pro Pro Gly Ala Asn Pro Lys His Asp Pro Pro
            20                  25                  30

Pro Arg Asn Pro Gly His His
        35
```

<210> SEQ ID NO 4
<211> LENGTH: 15
<212> TYPE: PRT
<213> ORGANISM: Artificial Sequence
<220> FEATURE:
<223> OTHER INFORMATION: Synthetic construct

<400> SEQUENCE: 4

```
His Val Gly Gly Gly Asp Tyr Pro Pro Pro Gly Ala Asn Pro Lys
1               5                   10                  15
```

<210> SEQ ID NO 5
<211> LENGTH: 180
<212> TYPE: DNA
<213> ORGANISM: Xanthomonas axonopodis

<400> SEQUENCE: 5

```
atgaatctgt cgaaaaaatc gccaaccaat ggtgcgcaag cgctgcagcg gcccgccggg      60

gccaagggcc agctggagcc cctggaccag cggctgtgga agcatgtcgg cggtggggac     120
```

tatcccccgc cgggcgccaa taccaagcac gatccgccgc ccaagaacgg gcaccactga 180

<210> SEQ ID NO 6
<211> LENGTH: 180
<212> TYPE: DNA
<213> ORGANISM: Xanthomonas axonopodis

<400> SEQUENCE: 6
atgaacctgt cgaaaaaatc gccaaccaat ggtgcgcaag cgctgcagcg gcccgccggg 60
gccaagggcc agctggagcc cctggaccag cgtatgtgga agcatgtcgg cggtggggac 120
tatcccccgc cgggcgccaa taccaagcac gatccgccgc ccaagaacgg gcaccactga 180

<210> SEQ ID NO 7
<211> LENGTH: 189
<212> TYPE: DNA
<213> ORGANISM: Xanthomonas campestris

<400> SEQUENCE: 7
atgaaactat tgaaaaaatc gccatccaat ggcgcgggat cgctccagcg gtcggccggc 60
gccaagggcc ggctagagcc gctggaccag cgtctgtgga agcatgtcgg gggtggggac 120
tatgccccgc cgggctcgaa tgaccgccac gacccaccaa agccgccgcc caaaaaaggg 180
aacccttga 189

<210> SEQ ID NO 8
<211> LENGTH: 189
<212> TYPE: DNA
<213> ORGANISM: Xanthomonas campestris

<400> SEQUENCE: 8
atggaactat tgaaaaaatc gccatccaat ggcgtgggat cgctccagcg gtcggccggc 60
gccaagggcc ggctagagcc gctggaccag cgtctgtgga agcatgtcgg gggtggggac 120
tatgccccgc cgggctcgaa tgaccgccac gacccaccaa agccgccgcc caaaaaaggg 180
aacccttga 189

<210> SEQ ID NO 9
<211> LENGTH: 180
<212> TYPE: DNA
<213> ORGANISM: Xanthomonas euvesicatoria

<400> SEQUENCE: 9
atgaatctgt cgaaaaaatc gccaaccaat ggtgcgcaag cgctgcagcg gcccgccggg 60
gccaagggcc agctggagcc cctggaccag cgtctgtgga agcatgtcgg cggtggggac 120
tatcccccgc cgggcgccaa taccaagcac gatccgccgc ccaagaacgg gcaccactga 180

<210> SEQ ID NO 10
<211> LENGTH: 183
<212> TYPE: DNA
<213> ORGANISM: Xanthomonas oryzae

<400> SEQUENCE: 10
atgaaccact cgaaaaaatc gcccaccaag ggtgcggcat cgctgcagcg gcccgccggg 60
gccaagggcc gaccggagcc gctcgaccag cgtctgtgga agcatgtcgg cggtggggac 120
tatcccccgc cgggcgcgaa tcccaagcac gatccgccgc cgcgcaaccc cgggcaccat 180
tga 183

<210> SEQ ID NO 11
<211> LENGTH: 180
<212> TYPE: DNA
<213> ORGANISM: Xanthomonas oryzae

<400> SEQUENCE: 11
atgaacctgt cgaaaaaatc gccaaccaag ggtgcggcat cgctgcagcg gcccgccggg 60
gccaagggcc gaccggagcc gctggaccag cgtctgtgga agcatgtcgg cggtggggac 120
tatcccccgt cgggcccgaa tcccaagcac gatccaccgg gcaacaacgg gcaccattga 180

<210> SEQ ID NO 12
<211> LENGTH: 165
<212> TYPE: DNA
<213> ORGANISM: Xanthomonas oryzae

<400> SEQUENCE: 12
atgaacctgt cgaaaaaatc gccaaccaag ggtgcggcat cgctgcagcg gtccgccggg 60
gccaagggcc gaccggagcc gctggaccag cgtctgtgga agcatgtcgg cggtggggac 120
tatcccccgg cgggcccgag taccaagcac gatccgcacc attga 165

<210> SEQ ID NO 13
<211> LENGTH: 183
<212> TYPE: DNA
<213> ORGANISM: Xanthomonas oryzae

<400> SEQUENCE: 13
atgaacctct tgaaaaaatc gccaaccaag gggcggcat cgctgcagcg gcccgccggg 60
gccaagggcc gaccggagcc gctcgaccag cgtctgtgga aacatgtcgg cggtggggac 120
taccccccgt cgggcccgaa taccaagcac gatccgccgc cgcccaacaa cgggcaccat 180
tga 183

<210> SEQ ID NO 14
<211> LENGTH: 183
<212> TYPE: DNA
<213> ORGANISM: Xanthomonas oryzae

<400> SEQUENCE: 14
atgaacctct cgaaaaaatc gccaaccaag gggcggcat cgctgcagcg gcccgccggg 60
gccaagggcc gaccggagcc gctcgaccag cgtctgtgga aacatgtcgg cggtggggac 120
taccccccgt cgggcccgaa taccaagcac gatccgccgc cgcccaacaa cgggcaccat 180
tga 183

<210> SEQ ID NO 15
<211> LENGTH: 183
<212> TYPE: DNA
<213> ORGANISM: Artificial Sequence
<220> FEATURE:
<223> OTHER INFORMATION: Synthetic construct

<400> SEQUENCE: 15
atgaacctct cgaaaaaatc gccaaccaag ggtgcggcat cgctgcagcg gcccgccggg 60
gccaaggtcc gaccggagcc gctcgaccag cgtctgtgga agcatgtcgg cggtggggac 120
taccccccgt cgggcccgaa tcccaagcac gatccgccgc cgcgcaacaa cgggcaccat 180
tga 183

<210> SEQ ID NO 16
<211> LENGTH: 183
<212> TYPE: DNA
<213> ORGANISM: Xanthomonas oryzae

<400> SEQUENCE: 16
atgaacctct cgaaaaaatc gccaaccaag ggtgcggcat cgctgcagtg gcccgccagg 60
gccaagggcc gaccggagcc gctcgaccag cgcctgtgga agcatgtcgg cggtggggac 120
taccccccgt cgggcccgaa taccaagcac gatccgccgc cgcccaacaa cgggcaccat 180
tga 183

<210> SEQ ID NO 17
<211> LENGTH: 183
<212> TYPE: DNA
<213> ORGANISM: Artificial Sequence
<220> FEATURE:
<223> OTHER INFORMATION: Synthetic construct

<400> SEQUENCE: 17
atgaaccact cgaaaaaatc gcccaccaag ggtgcggcat cgctgcagcg gcccgccggg 60
gccaagggcc gaccggagca gctcgaccag cgtctgtgga agcatgtcgg cggtggggac 120
tatcccccgc cgggcgcgaa tcccaagcac gatccgccgc cgcgcaaccc cgggcaccat 180
tga 183

<210> SEQ ID NO 18
<211> LENGTH: 192
<212> TYPE: DNA
<213> ORGANISM: Xanthomonas oryzae

<400> SEQUENCE: 18
atgaacctct cgaaaaaatc gccaaccaag ggtgcggcat cgctgcagcc gcccgccggg 60
gccaagggcc gaccggagcc gctcgaccag cgtctgtgga agcatgtcgg cggtggggac 120
taccccccgt cgggcccgaa tcccaagcac gatccgccgc atccgccgcc gcgcaacaac 180
gggcaccatt ga 192

<210> SEQ ID NO 19
<211> LENGTH: 183
<212> TYPE: DNA
<213> ORGANISM: Xanthomonas oryzae

<400> SEQUENCE: 19
atgaaccact cgaaaaaatc gcccgccaag ggtgcggcat cgctgcagcg gcccgccggg 60
gccaagggcc gaccggagcc gctcgaccag cgtctgtgga agcatgtcgg cggtggggac 120
tatcccccgc cgggcgcgaa tcccaagcac gatccgccgc cgcgcaaccc cgggcaccat 180
tga 183

<210> SEQ ID NO 20
<211> LENGTH: 189
<212> TYPE: DNA
<213> ORGANISM: Unknown
<220> FEATURE:
<223> OTHER INFORMATION: Xanthomonas sp. M97

<400> SEQUENCE: 20
atgaacctgt cgaagaaatc gccaacctat ggcgcgcaat cgctgcagcg gcccgccggg 60
gccaagggcc ggctggagcc cctggaccag cgtctgtgga agcatgtcgg cggtggggac 120

```
tatccccgc cgggcgcgaa cgaccgccac aacccgccac cgccgccgtc caacggcgga    180

caccactga                                                           189


<210> SEQ ID NO 21
<211> LENGTH: 189
<212> TYPE: DNA
<213> ORGANISM: Xanthomonas vesicatoria

<400> SEQUENCE: 21

atggaactat tgaaaaaatc gccatccaat ggcgtgggat cgctccagcg gtcggccggc     60

gccaagggcc ggctagagcc gctggaccag cgtctgtgga agcatgtcgg gggtggggac    120

tatcccccac cgggctcgaa taaccgccac gatccaacac agccgccgcc caaaaaaggg    180

aaaccttga                                                           189


<210> SEQ ID NO 22
<211> LENGTH: 59
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (46)..(46)
<223> OTHER INFORMATION: Xaa can be any naturally occurring amino acid

<400> SEQUENCE: 22

Met Asn Leu Ser Lys Lys Ser Pro Thr Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Pro Gly Xaa Asn Thr
        35                  40                  45

Lys His Asp Pro Pro Pro Asn Asn Gly His His
    50                  55


<210> SEQ ID NO 23
<211> LENGTH: 56
<212> TYPE: PRT
<213> ORGANISM: Xanthomonas translucens

<400> SEQUENCE: 23

Met His Leu Leu Asn Lys Arg Lys Pro Thr Gly Leu Arg Pro Leu Gln
1               5                   10                  15

Thr Glu Ser Gln Pro Lys Arg Val Ala Pro Leu Asp Glu Ala Leu Trp
            20                  25                  30

Lys Lys Val Gly Gly Gly Asp Tyr Pro Pro Pro Ser Ser Asn Gly Arg
        35                  40                  45

His Asp Pro Pro Gly His His His
    50                  55


<210> SEQ ID NO 24
<211> LENGTH: 62
<212> TYPE: PRT
<213> ORGANISM: Xanthomonas vesicatoria

<400> SEQUENCE: 24

Met Glu Leu Leu Lys Lys Ser Pro Ser Asn Gly Val Gly Ser Leu Gln
1               5                   10                  15

Arg Ser Ala Gly Ala Lys Gly Arg Leu Glu Pro Leu Asp Gln Arg Leu
            20                  25                  30
```

```
Trp Lys His Val Gly Gly Gly Asp Tyr Pro Pro Pro Gly Ser Asn Asn
        35                  40                  45

Arg His Asp Pro Thr Gln Pro Pro Pro Lys Lys Gly Lys Pro
    50                  55                  60


<210> SEQ ID NO 25
<211> LENGTH: 62
<212> TYPE: PRT
<213> ORGANISM: Xanthomonas campestris

<400> SEQUENCE: 25

Met Lys Leu Leu Lys Lys Ser Pro Ser Asn Gly Ala Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Ala Pro Pro Gly Ser Asn Asp
        35                  40                  45

Arg His Asp Pro Pro Lys Pro Pro Pro Lys Lys Gly Asn Pro
    50                  55                  60


<210> SEQ ID NO 26
<211> LENGTH: 62
<212> TYPE: PRT
<213> ORGANISM: Xanthomonas campestris

<400> SEQUENCE: 26

Met Glu Leu Leu Lys Lys Ser Pro Ser Asn Gly Val Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Ala Pro Pro Gly Ser Asn Asp
        35                  40                  45

Arg His Asp Pro Pro Lys Pro Pro Pro Lys Lys Gly Asn Pro
    50                  55                  60


<210> SEQ ID NO 27
<211> LENGTH: 62
<212> TYPE: PRT
<213> ORGANISM: Artificial Sequence
<220> FEATURE:
<223> OTHER INFORMATION: Synthetic construct

<400> SEQUENCE: 27

Met Glu Leu Leu Lys Lys Ser Pro Ser Asn Gly Val Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Ala Pro Pro Gly Ser Asn Asp
        35                  40                  45

Arg His Asp Pro Pro Lys Pro Pro Pro Lys Lys Gly Asn Pro
    50                  55                  60


<210> SEQ ID NO 28
<211> LENGTH: 62
<212> TYPE: PRT
<213> ORGANISM: Unknown
<220> FEATURE:
<223> OTHER INFORMATION: Xanthomonas sp. M97

<400> SEQUENCE: 28
```

-continued

```
Met Asn Leu Ser Lys Lys Ser Pro Thr Tyr Gly Ala Gln Ser Leu Gln
1               5                   10                  15

Arg Pro Ala Gly Ala Lys Gly Arg Leu Glu Pro Leu Asp Gln Arg Leu
            20                  25                  30

Trp Lys His Val Gly Gly Gly Asp Tyr Pro Pro Pro Gly Ala Asn Asp
        35                  40                  45

Arg His Asn Pro Pro Pro Pro Pro Ser Asn Gly Gly His His
    50                  55                  60
```

<210> SEQ ID NO 29
<211> LENGTH: 59
<212> TYPE: PRT
<213> ORGANISM: Xanthomonas axonopodis

<400> SEQUENCE: 29

```
Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55
```

<210> SEQ ID NO 30
<211> LENGTH: 59
<212> TYPE: PRT
<213> ORGANISM: Xanthomonas axonopodis

<400> SEQUENCE: 30

```
Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55
```

<210> SEQ ID NO 31
<211> LENGTH: 59
<212> TYPE: PRT
<213> ORGANISM: Xanthomonas euvesicatoria

<400> SEQUENCE: 31

```
Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55
```

<210> SEQ ID NO 32
<211> LENGTH: 59
<212> TYPE: PRT
<213> ORGANISM: Xanthomonas perforans

<400> SEQUENCE: 32

Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55

<210> SEQ ID NO 33
<211> LENGTH: 59
<212> TYPE: PRT
<213> ORGANISM: Xanthomonas axonopodis

<400> SEQUENCE: 33

Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Met
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55

<210> SEQ ID NO 34
<211> LENGTH: 60
<212> TYPE: PRT
<213> ORGANISM: Artificial Sequence
<220> FEATURE:
<223> OTHER INFORMATION: Synthetic construct

<400> SEQUENCE: 34

Met Asn His Ser Lys Lys Ser Pro Thr Lys Gly Ala Ala Ser Leu Gln
1               5                   10                  15

Arg Pro Ala Gly Ala Lys Gly Arg Pro Glu Gln Leu Asp Gln Arg Leu
            20                  25                  30

Trp Lys His Val Gly Gly Gly Asp Tyr Pro Pro Pro Gly Ala Asn Pro
        35                  40                  45

Lys His Asp Pro Pro Pro Arg Asn Pro Gly His His
    50                  55                  60

<210> SEQ ID NO 35
<211> LENGTH: 60
<212> TYPE: PRT
<213> ORGANISM: Xanthomonas oryzae

<400> SEQUENCE: 35

Met Asn His Ser Lys Lys Ser Pro Thr Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Pro Gly Ala Asn Pro
        35                  40                  45

Lys His Asp Pro Pro Pro Arg Asn Pro Gly His His
    50                  55                  60

<210> SEQ ID NO 36
<211> LENGTH: 60
<212> TYPE: PRT

<213> ORGANISM: Xanthomonas oryzae

<400> SEQUENCE: 36

Met Asn His Ser Lys Lys Ser Pro Ala Lys Gly Ala Ala Ser Leu Gln
1 5 10 15

Arg Pro Ala Gly Ala Lys Gly Arg Pro Glu Pro Leu Asp Gln Arg Leu
20 25 30

Trp Lys His Val Gly Gly Gly Asp Tyr Pro Pro Pro Gly Ala Asn Pro
35 40 45

Lys His Asp Pro Pro Pro Arg Asn Pro Gly His His
50 55 60

<210> SEQ ID NO 37
<211> LENGTH: 54
<212> TYPE: PRT
<213> ORGANISM: Artificial Sequence
<220> FEATURE:
<223> OTHER INFORMATION: Synthetic construct

<400> SEQUENCE: 37

Met Asn Leu Ser Lys Lys Ser Pro Thr Lys Gly Ala Ala Ser Leu Gln
1 5 10 15

Arg Ser Ala Gly Ala Lys Gly Arg Pro Glu Pro Leu Asp Gln Arg Leu
20 25 30

Trp Lys His Val Gly Gly Gly Asp Tyr Pro Pro Ala Gly Pro Ser Thr
35 40 45

Lys His Asp Pro His His
50

<210> SEQ ID NO 38
<211> LENGTH: 60
<212> TYPE: PRT
<213> ORGANISM: Artificial Sequence
<220> FEATURE:
<223> OTHER INFORMATION: Synthetic construct

<400> SEQUENCE: 38

Met Asn Leu Ser Lys Lys Ser Pro Thr Lys Gly Ala Ala Ser Leu Gln
1 5 10 15

Trp Pro Ala Arg Ala Lys Gly Arg Pro Glu Pro Leu Asp Gln Arg Leu
20 25 30

Trp Lys His Val Gly Gly Gly Asp Tyr Pro Pro Ser Gly Pro Asn Thr
35 40 45

Lys His Asp Pro Pro Pro Pro Asn Asn Gly His His
50 55 60

<210> SEQ ID NO 39
<211> LENGTH: 60
<212> TYPE: PRT
<213> ORGANISM: Xanthomonas oryzae

<400> SEQUENCE: 39

Met Asn Leu Ser Lys Lys Ser Pro Thr Lys Gly Ala Ala Ser Leu Gln
1 5 10 15

Trp Pro Ala Arg Ala Lys Gly Arg Pro Glu Pro Leu Asp Gln Arg Leu
20 25 30

Trp Lys His Val Gly Gly Gly Asp Tyr Pro Pro Ser Gly Pro Asn Thr
35 40 45

Lys His Asp Pro Pro Pro Pro Asn Asn Gly His His
50 55 60

<210> SEQ ID NO 40
<211> LENGTH: 60
<212> TYPE: PRT
<213> ORGANISM: Artificial Sequence
<220> FEATURE:
<223> OTHER INFORMATION: Synthetic construct

<400> SEQUENCE: 40

```
Met Asn Leu Ser Lys Lys Ser Pro Thr Lys Gly Ala Ala Ser Leu Gln
1               5                   10                  15

Trp Pro Ala Arg Ala Lys Gly Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 41
<211> LENGTH: 60
<212> TYPE: PRT
<213> ORGANISM: Xanthomonas oryzae

<400> SEQUENCE: 41

```
Met Asn Leu Leu Lys Lys Ser Pro Thr Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 42
<211> LENGTH: 60
<212> TYPE: PRT
<213> ORGANISM: Xanthomonas oryzae

<400> SEQUENCE: 42

```
Met Asn Leu Ser Lys Lys Ser Pro Thr Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 43
<211> LENGTH: 63
<212> TYPE: PRT
<213> ORGANISM: Artificial Sequence
<220> FEATURE:
<223> OTHER INFORMATION: Synthetic construct

<400> SEQUENCE: 43

```
Met Asn Leu Ser Lys Lys Ser Pro Thr Lys Gly Ala Ala Ser Leu Gln
1               5                   10                  15

Pro Pro Ala Gly Ala Lys Gly Arg Pro Glu Pro Leu Asp Gln Arg Leu
            20                  25                  30
```

Trp Lys His Val Gly Gly Gly Asp Tyr Pro Pro Ser Gly Pro Asn Pro
35 40 45

Lys His Asp Pro Pro His Pro Pro Pro Arg Asn Asn Gly His His
50 55 60

<210> SEQ ID NO 44
<211> LENGTH: 60
<212> TYPE: PRT
<213> ORGANISM: Artificial Sequence
<220> FEATURE:
<223> OTHER INFORMATION: Synthetic construct

<400> SEQUENCE: 44

Met Asn Leu Ser Lys Lys Ser Pro Thr Lys Gly Ala Ala Ser Leu Gln
1 5 10 15

Arg Pro Ala Gly Ala Lys Val Arg Pro Glu Pro Leu Asp Gln Arg Leu
20 25 30

Trp Lys His Val Gly Gly Gly Asp Tyr Pro Pro Ser Gly Pro Asn Pro
35 40 45

Lys His Asp Pro Pro Pro Arg Asn Asn Gly His His
50 55 60

<210> SEQ ID NO 45
<211> LENGTH: 59
<212> TYPE: PRT
<213> ORGANISM: Artificial Sequence
<220> FEATURE:
<223> OTHER INFORMATION: Synthetic construct

<400> SEQUENCE: 45

Met Asn Leu Ser Lys Lys Ser Pro Thr Lys Gly Ala Ala Ser Leu Gln
1 5 10 15

Arg Pro Ala Gly Ala Lys Gly Arg Pro Glu Pro Leu Asp Gln Arg Leu
20 25 30

Trp Lys His Val Gly Gly Gly Asp Tyr Pro Pro Ser Gly Pro Asn Pro
35 40 45

Lys His Asp Pro Pro Gly Asn Asn Gly His His
50 55

<210> SEQ ID NO 46
<211> LENGTH: 13
<212> TYPE: PRT
<213> ORGANISM: Artificial Sequence
<220> FEATURE:
<223> OTHER INFORMATION: Synthetic construct

<400> SEQUENCE: 46

Asp Tyr Pro Pro Pro Gly Ala Asn Pro Lys His Asp Pro
1 5 10

<210> SEQ ID NO 47
<211> LENGTH: 13
<212> TYPE: PRT
<213> ORGANISM: Artificial Sequence
<220> FEATURE:
<223> OTHER INFORMATION: Synthetic construct

<400> SEQUENCE: 47

Asp Tyr Gly Asp Pro Ser Ala Asn Pro Lys His Asp Pro
1 5 10

<210> SEQ ID NO 48
<211> LENGTH: 13

<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa = Pro or Gly
<220> FEATURE:
<221> NAME/KEY: MISC_FEATURE
<222> LOCATION: (4)..(4)
<223> OTHER INFORMATION: Xaa = Pro or Asp
<220> FEATURE:
<221> NAME/KEY: MISC_FEATURE
<222> LOCATION: (6)..(6)
<223> OTHER INFORMATION: Xaa = Gly or Ser

<400> SEQUENCE: 48

```
Asp Tyr Xaa Xaa Pro Xaa Ala Asn Pro Lys His Asp Pro
1               5                   10
```

<210> SEQ ID NO 49
<211> LENGTH: 182
<212> TYPE: DNA
<213> ORGANISM: Artificial Sequence
<220> FEATURE:
<223> OTHER INFORMATION: Synthetic construct

<400> SEQUENCE: 49

```
atgaacctgt cgaaaaaatc gccaaccaat ggtgcggaat cgctgcagcg gcccgccggg     60

gccaagggcc ggctggagcc gctggaccag cgtctgtgga agcatgtcgg cggtggggac    120

tatcccccgc cgggcgcgaa taccaagcac gaccgccgcc gcccaacaac gggcaccatt    180

ga                                                                   182
```

<210> SEQ ID NO 50
<211> LENGTH: 60
<212> TYPE: PRT
<213> ORGANISM: Artificial Sequence
<220> FEATURE:
<223> OTHER INFORMATION: Synthetic construct

<400> SEQUENCE: 50

```
Met Asn Leu Ser Lys Lys Ser Pro Thr Asn Gly Ala Glu Ser Leu Gln
1               5                   10                  15

Arg Pro Ala Gly Ala Lys Gly Arg Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Arg Arg Arg Pro Thr Thr Gly Thr Ile
    50                  55                  60
```

<210> SEQ ID NO 51
<211> LENGTH: 171
<212> TYPE: DNA
<213> ORGANISM: Xanthomonas translucens

<400> SEQUENCE: 51

```
atgcatctac tgaacaagcg caagccgacc ggccttcgcc cgctgcagac ggaatcgcag     60

cccaagcgcg tggccccgct ggacgaagcc ctgtggaaga aagtgggcgg cggcgattac    120

ccgcctccga gctccaacgg taggcacgac ccgcctgggc atcatcactg a             171
```

<210> SEQ ID NO 52
<211> LENGTH: 180

<212> TYPE: DNA
<213> ORGANISM: Xanthomonas axonopodis

<400> SEQUENCE: 52
atgaatctgt cgaaaaaatc gccaaccaat ggtgcgcaag cgctgcagcg gcccgccggg 60
gccaagggcc agctggagcc cctggaccag cgtctgtgga agcatgtcgg cggtggggac 120
tatcccccgc cgggcgccaa taccaagcac gatccgccgc ccaagaacgg gcaccactga 180

<210> SEQ ID NO 53
<211> LENGTH: 180
<212> TYPE: DNA
<213> ORGANISM: Xanthomonas perforans

<400> SEQUENCE: 53
atgaatctgt cgaaaaaatc gccaaccaat ggtgcgcaag cgctgcagcg gcccgccggg 60
gccaagggcc agctggagcc cctggaccag cgtctgtgga agcatgtcgg cggtggggac 120
tatcccccgc cgggcgccaa taccaagcac gatccgccgc ccaagaacgg gcaccactga 180

<210> SEQ ID NO 54
<211> LENGTH: 26
<212> TYPE: PRT
<213> ORGANISM: Xanthomonas oryzae

<400> SEQUENCE: 54

Val Asp Tyr His Phe Ile Ser Gly Leu Pro Arg Ala Gly Ser Ser Leu
1 5 10 15

Leu Ala Ala Leu Leu Arg Gln Asn Pro Gln
20 25

<210> SEQ ID NO 55
<211> LENGTH: 26
<212> TYPE: PRT
<213> ORGANISM: Homo sapiens

<400> SEQUENCE: 55

Met Pro Leu Ile Phe Ile Gly Gly Val Pro Arg Ser Gly Thr Thr Leu
1 5 10 15

Met Arg Ala Met Leu Asp Ala His Pro Asp
20 25

<210> SEQ ID NO 56
<211> LENGTH: 26
<212> TYPE: PRT
<213> ORGANISM: Homo sapiens

<400> SEQUENCE: 56

Met Pro Leu Ile Phe Val Gly Gly Val Pro Arg Ser Gly Thr Thr Leu
1 5 10 15

Met Arg Ala Met Leu Asp Ala His Pro Glu
20 25

<210> SEQ ID NO 57
<211> LENGTH: 9
<212> TYPE: PRT
<213> ORGANISM: Artificial Sequence
<220> FEATURE:
<223> OTHER INFORMATION: Synthetic construct

<400> SEQUENCE: 57

Gly Arg Pro Glu Pro Leu Asp Gln Arg
1 5

<210> SEQ ID NO 58
<211> LENGTH: 11
<212> TYPE: PRT
<213> ORGANISM: Escherichia coli

<400> SEQUENCE: 58

Asp Tyr Pro Pro Pro Gly Ala Asn Pro Lys His
1               5                   10

<210> SEQ ID NO 59
<211> LENGTH: 21
<212> TYPE: PRT
<213> ORGANISM: Xanthomonas oryzae

<400> SEQUENCE: 59

His Val Gly Gly Gly Asp Tyr Pro Pro Pro Gly Ala Asn Pro Lys His
1               5                   10                  15

Asp Pro Pro Pro Arg
            20

<210> SEQ ID NO 60
<211> LENGTH: 18
<212> TYPE: PRT
<213> ORGANISM: Arabidopsis thaliana

<400> SEQUENCE: 60

Asp Tyr Asp Asp Pro Ser Ala Asn Thr Arg His Asp Pro Ser Val Pro
1               5                   10                  15

Thr Asn

<210> SEQ ID NO 61
<211> LENGTH: 22
<212> TYPE: PRT
<213> ORGANISM: Arabidopsis thaliana

<400> SEQUENCE: 61

Asp Tyr Ser Asp Pro Thr Ala Asn Gly Arg His Asp Pro Pro Arg Gly
1               5                   10                  15

Gly Arg Gly Arg Arg Arg
            20

<210> SEQ ID NO 62
<211> LENGTH: 18
<212> TYPE: PRT
<213> ORGANISM: Arabidopsis thaliana

<400> SEQUENCE: 62

Asp Tyr Gly Asp Pro Ser Ala Asn Pro Lys His Asp Pro Gly Val Pro
1               5                   10                  15

Pro Ser

<210> SEQ ID NO 63
<211> LENGTH: 18
<212> TYPE: PRT
<213> ORGANISM: Oryza sativa

<400> SEQUENCE: 63

Asp Tyr Pro Ala Pro Gly Ala Asn Pro Arg His Asn Pro Lys Arg Pro
1               5                   10                  15

Pro Gly

<210> SEQ ID NO 64
<211> LENGTH: 18
<212> TYPE: PRT
<213> ORGANISM: Oryza sativa

<400> SEQUENCE: 64

Asp Tyr Pro Ala Pro Gly Ala Asn Pro Arg His Asn Pro Lys Ser Pro
1 5 10 15

Pro Gly

<210> SEQ ID NO 65
<211> LENGTH: 18
<212> TYPE: PRT
<213> ORGANISM: Oryza sativa

<400> SEQUENCE: 65

Asp Tyr Pro Ala Pro Gly Ala Asn Pro Arg His Asn Pro Lys Arg Pro
1 5 10 15

Pro Gly

<210> SEQ ID NO 66
<211> LENGTH: 18
<212> TYPE: PRT
<213> ORGANISM: Oryza sativa

<400> SEQUENCE: 66

Asp Tyr Leu Ala Pro Gly Ala Asn Pro Arg His Asn Pro Lys Arg Pro
1 5 10 15

Pro Gly

<210> SEQ ID NO 67
<211> LENGTH: 17
<212> TYPE: PRT
<213> ORGANISM: Oryza sativa

<400> SEQUENCE: 67

Asp Tyr Pro Ser Ser Gly Ala Asn Ser Arg His Asp Pro Arg Asn Pro
1 5 10 15

His

<210> SEQ ID NO 68
<211> LENGTH: 18
<212> TYPE: PRT
<213> ORGANISM: Oryza sativa

<400> SEQUENCE: 68

Asp Tyr Pro Gly Ser Gly Ala Asn Asn Arg His Asp Pro Lys Ser Pro
1 5 10 15

Gly Arg

<210> SEQ ID NO 69
<211> LENGTH: 18
<212> TYPE: PRT
<213> ORGANISM: Oryza sativa

<400> SEQUENCE: 69

Asp Tyr Pro Gly Ser Gly Pro Asn Asn Arg His Asp Pro Pro Lys Gly
1 5 10 15

Pro Gly

```
<210> SEQ ID NO 70
<211> LENGTH: 16
<212> TYPE: PRT
<213> ORGANISM: Artificial Sequence
<220> FEATURE:
<223> OTHER INFORMATION: Synthetic construct

<400> SEQUENCE: 70

Asp Tyr Pro Pro Pro Gly Ala Asn Pro Lys His Asp Pro Pro Pro Arg
1               5                   10                  15


<210> SEQ ID NO 71
<211> LENGTH: 138
<212> TYPE: PRT
<213> ORGANISM: Triticum aestivum

<400> SEQUENCE: 71

Met Gly Arg Ala Asn Cys Ser Val Pro Leu Leu Leu Val Leu Leu Ala
1               5                   10                  15

Phe Leu Ser Cys Phe Phe Leu Ala His Gly Leu Tyr Gly Leu Thr Glu
            20                  25                  30

Leu Phe Gly Ser Pro Asp Leu Ser Pro Glu Ala Ile Leu Leu Ile Phe
        35                  40                  45

Ala Leu Ser Phe Leu Val Leu Ala Ala Ala Val Ala Gly Ala Ser Gly
    50                  55                  60

Asn Arg Lys Met Phe Leu Pro Arg Glu Gly Ala Ala Ala Ala Ala Gly
65                  70                  75                  80

Ser Asn Asp Gly Gly Gln Ala Met Leu Thr Thr Ala Glu Glu Val Ala
                85                  90                  95

Val Gly Gly Glu Met His Leu Leu Leu Ser Asp Asp Glu Glu Met Leu
            100                 105                 110

Ala Arg Arg Val Asp Leu Gln Thr Gln Asp Tyr Pro Gly Ser Gly Ala
        115                 120                 125

Asn Gly Arg His Asp Pro Arg Asn Pro His
    130                 135


<210> SEQ ID NO 72
<211> LENGTH: 131
<212> TYPE: PRT
<213> ORGANISM: Musa acuminata

<400> SEQUENCE: 72

Met Ser Ile Cys Ile Asp Thr Gly Cys Leu Ser Ser Ser Phe Leu Thr
1               5                   10                  15

Phe Leu Ser Pro Lys Gly Gly Lys Val Gly Asp Gln Thr Glu Ser Ala
            20                  25                  30

Ser Gly Arg Glu His Ser Leu Lys Gly Asp His Phe Gly Phe Val Leu
        35                  40                  45

Gly Glu Met Glu Arg Val Ser Leu His Leu Leu Val Ile Leu Leu Ala
    50                  55                  60

Leu Ser His Leu Leu Val Ser Ser Gln Ala Ile Pro Ala Thr Glu Lys
65                  70                  75                  80

Glu Pro Lys Asp Leu Ala Thr Ile Ser Glu Pro Leu Lys Val Val Glu
                85                  90                  95

Asp Asp Ala Ala Thr Glu Asp Val Val Gly Gly Arg Met Asn Val Glu
            100                 105                 110

Ile Ser Asp Tyr Pro Ile Ser Gly Ala Asn Asn Arg His Thr Pro Pro
        115                 120                 125
```

Gly Arg Ser
    130

<210> SEQ ID NO 73
<211> LENGTH: 122
<212> TYPE: PRT
<213> ORGANISM: Oryza sativa

<400> SEQUENCE: 73

Met Arg Thr Ala Ala Ala Lys Ala Arg Cys Ser Val Pro Phe Ile Leu
1               5                   10                  15

Ala Ala Leu Ala Ala Leu Ser Cys Val Phe Leu Val His Ala Ala Ala
            20                  25                  30

Ala Ala Ala Ala Ala Ala Val Thr Thr Thr Thr Thr Ser Val Val Gly
        35                  40                  45

Tyr Arg Arg Ala Leu Leu Pro Arg Glu Ala Ala Ala Val Val Met Pro
    50                  55                  60

Thr Thr Ser Thr Ala Glu Asp Ala Ala Val Val Gly Met Ala Gly Val
65                  70                  75                  80

Glu Gly Glu Leu Pro Val Val Ala Asp Glu Ala Ala Ala Ala Ala Ala
                85                  90                  95

Arg Arg Met Asp Met Gln Thr Thr Gln Asp Tyr Pro Ser Ser Gly Ala
            100                 105                 110

Asn Ser Arg His Asp Pro Arg Asn Pro His
        115                 120

<210> SEQ ID NO 74
<211> LENGTH: 100
<212> TYPE: PRT
<213> ORGANISM: Oryza sativa

<400> SEQUENCE: 74

Met Ala Gln Gln Gln Arg Arg Arg Arg Arg Gly Gly Ser Leu Ala Val
1               5                   10                  15

Leu Leu Leu Leu Leu Leu Leu Ala Ala Leu Leu Leu Ser Leu Ser Leu
            20                  25                  30

Leu Ala Arg Val Asp Ala Ala Ala Thr Val Ser Ser Ala Asn Leu Asp
        35                  40                  45

Trp Asn Glu Gly Glu Val Ala Val Ala Thr Pro Leu Gly Gln Glu Ala
    50                  55                  60

Val Ala Ala Ala Glu Glu Glu Gly Asp Arg Pro Pro Glu Arg Val Glu
65                  70                  75                  80

Met Glu Ser Ile Asn Asp Tyr Gly Gln Ala Ser Ala Asn Asn Arg His
                85                  90                  95

Asn Pro His Pro
            100

<210> SEQ ID NO 75
<211> LENGTH: 104
<212> TYPE: PRT
<213> ORGANISM: Arabidopsis thaliana

<400> SEQUENCE: 75

Met Pro Leu Arg Ile Glu Pro Leu Ser Leu Leu Phe Leu Ile Leu Ile
1               5                   10                  15

Ile Cys Ser Ser Ser Leu Gly Met Thr Ile Asn Leu Ala Ser Gln His
            20                  25                  30

Ile His Leu Ser Pro Arg Ser Ala Phe Ala Ile Val Glu Gly Ser Ile

```
        35                  40                  45

Gln Leu Asp Gly Ala Lys Met His Glu Ser Ser Met Leu Tyr Lys Ser
    50                  55                  60

Glu Glu Val Gly Val Lys Lys Met Gly His Arg Lys Leu Met Phe His
65                  70                  75                  80

Ser Thr Ala Asp Tyr Asp Asp Ala Gly Pro Asn Pro Lys His Asp Pro
                85                  90                  95

Arg Arg Arg Pro Gly Gly Lys Gly
            100


<210> SEQ ID NO 76
<211> LENGTH: 101
<212> TYPE: PRT
<213> ORGANISM: Triticum aestivum

<400> SEQUENCE: 76

Met Glu Cys Arg Lys Met Lys Pro Val Leu Ala Leu Val Leu Leu Leu
1               5                   10                  15

Ser Cys His Leu Leu Leu Pro Leu Val Ser Ser Val Pro Val Ser Arg
            20                  25                  30

Ser Val Ser Leu Glu Asn His Gln Ala Ser Ala Ser Ser Leu Thr Pro
        35                  40                  45

Glu Ala Val Pro Val Gln Gly Val Val Thr Val Ala Ala Ala Ala Glu
    50                  55                  60

Glu Arg Ser Val Val Gly Glu Val Val Ala Arg Met Asp Ile Glu Val
65                  70                  75                  80

Asn Asp Tyr Pro Gly Ser Ser Ala Asn Gly Arg His Glu Pro Pro Arg
                85                  90                  95

Gly Pro Gly Arg Gly
            100


<210> SEQ ID NO 77
<211> LENGTH: 100
<212> TYPE: PRT
<213> ORGANISM: Oryza sativa

<400> SEQUENCE: 77

Met Arg Arg Ala Met Glu Arg Arg Pro Arg Asp Leu Val Ala Val Leu
1               5                   10                  15

Ala Leu Ser Cys Leu Leu Leu Leu Leu Pro Leu Leu Val Ser Ser Val
            20                  25                  30

Pro Met Ser Arg Ser Leu His Leu Ser Ser Gln Gln Gln Gln His Pro
        35                  40                  45

Pro Ser Leu Asn Leu Ser Pro Asp Glu Met Ala Ala Ala Ala Ala Ala
    50                  55                  60

Arg Gly Leu Gly Arg Arg Pro Ala Ala Arg Met Asp Val Glu Val Asn
65                  70                  75                  80

Asp Tyr Pro Gly Ser Gly Pro Asn Asn Arg His Asp Pro Pro Lys Gly
                85                  90                  95

Pro Gly Arg Ala
            100


<210> SEQ ID NO 78
<211> LENGTH: 97
<212> TYPE: PRT
<213> ORGANISM: Oryza sativa

<400> SEQUENCE: 78
```

```
Met Lys Met Glu Gln Val Ser Gln Arg Lys Ala Pro Leu Leu Val Leu
1               5                   10                  15

Val Ile Leu Cys Gly Leu Leu Leu Leu Leu Pro Leu Val Ser Ser Val
            20                  25                  30

Pro Leu Ser Arg Ser Val Ser Leu Arg Asn His Gln Ala Ser Val Ser
        35                  40                  45

Ala Leu Glu Ala Pro Val Gln Val Val Ala Ala Ala Ala Glu Glu Arg
    50                  55                  60

Asp Leu Asp Glu Val Ala Ala Arg Met Val Ile Glu Val Asn Asp Tyr
65                  70                  75                  80

Pro Gly Ser Gly Ala Asn Asn Arg His Asp Pro Lys Ser Pro Gly Arg
                85                  90                  95

Ala


<210> SEQ ID NO 79
<211> LENGTH: 95
<212> TYPE: PRT
<213> ORGANISM: Oryza sativa

<400> SEQUENCE: 79

Met Ala Arg Ser Ala Ser Gly Arg Ser Leu Leu Val Ile Leu Leu Ala
1               5                   10                  15

Val Ser Leu Leu Leu Val Ala Ser Ser Asp Ala Ala Arg Phe Thr Arg
            20                  25                  30

Ser Asn Arg Met Ala Met Met Val Val Glu Ala Pro Ala Arg Pro Gly
        35                  40                  45

Val Gly Val Ser Gly Ser Ala Glu Asp Asp Val Ser Thr Ser Asp Ala
    50                  55                  60

Ile Val Glu Met Phe Gly Arg Met Ala Leu Gln Thr Thr Asp Tyr Pro
65                  70                  75                  80

Pro Ser Gly Pro Asn Asp Arg His Thr Pro Lys Ala Pro Gly Thr
                85                  90                  95


<210> SEQ ID NO 80
<211> LENGTH: 95
<212> TYPE: PRT
<213> ORGANISM: Oryza sativa

<400> SEQUENCE: 80

Met Glu Arg Val Pro Ala Val His Leu Ala Val Val Leu Leu Ala Phe
1               5                   10                  15

Cys Cys Leu Ile His Ala Ser Ser Ser Ala Glu Thr Pro Leu Pro Pro
            20                  25                  30

Ala Leu Lys Val Met Gln Arg Phe Glu Ala Thr Pro Val Ser Ser Arg
        35                  40                  45

Gly Asp Asp Gln Ala Ala Ala Val Ile Ala Gly Glu Pro Glu Ala Gly
    50                  55                  60

Glu Val Asn Gly Arg Met Glu Leu Glu Leu Thr Asp Tyr Pro Gly Ser
65                  70                  75                  80

Gly Ala Asn Asp Arg His Ser Pro Trp Gly Gln Glu Arg Arg Asn
                85                  90                  95


<210> SEQ ID NO 81
<211> LENGTH: 88
<212> TYPE: PRT
<213> ORGANISM: Musa acuminata
```

<400> SEQUENCE: 81

```
Met Glu Gln Lys Lys Pro Leu Ser His Leu Leu Ala Leu Leu Leu Leu
1               5                   10                  15

Ser Cys Leu Leu Ser Val Asp Ala Ala Pro Leu Ser Gly Thr Phe Ala
            20                  25                  30

Leu Lys Asn Gln Asp Glu Ala Glu Met Lys Val Ala Asp Gln Val Ile
        35                  40                  45

Asn Lys Glu Thr Pro Glu Glu Gly Gly Val Ser Leu Asn Glu Arg Met
    50                  55                  60

Asp Phe Glu Leu Asp Asp Tyr Pro Gly Ser Gly Ala Asn Ser Arg His
65                  70                  75                  80

Asp Pro Lys Asn Pro Gly Lys Pro
                85
```

<210> SEQ ID NO 82
<211> LENGTH: 88
<212> TYPE: PRT
<213> ORGANISM: Musa acuminata

<400> SEQUENCE: 82

```
Met Asp Gln Arg Lys Pro Ala Ile Cys Leu Cys Thr Leu Leu Cys Phe
1               5                   10                  15

Ser Trp Ile Leu Ser Leu Val Ala Val Pro Leu Pro Gly Lys Leu Asp
            20                  25                  30

Leu Arg Asn Gln Lys Ile Ser Val Met Lys Val Ala Asp Gln Val Ile
        35                  40                  45

Asn Arg Lys Ile Leu Ile Asn Glu Lys Ala Ile Ala Asp Arg Arg Met
    50                  55                  60

Asp Ile Glu Leu Asn Asp Tyr Pro Val Ser Gly Ala Asn Ser Arg His
65                  70                  75                  80

Asp Pro Lys Ser Pro Gly Lys Pro
                85
```

<210> SEQ ID NO 83
<211> LENGTH: 92
<212> TYPE: PRT
<213> ORGANISM: Solanum lycopericum

<400> SEQUENCE: 83

```
Met Ala Ala Pro Phe Phe Arg Leu Phe Ile Ser Phe Leu Cys Phe Ser
1               5                   10                  15

Tyr Thr Ile Asn Ser Phe Ile Asn Ala Val Pro Val Thr Arg Ser Lys
            20                  25                  30

Ser Leu Val Leu Leu Asp Ile Ser Gln Glu His Asn Val Leu Ser Glu
        35                  40                  45

Asn Ile Ile Leu Met Asp Lys Thr Arg Arg Glu Val Leu Glu Ala Glu
    50                  55                  60

Glu Ile Ile Asn Asp Tyr Pro Gly Ser Gly Ala Asn Asn Arg His Thr
65                  70                  75                  80

Pro Arg Pro Gln Leu Gly Arg Gly Cys Val Glu Cys
                85                  90
```

<210> SEQ ID NO 84
<211> LENGTH: 84
<212> TYPE: PRT
<213> ORGANISM: Musa acuminata

<400> SEQUENCE: 84

Met Val Asp Thr Lys Gly Met Thr Ser Leu Arg Leu Leu Leu Ile Ser
1               5                   10                  15

Leu Ala Leu Ala His Leu Ile Ala Ala Ser His Ala Val Pro Ser Thr
            20                  25                  30

Arg Asp Gly Arg Met Leu Arg Gly Cys Arg Ser Val Gly Asp Ala Val
        35                  40                  45

Gln Val Ile Asn Glu Asp Glu Glu Ala Lys Ile Gln Arg Met Asp Ile
    50                  55                  60

Glu Ile Asn Asp Tyr Pro Gly Ser Gly Ala Asn Asp Arg His Thr Pro
65                  70                  75                  80

Lys Pro Pro Glu

<210> SEQ ID NO 85
<211> LENGTH: 88
<212> TYPE: PRT
<213> ORGANISM: Oryza sativa

<400> SEQUENCE: 85

Met Arg Arg Val Met Glu Met Arg Ser Arg Asp Leu Val Ala Val Leu
1               5                   10                  15

Ala Met Ser Ser Leu Leu Leu Leu Pro Leu Leu Val Ser Ser Val Pro
            20                  25                  30

Met Ser Gly Ser Leu His Leu Ser Ser Gln Gln Gln His Leu Ser Ser
        35                  40                  45

Pro Asn Ile Ser Ala Asp Asp Met Val Ala Ala Thr Thr Thr Asp Val
    50                  55                  60

Glu Val Asn Asp Tyr Pro Ala Pro Gly Ala Asn Pro Arg His Asn Pro
65                  70                  75                  80

Lys Arg Pro Pro Gly Arg Glu Met
                85

<210> SEQ ID NO 86
<211> LENGTH: 37
<212> TYPE: PRT
<213> ORGANISM: Oryza sativa

<400> SEQUENCE: 86

Ser Val Gln Gly Met Val Ala Ala Ala Thr Asn Asn Val Glu Val Asn
1               5                   10                  15

Asp Tyr Pro Ala Pro Gly Ala Asn Pro Arg His Asn Pro Lys Ser Pro
            20                  25                  30

Pro Gly Arg Glu Met
        35

<210> SEQ ID NO 87
<211> LENGTH: 36
<212> TYPE: PRT
<213> ORGANISM: Oryza sativa

<400> SEQUENCE: 87

Ser Val Gln Gly Met Val Ala Ala Ala Thr Asp Val Glu Val Asn Asp
1               5                   10                  15

Tyr Pro Ala Pro Gly Ala Asn Pro Arg His Asn Pro Lys Arg Pro Pro
            20                  25                  30

Gly Arg Glu Met
        35

<210> SEQ ID NO 88
<211> LENGTH: 35
<212> TYPE: PRT
<213> ORGANISM: Oryza sativa

<400> SEQUENCE: 88

Ser Val Gln Gly Met Val Ala Ala Thr Thr Asp Val Glu Val Asn Asp
1 5 10 15

Tyr Leu Ala Pro Gly Ala Asn Pro Arg His Asn Pro Lys Arg Pro Pro
20 25 30

Gly Arg Glu
35

<210> SEQ ID NO 89
<211> LENGTH: 81
<212> TYPE: PRT
<213> ORGANISM: Solanum lycopericum

<400> SEQUENCE: 89

Met Ala Thr Thr Leu Phe Leu Ala Phe Leu Cys Phe Ser Gln Val Ile
1 5 10 15

Tyr Leu Asn Thr Ile Pro Ile Thr Arg Cys Ser Asn Leu Val Tyr Lys
20 25 30

Ala Gln Gln His Glu Asn Thr Arg Thr Met Glu Asn Ile Glu Ala Glu
35 40 45

Asn Met Lys Leu Gly Asp Val Val Ile Arg Arg Met Asp Val Glu Val
50 55 60

Asn Asp Tyr Pro Ser Ser Gly Ala Asn Asn Arg His Thr Pro Ser His
65 70 75 80

Pro

<210> SEQ ID NO 90
<211> LENGTH: 85
<212> TYPE: PRT
<213> ORGANISM: Oryza sativa

<400> SEQUENCE: 90

Met Pro Ser Val Ser Val Ala Ser Ser Met Ser Lys Leu Lys Phe Leu
1 5 10 15

Val Thr Val Val Leu Val Ile Leu Leu Leu Phe Asp Ser Ser Ser Ser
20 25 30

Gly Gln Ala Glu Thr Ala Tyr Thr Asn Tyr Glu Val Thr Ser Lys Val
35 40 45

Lys Glu Arg Ile Gln Lys His Ser Arg Arg Val Leu Thr Asp Val Gln
50 55 60

Asp Tyr Asp Tyr Gly Gly Pro Asn Pro Arg His Glu Pro Arg Lys Lys
65 70 75 80

Pro Gly Asn Gly His
85

<210> SEQ ID NO 91
<211> LENGTH: 87
<212> TYPE: PRT
<213> ORGANISM: Solanum lycopericum

<400> SEQUENCE: 91

Met Glu Lys Lys Val Ser Phe Leu Ser Leu Leu Leu Leu Ile Phe Val
1 5 10 15

Gly Phe Ser Leu Leu Ile Ser Thr Ile Ala Val Pro Ser Ser Arg Ser

```
            20                  25                  30

Ile Lys Thr Asn Thr Glu Asn Gln Val Ser His Asp Lys Val Val Leu
        35                  40                  45

Met Asp Glu Leu Glu Lys Lys Arg Glu Leu Leu Val Glu Arg Asp Asp
    50                  55                  60

Tyr Ala Gly Thr Gly Ala Asn Asn His His Asp Pro Lys Pro Pro Gly
65                  70                  75                  80

Ser Gln Trp Ser Asn Leu Asn
                85


<210> SEQ ID NO 92
<211> LENGTH: 78
<212> TYPE: PRT
<213> ORGANISM: Solanum lycopericum

<400> SEQUENCE: 92

Met Val Gln Lys Ile Gly Phe His Leu Leu Leu Leu Phe Ile Phe Ala
1               5                   10                  15

Thr Ile Ile Ser Thr Ala Ser Ser Ser Arg Ile Leu Lys Glu Ser Ile
            20                  25                  30

Asp Glu Thr Ser Asp Phe Asp Leu Pro Ser Gln Asp Thr Ser Asp Leu
        35                  40                  45

Thr Asp Glu Glu Leu Ser Ile Ala Arg Arg Ile Asp Leu Val Leu Asp
    50                  55                  60

Tyr Ala Asn Ala Gly Ala Asn Asp Gln His Lys Pro Lys Pro
65                  70                  75


<210> SEQ ID NO 93
<211> LENGTH: 77
<212> TYPE: PRT
<213> ORGANISM: Solanum lycopericum

<400> SEQUENCE: 93

Met Ala Ala Gly Phe Gly Ile Arg His Tyr Leu Cys Met Met Phe Leu
1               5                   10                  15

Leu Ser Ile Ile Phe Cys Val Ser Ala Arg Asn Phe Ile Ser Ile Ser
            20                  25                  30

Asp Asp Glu Met Ala Met Leu Gln Val Glu Val Lys Arg Ser Leu Leu
        35                  40                  45

Ser Val Gln Leu Asp Asp Tyr Gly Ser Pro Ser Ala Asn Arg Asn His
    50                  55                  60

Tyr Pro Gly Lys Pro Ser Lys Ser Lys Gly Gly Arg Gly
65                  70                  75


<210> SEQ ID NO 94
<211> LENGTH: 75
<212> TYPE: PRT
<213> ORGANISM: Musa acuminata

<400> SEQUENCE: 94

Met Pro Arg Val Lys Thr Phe Leu Ile Phe Leu Leu Leu Ile Leu Leu
1               5                   10                  15

Leu Ala Ser Ser Ser Cys Gln Ala Gly Arg Thr Gln Thr Gly Lys Glu
            20                  25                  30

Pro Ala Tyr Leu Val Ala Arg Met Asn Ser Arg Lys Ala Leu Leu Glu
        35                  40                  45

Thr Thr Leu Asp Tyr Asp Tyr Gly Gly Ala Asn Pro Lys His Asp Pro
    50                  55                  60
```

```
Lys Lys Gly Lys Pro Gly Ile Gly Gly Lys Pro
65                  70                  75


<210> SEQ ID NO 95
<211> LENGTH: 75
<212> TYPE: PRT
<213> ORGANISM: Arabidopsis thaliana

<400> SEQUENCE: 95

Met Phe Ser Lys Met Gln Leu Val Val Leu Met Ser Phe Leu Leu Leu
1               5                   10                  15

Leu Pro Leu Cys Ser Ser Arg Phe Gly Glu Ser His Glu Asp Gly Val
            20                  25                  30

Pro His Thr Asp Gln Tyr Ser Leu Asn Met Val Glu Glu Ser Ile Pro
        35                  40                  45

Lys Met Met Glu Thr Gly Thr Asn Pro Ser His Asp Gln Thr Thr Asn
    50                  55                  60

Gly Trp Gly Arg Pro Thr Arg Pro Pro Pro Ser
65                  70                  75


<210> SEQ ID NO 96
<211> LENGTH: 29
<212> TYPE: PRT
<213> ORGANISM: Arabidopsis thaliana

<400> SEQUENCE: 96

Arg Met Met Asp Tyr Pro Lys Thr Tyr Pro Asn Pro Ser Arg Gly Gln
1               5                   10                  15

Thr Thr Asn Arg Val Ile Arg Leu Ser Pro Pro Pro Pro
            20                  25


<210> SEQ ID NO 97
<211> LENGTH: 29
<212> TYPE: PRT
<213> ORGANISM: Arabidopsis thaliana

<400> SEQUENCE: 97

Arg Met Met Asp Tyr Pro Lys Lys Asp Pro Asn Pro Ser His Asp Gln
1               5                   10                  15

Thr Ile Asn Arg Val Ile Arg Leu Ser Pro Pro Pro Pro
            20                  25


<210> SEQ ID NO 98
<211> LENGTH: 15
<212> TYPE: PRT
<213> ORGANISM: Arabidopsis thaliana

<400> SEQUENCE: 98

Arg Met Met Asp Tyr Pro Lys Ala Tyr Pro Asn Pro Ser Arg Gly
1               5                   10                  15


<210> SEQ ID NO 99
<211> LENGTH: 71
<212> TYPE: PRT
<213> ORGANISM: Triticum aestivum

<400> SEQUENCE: 99

Met Pro Lys Pro Thr Phe Val Leu Ala Ile Ile Leu Leu Ile Ala Leu
1               5                   10                  15

Phe Ser Ala Ser Ala Gly Gln Thr Ile Val Val Glu Ile Asp Asn Asp
            20                  25                  30
```

Val Pro Pro Lys Phe Ile Lys Gly His Ser Arg Lys Ile Leu Thr Glu
35 40 45

Ile Gln Asp Tyr Asp Tyr Gly Gly Ala Asn Ser Arg His Asp Pro Arg
50 55 60

Arg Arg Pro Gly Arg Asn Gly
65 70

<210> SEQ ID NO 100
<211> LENGTH: 86
<212> TYPE: PRT
<213> ORGANISM: Arabidopsis thaliana

<400> SEQUENCE: 100

Met Leu Ser Lys Ile Lys Pro Val Val Leu Met Ser Phe Leu Leu Leu
1 5 10 15

Phe Pro Leu Cys Ser Ser Gly Phe Arg Glu Gly His Gly Val Thr His
20 25 30

Thr Asp Gln Asn Ser Leu Asn Lys Val Glu Glu Ser Ile Pro Thr Ile
35 40 45

Met Asp Tyr Pro Glu Pro Gly Pro Asp Pro Lys His Asp Pro Thr Lys
50 55 60

Pro Gly Tyr Gly Phe Pro Pro Pro Pro Pro Pro Pro Leu Ser Pro Pro
65 70 75 80

Pro Pro Pro Lys Met Asn
85

<210> SEQ ID NO 101
<211> LENGTH: 78
<212> TYPE: PRT
<213> ORGANISM: Arabidopsis thaliana

<400> SEQUENCE: 101

Met Leu Ser Lys Met Lys Leu Val Val Leu Met Ser Phe Leu Leu Leu
1 5 10 15

Leu Pro Leu Cys Ser Ser Gly Phe Gly Glu Gly His Gly Val Thr His
20 25 30

Thr Asn Gln Tyr Ser Leu Asn Asn Leu Glu Glu Ser Ile Pro Thr Ile
35 40 45

Met Asp Tyr Pro Glu Pro Gly Pro Asn Pro Ile His Asp Pro Thr Lys
50 55 60

Pro Gly Tyr Gly Arg Pro Pro Pro Pro Pro Pro Lys Met Asn
65 70 75

<210> SEQ ID NO 102
<211> LENGTH: 71
<212> TYPE: PRT
<213> ORGANISM: Arabidopsis thaliana

<400> SEQUENCE: 102

Met Gly Tyr Ser Ser Ser Ser Arg Ile Gly Leu Cys Leu Phe Leu Phe
1 5 10 15

Phe Thr Phe Ala Leu Leu Ser Ser Ala Arg Ile Ser Leu Ser Phe Ser
20 25 30

Glu Asn Glu Met Thr Val Val Pro Glu Arg Ser Leu Met Val Ser Thr
35 40 45

Asn Asp Tyr Ser Asp Pro Thr Ala Asn Gly Arg His Asp Pro Pro Arg
50 55 60

Gly Gly Arg Gly Arg Arg Arg
65 70

<210> SEQ ID NO 103
<211> LENGTH: 75
<212> TYPE: PRT
<213> ORGANISM: Arabidopsis thaliana

<400> SEQUENCE: 103

Met Thr Phe Val Val Arg Leu Leu Val Cys Leu Leu Leu Thr Leu Thr
1 5 10 15

Ile Thr Ser Ser Leu Ala Arg Asn Pro Val Ser Val Ser Gly Gly Phe
20 25 30

Glu Asn Ser Gly Phe Gln Arg Ser Leu Leu Met Val Asn Val Glu Asp
35 40 45

Tyr Gly Asp Pro Ser Ala Asn Pro Lys His Asp Pro Gly Val Pro Pro
50 55 60

Ser Ala Thr Gly Gln Arg Val Val Gly Arg Gly
65 70 75

<210> SEQ ID NO 104
<211> LENGTH: 71
<212> TYPE: PRT
<213> ORGANISM: Arabidopsis thaliana

<400> SEQUENCE: 104

Met Val Phe Cys Tyr Ala Ile Arg Leu Cys Leu Cys Ile Phe Leu Ala
1 5 10 15

Leu Ser Ile Val Ser Ser Ala Arg Leu Thr Phe Ser Phe Ser Glu Asn
20 25 30

Glu Lys Met Met Val Arg Gly Arg Ser Leu Met Val Ser Thr Asn Asp
35 40 45

Tyr Gly Glu Pro Ser Ala Asn Ala Lys His Asn Pro Pro Gly Arg Arg
50 55 60

Arg Gly Gly Gly Arg Arg Gly
65 70

<210> SEQ ID NO 105
<211> LENGTH: 71
<212> TYPE: PRT
<213> ORGANISM: Arabidopsis thaliana

<400> SEQUENCE: 105

Met Ser Phe Gly Thr Arg Leu Leu Leu Phe Leu Ile Leu Thr Leu Pro
1 5 10 15

Leu Val Thr Ser Ser Ser Pro Asn Thr Leu His Val Ser Gly Ile Val
20 25 30

Lys Thr Gly Thr Thr Ser Arg Phe Leu Met Met Thr Ile Glu Asp Tyr
35 40 45

Asp Asp Pro Ser Ala Asn Thr Arg His Asp Pro Ser Val Pro Thr Asn
50 55 60

Ala Lys Ala Asp Thr Thr Pro
65 70

<210> SEQ ID NO 106
<211> LENGTH: 56
<212> TYPE: PRT
<213> ORGANISM: Xanthomonas oryzae

<400> SEQUENCE: 106

```
Met Asn His Ser Lys Lys Ser Pro Ala Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Pro Gly Ala Asn Pro
        35                  40                  45

Lys His Asp Pro Pro Pro Arg Asn
    50                  55
```

<210> SEQ ID NO 107
<211> LENGTH: 60
<212> TYPE: PRT
<213> ORGANISM: Xanthomonas oryzae

<400> SEQUENCE: 107

```
Met Asn His Ser Lys Lys Ser Pro Ala Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Pro Gly Ala Asn Pro
        35                  40                  45

Lys His Asp Pro Pro Pro Arg Asn Pro Gly His His
    50                  55                  60
```

<210> SEQ ID NO 108
<211> LENGTH: 60
<212> TYPE: PRT
<213> ORGANISM: Xanthomonas oryzae

<400> SEQUENCE: 108

```
Met Asn His Ser Lys Lys Ser Pro Thr Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Pro Gly Ala Asn Pro
        35                  40                  45

Lys His Asp Pro Pro Pro Arg Asn Pro Gly His His
    50                  55                  60
```

<210> SEQ ID NO 109
<211> LENGTH: 60
<212> TYPE: PRT
<213> ORGANISM: Xanthomonas oryzae

<400> SEQUENCE: 109

```
Met Asn His Ser Lys Lys Ser Pro Thr Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Pro Gly Ala Asn Pro
        35                  40                  45

Lys His Asp Pro Pro Pro Arg Asn Pro Gly His His
    50                  55                  60
```

<210> SEQ ID NO 110
<211> LENGTH: 60
<212> TYPE: PRT
<213> ORGANISM: Xanthomonas oryzae -continued

<400> SEQUENCE: 110

```
Met Asn His Ser Lys Lys Ser Pro Thr Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Pro Gly Ala Asn Pro
        35                  40                  45

Lys His Asp Pro Pro Pro Arg Asn Pro Gly His His
    50                  55                  60
```

<210> SEQ ID NO 111
<211> LENGTH: 60
<212> TYPE: PRT
<213> ORGANISM: Xanthomonas oryzae

<400> SEQUENCE: 111

```
Met Asn His Ser Lys Lys Ser Pro Thr Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Pro Gly Ala Asn Pro
        35                  40                  45

Lys His Asp Pro Pro Pro Arg Asn Pro Gly His His
    50                  55                  60
```

<210> SEQ ID NO 112
<211> LENGTH: 60
<212> TYPE: PRT
<213> ORGANISM: Xanthomonas oryzae

<400> SEQUENCE: 112

```
Met Asn His Ser Lys Lys Ser Pro Thr Lys Gly Ala Ala Ser Leu Gln
1               5                   10                  15

Arg Pro Ala Gly Ala Lys Gly Arg Pro Glu Pro Leu Asp Gln Arg Leu
            20                  25                  30

Trp Lys His Val Gly Gly Gly Asp Tyr Pro Pro Pro Gly Ala Asn Pro
        35                  40                  45

Lys His Asp Pro Pro Pro Arg Asn Pro Gly His His
    50                  55                  60
```

<210> SEQ ID NO 113
<211> LENGTH: 63
<212> TYPE: PRT
<213> ORGANISM: Xanthomonas oryzae

<400> SEQUENCE: 113

```
Met Asn Leu Ser Lys Lys Ser Pro Thr Lys Gly Ala Ala Ser Leu Gln
1               5                   10                  15

Pro Pro Ala Gly Ala Lys Gly Arg Pro Glu Pro Leu Asp Gln Arg Leu
            20                  25                  30

Trp Lys His Val Gly Gly Gly Asp Tyr Pro Pro Ser Gly Pro Asn Pro
        35                  40                  45

Lys His Asp Pro Pro His Pro Pro Pro Arg Asn Asn Gly His His
    50                  55                  60
```

<210> SEQ ID NO 114
<211> LENGTH: 60
<212> TYPE: PRT
<213> ORGANISM: Xanthomonas oryzae

<400> SEQUENCE: 114

Met Asn Leu Ser Lys Lys Ser Pro Thr Lys Gly Ala Ala Ser Leu Gln
1 5 10 15

Arg Pro Ala Gly Ala Lys Val Arg Pro Glu Pro Leu Asp Gln Arg Leu
20 25 30

Trp Lys His Val Gly Gly Gly Asp Tyr Pro Pro Ser Gly Pro Asn Pro
35 40 45

Lys His Asp Pro Pro Pro Arg Asn Asn Gly His His
50 55 60

<210> SEQ ID NO 115
<211> LENGTH: 59
<212> TYPE: PRT
<213> ORGANISM: Xanthomonas oryzae

<400> SEQUENCE: 115

Met Asn Leu Ser Lys Lys Ser Pro Thr Lys Gly Ala Ala Ser Leu Gln
1 5 10 15

Arg Pro Ala Gly Ala Lys Gly Arg Pro Glu Pro Leu Asp Gln Arg Leu
20 25 30

Trp Lys His Val Gly Gly Gly Asp Tyr Pro Pro Ser Gly Pro Asn Pro
35 40 45

Lys His Asp Pro Pro Gly Asn Asn Gly His His
50 55

<210> SEQ ID NO 116
<211> LENGTH: 54
<212> TYPE: PRT
<213> ORGANISM: Xanthomonas oryzae

<400> SEQUENCE: 116

Met Asn Leu Ser Lys Lys Ser Pro Thr Lys Gly Ala Ala Ser Leu Gln
1 5 10 15

Arg Ser Ala Gly Ala Lys Gly Arg Pro Glu Pro Leu Asp Gln Arg Leu
20 25 30

Trp Lys His Val Gly Gly Gly Asp Tyr Pro Pro Ala Gly Pro Ser Thr
35 40 45

Lys His Asp Pro His His
50

<210> SEQ ID NO 117
<211> LENGTH: 60
<212> TYPE: PRT
<213> ORGANISM: Xanthomonas oryzae

<400> SEQUENCE: 117

Met Asn Leu Ser Lys Lys Ser Pro Thr Lys Gly Ala Ala Ser Leu Gln
1 5 10 15

Arg Pro Ala Gly Ala Lys Val Arg Pro Glu Pro Leu Asp Gln Arg Leu
20 25 30

Trp Lys His Val Gly Gly Gly Asp Tyr Pro Pro Ser Gly Pro Asn Thr
35 40 45

Lys His Asp Pro Pro Pro Pro Asn Asn Gly His His
50 55 60

<210> SEQ ID NO 118
<211> LENGTH: 60
<212> TYPE: PRT

<213> ORGANISM: Xanthomonas oryzae

<400> SEQUENCE: 118

Met Asn Leu Ser Lys Lys Ser Pro Thr Lys Gly Ala Ala Ser Leu Gln
1 5 10 15

Arg Pro Ala Gly Ala Lys Val Arg Pro Glu Pro Leu Asp Gln Arg Leu
20 25 30

Trp Lys His Val Gly Gly Gly Asp Tyr Pro Pro Ser Gly Pro Asn Thr
35 40 45

Lys His Asp Pro Pro Pro Pro Asn Asn Gly His His
50 55 60

<210> SEQ ID NO 119
<211> LENGTH: 60
<212> TYPE: PRT
<213> ORGANISM: Xanthomonas oryzae

<400> SEQUENCE: 119

Met Asn Leu Ser Lys Lys Ser Pro Thr Lys Gly Ala Ala Ser Leu Gln
1 5 10 15

Arg Pro Ala Gly Ala Lys Val Arg Pro Glu Pro Leu Asp Gln Arg Leu
20 25 30

Trp Lys His Val Gly Gly Gly Asp Tyr Pro Pro Ser Gly Pro Asn Thr
35 40 45

Lys His Asp Pro Pro Pro Pro Asn Asn Gly His His
50 55 60

<210> SEQ ID NO 120
<211> LENGTH: 60
<212> TYPE: PRT
<213> ORGANISM: Xanthomonas oryzae

<400> SEQUENCE: 120

Met Asn Leu Ser Lys Lys Ser Pro Thr Lys Gly Ala Ala Ser Leu Gln
1 5 10 15

Arg Pro Ala Gly Ala Lys Val Arg Pro Glu Pro Leu Asp Gln Arg Leu
20 25 30

Trp Lys His Val Gly Gly Gly Asp Tyr Pro Pro Ser Gly Pro Asn Thr
35 40 45

Lys His Asp Pro Pro Pro Pro Asn Asn Gly His His
50 55 60

<210> SEQ ID NO 121
<211> LENGTH: 60
<212> TYPE: PRT
<213> ORGANISM: Xanthomonas oryzae

<400> SEQUENCE: 121

Met Asn Leu Ser Lys Lys Ser Pro Thr Lys Gly Ala Ala Ser Leu Gln
1 5 10 15

Arg Pro Ala Gly Ala Lys Val Arg Pro Glu Pro Leu Asp Gln Arg Leu
20 25 30

Trp Lys His Val Gly Gly Gly Asp Tyr Pro Pro Ser Gly Pro Asn Thr
35 40 45

Lys His Asp Pro Pro Pro Pro Asn Asn Gly His His
50 55 60

<210> SEQ ID NO 122
<211> LENGTH: 60

-continued

<212> TYPE: PRT
<213> ORGANISM: Xanthomonas oryzae

<400> SEQUENCE: 122

```
Met Asn Leu Ser Lys Lys Ser Pro Thr Lys Gly Ala Ala Ser Leu Gln
1               5                   10                  15

Arg Pro Ala Gly Ala Lys Val Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 123
<211> LENGTH: 60
<212> TYPE: PRT
<213> ORGANISM: Xanthomonas oryzae

<400> SEQUENCE: 123

```
Met Asn Leu Ser Lys Lys Ser Pro Thr Lys Gly Ala Ala Ser Leu Gln
1               5                   10                  15

Arg Pro Ala Gly Ala Lys Val Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 124
<211> LENGTH: 60
<212> TYPE: PRT
<213> ORGANISM: Xanthomonas oryzae

<400> SEQUENCE: 124

```
Met Asn Leu Ser Lys Lys Ser Pro Thr Lys Gly Ala Ala Ser Leu Gln
1               5                   10                  15

Arg Pro Ala Gly Ala Lys Val Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 125
<211> LENGTH: 60
<212> TYPE: PRT
<213> ORGANISM: Xanthomonas oryzae

<400> SEQUENCE: 125

```
Met Asn Leu Ser Lys Lys Ser Pro Thr Lys Gly Ala Ala Ser Leu Gln
1               5                   10                  15

Arg Pro Ala Gly Ala Lys Val Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 126

```
<211> LENGTH: 60
<212> TYPE: PRT
<213> ORGANISM: Xanthomonas oryzae

<400> SEQUENCE: 126

Met Asn Leu Ser Lys Lys Ser Pro Thr Lys Gly Ala Ala Ser Leu Gln
1               5                   10                  15

Arg Pro Ala Gly Ala Lys Val Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60


<210> SEQ ID NO 127
<211> LENGTH: 60
<212> TYPE: PRT
<213> ORGANISM: Xanthomonas oryzae

<400> SEQUENCE: 127

Met Asn Leu Leu Lys Lys Ser Pro Thr Lys Gly Ala Ala Ser Leu Gln
1               5                   10                  15

Arg Pro Ala Gly Ala Lys Val Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60


<210> SEQ ID NO 128
<211> LENGTH: 60
<212> TYPE: PRT
<213> ORGANISM: Xanthomonas oryzae

<400> SEQUENCE: 128

Met Asn Leu Leu Lys Lys Ser Pro Thr Lys Gly Ala Ala Ser Leu Gln
1               5                   10                  15

Arg Pro Ala Gly Ala Lys Val Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60


<210> SEQ ID NO 129
<211> LENGTH: 60
<212> TYPE: PRT
<213> ORGANISM: Xanthomonas oryzae

<400> SEQUENCE: 129

Met Asn Leu Ser Lys Lys Ser Pro Thr Lys Gly Ala Ala Leu Leu Gln
1               5                   10                  15

Trp Pro Ala Arg Ala Lys Val Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 130
<211> LENGTH: 60
<212> TYPE: PRT
<213> ORGANISM: Xanthomonas oryzae

<400> SEQUENCE: 130

```
Met Asn Leu Ser Lys Lys Ser Pro Thr Lys Gly Ala Ala Leu Leu Gln
1               5                   10                  15

Trp Pro Ala Arg Ala Lys Gly Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 131
<211> LENGTH: 60
<212> TYPE: PRT
<213> ORGANISM: Xanthomonas oryzae

<400> SEQUENCE: 131

```
Met Asn Leu Ser Lys Lys Ser Pro Thr Lys Gly Ala Ala Ser Leu Gln
1               5                   10                  15

Trp Pro Ala Arg Ala Lys Gly Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 132
<211> LENGTH: 60
<212> TYPE: PRT
<213> ORGANISM: Xanthomonas oryzae

<400> SEQUENCE: 132

```
Met Asn Leu Ser Lys Lys Ser Pro Thr Lys Gly Ala Ala Ser Leu Gln
1               5                   10                  15

Trp Pro Ala Arg Ala Lys Gly Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

<210> SEQ ID NO 133
<211> LENGTH: 60
<212> TYPE: PRT
<213> ORGANISM: Xanthomonas oryzae

<400> SEQUENCE: 133

```
Met Asn Leu Ser Lys Lys Ser Pro Thr Lys Gly Ala Ala Ser Leu Gln
1               5                   10                  15

Trp Pro Ala Arg Ala Lys Gly Arg Pro Glu Pro Leu Asp Gln Arg Leu
            20                  25                  30

Trp Lys His Val Gly Gly Gly Asp Tyr Pro Pro Ser Gly Pro Asn Thr
        35                  40                  45

Lys His Asp Pro Pro Pro Pro Asn Asn Gly His His
    50                  55                  60
```

```
<210> SEQ ID NO 134
<211> LENGTH: 59
<212> TYPE: PRT
<213> ORGANISM: Unknown
<220> FEATURE:
<223> OTHER INFORMATION: Other Xanthomonas

<400> SEQUENCE: 134

Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55


<210> SEQ ID NO 135
<211> LENGTH: 59
<212> TYPE: PRT
<213> ORGANISM: Unknown
<220> FEATURE:
<223> OTHER INFORMATION: Other Xanthomonas

<400> SEQUENCE: 135

Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55


<210> SEQ ID NO 136
<211> LENGTH: 59
<212> TYPE: PRT
<213> ORGANISM: Unknown
<220> FEATURE:
<223> OTHER INFORMATION: Other Xanthomonas

<400> SEQUENCE: 136

Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55


<210> SEQ ID NO 137
<211> LENGTH: 59
<212> TYPE: PRT
<213> ORGANISM: Unknown
<220> FEATURE:
<223> OTHER INFORMATION: Other Xanthomonas

<400> SEQUENCE: 137

Met Asn Leu Ser Lys Lys Ser Pro Thr Asn Gly Ala Gln Ala Leu Gln
1               5                   10                  15
```

```
Arg Pro Ala Gly Ala Lys Gly Gln Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55


<210> SEQ ID NO 138
<211> LENGTH: 59
<212> TYPE: PRT
<213> ORGANISM: Unknown
<220> FEATURE:
<223> OTHER INFORMATION: Other Xanthomonas

<400> SEQUENCE: 138

Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55


<210> SEQ ID NO 139
<211> LENGTH: 59
<212> TYPE: PRT
<213> ORGANISM: Unknown
<220> FEATURE:
<223> OTHER INFORMATION: Other Xanthomonas

<400> SEQUENCE: 139

Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Leu
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55


<210> SEQ ID NO 140
<211> LENGTH: 59
<212> TYPE: PRT
<213> ORGANISM: Unknown
<220> FEATURE:
<223> OTHER INFORMATION: Other Xanthomonas

<400> SEQUENCE: 140

Met Asn Leu Ser Lys Lys Ser Pro Thr Asn Gly Ala Gln Ala Leu Gln
1               5                   10                  15

Arg Pro Ala Gly Ala Lys Gly Gln Leu Glu Pro Leu Asp Gln Arg Met
            20                  25                  30

Trp Lys His Val Gly Gly Gly Asp Tyr Pro Pro Pro Gly Ala Asn Thr
        35                  40                  45

Lys His Asp Pro Pro Pro Lys Asn Gly His His
    50                  55


<210> SEQ ID NO 141
<211> LENGTH: 59
<212> TYPE: PRT
```

<213> ORGANISM: Unknown
<220> FEATURE:
<223> OTHER INFORMATION: Other Xanthomonas

<400> SEQUENCE: 141

Met Asn Leu Ser Lys Lys Ser Pro Thr Asn Gly Ala Gln Ala Leu Gln
1 5 10 15

Arg Pro Ala Gly Ala Lys Gly Gln Leu Glu Pro Leu Asp Gln Arg Met
20 25 30

Trp Lys His Val Gly Gly Gly Asp Tyr Pro Pro Pro Gly Ala Asn Thr
35 40 45

Lys His Asp Pro Pro Pro Lys Asn Gly His His
50 55

<210> SEQ ID NO 142
<211> LENGTH: 59
<212> TYPE: PRT
<213> ORGANISM: Unknown
<220> FEATURE:
<223> OTHER INFORMATION: Other Xanthomonas

<400> SEQUENCE: 142

Met Asn Leu Ser Lys Lys Ser Pro Thr Asn Gly Ala Gln Ala Leu Gln
1 5 10 15

Arg Pro Ala Gly Ala Lys Gly Gln Leu Glu Pro Leu Asp Gln Arg Met
20 25 30

Trp Lys His Val Gly Gly Gly Asp Tyr Pro Pro Pro Gly Ala Asn Thr
35 40 45

Lys His Asp Pro Pro Pro Lys Asn Gly His His
50 55

<210> SEQ ID NO 143
<211> LENGTH: 59
<212> TYPE: PRT
<213> ORGANISM: Unknown
<220> FEATURE:
<223> OTHER INFORMATION: Other Xanthomonas

<400> SEQUENCE: 143

Met Asn Leu Ser Lys Lys Ser Pro Thr Asn Gly Ala Gln Ala Leu Gln
1 5 10 15

Arg Pro Ala Gly Ala Lys Gly Gln Leu Glu Pro Leu Asp Gln Arg Met
20 25 30

Trp Lys His Val Gly Gly Gly Asp Tyr Pro Pro Pro Gly Ala Asn Thr
35 40 45

Lys His Asp Pro Pro Pro Lys Asn Gly His His
50 55

<210> SEQ ID NO 144
<211> LENGTH: 59
<212> TYPE: PRT
<213> ORGANISM: Unknown
<220> FEATURE:
<223> OTHER INFORMATION: Other Xanthomonas

<400> SEQUENCE: 144

Met Asn Leu Ser Lys Lys Ser Pro Thr Asn Gly Ala Gln Ala Leu Gln
1 5 10 15

Arg Pro Ala Gly Ala Lys Gly Gln Leu Glu Pro Leu Asp Gln Arg Met
20 25 30

Trp Lys His Val Gly Gly Gly Asp Tyr Pro Pro Pro Gly Ala Asn Thr 35 40 45

Lys His Asp Pro Pro Pro Lys Asn Gly His His
50 55

<210> SEQ ID NO 145
<211> LENGTH: 62
<212> TYPE: PRT
<213> ORGANISM: Unknown
<220> FEATURE:
<223> OTHER INFORMATION: Other Xanthomonas

<400> SEQUENCE: 145

Met Asn Leu Ser Lys Lys Ser Pro Thr Tyr Gly Ala Gln Ser Leu Gln
1 5 10 15

Arg Pro Ala Gly Ala Lys Gly Arg Leu Glu Pro Leu Asp Gln Arg Leu
20 25 30

Trp Lys His Val Gly Gly Gly Asp Tyr Pro Pro Pro Gly Ala Asn Asp
35 40 45

Arg His Asn Pro Pro Pro Pro Pro Ser Asn Gly Gly His His
50 55 60

<210> SEQ ID NO 146
<211> LENGTH: 62
<212> TYPE: PRT
<213> ORGANISM: Unknown
<220> FEATURE:
<223> OTHER INFORMATION: Other Xanthomonas

<400> SEQUENCE: 146

Met Lys Leu Leu Lys Lys Ser Pro Ser Asn Gly Ala Gly Ser Leu Gln
1 5 10 15

Arg Ser Ala Gly Ala Lys Gly Arg Leu Glu Pro Leu Asp Gln Arg Leu
20 25 30

Trp Lys His Val Gly Gly Gly Asp Tyr Ala Pro Pro Gly Ser Asn Asp
35 40 45

Arg His Asp Pro Pro Lys Pro Pro Pro Lys Lys Gly Asn Pro
50 55 60

<210> SEQ ID NO 147
<211> LENGTH: 62
<212> TYPE: PRT
<213> ORGANISM: Unknown
<220> FEATURE:
<223> OTHER INFORMATION: Other Xanthomonas

<400> SEQUENCE: 147

Met Lys Leu Leu Lys Lys Ser Pro Ser Asn Gly Ala Gly Ser Leu Gln
1 5 10 15

Arg Ser Ala Gly Ala Lys Gly Arg Leu Glu Pro Leu Asp Gln Arg Leu
20 25 30

Trp Lys His Val Gly Gly Gly Asp Tyr Ala Pro Pro Gly Ser Asn Asp
35 40 45

Arg His Asp Pro Pro Lys Pro Pro Pro Lys Lys Gly Asn Pro
50 55 60

<210> SEQ ID NO 148
<211> LENGTH: 62
<212> TYPE: PRT
<213> ORGANISM: Unknown
<220> FEATURE:
<223> OTHER INFORMATION: Other Xanthomonas

<400> SEQUENCE: 148

Met Lys Leu Leu Lys Lys Ser Pro Ser Asn Gly Ala Gly Ser Leu Gln
1 5 10 15

Arg Ser Ala Gly Ala Lys Gly Arg Leu Glu Pro Leu Asp Gln Arg Leu
20 25 30

Trp Lys His Val Gly Gly Gly Asp Tyr Ala Pro Pro Gly Ser Asn Asp
35 40 45

Arg His Asp Pro Pro Lys Pro Pro Pro Lys Lys Gly Asn Pro
50 55 60

<210> SEQ ID NO 149
<211> LENGTH: 62
<212> TYPE: PRT
<213> ORGANISM: Unknown
<220> FEATURE:
<223> OTHER INFORMATION: Other Xanthomonas

<400> SEQUENCE: 149

Met Lys Leu Leu Lys Lys Ser Pro Ser Asn Gly Ala Gly Ser Leu Gln
1 5 10 15

Arg Ser Ala Gly Ala Lys Gly Arg Leu Glu Pro Leu Asp Gln Arg Leu
20 25 30

Trp Lys His Val Gly Gly Gly Asp Tyr Ala Pro Pro Gly Ser Asn Asp
35 40 45

Arg His Asp Pro Pro Lys Pro Pro Pro Lys Lys Gly Asn Pro
50 55 60

<210> SEQ ID NO 150
<211> LENGTH: 62
<212> TYPE: PRT
<213> ORGANISM: Unknown
<220> FEATURE:
<223> OTHER INFORMATION: Other Xanthomonas

<400> SEQUENCE: 150

Met Lys Leu Leu Lys Lys Ser Pro Ser Asn Gly Ala Gly Ser Leu Gln
1 5 10 15

Arg Ser Ala Gly Ala Lys Gly Arg Leu Glu Pro Leu Asp Gln Arg Leu
20 25 30

Trp Lys His Val Gly Gly Gly Asp Tyr Ala Pro Pro Gly Ser Asn Asp
35 40 45

Arg His Asp Pro Pro Lys Pro Pro Pro Lys Lys Gly Asn Pro
50 55 60

<210> SEQ ID NO 151
<211> LENGTH: 62
<212> TYPE: PRT
<213> ORGANISM: Unknown
<220> FEATURE:
<223> OTHER INFORMATION: Other Xanthomonas

<400> SEQUENCE: 151

Met Lys Leu Leu Lys Lys Ser Pro Ser Asn Gly Ala Gly Ser Leu Gln
1 5 10 15

Arg Ser Ala Gly Ala Lys Gly Arg Leu Glu Pro Leu Asp Gln Arg Leu
20 25 30

Trp Lys His Val Gly Gly Gly Asp Tyr Ala Pro Pro Gly Ser Asn Asp
35 40 45

Arg His Asp Pro Pro Lys Pro Pro Pro Lys Lys Gly Asn Pro
50 55 60

<210> SEQ ID NO 152
<211> LENGTH: 62
<212> TYPE: PRT
<213> ORGANISM: Unknown
<220> FEATURE:
<223> OTHER INFORMATION: Other Xanthomonas

<400> SEQUENCE: 152

```
Met Lys Leu Leu Lys Lys Ser Pro Ser Asn Gly Ala Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Ala Pro Pro Gly Ser Asn Asp
        35                  40                  45

Arg His Asp Pro Pro Lys Pro Pro Pro Lys Lys Gly Asn Pro
    50                  55                  60
```

<210> SEQ ID NO 153
<211> LENGTH: 62
<212> TYPE: PRT
<213> ORGANISM: Unknown
<220> FEATURE:
<223> OTHER INFORMATION: Other Xanthomonas

<400> SEQUENCE: 153

```
Met Glu Leu Leu Lys Lys Ser Pro Ser Asn Gly Val Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Ala Pro Pro Gly Ser Asn Asp
        35                  40                  45

Arg His Asp Pro Pro Lys Pro Pro Pro Lys Lys Gly Asn Pro
    50                  55                  60
```

<210> SEQ ID NO 154
<211> LENGTH: 62
<212> TYPE: PRT
<213> ORGANISM: Unknown
<220> FEATURE:
<223> OTHER INFORMATION: Other Xanthomonas

<400> SEQUENCE: 154

```
Met Glu Leu Leu Lys Lys Ser Pro Ser Asn Gly Val Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Ala Pro Pro Gly Ser Asn Asp
        35                  40                  45

Arg His Asp Pro Pro Lys Pro Pro Pro Lys Lys Gly Asn Pro
    50                  55                  60
```

<210> SEQ ID NO 155
<211> LENGTH: 62
<212> TYPE: PRT
<213> ORGANISM: Unknown
<220> FEATURE:
<223> OTHER INFORMATION: Other Xanthomonas

<400> SEQUENCE: 155

```
Met Glu Leu Leu Lys Lys Ser Pro Ser Asn Gly Val Gly Ser Leu Gln
1               5                   10                  15
```

```
Arg Ser Ala Gly Ala Lys Gly Arg Leu Glu Pro Leu Asp Gln Arg Leu
            20                  25                  30

Trp Lys His Val Gly Gly Gly Asp Tyr Ala Pro Pro Gly Ser Asn Asp
        35                  40                  45

Arg His Asp Pro Pro Lys Pro Pro Pro Lys Lys Gly Asn Pro
    50                  55                  60


<210> SEQ ID NO 156
<211> LENGTH: 62
<212> TYPE: PRT
<213> ORGANISM: Unknown
<220> FEATURE:
<223> OTHER INFORMATION: Other Xanthomonas

<400> SEQUENCE: 156

Met Glu Leu Leu Lys Lys Ser Pro Ser Asn Gly Val Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Ala Pro Pro Gly Ser Asn Asp
        35                  40                  45

Arg His Asp Pro Pro Lys Pro Pro Pro Lys Lys Gly Asn Pro
    50                  55                  60


<210> SEQ ID NO 157
<211> LENGTH: 62
<212> TYPE: PRT
<213> ORGANISM: Unknown
<220> FEATURE:
<223> OTHER INFORMATION: Other Xanthomonas

<400> SEQUENCE: 157

Met Glu Leu Leu Lys Lys Ser Pro Ser Asn Gly Val Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Ala Pro Pro Gly Ser Asn Asp
        35                  40                  45

Arg His Asp Pro Pro Lys Pro Pro Pro Lys Lys Gly Asn Pro
    50                  55                  60


<210> SEQ ID NO 158
<211> LENGTH: 62
<212> TYPE: PRT
<213> ORGANISM: Unknown
<220> FEATURE:
<223> OTHER INFORMATION: Other Xanthomonas

<400> SEQUENCE: 158

Met Glu Leu Leu Lys Lys Ser Pro Ser Asn Gly Val Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Pro Pro Pro Gly Ser Asn Asn
        35                  40                  45

Arg His Asp Pro Thr Gln Pro Pro Pro Lys Lys Gly Lys Pro
    50                  55                  60


<210> SEQ ID NO 159
<211> LENGTH: 62
```

```
<212> TYPE: PRT
<213> ORGANISM: Unknown
<220> FEATURE:
<223> OTHER INFORMATION: Other Xanthomonas

<400> SEQUENCE: 159

Met Glu Leu Leu Lys Lys Ser Pro Ser Asn Gly Val Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Pro Pro Pro Gly Ser Asn Asn
        35                  40                  45

Arg His Asp Pro Thr Gln Pro Pro Pro Lys Lys Gly Lys Pro
    50                  55                  60


<210> SEQ ID NO 160
<211> LENGTH: 60
<212> TYPE: PRT
<213> ORGANISM: Unknown
<220> FEATURE:
<223> OTHER INFORMATION: Other Xanthomonas

<400> SEQUENCE: 160

Met Asn Leu Ser Lys Lys Thr Pro Ser Asn Gly Ala Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Pro Pro Thr Gly Pro Asn Thr
        35                  40                  45

Arg His Asp Pro Pro Gln Pro Pro Pro Pro Glu His
    50                  55                  60


<210> SEQ ID NO 161
<211> LENGTH: 55
<212> TYPE: PRT
<213> ORGANISM: Unknown
<220> FEATURE:
<223> OTHER INFORMATION: Other Xanthomonas

<400> SEQUENCE: 161

Met Asn Leu Ser Lys Lys Thr Pro Ser Asn Gly Ala Gly Ser Leu Gln
1               5                   10                  15

Arg Ser Ala Gly Ala Lys Gly Arg Leu Glu Pro Leu Asp Gln Arg Leu
            20                  25                  30

Trp Lys His Val Gly Gly Gly Asp Tyr Pro Pro Ser Ala Ala Asn Asp
        35                  40                  45

Arg His Asp Pro Pro Lys Lys
    50                  55


<210> SEQ ID NO 162
<211> LENGTH: 56
<212> TYPE: PRT
<213> ORGANISM: Xanthomonas translucens

<400> SEQUENCE: 162

Met His Leu Leu Asn Lys Arg Lys Pro Thr Gly Leu Arg Pro Leu Gln
1               5                   10                  15

Thr Glu Ser Gln Pro Lys Arg Val Ala Pro Leu Asp Glu Ala Leu Trp
            20                  25                  30

Lys Lys Val Gly Gly Gly Asp Tyr Pro Pro Pro Ser Ser Asn Gly Arg
        35                  40                  45
```

His Asp Pro Pro Gly His His His
50 55

<210> SEQ ID NO 163
<211> LENGTH: 56
<212> TYPE: PRT
<213> ORGANISM: Xanthomonas translucens

<400> SEQUENCE: 163

Met His Leu Leu Asn Lys Arg Lys Pro Thr Gly Leu Arg Pro Leu Gln
1 5 10 15

Thr Glu Ser Gln Pro Lys Arg Val Ala Pro Leu Asp Glu Ala Leu Trp
20 25 30

Lys Lys Val Gly Gly Gly Asp Tyr Pro Pro Pro Ser Ser Asn Gly Arg
35 40 45

His Asp Pro Pro Gly His His His
50 55

<210> SEQ ID NO 164
<211> LENGTH: 56
<212> TYPE: PRT
<213> ORGANISM: Xanthomonas translucens

<400> SEQUENCE: 164

Met His Leu Leu Asn Lys Arg Lys Pro Thr Gly Leu Arg Pro Leu Gln
1 5 10 15

Thr Glu Ser Gln Pro Lys Arg Val Ala Pro Leu Asp Glu Ala Leu Trp
20 25 30

Lys Lys Val Gly Gly Gly Asp Tyr Pro Pro Pro Ser Ser Asn Gly Arg
35 40 45

His Asp Pro Pro Gly His His His
50 55

<210> SEQ ID NO 165
<211> LENGTH: 56
<212> TYPE: PRT
<213> ORGANISM: Xanthomonas translucens

<400> SEQUENCE: 165

Met His Leu Leu Asn Lys Arg Lys Pro Thr Gly Leu Arg Pro Leu Gln
1 5 10 15

Thr Glu Ser Gln Pro Lys Arg Val Ala Pro Leu Asp Glu Ala Leu Trp
20 25 30

Lys Lys Val Gly Gly Gly Asp Tyr Pro Pro Pro Ser Ser Asn Gly Arg
35 40 45

His Asp Pro Pro Gly His His His
50 55

<210> SEQ ID NO 166
<211> LENGTH: 56
<212> TYPE: PRT
<213> ORGANISM: Xanthomonas translucens

<400> SEQUENCE: 166

Met His Leu Leu Asn Lys Arg Lys Pro Thr Gly Leu Arg Pro Leu Gln
1 5 10 15

Thr Glu Ser Gln Pro Lys Arg Val Ala Pro Leu Asp Glu Ala Leu Trp
20 25 30

Lys Lys Val Gly Gly Gly Asp Tyr Pro Pro Pro Ser Ser Asn Gly Arg

```
        35                  40                  45

His Asp Pro Pro Gly His His His
    50                  55


<210> SEQ ID NO 167
<211> LENGTH: 56
<212> TYPE: PRT
<213> ORGANISM: Xanthomonas translucens

<400> SEQUENCE: 167

Met His Leu Leu Asn Lys Arg Lys Pro Thr Gly Leu Arg Pro Leu Gln
1               5                   10                  15

Thr Glu Ser Gln Pro Lys Arg Val Ala Pro Leu Asp Glu Ala Leu Trp
            20                  25                  30

Lys Lys Val Gly Gly Gly Asp Tyr Pro Pro Pro Ser Ser Asn Gly Arg
        35                  40                  45

His Asp Pro Pro Gly His His His
    50                  55


<210> SEQ ID NO 168
<211> LENGTH: 56
<212> TYPE: PRT
<213> ORGANISM: Xanthomonas translucens

<400> SEQUENCE: 168

Met His Leu Leu Asn Lys Arg Lys Pro Thr Gly Leu Arg Pro Leu Gln
1               5                   10                  15

Thr Glu Ser Gln Pro Lys Arg Val Ala Pro Leu Asp Glu Ala Leu Trp
            20                  25                  30

Lys Lys Val Gly Gly Gly Asp Tyr Pro Pro Pro Ser Ser Asn Gly Arg
        35                  40                  45

His Asp Pro Pro Gly His His His
    50                  55


<210> SEQ ID NO 169
<211> LENGTH: 56
<212> TYPE: PRT
<213> ORGANISM: Xanthomonas translucens

<400> SEQUENCE: 169

Met His Leu Leu Asn Lys Arg Lys Pro Thr Gly Leu Arg Pro Leu Gln
1               5                   10                  15

Thr Glu Ser Gln Pro Lys Arg Val Ala Pro Leu Asp Glu Ala Leu Trp
            20                  25                  30

Lys Lys Val Gly Gly Gly Asp Tyr Pro Pro Pro Ser Ser Asn Gly Arg
        35                  40                  45

His Asp Pro Pro Gly His His His
    50                  55


<210> SEQ ID NO 170
<211> LENGTH: 56
<212> TYPE: PRT
<213> ORGANISM: Xanthomonas translucens

<400> SEQUENCE: 170

Met His Leu Leu Asn Lys Arg Lys Pro Thr Gly Leu Arg Pro Leu Gln
1               5                   10                  15

Thr Glu Ser Gln Pro Lys Arg Val Ala Pro Leu Asp Glu Ala Leu Trp
            20                  25                  30
```

-continued

```
Lys Lys Val Gly Gly Gly Asp Tyr Pro Pro Pro Ser Ser Asn Gly Arg
        35                  40                  45

His Asp Pro Pro Gly His His His
    50                  55


<210> SEQ ID NO 171
<211> LENGTH: 56
<212> TYPE: PRT
<213> ORGANISM: Xanthomonas translucens

<400> SEQUENCE: 171

Met His Leu Leu Asn Lys Arg Lys Pro Thr Gly Leu Arg Pro Leu Gln
1               5                   10                  15

Thr Glu Ser Gln Pro Lys Arg Val Ala Pro Leu Asp Glu Ala Leu Trp
            20                  25                  30

Lys Lys Val Gly Gly Gly Asp Tyr Pro Pro Pro Ser Ser Asn Gly Arg
        35                  40                  45

His Asp Pro Pro Gly His His His
    50                  55


<210> SEQ ID NO 172
<211> LENGTH: 56
<212> TYPE: PRT
<213> ORGANISM: Xanthomonas translucens

<400> SEQUENCE: 172

Met His Leu Leu Asn Lys Arg Lys Pro Thr Gly Leu Arg Pro Leu Gln
1               5                   10                  15

Thr Glu Ser Gln Pro Lys Arg Val Ala Pro Leu Asp Glu Ala Leu Trp
            20                  25                  30

Lys Lys Val Gly Gly Gly Asp Tyr Pro Pro Pro Ser Ser Asn Gly Arg
        35                  40                  45

His Asp Pro Pro Gly His His His
    50                  55


<210> SEQ ID NO 173
<211> LENGTH: 56
<212> TYPE: PRT
<213> ORGANISM: Xanthomonas translucens

<400> SEQUENCE: 173

Met His Leu Leu Asn Lys Arg Lys Pro Thr Gly Leu Arg Pro Leu Gln
1               5                   10                  15

Thr Glu Ser Gln Pro Lys Arg Val Ala Pro Leu Asp Glu Ala Leu Trp
            20                  25                  30

Lys Lys Val Gly Gly Gly Asp Tyr Pro Pro Pro Ser Ser Asn Gly Arg
        35                  40                  45

His Asp Pro Pro Gly His His His
    50                  55


<210> SEQ ID NO 174
<211> LENGTH: 56
<212> TYPE: PRT
<213> ORGANISM: Xanthomonas translucens

<400> SEQUENCE: 174

Met His Leu Leu Asn Lys Arg Lys Pro Thr Gly Leu Arg Pro Leu Gln
1               5                   10                  15

Thr Glu Ser Gln Pro Lys Arg Val Ala Pro Leu Asp Glu Ala Leu Trp
            20                  25                  30
```

Lys Lys Val Gly Gly Gly Asp Tyr Pro Pro Pro Ser Ser Asn Gly Arg
35 40 45

His Asp Pro Pro Gly His His His
50 55

<210> SEQ ID NO 175
<211> LENGTH: 56
<212> TYPE: PRT
<213> ORGANISM: Xanthomonas translucens

<400> SEQUENCE: 175

Met His Leu Leu Asn Lys Arg Lys Pro Thr Gly Leu Arg Pro Leu Gln
1 5 10 15

Thr Glu Ser Gln Pro Lys Arg Val Ala Pro Leu Asp Glu Ala Leu Trp
20 25 30

Lys Lys Val Gly Gly Gly Asp Tyr Pro Pro Pro Ser Ser Asn Gly Arg
35 40 45

His Asp Pro Pro Gly His His His
50 55

<210> SEQ ID NO 176
<211> LENGTH: 56
<212> TYPE: PRT
<213> ORGANISM: Xanthomonas translucens

<400> SEQUENCE: 176

Met His Leu Leu Asn Lys Arg Lys Pro Thr Gly Leu Arg Pro Leu Gln
1 5 10 15

Thr Glu Ser Gln Pro Lys Arg Val Ala Pro Leu Asp Glu Ala Leu Trp
20 25 30

Lys Lys Val Gly Gly Gly Asp Tyr Pro Pro Pro Ser Ser Asn Gly Arg
35 40 45

His Asp Pro Pro Gly His His His
50 55

<210> SEQ ID NO 177
<211> LENGTH: 56
<212> TYPE: PRT
<213> ORGANISM: Xanthomonas translucens

<400> SEQUENCE: 177

Met His Leu Leu Asn Lys Arg Lys Pro Thr Gly Leu Arg Pro Leu Gln
1 5 10 15

Thr Glu Ser Gln Pro Lys Arg Val Ala Pro Leu Asp Glu Ala Leu Trp
20 25 30

Lys Lys Val Gly Gly Gly Asp Tyr Pro Pro Pro Ser Ser Asn Gly Arg
35 40 45

His Asp Pro Pro Gly His His His
50 55

<210> SEQ ID NO 178
<211> LENGTH: 56
<212> TYPE: PRT
<213> ORGANISM: Xanthomonas translucens

<400> SEQUENCE: 178

Met His Leu Leu Asn Lys Arg Lys Pro Thr Gly Leu Arg Pro Leu Gln
1 5 10 15

Thr Glu Ser Gln Pro Lys Arg Val Ala Pro Leu Asn Glu Ala Leu Trp

```
            20                  25                  30

Lys Lys Val Gly Gly Gly Asp Tyr Ala Pro Pro Ser Ser Asn Gly Arg
        35                  40                  45

His Asp Pro Pro Gly His His His
    50                  55


<210> SEQ ID NO 179
<211> LENGTH: 56
<212> TYPE: PRT
<213> ORGANISM: Xanthomonas translucens

<400> SEQUENCE: 179

Met His Leu Leu Asn Lys Arg Lys Pro Thr Gly Leu Arg Pro Leu Gln
1               5                   10                  15

Pro Glu Ser Gln Pro Lys Arg Val Ala Pro Leu Asp Glu Ser Leu Trp
            20                  25                  30

Lys Lys Val Gly Gly Gly Asp Tyr Pro Pro Pro His Ser Asn Asp Arg
        35                  40                  45

His Asp Pro Pro Gly Lys His His
    50                  55


<210> SEQ ID NO 180
<211> LENGTH: 56
<212> TYPE: PRT
<213> ORGANISM: Xanthomonas translucens

<400> SEQUENCE: 180

Met His Leu Leu Asn Lys Arg Lys Pro Thr Gly Leu Arg Pro Leu Gln
1               5                   10                  15

Pro Glu Ser Gln Pro Lys Arg Val Ala Pro Leu Asp Glu Ser Leu Trp
            20                  25                  30

Lys Lys Val Gly Gly Gly Asp Tyr Pro Pro Pro His Ser Asn Asp Arg
        35                  40                  45

His Asp Pro Pro Gly Lys His His
    50                  55


<210> SEQ ID NO 181
<211> LENGTH: 56
<212> TYPE: PRT
<213> ORGANISM: Xanthomonas translucens

<400> SEQUENCE: 181

Met His Leu Leu Asn Lys Arg Lys Pro Thr Gly Leu Arg Pro Leu Gln
1               5                   10                  15

Pro Glu Ser Gln Pro Lys Arg Val Ala Pro Leu Asp Glu Ser Leu Trp
            20                  25                  30

Lys Lys Val Gly Gly Gly Asp Tyr Pro Pro Pro His Ser Asn Asp Arg
        35                  40                  45

His Asp Pro Pro Gly Lys His His
    50                  55


<210> SEQ ID NO 182
<211> LENGTH: 56
<212> TYPE: PRT
<213> ORGANISM: Xanthomonas translucens

<400> SEQUENCE: 182

Met His Leu Leu Asn Lys Arg Lys Pro Thr Gly Leu Arg Pro Leu Gln
1               5                   10                  15
```

```
Pro Glu Ser Gln Pro Lys Arg Val Ala Pro Leu Asp Glu Ser Leu Trp
            20                  25                  30

Lys Lys Val Gly Gly Gly Asp Tyr Pro Pro Pro His Ser Asn Asp Arg
        35                  40                  45

His Asp Pro Pro Gly Lys His His
    50                  55


<210> SEQ ID NO 183
<211> LENGTH: 56
<212> TYPE: PRT
<213> ORGANISM: Xanthomonas translucens

<400> SEQUENCE: 183

Met His Leu Leu Asn Lys Arg Lys Pro Thr Gly Leu Arg Pro Leu Gln
1               5                   10                  15

Pro Glu Ser Gln Pro Lys Arg Val Ala Pro Leu Asp Glu Ser Leu Trp
            20                  25                  30

Lys Lys Val Gly Gly Gly Asp Tyr Pro Pro Pro His Ser Asn Asp Arg
        35                  40                  45

His Asp Pro Pro Gly Lys His His
    50                  55


<210> SEQ ID NO 184
<211> LENGTH: 56
<212> TYPE: PRT
<213> ORGANISM: Xanthomonas translucens

<400> SEQUENCE: 184

Met His Leu Leu Asn Lys Arg Lys Pro Ile Gly Leu Arg Pro Leu Gln
1               5                   10                  15

Pro Glu Ser Gln Pro Lys Arg Val Ala Pro Leu Asp Glu Ala Leu Trp
            20                  25                  30

Lys Lys Val Gly Gly Gly Asp Tyr Pro Pro Thr Gly Ala Asn Asp Lys
        35                  40                  45

His Asp Pro Pro Gly His His His
    50                  55


<210> SEQ ID NO 185
<211> LENGTH: 53
<212> TYPE: PRT
<213> ORGANISM: Xanthomonas translucens

<400> SEQUENCE: 185

Met His Leu Leu Asn Lys Arg Lys Pro Thr Gly Leu Arg Pro Leu Gln
1               5                   10                  15

Pro Glu Ser Gln Pro Lys Arg Val Ala Pro Leu Asp Glu Ala Leu Trp
            20                  25                  30

Lys Lys Val Gly Gly Gly Asp Tyr Pro Pro Ser Gly Pro Asn Thr Arg
        35                  40                  45

His Asp Pro Pro Gly
    50


<210> SEQ ID NO 186
<211> LENGTH: 51
<212> TYPE: PRT
<213> ORGANISM: Xanthomonas translucens

<400> SEQUENCE: 186

Met His Leu Leu Asn Lys Arg Lys Pro Thr Gly Leu Arg Pro Leu Gln
1               5                   10                  15
```

Pro Glu Ser Gln Pro Lys Arg Val Ala Pro Leu Asp Glu Ala Gln Trp
20 25 30

Lys Lys Val Gly Gly Gly Asp Tyr Pro Thr Ala Gly Ala Asn Arg Lys
35 40 45

His Asp Pro
50

<210> SEQ ID NO 187
<211> LENGTH: 50
<212> TYPE: PRT
<213> ORGANISM: Xanthomonas translucens

<400> SEQUENCE: 187

Met His Leu Leu Asn Lys Arg Lys Pro Thr Gly Leu Arg Pro Leu Gln
1 5 10 15

Pro Glu Ser Gln Arg Lys Arg Val Ala Pro Leu Asp Glu Ala Gln Trp
20 25 30

Lys Lys Val Gly Gly Gly Asp Tyr Pro Pro Ser Gly Pro Asn Gly Lys
35 40 45

His Asn
50

<210> SEQ ID NO 188
<211> LENGTH: 50
<212> TYPE: PRT
<213> ORGANISM: Xanthomonas translucens

<400> SEQUENCE: 188

Met His Leu Leu Asn Lys Arg Lys Pro Thr Gly Leu Arg Pro Leu Gln
1 5 10 15

Pro Glu Ser Gln Arg Lys Arg Val Ala Pro Leu Asp Glu Ala Gln Trp
20 25 30

Lys Lys Val Gly Gly Gly Asp Tyr Pro Pro Ser Gly Pro Asn Gly Lys
35 40 45

His Asn
50

<210> SEQ ID NO 189
<211> LENGTH: 19
<212> TYPE: DNA
<213> ORGANISM: Artificial Sequence
<220> FEATURE:
<223> OTHER INFORMATION: Synthetic construct

<400> SEQUENCE: 189
attttgccga tttcggaac 19

<210> SEQ ID NO 190
<211> LENGTH: 21
<212> TYPE: DNA
<213> ORGANISM: Artificial Sequence
<220> FEATURE:
<223> OTHER INFORMATION: Synthetic construct

<400> SEQUENCE: 190
gagaaccttt agctgcccaa c 21

<210> SEQ ID NO 191
<211> LENGTH: 21
<212> TYPE: DNA
<213> ORGANISM: Artificial Sequence
<220> FEATURE:
<223> OTHER INFORMATION: Synthetic construct

<400> SEQUENCE: 191
acaatgattt cagcggtgat c 21

<210> SEQ ID NO 192
<211> LENGTH: 23
<212> TYPE: DNA
<213> ORGANISM: Artificial Sequence
<220> FEATURE:
<223> OTHER INFORMATION: Synthetic construct

<400> SEQUENCE: 192
gcaatacaat cagctttcca gcc 23

<210> SEQ ID NO 193
<211> LENGTH: 23
<212> TYPE: DNA
<213> ORGANISM: Artificial Sequence
<220> FEATURE:
<223> OTHER INFORMATION: Synthetic construct

<400> SEQUENCE: 193
ggtaacattg tgctcagtgg tgg 23

<210> SEQ ID NO 194
<211> LENGTH: 23
<212> TYPE: DNA
<213> ORGANISM: Artificial Sequence
<220> FEATURE:
<223> OTHER INFORMATION: Synthetic construct

<400> SEQUENCE: 194
ggtgcaacga ccttaatctt cat 23

<210> SEQ ID NO 195
<211> LENGTH: 13
<212> TYPE: PRT
<213> ORGANISM: Xanthomonas oryzae

<400> SEQUENCE: 195

Asp Tyr Pro Pro Pro Gly Ala Asn Pro Lys His Asp Pro
1 5 10

<210> SEQ ID NO 196
<211> LENGTH: 13
<212> TYPE: PRT
<213> ORGANISM: Oryza sativa

<400> SEQUENCE: 196

Asp Tyr Pro Ala Pro Gly Ala Asn Pro Arg His Asn Pro
1 5 10

<210> SEQ ID NO 197
<211> LENGTH: 13
<212> TYPE: PRT
<213> ORGANISM: Xanthomonas oryzae

<400> SEQUENCE: 197

Asp Tyr Pro Pro Ser Gly Pro Asn Thr Lys His Asp Pro
1 5 10

<210> SEQ ID NO 198
<211> LENGTH: 13

<212> TYPE: PRT
<213> ORGANISM: Oryza sativa

<400> SEQUENCE: 198

Asp Tyr Pro Gly Ser Gly Pro Asn Asn Arg His Asp Pro
1 5 10

<210> SEQ ID NO 199
<211> LENGTH: 21
<212> TYPE: PRT
<213> ORGANISM: Artificial Sequence
<220> FEATURE:
<223> OTHER INFORMATION: Synthetic construct

<400> SEQUENCE: 199

His Val Gly Gly Gly Asp Tyr Pro Pro Pro Gly Ala Asn Pro Lys His
1 5 10 15

Asp Pro Pro Pro Arg
20

<210> SEQ ID NO 200
<211> LENGTH: 18
<212> TYPE: PRT
<213> ORGANISM: Artificial Sequence
<220> FEATURE:
<223> OTHER INFORMATION: Synthetic construct

<400> SEQUENCE: 200

Leu Trp Lys His Val Gly Gly Gly Asp Tyr Pro Pro Pro Gly Ala Asn
1 5 10 15

Pro Lys

<210> SEQ ID NO 201
<211> LENGTH: 20
<212> TYPE: DNA
<213> ORGANISM: Artificial Sequence
<220> FEATURE:
<223> OTHER INFORMATION: Synthetic construct

<400> SEQUENCE: 201
gtcgcggtgt cggtggagag 20

<210> SEQ ID NO 202
<211> LENGTH: 20
<212> TYPE: DNA
<213> ORGANISM: Artificial Sequence
<220> FEATURE:
<223> OTHER INFORMATION: Synthetic construct

<400> SEQUENCE: 202
acggcgtcga tgaatccggc 20

<210> SEQ ID NO 203
<211> LENGTH: 20
<212> TYPE: DNA
<213> ORGANISM: Artificial Sequence
<220> FEATURE:
<223> OTHER INFORMATION: Synthetic construct

<400> SEQUENCE: 203
aaatgatttg ggaccagtcg 20

<210> SEQ ID NO 204
<211> LENGTH: 20
<212> TYPE: DNA

<213> ORGANISM: Artificial Sequence
<220> FEATURE:
<223> OTHER INFORMATION: Synthetic construct

<400> SEQUENCE: 204
gatggaatgt cctcgcaaac 20

<210> SEQ ID NO 205
<211> LENGTH: 20
<212> TYPE: DNA
<213> ORGANISM: Artificial Sequence
<220> FEATURE:
<223> OTHER INFORMATION: Synthetic construct

<400> SEQUENCE: 205
gagaagctca tcctcgacgg 20

<210> SEQ ID NO 206
<211> LENGTH: 20
<212> TYPE: DNA
<213> ORGANISM: Artificial Sequence
<220> FEATURE:
<223> OTHER INFORMATION: Synthetic construct

<400> SEQUENCE: 206
gcatactcgg tagggtgagc 20

<210> SEQ ID NO 207
<211> LENGTH: 22
<212> TYPE: DNA
<213> ORGANISM: Artificial Sequence
<220> FEATURE:
<223> OTHER INFORMATION: Synthetic construct

<400> SEQUENCE: 207
tcggctctga atgtacctcc ta 22

<210> SEQ ID NO 208
<211> LENGTH: 24
<212> TYPE: DNA
<213> ORGANISM: Artificial Sequence
<220> FEATURE:
<223> OTHER INFORMATION: Synthetic construct

<400> SEQUENCE: 208
cacttgagta aagactgtca cttg 24

<210> SEQ ID NO 209
<211> LENGTH: 13
<212> TYPE: PRT
<213> ORGANISM: Xanthomonas oryzae

<400> SEQUENCE: 209

Asp Tyr Pro Pro Ser Gly Pro Asn Pro Lys His Asp Pro
1 5 10

<210> SEQ ID NO 210
<211> LENGTH: 13
<212> TYPE: PRT
<213> ORGANISM: Xanthomonas oryzae

<400> SEQUENCE: 210

Asp Tyr Pro Pro Ala Gly Pro Ser Thr Lys His Asp Pro
1 5 10

<210> SEQ ID NO 211
<211> LENGTH: 13
<212> TYPE: PRT
<213> ORGANISM: Unknown
<220> FEATURE:
<223> OTHER INFORMATION: Xanthomonas oryzae or X. campestris

<400> SEQUENCE: 211

Asp Tyr Pro Pro Ser Gly Pro Asn Thr Lys His Asp Pro
1 5 10

<210> SEQ ID NO 212
<211> LENGTH: 13
<212> TYPE: PRT
<213> ORGANISM: Unknown
<220> FEATURE:
<223> OTHER INFORMATION: Xanthomonas axonopodis, X. euvesicatoria, X. alfalfae, or X. perforans

<400> SEQUENCE: 212

Asp Tyr Pro Pro Pro Gly Ala Asn Thr Lys His Asp Pro
1 5 10

<210> SEQ ID NO 213
<211> LENGTH: 13
<212> TYPE: PRT
<213> ORGANISM: Xanthomonas axonopodis

<400> SEQUENCE: 213

Asp Tyr Pro Pro Pro Gly Ala Asn Thr Lys His Asp Pro
1 5 10

<210> SEQ ID NO 214
<211> LENGTH: 13
<212> TYPE: PRT
<213> ORGANISM: Xanthomonas maliensis

<400> SEQUENCE: 214

Asp Tyr Pro Pro Pro Gly Ala Asn Asp Arg His Asn Pro
1 5 10

<210> SEQ ID NO 215
<211> LENGTH: 13
<212> TYPE: PRT
<213> ORGANISM: Xanthomonas campestris

<400> SEQUENCE: 215

Asp Tyr Ala Pro Pro Gly Ser Asn Asp Arg His Asp Pro
1 5 10

<210> SEQ ID NO 216
<211> LENGTH: 13
<212> TYPE: PRT
<213> ORGANISM: Xanthomonas vasicola

<400> SEQUENCE: 216

Asp Tyr Ala Pro Pro Gly Ser Asn Asp Arg His Asp Pro
1 5 10

<210> SEQ ID NO 217
<211> LENGTH: 13
<212> TYPE: PRT
<213> ORGANISM: Xanthomonas vasicola

<400> SEQUENCE: 217

Asp Tyr Pro Pro Pro Gly Ser Asn Asn Arg His Asp Pro 1 5 10

<210> SEQ ID NO 218
<211> LENGTH: 13
<212> TYPE: PRT
<213> ORGANISM: Xanthomonas axonopodis

<400> SEQUENCE: 218

Asp Tyr Pro Pro Thr Gly Pro Asn Thr Arg His Asp Pro
1 5 10

<210> SEQ ID NO 219
<211> LENGTH: 13
<212> TYPE: PRT
<213> ORGANISM: Xanthomonas axonopodis

<400> SEQUENCE: 219

Asp Tyr Pro Pro Ser Ala Ala Asn Asp Arg His Asp Pro
1 5 10

<210> SEQ ID NO 220
<211> LENGTH: 13
<212> TYPE: PRT
<213> ORGANISM: Xanthomonas translucens

<400> SEQUENCE: 220

Asp Tyr Pro Pro Pro Ser Ser Asn Gly Arg His Asp Pro
1 5 10

<210> SEQ ID NO 221
<211> LENGTH: 13
<212> TYPE: PRT
<213> ORGANISM: Xanthomonas translucens

<400> SEQUENCE: 221

Asp Tyr Ala Pro Pro Ser Ser Asn Gly Arg His Asp Pro
1 5 10

<210> SEQ ID NO 222
<211> LENGTH: 13
<212> TYPE: PRT
<213> ORGANISM: Xanthomonas translucens

<400> SEQUENCE: 222

Asp Tyr Pro Pro Pro His Ser Asn Asp Arg His Asp Pro
1 5 10

<210> SEQ ID NO 223
<211> LENGTH: 13
<212> TYPE: PRT
<213> ORGANISM: Xanthomonas translucens

<400> SEQUENCE: 223

Asp Tyr Pro Pro Thr Gly Ala Asn Asp Lys His Asp Pro
1 5 10

<210> SEQ ID NO 224
<211> LENGTH: 13
<212> TYPE: PRT
<213> ORGANISM: Xanthomonas translucens

<400> SEQUENCE: 224

Asp Tyr Pro Pro Ser Gly Pro Asn Thr Arg His Asp Pro
1 5 10

<210> SEQ ID NO 225
<211> LENGTH: 13
<212> TYPE: PRT
<213> ORGANISM: Xanthomonas translucens

<400> SEQUENCE: 225

Asp Tyr Pro Thr Ala Gly Ala Asn Arg Lys His Asp Pro
1 5 10

<210> SEQ ID NO 226
<211> LENGTH: 16
<212> TYPE: PRT
<213> ORGANISM: Xanthomonas oryzae

<400> SEQUENCE: 226

Asp Tyr Pro Pro Pro Gly Ala Asn Pro Lys His Asp Pro Pro Pro Arg
1 5 10 15

<210> SEQ ID NO 227
<211> LENGTH: 5
<212> TYPE: PRT
<213> ORGANISM: Arabidopsis thaliana

<400> SEQUENCE: 227

Tyr Ile Tyr Thr Gln
1 5

<210> SEQ ID NO 228
<211> LENGTH: 24
<212> TYPE: PRT
<213> ORGANISM: Xanthomonas oryzae

<400> SEQUENCE: 228

Leu Trp Lys His Val Gly Gly Gly Asp Tyr Pro Pro Ser Gly Pro Asn
1 5 10 15

Thr Lys His Asp Pro Pro Pro Pro
20

<210> SEQ ID NO 229
<211> LENGTH: 24
<212> TYPE: PRT
<213> ORGANISM: Xanthomonas euvesicatoria

<400> SEQUENCE: 229

Leu Trp Lys His Val Gly Gly Gly Asp Tyr Pro Pro Pro Gly Ala Asn
1 5 10 15

Thr Lys His Asp Pro Pro Pro Lys
20

<210> SEQ ID NO 230
<211> LENGTH: 24
<212> TYPE: PRT
<213> ORGANISM: Xanthomonas campestris

<400> SEQUENCE: 230

Leu Trp Lys His Val Gly Gly Gly Asp Tyr Ala Pro Pro Gly Ser Asn
1 5 10 15

Asp Arg His Asp Pro Pro Lys Pro
20

<210> SEQ ID NO 231
<211> LENGTH: 13
<212> TYPE: PRT

<213> ORGANISM: Unknown
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Xaa = Pro or Ala
<220> FEATURE:
<221> NAME/KEY: MISC_FEATURE
<222> LOCATION: (4)..(4)
<223> OTHER INFORMATION: Xaa = Pro or Thr
<220> FEATURE:
<221> NAME/KEY: MISC_FEATURE
<222> LOCATION: (5)..(5)
<223> OTHER INFORMATION: Xaa = Pro or Ser or Ala or Thr
<220> FEATURE:
<221> NAME/KEY: MISC_FEATURE
<222> LOCATION: (6)..(6)
<223> OTHER INFORMATION: Xaa = Gly or Ala or Ser or His
<220> FEATURE:
<221> NAME/KEY: MISC_FEATURE
<222> LOCATION: (7)..(7)
<223> OTHER INFORMATION: Xaa = Ala or Pro or Ser
<220> FEATURE:
<221> NAME/KEY: MISC_FEATURE
<222> LOCATION: (8)..(8)
<223> OTHER INFORMATION: Xaa = Asn or Ser
<220> FEATURE:
<221> NAME/KEY: MISC_FEATURE
<222> LOCATION: (9)..(9)
<223> OTHER INFORMATION: Xaa = Pro or Thr or Asp or Asn or Gly or Arg
<220> FEATURE:
<221> NAME/KEY: MISC_FEATURE
<222> LOCATION: (10)..(10)
<223> OTHER INFORMATION: Xaa = Lys or Arg
<220> FEATURE:
<221> NAME/KEY: MISC_FEATURE
<222> LOCATION: (12)..(12)
<223> OTHER INFORMATION: Xaa = Asp or Asn

<400> SEQUENCE: 231

```
Asp Tyr Xaa Xaa Xaa Xaa Xaa Xaa Xaa Xaa His Xaa Pro
1               5                   10
```

<210> SEQ ID NO 232
<211> LENGTH: 11
<212> TYPE: PRT
<213> ORGANISM: Artificial sequence
<220> FEATURE:
<223> OTHER INFORMATION: Synthetic construct

<400> SEQUENCE: 232

```
Lys Gly Arg Pro Glu Pro Leu Asp Gln Arg Leu
1               5                   10
```

<210> SEQ ID NO 233
<211> LENGTH: 17
<212> TYPE: PRT
<213> ORGANISM: Artificial sequence
<220> FEATURE:
<223> OTHER INFORMATION: Synthetic construct

<400> SEQUENCE: 233

```
Lys His Val Gly Gly Gly Asp Tyr Pro Pro Pro Gly Ala Asn Pro Lys
1               5                   10                  15

His
```

<210> SEQ ID NO 234
<211> LENGTH: 26
<212> TYPE: PRT
<213> ORGANISM: Artificial sequence
<220> FEATURE:

-continued

```
<223> OTHER INFORMATION: Synthetic construct

<400> SEQUENCE: 234

Arg Leu Trp Lys His Val Gly Gly Gly Asp Tyr Pro Pro Pro Gly Ala
1               5                   10                  15

Asn Pro Lys His Asp Pro Pro Pro Arg Asn
            20                  25


<210> SEQ ID NO 235
<211> LENGTH: 13
<212> TYPE: PRT
<213> ORGANISM: Artificial Sequence
<220> FEATURE:
<223> OTHER INFORMATION: Synthetic construct

<400> SEQUENCE: 235

Gly Asp Tyr Pro Pro Pro Gly Ala Asn Pro Lys His Asp
1               5                   10
```

ENGINEERING PATHOGEN RESISTANCE IN PLANTS

CROSS-REFERENCED TO RELATED PATENT APPLICATIONS

This application is a continuation-in-part of PCT Patent Application No. PCT/US2015/036439, filed Jun. 18, 2015, which claims benefit of priority to U.S. Provisional Patent Application No. 62/013,709, filed Jun. 18, 2014, which is incorporated by reference for all purposes.

STATEMENT AS TO RIGHTS TO INVENTIONS MADE UNDER FEDERALLY SPONSORED RESEARCH AND DEVELOPMENT

This invention was made with government support under Grant No. RO1 GM59962, awarded by the National Institutes of Health. The government has certain rights in the invention.

REFERENCE TO A "SEQUENCE LISTING" SUBMITTED AS ASCII TEXT FILES VIA EFS-WEB

The Sequence Listing written in file 077429-0218020US-1033381_SubstituteSequenceListing.txt created on Sep. 19, 2017, 115,589 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Perception of extracellular signals by cell surface receptors is of central importance to eukaryotic development and immunity. Cell surface Pattern Recognition Receptors (PRRs), play an essential role in the innate immune responses in animals and plants. PRRs share conserved signaling domains, such as leucine-rich repeats (LRRs), and function via kinases, which are either integral to the receptor (plants) or associated with the receptor (animals). Many of these receptors regulate transcription of target genes through phosphorylation events after recognition of pathogen associated molecular patterns (PAMPs).

In animals, recognition of PAMPs in extracellular compartments or at the cell surface is largely carried out by the toll like receptor (TLR) family that contains LRRs in the extracellular domain and a TIR intracellular domain. All TLRs activate a common signaling pathway to induce a core set of defense responses via kinases. TLRs associate with the interleukin-1 receptor-associated kinase (IRAK) family and with receptor interacting-protein (RIP) kinases via adaptor proteins. In plants, cell surface recognition of PAMPS is largely carried out by receptor kinases (RKs).

Kinases can be divided into "RD" kinases, which have an arginine (R) immediately preceding the conserved catalytic aspartate (D), and a smaller group of "non-RD" kinases, which typically carry a cysteine or glycine before the aspartate residue. The RD class of kinases includes nearly all receptor tyrosine kinases (RTKs) and most characterized plant RSTKs. The non-RD class includes members of human IRAKs and RIPs, *Drosophila* Pelle, and members of plant RKs belonging to the IRAK family.

Plant genome analyses have revealed the presence of a large family of these non-RD IRAK RKs, with more than 45 encoded in the *Arabidopsis* genome and more than 370 found in the rice genome. Members include *Arabidopsis* FLS2 that detects the peptide flg22, a component of flagellin; the elongation factor Tu receptor (EFR) that detects elf18, a peptide corresponding to the bacterial elongation factor Tu; the rice XA26 and Pi-d2 RKs; and the rice XA21 RK that mediates recognition of *Xanthomonas oryzae* pv. *oryzae* (Xoo).

Activation of XA21 results in a robust immune response. XA21 biogenesis takes place in the endoplasmic reticulum. After processing and transit to the plasma membrane, XA21 binds to XB24 (XA21 binding protein 24). XB24 associates with the XA21 juxtamembrane domain and catalyzes the autophosphorylation of serine and threonine residues on XA21, maintaining XA21 in an inactive state. Following pathogen recognition, the XA21 kinase disassociates from XB24 and is activated. XA21 also binds to XB25, a plant-specific ankyrin-repeat protein. XB25 associates with the XA21 transmembrane domain in vitro and is weakly transphosphorylated by XA21. The XA21-mediated signaling pathway is attenuated by XB15, a protein phosphatase 2C, which dephosphorylates XA21. XA21-mediated immunity requires the presence of a co-receptor called OsSERK2 (somatic embryogenesis receptor kinase 2). OsSERK2 interacts with the intracellular domain of XA21 in a kinase activity dependent manner. OsSERK2 undergoes bidirectional transphosphorylation with XA21 in vitro and forms a constitutive complex with XA21 in vivo.

BRIEF SUMMARY OF THE INVENTION

The present results reveal a microbial molecule that activates XA21-mediated immunity (sulfated raxX), and molecular pathways involved in its processing (e.g., raxST) and release (e.g., membrane fusion protein (MFP) (e.g., raxA), ABC transporter protein (e.g., raxB and/or cvaB) and outer membrane protein (OMP) (e.g., raxC)).

Provided herein are isolated or purified or synthetic RaxX polypeptides or homologs thereof. In some embodiments, the polypeptide comprises a sequence of SEQ ID NO:46, or a sequence having at least 60% identity (e.g., at least 65%, 70%, 75%, 80%, 85%, or 90%) to SEQ ID NO:46, wherein the amino acid at the position corresponding to Tyr2 of SEQ ID NO:46—which corresponds to Tyr10 of SEQ ID NO:1—(i.e., when the sequences are optimally aligned) is Tyr. In some embodiments, the polypeptide comprises the sequence DY(P/G)(P/D)P(G/S)ANPKHDP (SEQ ID NO:48), wherein the amino acids in parentheses are options at that position. In some embodiments, the peptide is not DYGDPSANPKHDP (SEQ ID NO:47). In some embodiments, the polpeptide comprises any of the 13mer sequences depicted in FIG. 45 part 2 from the highlighted "D" through the highlighted "P" or an aligned sequence thereof in the Figure. In some embodiments, the polpeptide comprises a sequence from Table 51.

In some embodiments, the polypeptide comprises a sequence of SEQ ID NO:1, or a sequence having at least 60% identity (e.g., at least 65%, 70%, 75%, 80%, 85%, 90%, or 95%) to SEQ ID NO:1, wherein the amino acid at the position corresponding to Tyr10 of SEQ ID NO:1 (i.e., when the sequences are optimally aligned) is Tyr.

In some embodiments, the polypeptide as described above or elsewhere herein is 13, 14, 15, 16, 17, 18, 19, 20, 13-20, 13-75, 15-75, 20-50, 50-100, 50-75, or about 60 amino acids in length. In some embodiments, the Tyr corresponding to Tyr10 of SEQ ID NO:1 is sulfated. In some embodiments, the polypeptide comprises a sequence of any one of SEQ ID NOs: 22-45, or amino acids 20-60, 25-55, or 30-55 of any one of SEQ ID NOs: 22-45. In some embodiments, the polypeptide comprises amino acids 32-51 of SEQ ID NO:22. In some embodiments, the polypeptide is encoded by a polynucleotide selected from the group of sequences consisting of SEQ ID NOs: 5-21.

Further provided are agricultural compositions comprising the polypeptide described above formulated for application to a plant (e.g., directly, or via soil or water). In some embodiments, the agricultural composition further comprises an agriculturally suitable carrier, surfactant, herbicide, fungicide, pesticide, or fertilizer. In some embodiments, the polypeptide or agricultural composition enhances the disease resistance of a plant expressing XA21 or a homolog thereof (endogenously or heterologously expressed) when contacted with the plant, compared to a plant that is not contacted with the polypeptide or agricultural composition. In some embodiments, the tyrosine corresponding to Tyr10 of SEQ ID NO:1 or Tyr2 of SEQ ID NO: 46, is sulfated. In some embodiments, the polypeptide is 13, 14, 15, 16, 17, 18, 19, 20, 13-20, 13-75, 15-75, 20-50, 50-100, 50-75, or about 60 amino acids in length.

Additionally provided are plants contacted with the polypeptide or agricultural composition as described above. In some embodiments, the plant expresses XA21 or a homolog thereof (endogenously or heterologously). In some embodiments, the plant has enhanced disease resistance compared to a plant not contacted with the polypeptide or agricultural composition. In some embodiments, the plant is of a species selected from the group consisting of: *Asparagus, Atropa, Avena, Brassica, Citrus, Citrullus, Capsicum, Cucumis, Cucurbita, Daucus, eucalyptus, Fragaria, Glycine, Gossypium, Helianthus, Heterocallis, Hordeum, Hyoscyamus, Lactuca, Linum, Lolium, Lycopersicon, Malta, Manihot, Majorana, Medicago, Setaria, Miscanthus, Nicotiana, Oryza, Panicum, Pennisetum, Persea, Pisum, Populus, Pyrus, Prunus, Raphanus, Secale, Senecio, Sinapis, Solanum, Sorghum, Trigonella, Triticum, Vitis, Vigna*, and, *Zea.*

Provided herein are methods of making the polypeptide as described above comprising introducing an expression cassette comprising a promoter operably linked to a polynucleotide sequence encoding the polypeptide to a heterologous cell, expressing the polypeptide in the cell, and purifying the polypeptide. In some embodiments, the promoter is a pathogen-inducible promoter. In some embodiments, the polypeptide comprises a cleavable tag to ease purification, e.g., a maltose binding protein (MBP) or poly-His tag. After the expressed polypeptide is separated from extraneous material, the tag can be removed enzymatically or chemically according to common techniques.

In some embodiments, the polynucleotide sequence encoding the polypeptide comprises an amber codon at the amino acid position corresponding to Tyr10 of SEQ ID NO:1, and the heterologous cell comprises an orthogonal aminoacyl-tRNA synthetase/tRNA pair, and sulfotyrosine. In some embodiments, the heterologous cell comprises an enzyme that sulfates the Tyr at the position corresponding to Tyr10 of SEQ ID NO: 1. In some embodiments, the method further comprises introducing to the cell an expression cassette comprising a promoter operably linked to a polynucleotide sequence encoding the enzyme. In some embodiments, this orthogonal expression system is carried out in bacteria, e.g., *E. coli.*

Further provided are methods of making the polypeptides as described herein using chemical synthesis. The length of the raxX polypeptide required to activate XA21-mediated immunity is small (e.g., about 20 amino acids), making chemical synthesis an economically viable option. In some embodiments, the method comprises adding a sulfated tyrosine to the nascent polypeptide chain at the amino acid position corresponding to Tyr10 of SEQ ID NO:1.

Also provided are transgenic plants, wherein the plant comprises a heterologous expression cassette comprising a promoter (e.g., a pathogen-inducible promoter) operably linked to a polynucleotide encoding a polypeptide as described above. In some embodiments, the plant expresses endogenous XA21 or a homolog thereof. In some embodiments, the plant further comprises a heterologous expression cassette comprising a promoter operably linked to a polynucleotide encoding XA21 or a homolog thereof. In some embodiments, the plant further comprises a heterologous expression cassette comprising a promoter operably linked to a polynucleotide encoding a sulfotransferase (e.g., RaxST or a homolog thereof). In some embodiments, one, two, or three of the promoters are pathogen-inducible promoters. In some embodiments, the plant is of a species selected from the group consisting of: *Asparagus, Atropa, Avena, Brassica, Citrus, Citrullus, Capsicum, Cucumis, Cucurbita, Daucus, eucalyptus, Fragaria, Glycine, Gossypium, Helianthus, Heterocallis, Hordeum, Hyoscyamus, Lactuca, Linum, Lolium, Lycopersicon, Malta, Manihot, Majorana, Medicago, Setaria, Miscanthus, Nicotiana, Oryza, Panicum, Pennisetum, Persea, Pisum, Populus, Pyrus, Prunus, Raphanus, Secale, Senecio, Sinapis, Solanum, Sorghum, Trigonella, Triticum, Vitis, Vigna*, and, *Zea.*

Provided herein are methods for enhancing disease resistance and/or enhancing root growth in a plant. In some embodiments, the method comprises contacting the plant with a sufficient amount of the polypeptide or the agricultural composition as described above to enhance the disease resistance and/or root growth of the plant compared to a plant that is not contacted by the polypeptide or agricultural composition. In some embodiments, the plant expresses XA21 or a homolog thereof (endogenously or heterologously). In some embodiments, the plant is of a species selected from the group consisting of: *Asparagus, Atropa, Avena, Brassica, Citrus, Citrullus, Capsicum, Cucumis, Cucurbita, Daucus, eucalyptus, Fragaria, Glycine, Gossypium, Helianthus, Heterocallis, Hordeum, Hyoscyamus, Lactuca, Linum, Lolium, Lycopersicon, Malta, Manihot, Majorana, Medicago, Setaria, Miscanthus, Nicotiana, Oryza, Panicum, Pennisetum, Persea, Pisum, Populus, Pyrus, Prunus, Raphanus, Secale, Senecio, Sinapis, Solanum, Sorghum, Trigonella, Triticum, Vitis, Vigna*, and, *Zea.* In some embodiments, the method further comprises contacting the plant with a pathogen (e.g., *Xanthomonas* bacteria, a non-*Xanthomonas* pathogen, or supernatants or extracts from the pathogen) and determining disease resistance to the pathogen.

Also provided are recombinant host cells, wherein the host cell comprises a heterologous expression cassette comprising a promoter operably linked to a polynucleotide encoding a RaxX polypeptide or homolog thereof as described above. In some embodiments, the host cell is selected from the group consisting of a plant cell, a fungal cell, a bacterial cell, a yeast cell, an insect cell and a mammalian cell. In some embodiments, the host cell expresses (endogenously or heterologously) an enzyme that sulfates the Tyr corresponding to Tyr10 in SEQ ID NO:1 (if present), e.g., RaxST or a homolog thereof (e.g., having an Arg at the amino acid position corresponding to Arg35 in Xoo RaxST). In some embodiments, the host cell expresses (endogenously or heterologously) a membrane fusion protein, ATP binding cassette transporter protein, and outer membrane protein, e.g., RaxA, RaxB, and RaxC, or homologs thereof.

Further provided is a method of screening for a polypeptide that enhances disease resistance (e.g., XA21-mediated disease resistance or resistance mediated by a XA21 homolog) and/or root growth in a plant. In some embodiments, the method comprises a) detecting polypeptides released from a bacterial cell lacking functional raxB and cvaB (raxB/cvaB deficient); b) detecting polypeptides secreted from a bacterial cell having functional raxb and cvaB; c) identifying polypeptides released in b) that are not released in a); d) applying a polypeptide identified in c) to the plant; and e) selecting the polypeptide that enhances disease resistance compared to a plant not contacted with the polypeptide. In some embodiments, the plant expresses XA21 or a homolog thereof (endogenously or heterologously). In some embodiments, the method further comprises contacting the plant with a pathogen, e.g., a Gram negative bacteria such as *Xanthomonas*, or supernatants or extracts from the bacteria.

Also provided are methods of screening for compounds that affect expression of Rax genes. In some embodiments, the method comprises (i) contacting a test compound with a cell comprising an expression cassette having a Rax gene promoter and either a Rax-encoding sequence, or a reporter-encoding sequence (e.g., GFP); (ii) detecting the level of Rax expression by detecting the level of Rax gene product (e.g., RNA or protein) or reporter; and (iii) comparing the level detected in step (ii) to the level of Rax expression in a control cell. In some embodiments, the control cell is not contacted with the test compound. In some embodiments, the Rax gene is RaxX. In some embodiments, the Rax gene is RaxST. In some embodiments, the expression cassette is an endogenous gene in the cell (e.g., a Gram-negative bacterial cell). In some embodiments, the expression cassette is heterologous to the cell.

The following Xoo strains were used: PXO99A WT [PXO99A], PXO99A ΔraxST [RaxST], PXO99A ΔraxST complemented with RaxST [RaxST (RaxST)], and PXO99A ΔraxST complemented with catalytic inactive RaxST (R35a) [RaxST (STr35a)].

Figure 3:
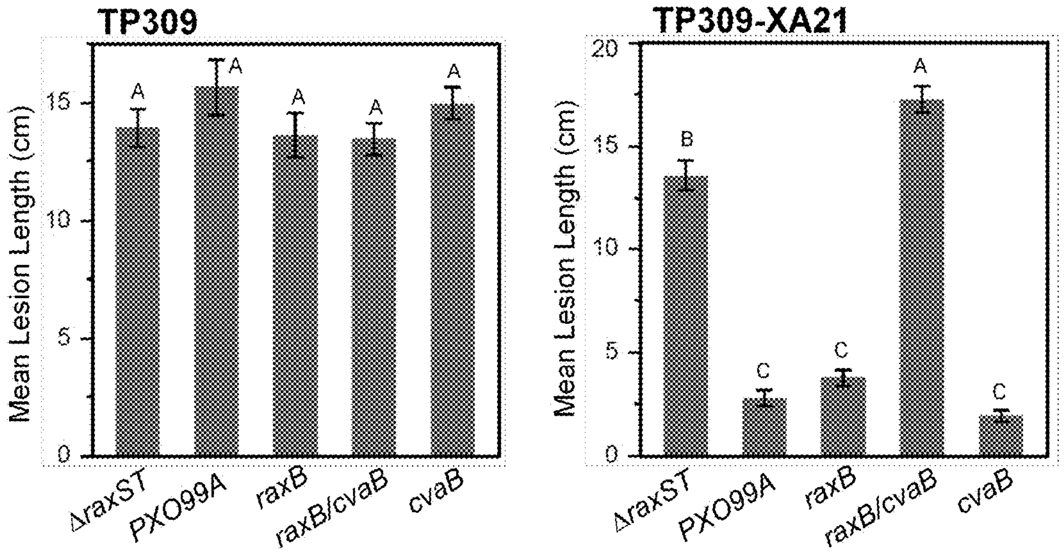

FIG. 3. The raxB/cvaB double mutant overcomes XA21-mediated immunity. The standard clipping method was used to inoculate rice plants (TP309 and TP309-XA21) with a $10^8$ CFU/mL suspension. Lesion lengths were measured 14 days post inoculation. Bars represent mean of 20-30 leaves±SE. Statistical significance was calculated using the Tukey-Kramer HSD test. Different letters indicate significant difference ($p<0.01$). This experiment was repeated 3 times with similar results.

The following Xoo strains were used: PXO99A ΔraxST [ΔraxST], PXO99A WT [PXO99A], PXO99A ΔraxB [raxB], PXO99A ΔraxB/ΔcvaB [raxB/cvaB] and PXO99A ΔcvaB [cvaB].

Figure 4:
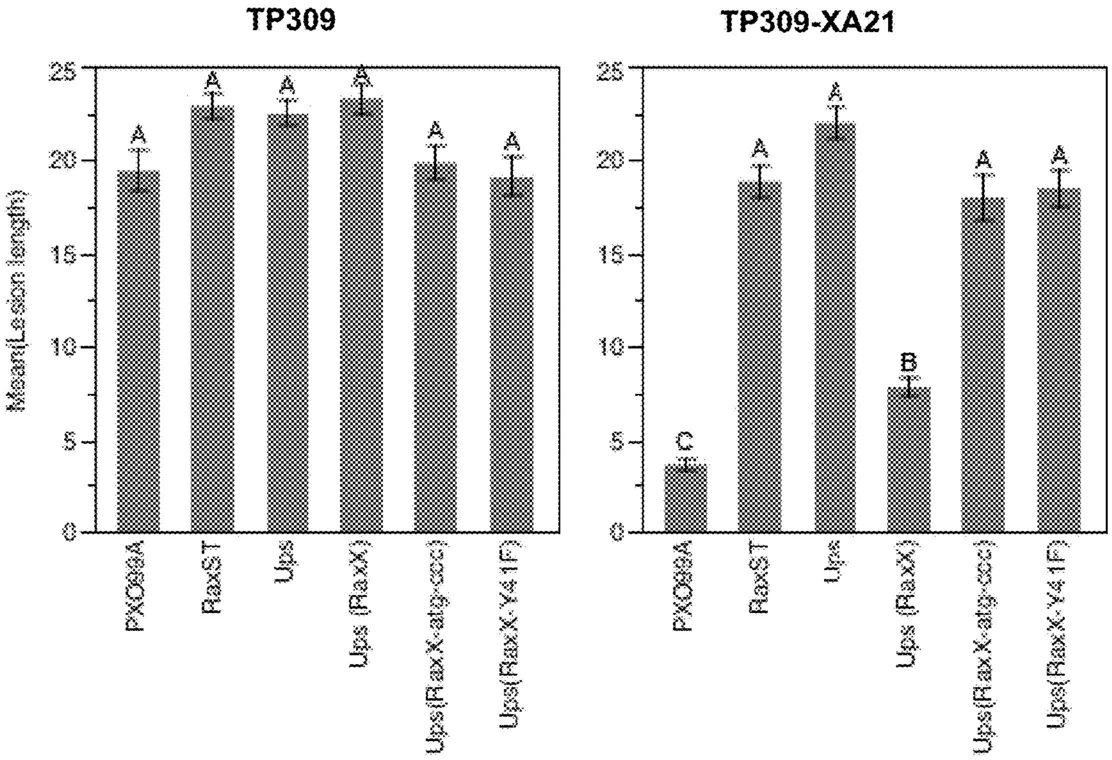

FIG. 4. raxX is required for activation of XA21-mediated immunity. The standard clipping method was used to inoculate rice plants (TP309 and TP309-XA21) with a $10^8$ CFU/mL bacterial suspension. Lesion lengths were measured 14 days post inoculation. Bars represent mean of at least 10 leaves±SE. The experiment was repeated 3 times with similar results.

The following Xoo strains were used: PXO99A WT [PXO99A], PXO99A ΔraxST [RaxST], PXO99A carrying a deletion of 1 kb located 300 bp upstream of the start site of RaxST [Ups], PXO99A Ups complemented with the open reading frame of RaxX [Ups(RaxX)] and PXO99A Ups complemented with the open reading frame of RaxX with a mutation in the presumed start codon (atg-ccc) [Ups(RaxX-atg-ccc)] and PXO99A Ups complemented with the open reading frame of RaxX(Y41F) [Ups(RaxX-Y41F)].

Figure 5B:
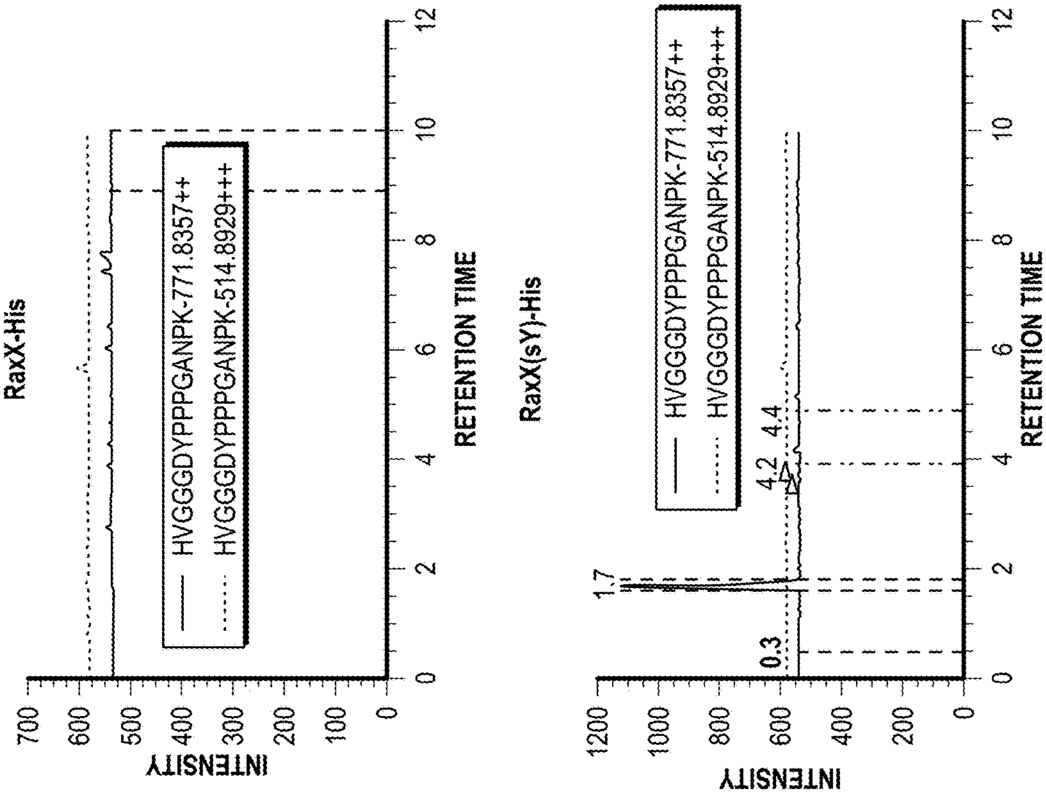
Figure 5A:
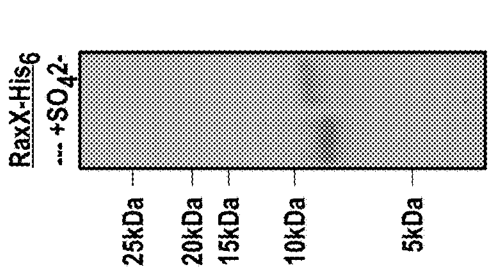

FIGS. 5A and 5B. Expression and purification of RaxX-His and RaxX(sY)-His. A specifically engineered orthogonal aminoacyl-tRNA synthetase/tRNA (aaRS/tRNA) pair was co-expressed from the pULTRA_SYP29 plasmid. This tRNA recognizes the amber codon and incorporates sulfotyrosine, which is supplied in the media, at the desired position MBP-3C-RaxX-His or MBP-3C-RaxX(sY)-His were expressed in pMAL vector in *E. coli* BL21 cells in the presence of 1 mM IPTG for 16 h at 20° C. Both proteins were two-step purified and RaxX-His released from the N-terminal MBP-tag by 3C protease treatment. (FIG. 5A) Sulfated RaxX(sY)-His (+$504^{2}$") runs at a slightly higher molecular weight than RaxX-His most likely due to its additional negative charge. (FIG. 5B) Sulfation of the central tyrosine of RaxX can only be detected on trypsin peptides of RaxX(sY)-His (lower panel) but not of RaxX-His. SEQ ID NO:4 is the 15-mer peptide used in this test, as shown in the legends for both graphs in FIG. 5B.

Figure 6:
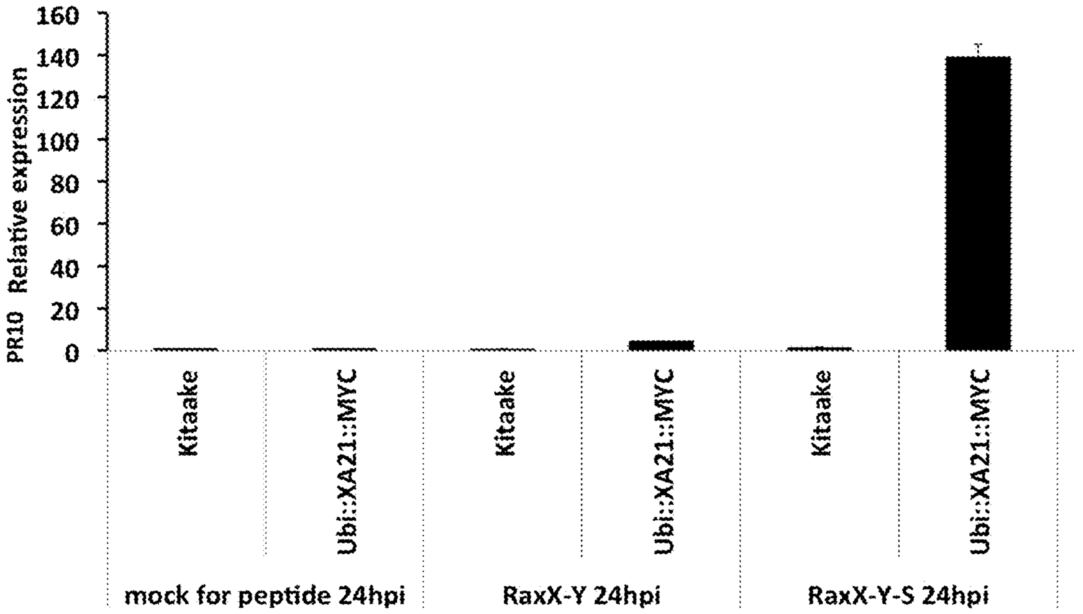

FIG. 6. RaxX-His induces defense gene expression in a tyrosine sulfation and XA21-dependent manner. Leaves of Kitaake or Kitaake expressing Ubi::XA21::MYC were treated with about 200 nM purified mock, RaxX-His (designated RaxX-Y) and RaxX(sY)-His) designated RaxX-Y-S) for 24 h. PR10b marker expression was measured by qPCR, and normalized to actin expression. Defense gene expression is only induced in XA21 plants in the presence of sulfated RaxX but not nonsulfated RaxX. Similar gene expression patterns were observed for Os04g10010. The experiment was repeated 8 times with similar results.

Figure 7A:
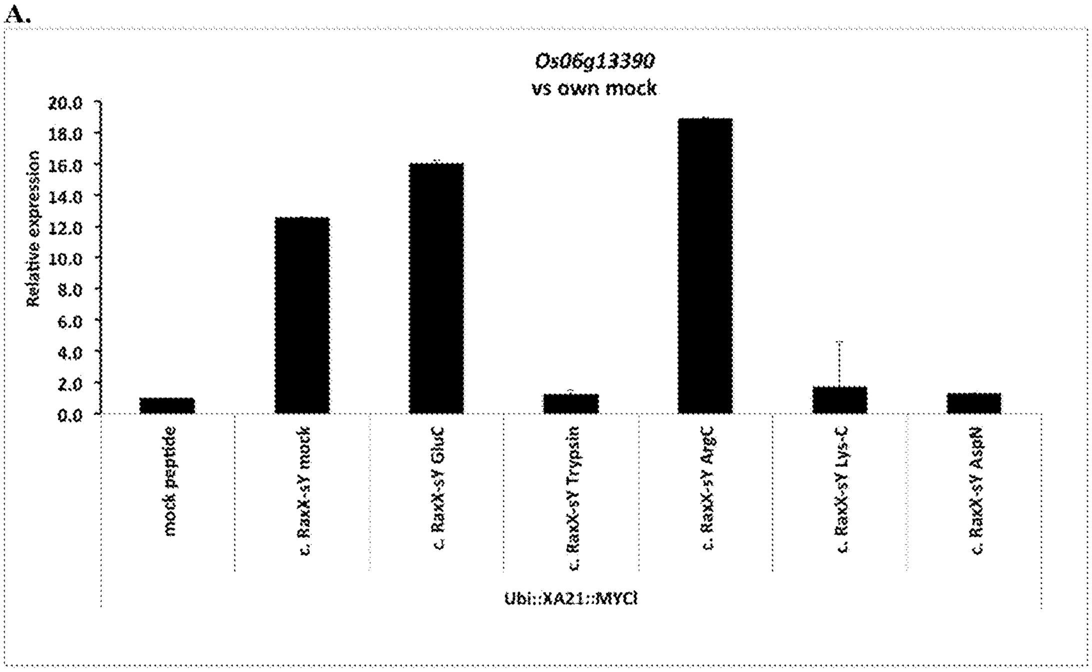
Figure 7B:
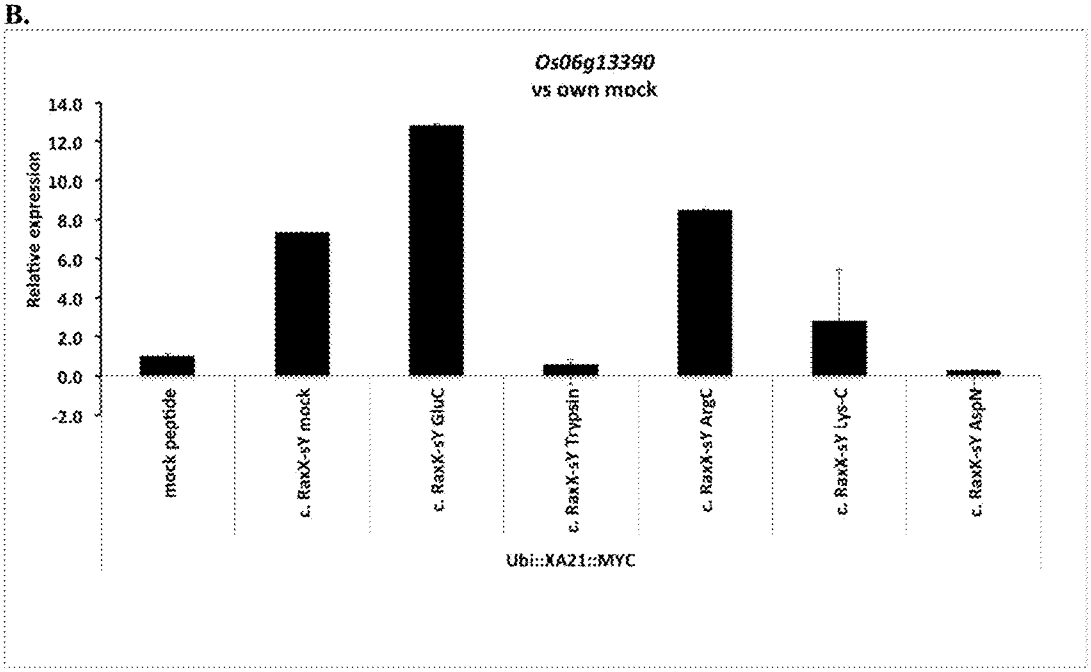

FIGS. 7A-7C: Amino acids 32-55 of Xoo RaxX-Y are sufficient for activating XA21-mediated gene expression. Amino acids 21-60 of RaxX (SEQ ID NO:3) were digested with the indicated proteases as shown in FIG. 7C. Leaves of Kitaake expressing Ubi::XA21::MYC were treated with about 500 nM or 1 uM of the resulting peptides. Os06g13390 marker expression was measured by qPCR. FIG. 7A shows results for 500 nM and FIG. 7B shows results for 1 uM.

FIG. 8 shows the percent identity of amino acid sequences of RaxX proteins for the indicated strains.

FIG. 9 shows the percent identity of nucleic acid sequence encoding RaxX proteins for the indicated strains.

Figure 10A:
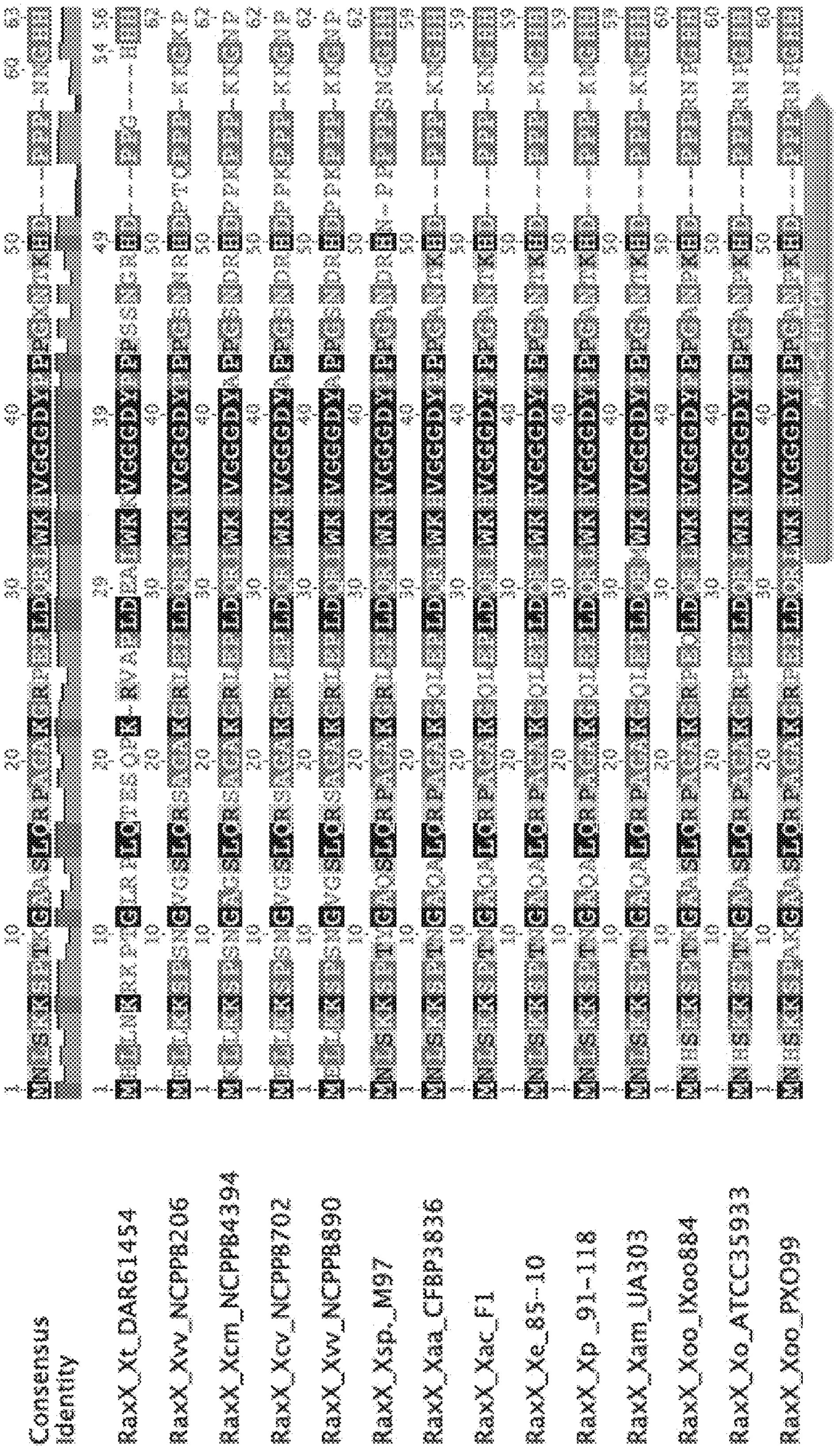
Figure 10B:
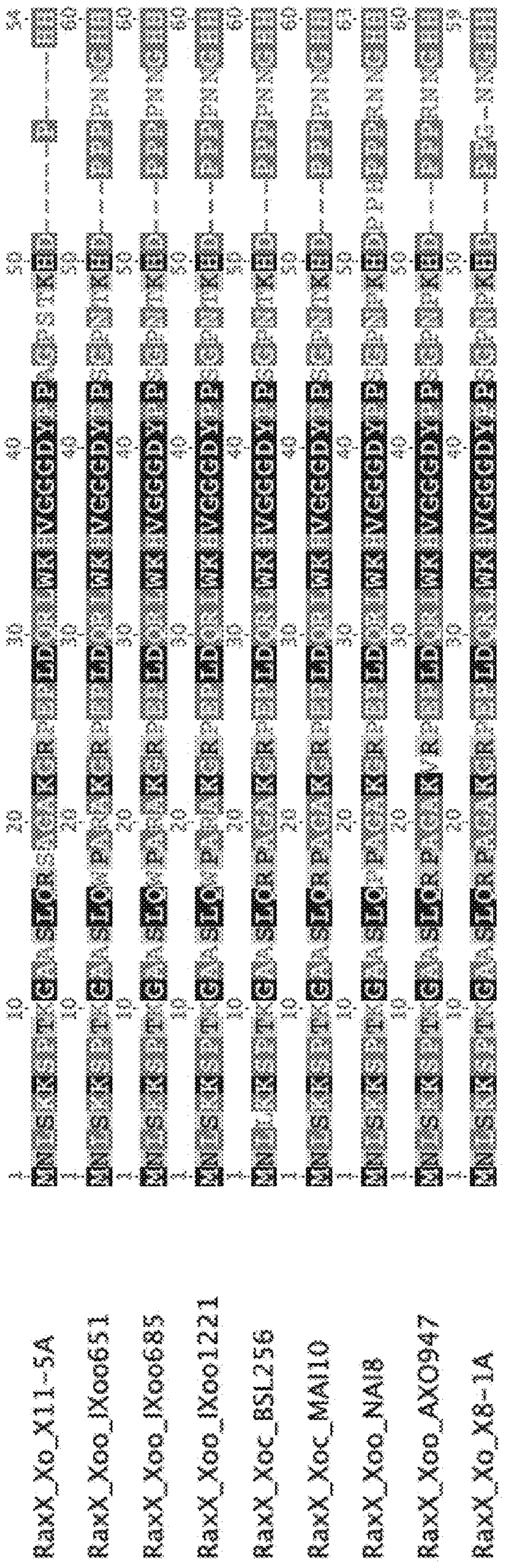

FIGS. 10A and 10B show an alignment of RaxX polypeptide sequences from various Gram negative bacteria. The amino acid sequences are designated SEQ ID NO:22 (consensus sequence) to SEQ ID NO:45, respectively, from top to bottom.

FIGS. 11A to 11D. raxX, a small ORF located upstream of the raxSTAB operon, is required for activation of XA21-mediated immunity. (FIG. 11A). raxST, raxA, and raxB are encoded in a single operon. A 1.0 kb region upstream of raxST and a 1.7 kb region downstream of raxB were deleted in PXO99Δ1.0$^{Sp}$ and PXO99Δ1.7$^{Sp}$, respectively. The raxX ORF is located ~0.4 kb upstream of raxST and in the opposite orientation. (FIG. 11B) TP309 (open bars) or XA21-TP309 (black bars) were inoculated by clipping with scissors dipped in Xoo suspensions. Bars indicate the mean lesion length±standard error (SE) measured 14 days after inoculation (n≥14). The '*' indicates statistically significant difference from PXO99 using Dunnett's test (α=0.01). No statistical differences in lesion length were observed on TP309 inoculated with the different strains. The experiment was repeated at least 3 times with similar results. (FIG. 11C) XA21-TP309 rice leaves display water soaked lesions two weeks after inoculation with the indicated strains. (FIG. 11D) Growth of PXO99 (□), PXO99ΔraxX (Δ), and PXO99ΔraxX(praxX) (○) in rice leaves inoculated as in FIG. 11B. In planta bacterial growth analysis was carried out as described (Bahar O, et al. (2014) *Peer J* 2:e242). Bacterial quantification was determined as the number of colony forming units (CFU) extracted per inoculated leaf. For the final data point, '*' indicates statistically significant difference from PXO99 using Dunnett's test (α=0.01, n=4). The experiment was repeated twice with similar results.

FIGS. 12A-12D. RaxST sulfates RaxX on tyrosine 41. (FIG. 12A) The predicted PAPS binding residue R35 of RaxST and Y41 of RaxX are required for activation of XA21-mediated immunity. TP309 (open bars) and XA21-TP309 (black bars) were inoculated with the indicated Xoo strains, and lesion lengths were measured 14 days later as described in FIG. 11B. Bars indicate the mean lesion length±SE (n>14). The '*' indicates statistically significant difference from PX099 using Dunnett's test (α=0.01). (FIG. 12B) UV photodissociation (UVPD) mass spectrum of a tyrosine sulfated peptide (HVGGGDsYPPPGANPK (SEQ ID NO:4)), 2-, m/z 770) from trypsin digestion of in vitro sulfated Rax39. After incubation with *E. coli*-expressed and purified His-RaxST, RaxX39 was digested with trypsin and analyzed by LC-UVPD-MS/MS in the negative nanoelectrospray mode to generate a, c, x, y, and z product ions, which are defined in the fragmentation key in the upper left corner of the spectrum. $SO_3$ is retained on all product ions allowing the sulfate modification to be localized to Y41. Neutral losses of $SO_3$ from the precursor ion and charge reduced radical precursor ion are denoted as $(M\text{-}2H\text{-}SO_3)^{2-}$ and $(M\text{-}2H\text{-}SO_3)^{1+\cdot}$, respectively in the spectrum. The ion labeled "m7" refers to the neutral loss of the sulfo-tyrosine side chain without additional fragmentation of the peptide backbone. Examination of extracted ion chromatograms of the sulfated and non-sulfated peptides suggest that the sulfated peptide is 100× lower in abundance than the non-sulfated peptide. (see FIG. 23). (FIGS. 12C-D) RaxX-His proteins purified from PX099(praxX-His) and PXO99ΔraxST(praxX-His) were analyzed by selected reaction monitoring-mass spectrometry (SRM-MS) (see FIG. 22). Total peak areas (arbitrary units) were quantitated for sulfated (SEQ ID NO:4) (FIG. 12C) and nonsulfated (SEQ ID NO:4) (FIG. 12D) tryptic RaxX peptides covering Y41.

FIGS. 13A-13D. Sulfated RaxX triggers XA21-mediated defense responses. (FIG. 13A) The 60 amino acid RaxX sequence is shown (SEQ ID NO:36). RaxX derivative peptides of varying lengths were tested for their ability to activate XA21-dependent signaling. Sulfated peptides (RaxX_60, RaxX_39, RaxX_24 and RaxX_21) trigger XA21-mediated defense responses, whereas nonsulfated peptides (RaxX_18) do not. "EC50 value on Ubi-XA21" refers to the EC50 values determined by monitoring total ROS production over 3 hours following application of the RaxX protein and peptide derivatives (see FIGS. 34A-34E) at different concentrations on Kitaake rice expressing XA21 under the control of the ubiquitin promoter (Ubi::XA21) (n=6). (FIG. 13B) ROS production in leaves of Kitaake and Ubi::XA21 rice plants treated with $H_2O$ (mock), RaxX21-Y or RaxX21-sY (250 nM) (n=3). RLU stands for relative light units. (FIG. 13C) Ethylene production in leaves of Kitaake and Ubi::XA21 rice plants after 4 hours of treatment with $H_2O$ (mock), RaxX21-Y or RaxX21-sY (1 μM). The '*' indicates statistically significant difference from mock treatment using Dunnett's test (α=0.01, n=3). (FIG. 13D) Temporal changes in defense marker gene (Os04g10100, PR10b, and Os12g36830) expression in leaves of Kitaake and Ubi::XA21 rice plants treated with $H_2O$ (mock), RaxX21-Y or RaxX21-sY (500 nM, n=3). All data points depict means±SE. These experiments were repeated at least 3 times with similar results.

FIGS. 14A-14E. Comparative genomics and mutational analyses identify key amino acids required for RaxX activity. (FIG. 14A) Alignment of amino acid sequences of RaxX from PX099 (SEQ ID NO:36) and IXO685 (SEQ ID NO:39). The region corresponding to RaxX21 is boxed. (FIGS. 14B-C) RaxX from the field strain IXO685 does not trigger XA21-mediated immune response. (FIG. 14B) TP309 (open bars) and XA21-TP309 (black bars) were inoculated with the indicated Xoo strains, and lesion lengths were measured 14 days later as described in FIG. 1B. Bars indicate the mean lesion length±SE (n>14). (FIG. 14C) ROS production in leaves of Kitaake (open bars) and Ubi::XA21 (black bars) rice plants treated with the indicated peptides (250 nM) or mock treatment. Bars depict mean relative light production (RLU) over 3 h±SE (n=6). (FIGS. 14D-E) RaxX point mutation analysis reveals that P44 and P48 are required for activation of XA21-mediated immune response. (FIG. 14D) TP309 (open bars) and XA21-TP309 (black bars) were inoculated with the indicated Xoo strains, and lesions were measured 14 days later as described in FIG. 11B. Bars indicate the mean lesion length±SE (n>14). (FIG. 14E) ROS production in leaves of Kitaake (open bars) and Ubi::XA21 (black bars) rice plants treated with the indicated peptides (250 nM) or mock treatment. Bars depict average relative light production±SE (n=6). For FIGS. 14B-D, the '*' indicates statistically significant difference from mock treatments using Dunnett's test (α=0.01). These experiments were repeated at least 3 times with similar results.

Figure 15A:
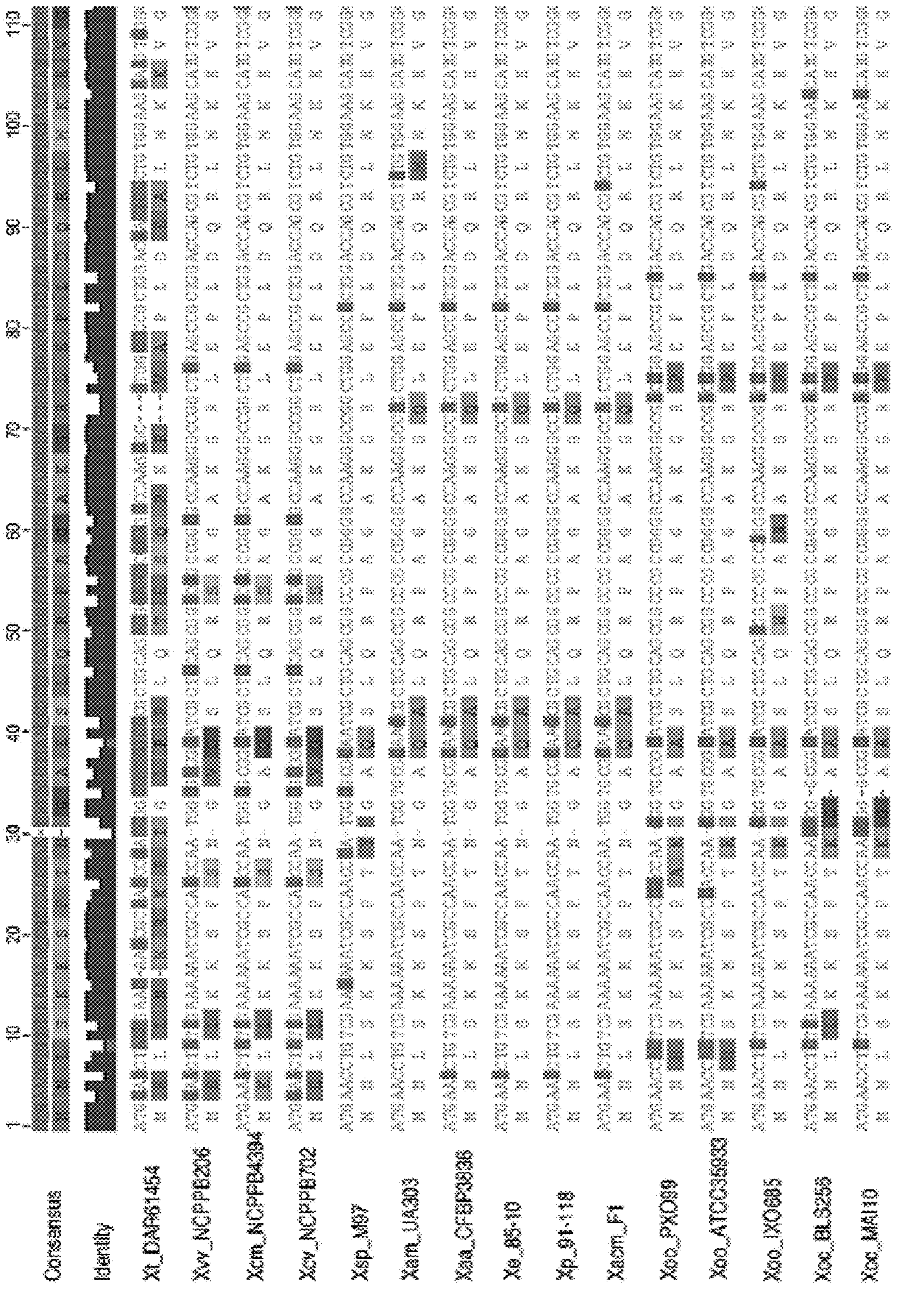
Figure 15B:
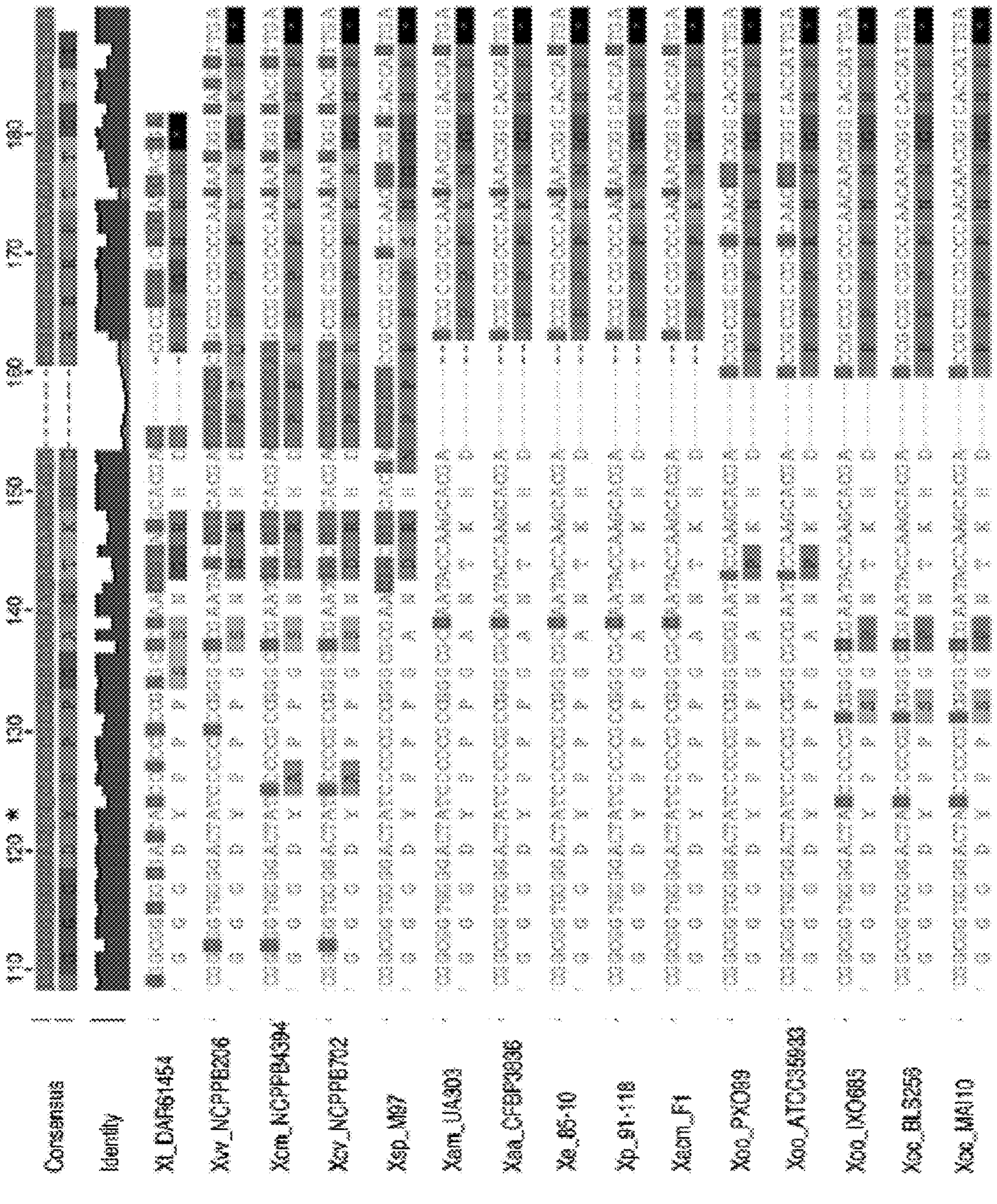

FIGS. 15A and 15B. Sequence alignment of 15 raxX alleles. raxX sequences (consensus nucleotide sequence=SEQ ID NO:49, consenus amino acid sequence=SEQ ID NO:50) were identified and aligned for the following *Xanthomonas* strains: *X. translucens DAR*61454 (nucleotide=SEQ ID NO:51, amino acid=SEQ ID NO:23), *X. vesicatoria* pv. *vasculorum* NCPPB206 (nucleotide=SEQ ID NO:21, amino acid=SEQ ID NO:24), *X. campestris* pv. *musacearum* NCPPB4394

(nucleotide=SEQ ID NO:7, amino acid=SEQ ID NO:25), *X. campestris* pv. *vasculorum* NCPPB792 (nucleotide=SEQ ID NO:8, amino acid=SEQ ID NO:26), X sp. M97 (nucleotide=SEQ ID NO:20, amino acid=SEQ ID NO:28), *X. axonopodis* pv. *manihotis* UA303 (nucleotide=SEQ ID NO:6, amino acid=SEQ ID NO:33), *X. axonopodis* pv. *alfalfae* CFBP3836 (nucleotide=SEQ ID NO:52, amino acid=SEQ ID NO:29), *X. euvesicatoria* 85-10 (nucleotide=SEQ ID NO:9, amino acid=SEQ ID NO:31), *X. perforans* 91-118 (nucleotide=SEQ ID NO:53, amino acid=SEQ ID NO:32), *X. axonopodis* pv. *citrumelo* F1 (nucleotide=SEQ ID NO:5, amino acid=SEQ ID NO:30), *X. oryzae* pv. *oryzae* PXO99 (nucleotide=SEQ ID NO:19, amino acid=SEQ ID NO:36), *X. oryzae* pv. *oryzae* ATCC35933 (nucleotide=SEQ ID NO:10, amino acid=SEQ ID NO:35), *X. oryzae* pv. *oryzae* IXO685 (nucleotide=SEQ ID NO:16, amino acid=SEQ ID NO:39), *X. oryzae* pv. *oryzicola* BLS256 (nucleotide=SEQ ID NO:13, amino acid=SEQ ID NO:41), and *X. oryzae* pv. *oryzicola* MAI10 (nucleotide=SEQ ID NO:14, amino acid=SEQ ID NO:42). The alignment was created using Geneious software (Kearse M, et al. (2012) *Bioinformatics* 28(12):1647-1649). The raxX sequence from IXO685 was determined by Sanger sequencing. All other sequences were downloaded from NCBI, which was last accessed Dec. 14, 2014.

Figure 16:
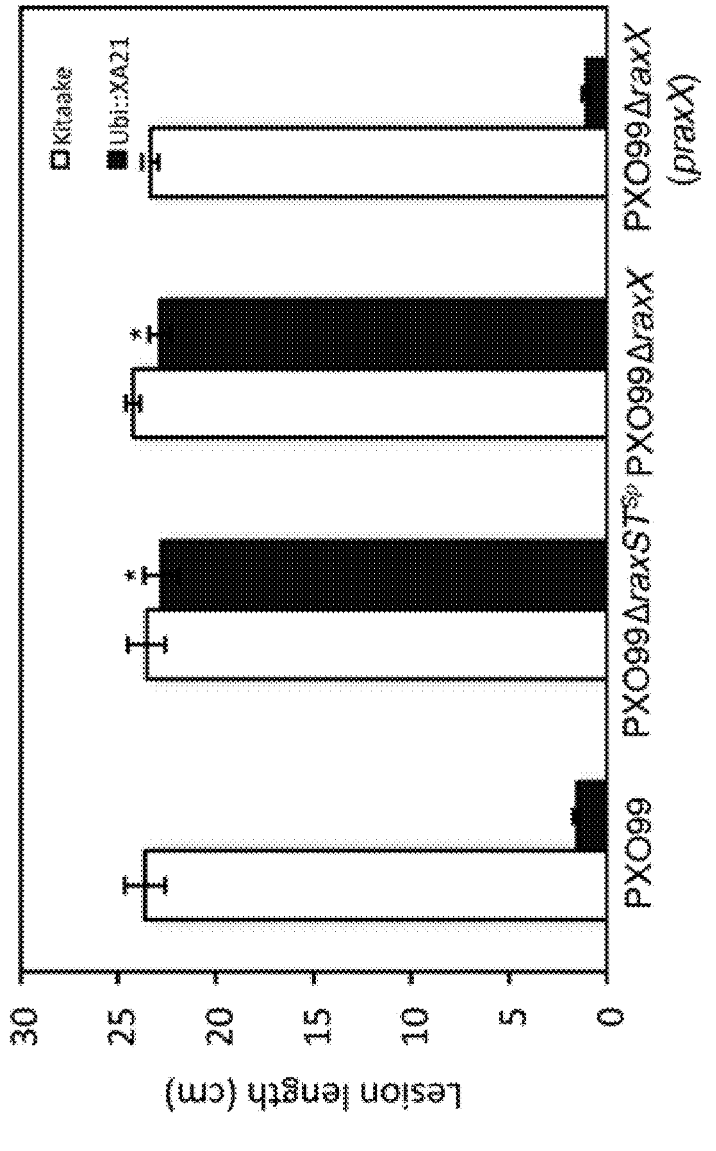

FIG. 16. raxX is required for activation of XA21-mediated immunity in the Ubi::XA21 Kitaake (Ubi::XA21) genetic background. Kitaake (open bars) or Ubi::XA21 (black bars) were inoculated by clipping with scissors dipped in Xoo suspensions ($10^8$ CFU/mL). Bars indicate the mean lesion length±SE 14 days after inoculation (n≥4). The '*' indicates statistically significant difference from PXO99 using Dunnett's test (α=0.01). There were no statistical differences in lesion length on Kitaake inoculated with the four strains.

Figure 17:
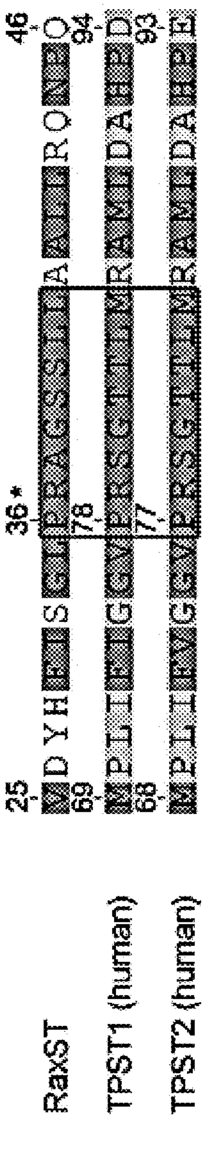

FIG. 17. Alignment of the PAPS binding motif of RaxST from PXO99 (SEQ ID NO:54), TPST1 from human (SEQ ID NO:55), and TPST2 from human (SEQ ID NO:56). The conserved PAPS binding motif is boxed, and the conserved arginine in the PAPS biding motif is noted with an asterisk.

Figure 18A:
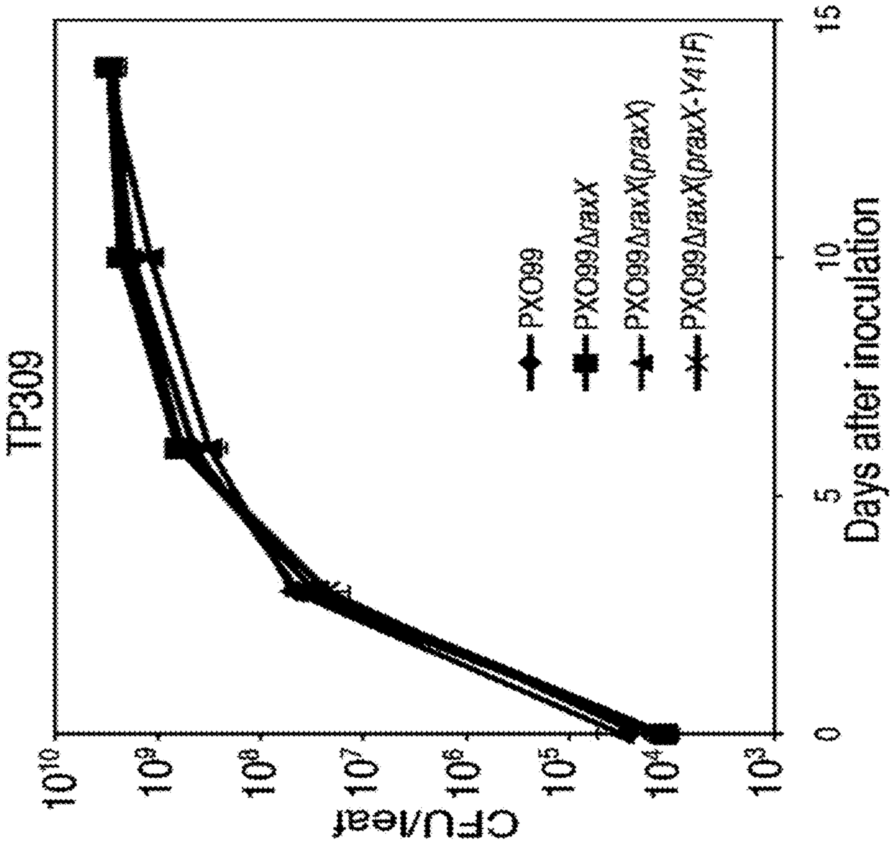
Figure 18B:
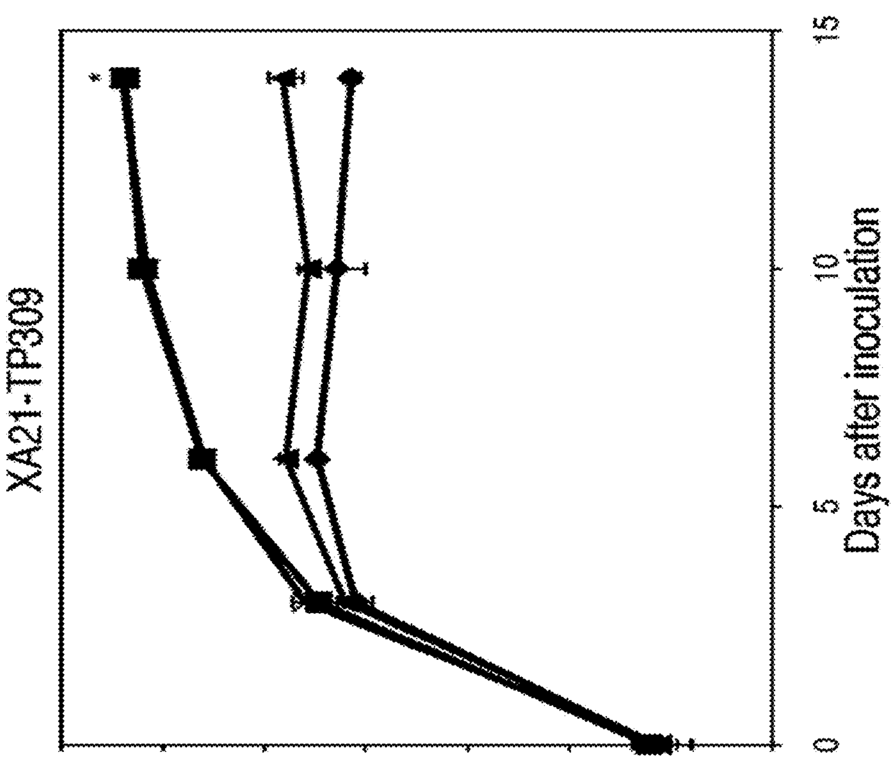

FIGS. 18A to 18B. RaxX Y41 is required for activation of XA21-mediated immunity. In planta bacterial growth analysis was carried out as described (Bahar O, et al. (2014) *Peer J* 2:e242). Bacteria were extracted from leaves 0, 3, 6, 10, and 14 days after inoculation and plated on selective media. Colonies were counted after 2 days incubation at 28° C. Data points indicate the mean±SE (n=4). For the final time point, the '*' indicates a statistically significant difference from PXO99 using Dunnett's test (α=0.01). This experiment was performed twice with similar results.

Figure 19:
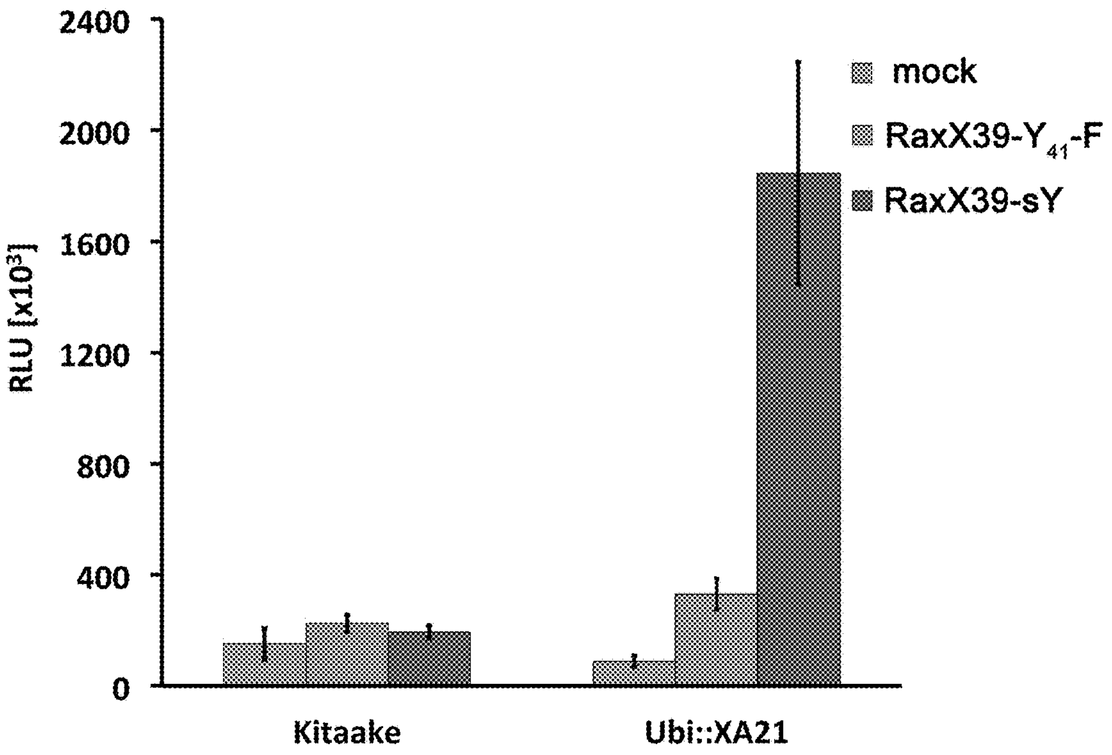

FIG. 19. RaxX Y41F does not trigger the XA21-mediated immune response. Total ROS production over 3 h in response to chemically synthesized sulfated RaxX peptide variants. Leaf strips of Kitaake and Ubi::XA21 were treated with the indicated peptide (250 nM) for 3 h. Bars depict mean relative light production (RLU)±SE (n=6). This experiment was repeated four times with similar results.

Figure 20:
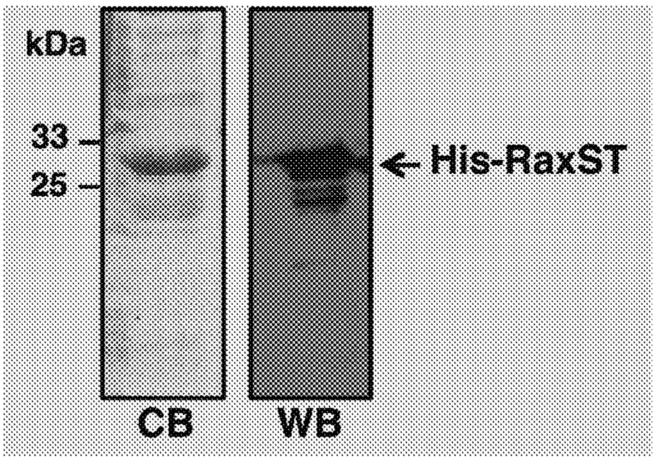

FIG. 20. Purification of the full-length RaxST protein carrying an N-terminal His-tag. RaxST was expressed with an N-terminal His-tag (His-RaxST) in *E. coli* BL21(DE3) and purified using Ni-NTA agarose beads. The purified His-RaxST was resolved by SDS-PAGE for both Coomassie-blue staining (CB) and western blot analysis with an anti-His antibody (WB). The purified His-RaxST was detected at the predicted size of 32 kDa.

Figure 21:
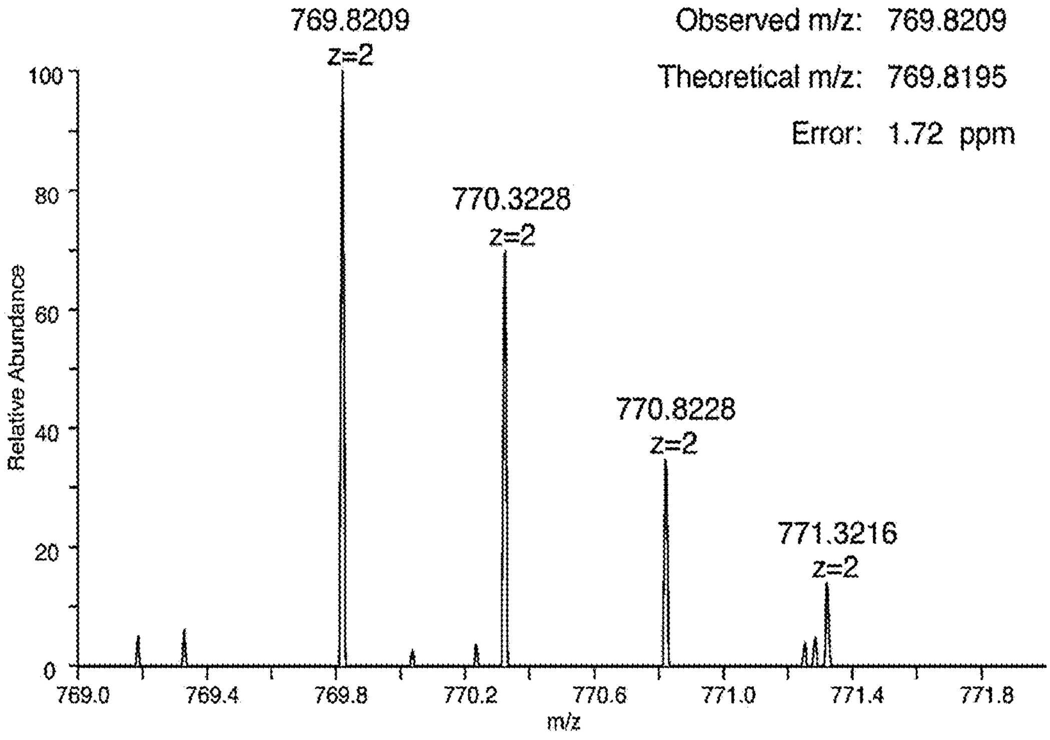

FIG. 21. Expanded MS1 spectrum of HVGGGDsYPPPGANPK (SEQ ID NO:4) from trypsin digestion of in vitro sulfated RaxX39. Negative mode MS1 spectrum expanded between m/z 769 and 772 showing an accurate mass measurement for doubly deprotonated HVGGGDsYPPPGANPK (2-) (SEQ ID NO:4) acquired using an Orbitrap Elite mass spectrometer operated at an FT resolution of 120,000 at m/z 400.

Figure 12A:
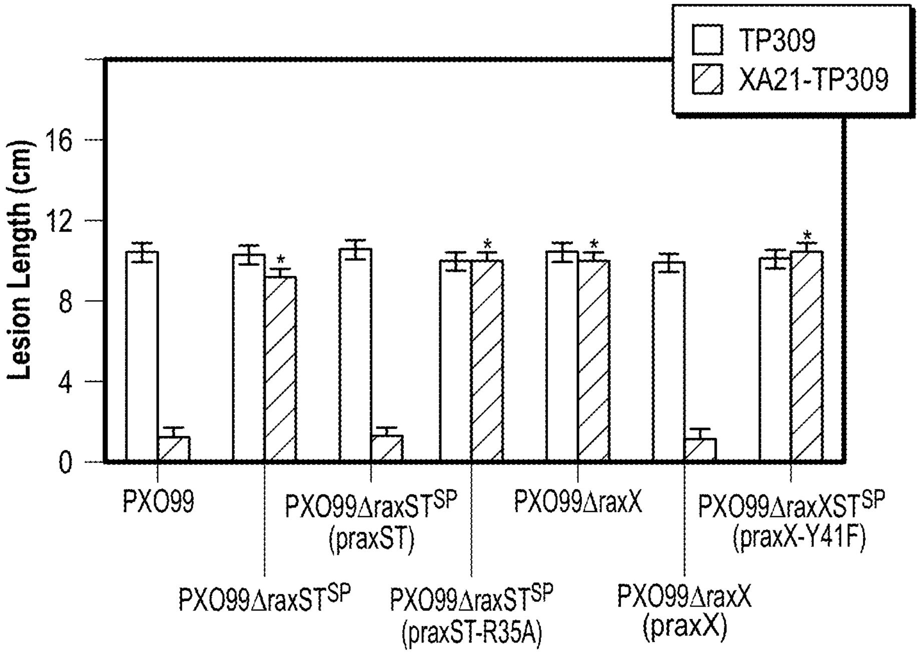
Figure 12B:
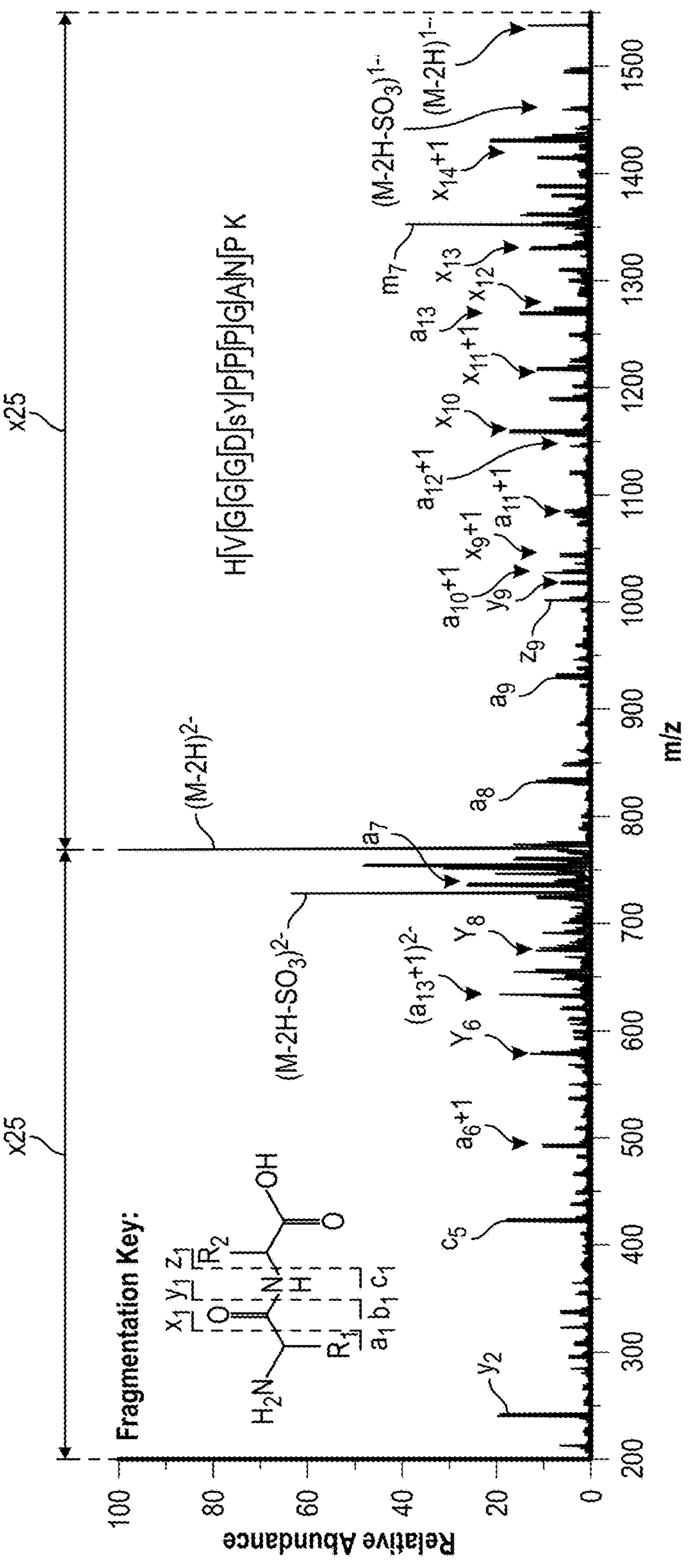
Figure 22:
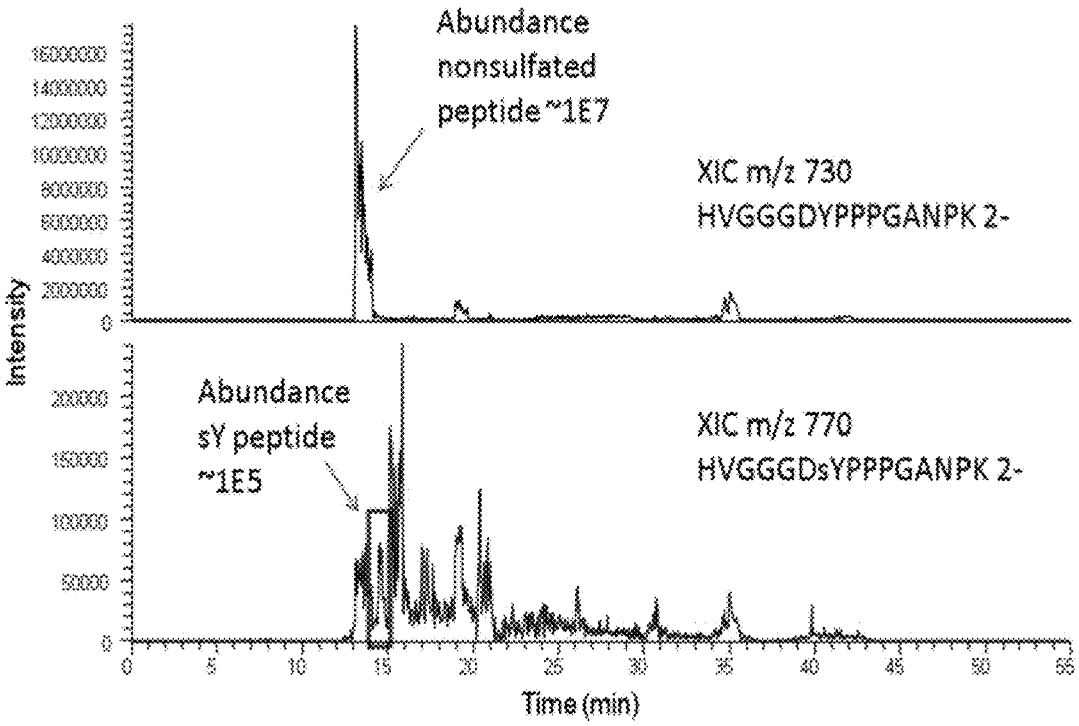

FIG. 22. Extracted ion chromatograms (XIC) showing the difference in ion abundances for the sulfated (SEQ ID NO:4) and nonsulfated peptide HVGGGDYPPPGANPK (2—charge state; SEQ ID NO:4) After incubation with *E. coli*-expressed and purified His-RaxST, RaxX39 was digested with trypsin and analyzed by LC-UVPD-MS/MS (FIG. 12B). XICs of the sulfated (lower panel) and nonsulfated (upper panel) peptides suggest that the sulfated peptide is 100× lower in abundance than the non-sulfated peptide. Nonsulfated peptide and sulfated peptide are marked by arrows.

Figure 23:
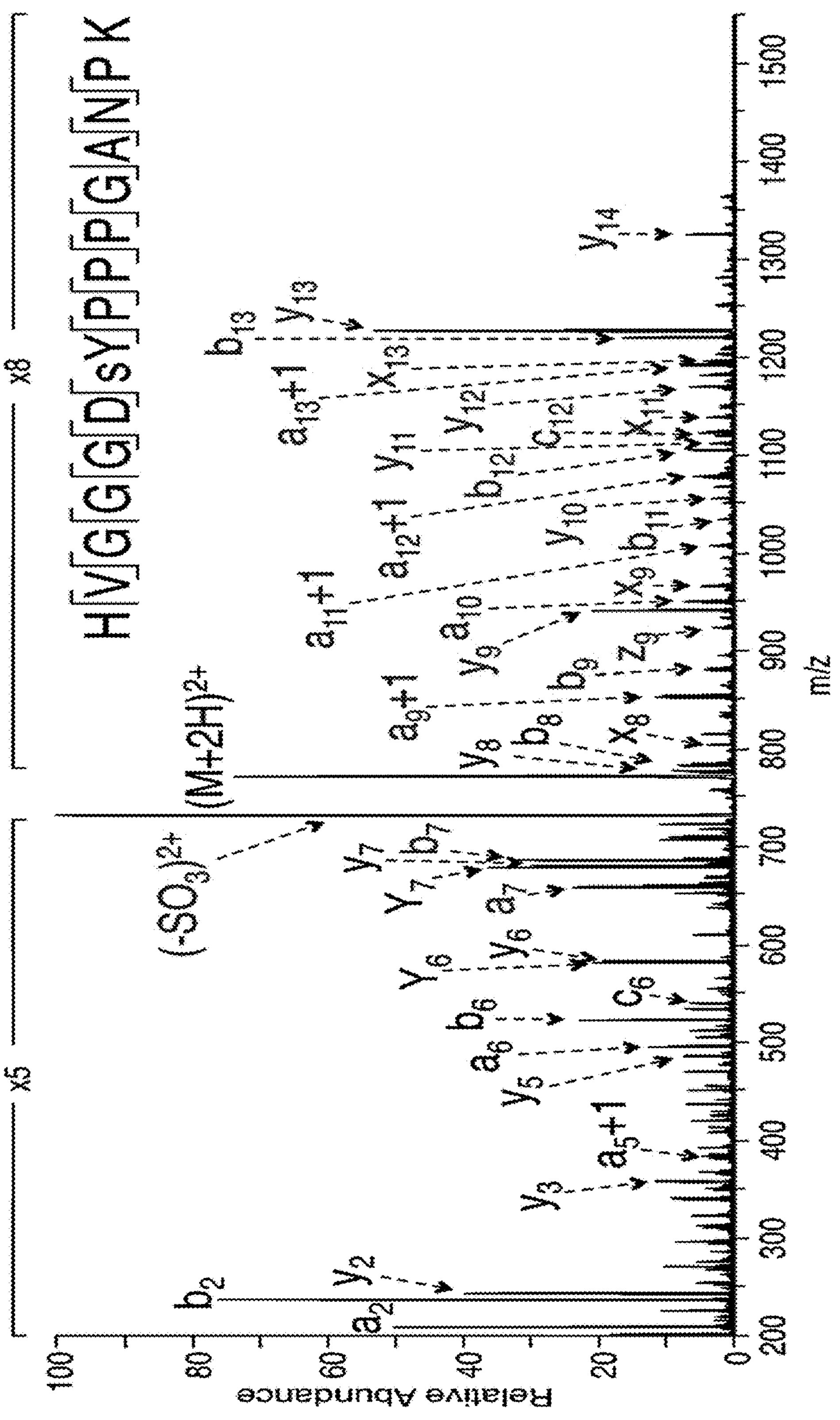

FIG. 23. Positive UVPD mass spectrum of HVGGGDsYPPPGANPK (SEQ ID NO:4) from trypsin digestion of in vitro sulfated RaxX39. 30 MS/MS scans were averaged during peptide elution between 14.23-14.53 min. Two pulses at 2 mJ was used for fragmentation. Neutral loss of $SO_3$ from the precursor ion is denoted as $(—SO_3)^{2+}$. All product ions containing the tyrosine residue undergo the neutral loss of $SO_3$; these ions are denoted in red font.

FIG. 24. RaxX-His proteins were purified from PXO99 (praxX-His) and PXO99ΔraxST(praxX-His).PXO99 (praxX-His) and PXO99ΔraxST(praxX-His) were grown in XVM2 media for 40 h at 28° C. RaxX-His proteins were purified from Xoo cell lysates. The purified RaxX-His proteins were resolved by SDS-PAGE and subjected to western blot analysis with an anti-His antibody.

FIGS. 25A-25D. Expression and sulfation of RaxX60-Y and RaxX60-sY. (FIG. 25A) Purity assessment of 1 μg of RaxX60-Y and RaxX60-sY by coomassie colloidal blue stain (SimplyBlue SafeStain). RaxX60-Y and RaxX60-sY proteins purified from *E. coli* were analyzed by selected reaction monitoring-mass spectrometry (SRM-MS). Total peak areas (arbitrary units) were quantitated for an unmodified internal control peptide [K.GRPEPLDQR.L] (SEQ ID NO:232), GRPEPLDQR (SEQ ID NO:57) (FIG. 25B) as well as nonsulfated (FIG. 25C) (SEQ ID NO:4) and sulfated (FIG. 25D) (SEQ ID NO:4) tryptic RaxX peptides [K.HVGGGDYPPPGANPK.H] (SEQ ID NO:233) covering Y41 (SEQ ID NO:4).

Figures 26A, 26B:
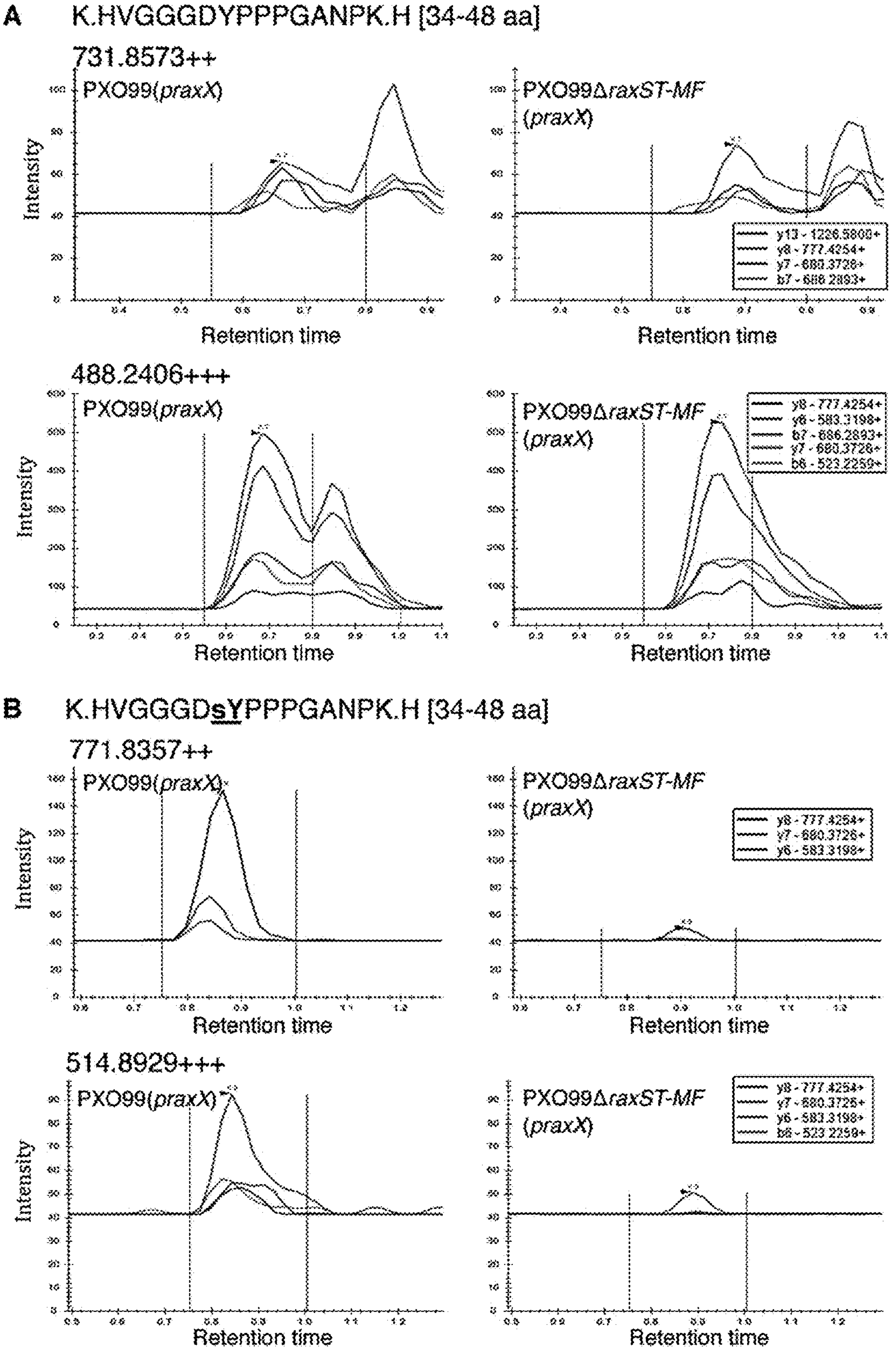

FIGS. 26A and 26B. SRM-MS analysis of the tryptic RaxX peptide HVGGGDYPPPGANPK (SEQ ID NO:4) from PX099(praxX-His) and PX099ΔraxST(praxX-His). RaxX-His was isolated from PX099(praxX-His) and PXO99ΔraxST(praxX-His), digested with trypsin and analyzed by SRM-MS as described in the materials and methods. (FIG. 26A (SEQ ID NO:233)) LC-SRM-MS chromatograms of the doubly and triply charged nonsulfated peptide HVGGGDYPPPGANPK (SEQ ID NO:4). (FIG. 26B (SEQ ID NO:233)) LC-SRM-MS chromatograms of the doubly and triply charged sulfated peptide HVGGGDsYPPPGANPK(SEQ ID NO:4). The lines correspond to individual SRM transitions that were monitored for each peptide. The peptide y-series fragment ion detected is indicated in the legend of each panel. This experiment was repeated twice with similar results.

Figures 27A, 27B:
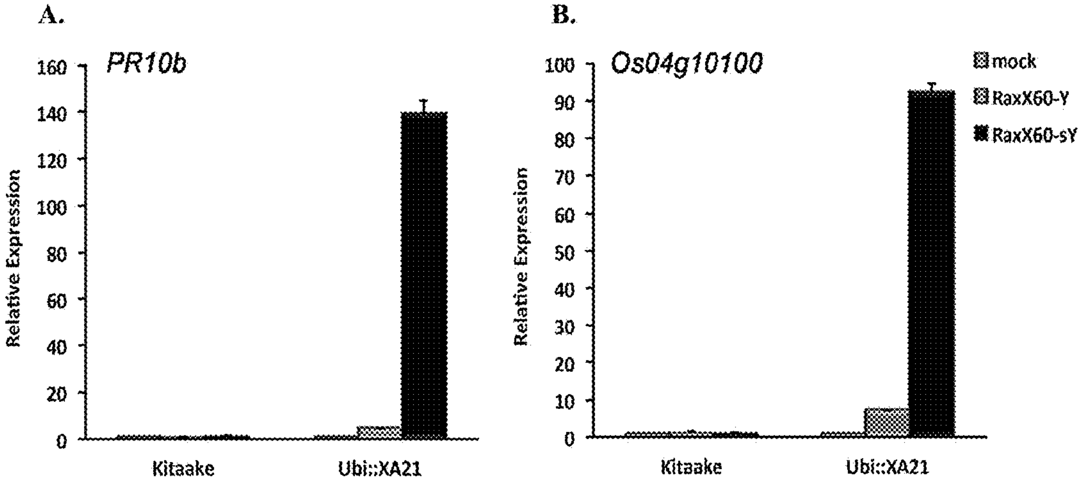

FIGS. 27A and 27B. Heterologously expressed, full length RaxX60-sY activates XA21-mediated defense gene expression. Defense gene (PR10b and Os04g10100) expression changes in leaves of Kitaake (FIG. 27A) and Ubi::XA21 (FIG. 27B) rice plants treated with $H_2O$ (mock), RaxX60-Y or RaxX60-sY (500 nM) for 24 h. Gene expression levels were measured by qRT-PCR and normalized to actin. Bars depict mean expression level±SD (n=2). This experiment was repeated at least 6 times with similar results.

Figures 28A, 28B:
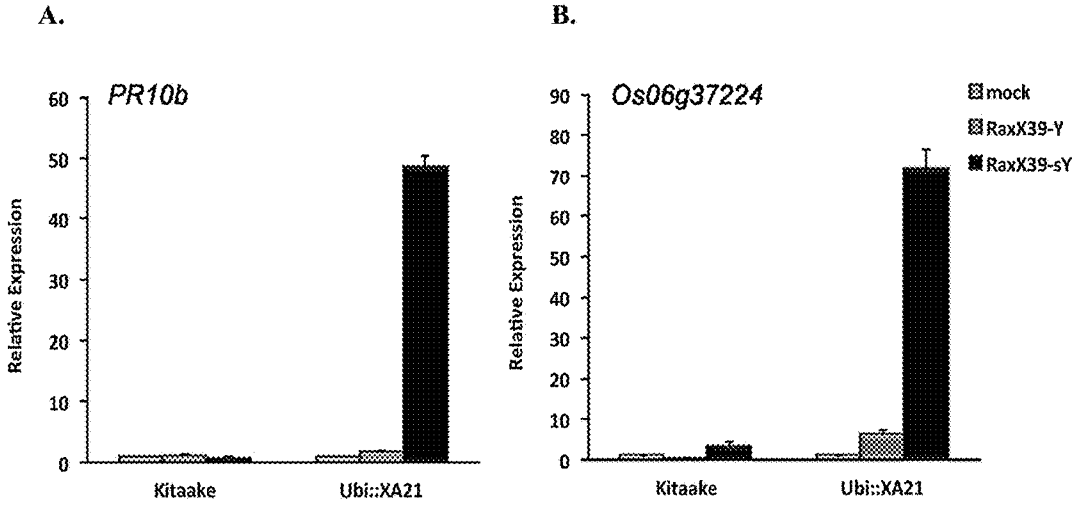
Figures 29A, 29B:
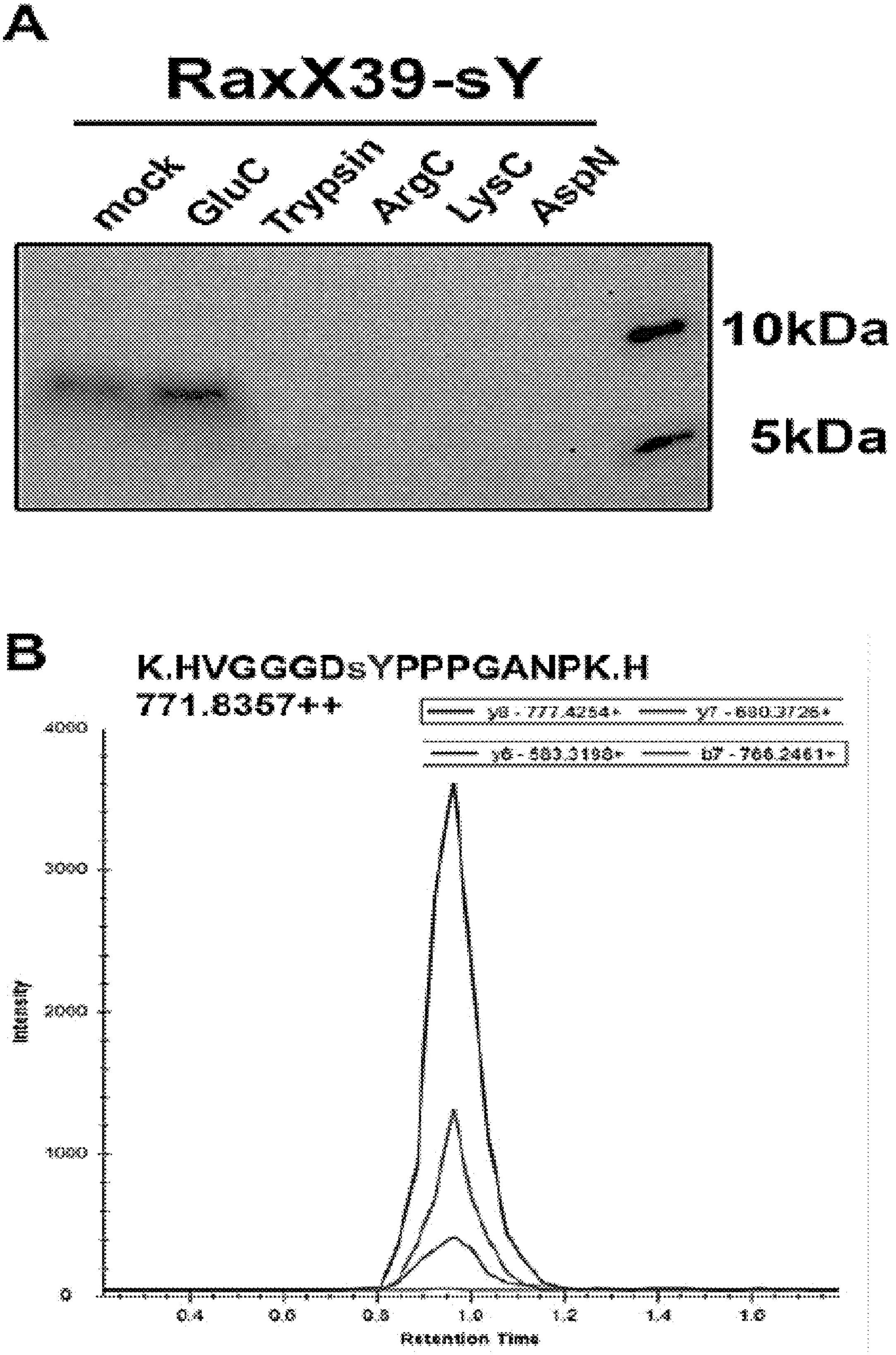
Figure 29C:
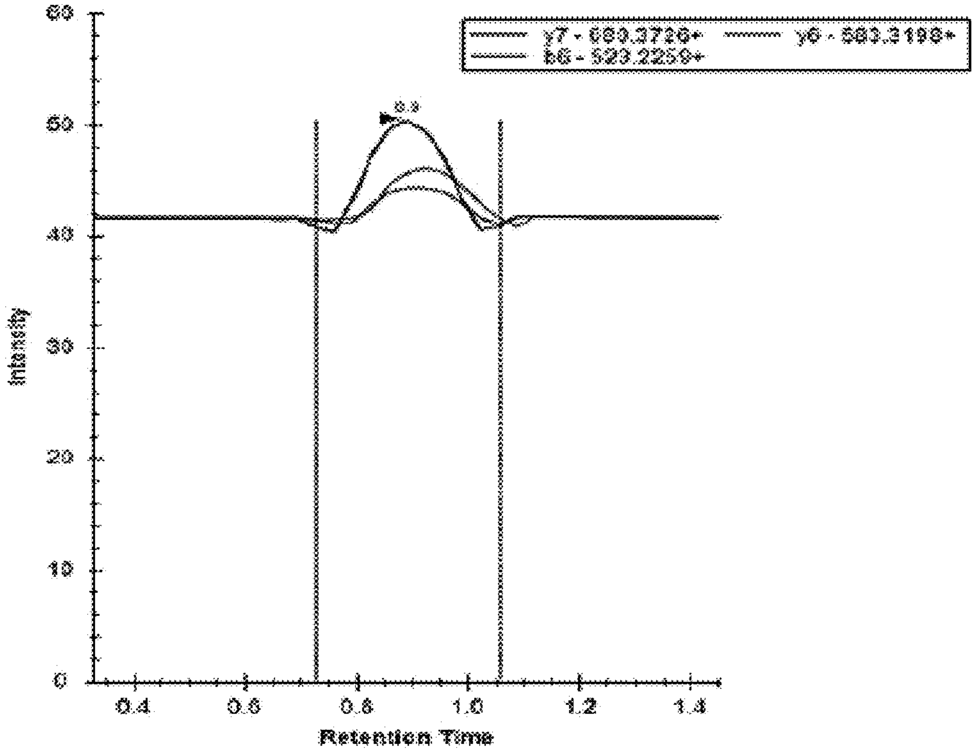
Figure 29D:
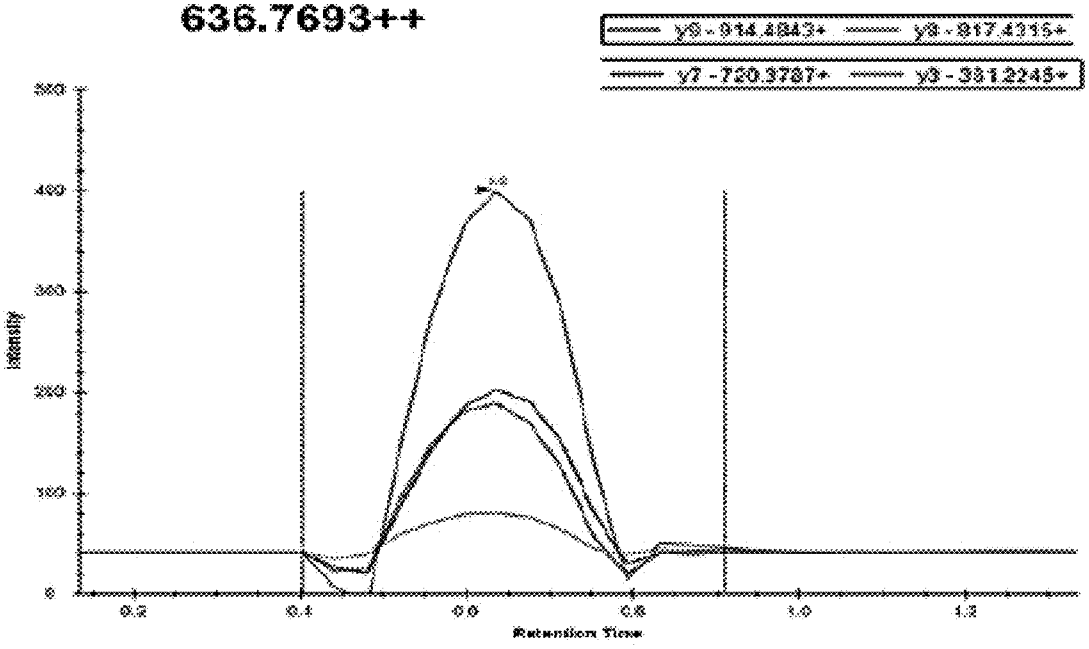

FIGS. 28A and 28B. Chemically synthesized RaxX39-sY activates XA21-mediated defense gene expression. Defense gene (PR10b (FIG. 28A) and Os06g37224 (FIG. 28B)) expression changes in leaves of Kitaake and Ubi::XA21 rice plants treated with $H_2O$ (mock), RaxX39-Y or RaxX39-sY (500 nM) for 24 h. Expression levels were measured by qRT-PCR and normalized to actin reference gene expression. Bars depict mean expression level±SD (n=2). This experiment was repeated at least 9 times with similar results.

FIGS. 29A-29D. Digestion of RaxX39-sY by the four site-specific proteases GluC, trypsin, ArgC and ApsN. (FIG. 29A) Tris-tricine gel of digestion products (4 μg) of RaxX39-sY treated with the indicated protease and stained with coommassie colloidal blue stain (SimplyBlue SafeStain). Digestion products of trypsin, ArgC and AspN were not resolved on tris-tricine gels due to small digestion product sizes (<2.6 kDa). Appropriate digestion for these three proteases was confirmed by selected reaction monitoring-mass spectrometry (SRM-MS). (FIGS. 29B-D) shows representative LC-SRM-MS chromatograms of trypsin [K.HVGGGDsYPPPGANPK.H] (SEQ ID NO:233), ArgC [R.LWKHVGGGDsYPPPGANPKHDPPPR.N] (SEQ ID NO:234), and AspN [G.DsYPPPGANPKH.D] (SEQ ID NO:235) RaxX digestion products covering the sulfated Y41 residue. The lines correspond to individual SRM transitions that were monitored for each peptide. The peptide y-series fragment ion detected is indicated in the legend at the top of the plot. This experiment was repeated twice with similar results.

Figures 30A, 30B:
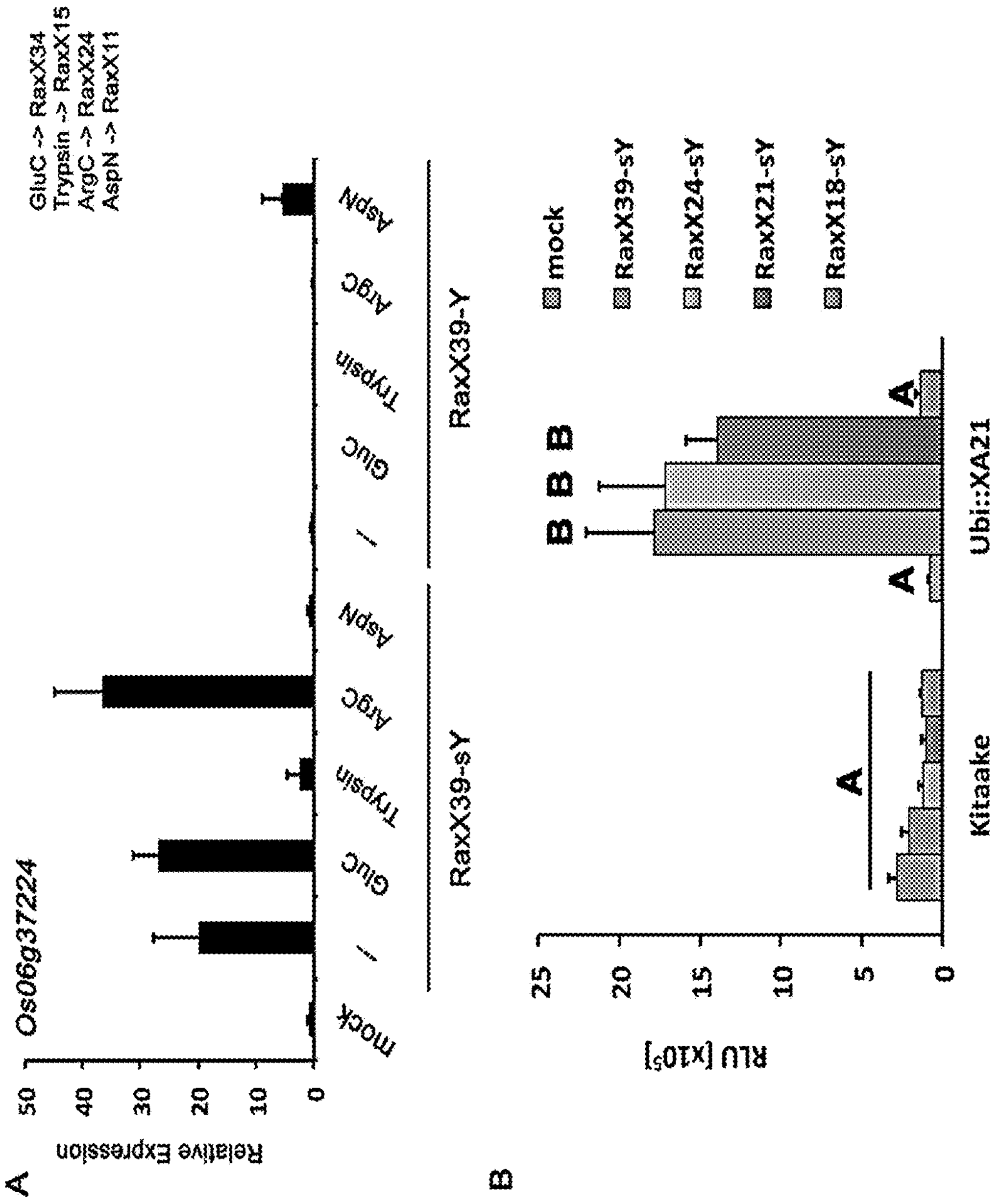

FIGS. 30A-30B. A 21 amino acid sulfated peptide derived from RaxX is sufficient to activate XA21-mediated defense gene expression and the production of reactive oxygen species. (FIG. 30A) Gene (Os06g37224) expression changes in leaves of Ubi::XA21 rice plants treated with protease digestion buffer (mock), RaxX39-sY, RaxX39-Y, or digestion products thereof produced using the indicated site specific proteases. Leaf strips were treated with peptides and their digests (1 μM) for 24 h. Expression levels were measured by qRT-PCR and normalized to actin. Bars depict mean expression level±SD (n=2). This experiment was repeated 3 times with similar results. (FIG. 30B) Total ROS production over 3 h in response to chemically synthesized sulfated RaxX peptide variants. Leaf strips of Kitaake and Ubi::XA21 were treated with the indicated peptide (250 nM) for 3 h. Bars depict mean relative light production (RLU) ±SE (n=6). Different letters indicate statistically significant differences using Tukey HSD test (α=0.01). This experiment was repeated at least twice with similar results.

Figures 31A, 31B:
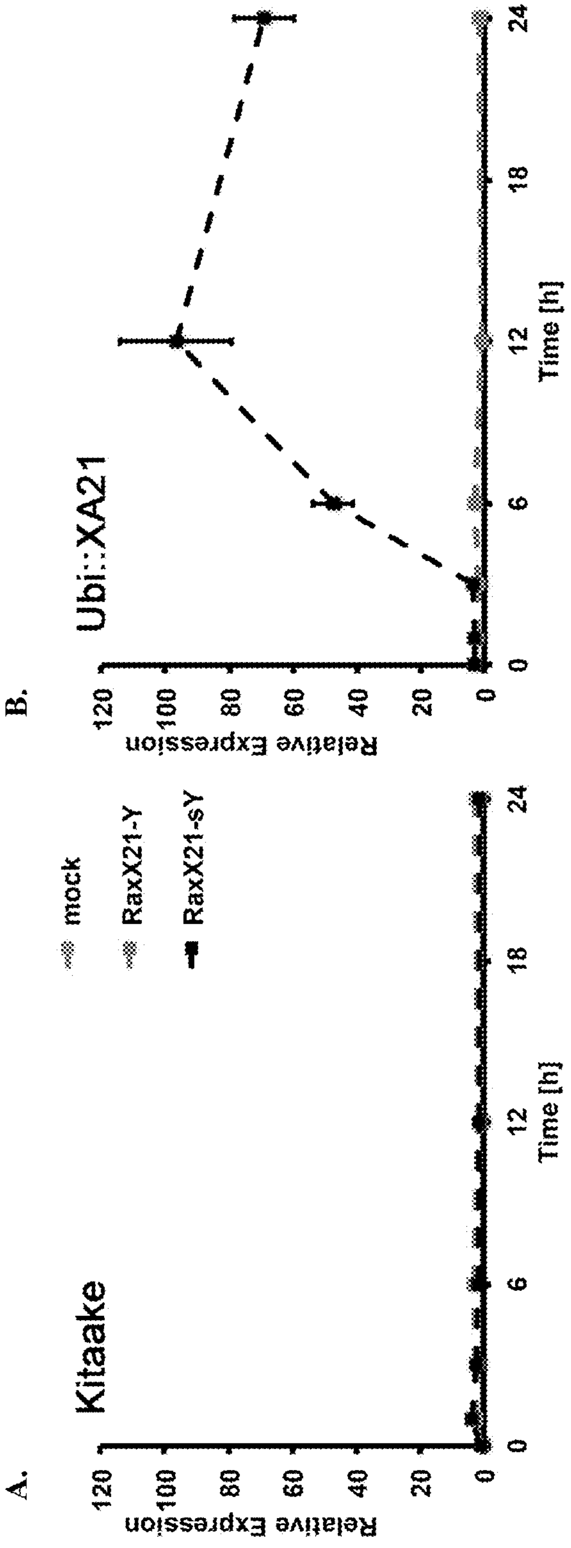

FIGS. 31A-31B. Chemically synthesized RaxX21-sY is sufficient to activate XA21-mediated defense gene expression. Temporal defense gene expression (Os06g37224) changes in leaves of Kitaake (FIG. 31A) and Ubi::XA21 (FIG. 31B) rice plants treated with $H_2O$ (mock), RaxX21-Y or RaxX21-sY (500 nM). Data points depict mean expression level±SE (n=3). This experiment was repeated at least 3 times with similar results.

Figure 32:
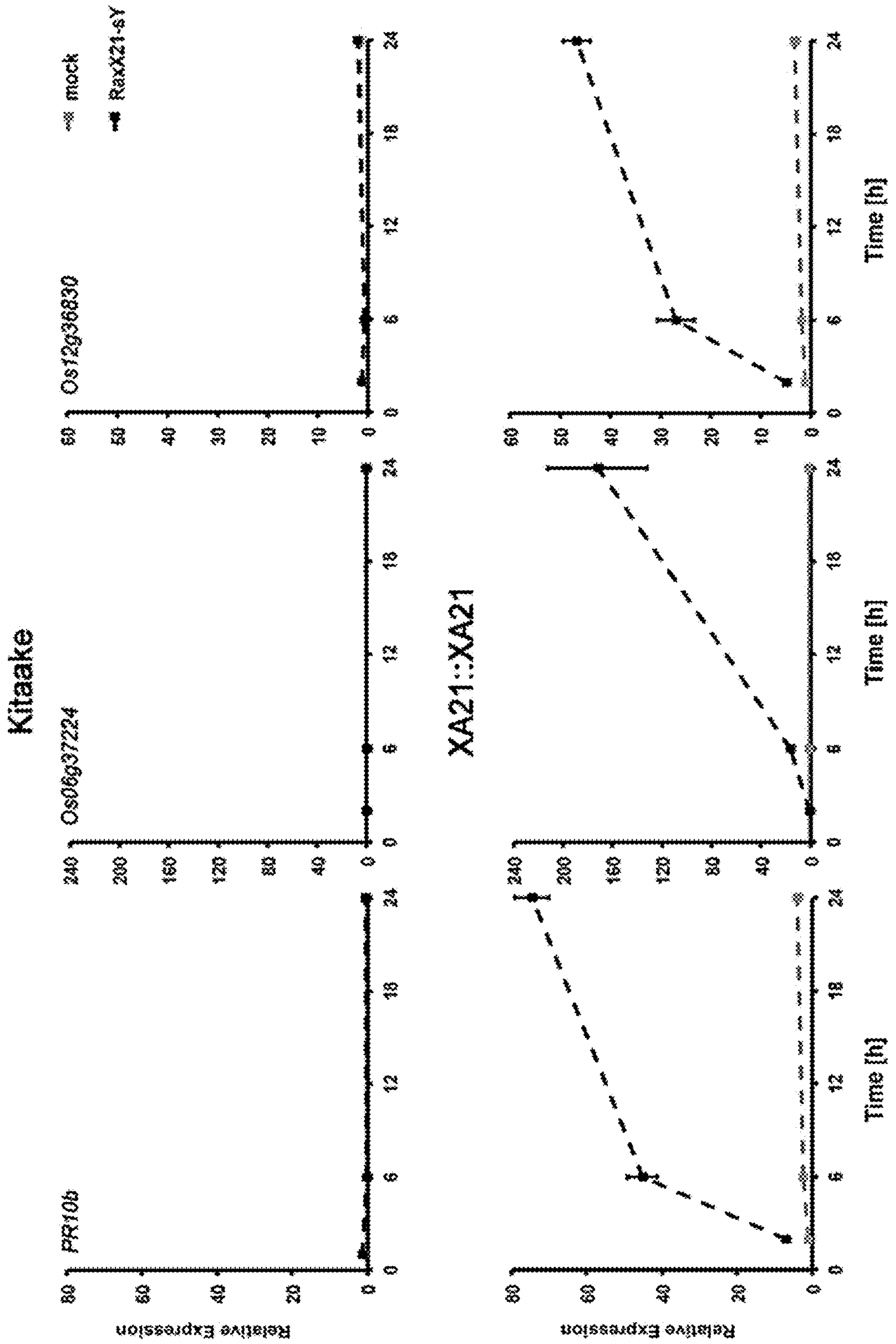

FIG. 32. Chemically synthesized RaxX21-sY activates gene expression in Kitaake lines expressing XA21 from its native promoter (XA21:XA21). Temporal gene expression changes in leaves of five week old XA21::XA21 rice plants treated with $H_2O$ (mock) or RaxX21-sY (500 nM). Data points depict mean expression level±SD (n=2). This experiment was repeated at least 3 times with similar results.

Figures 33A, 33B:
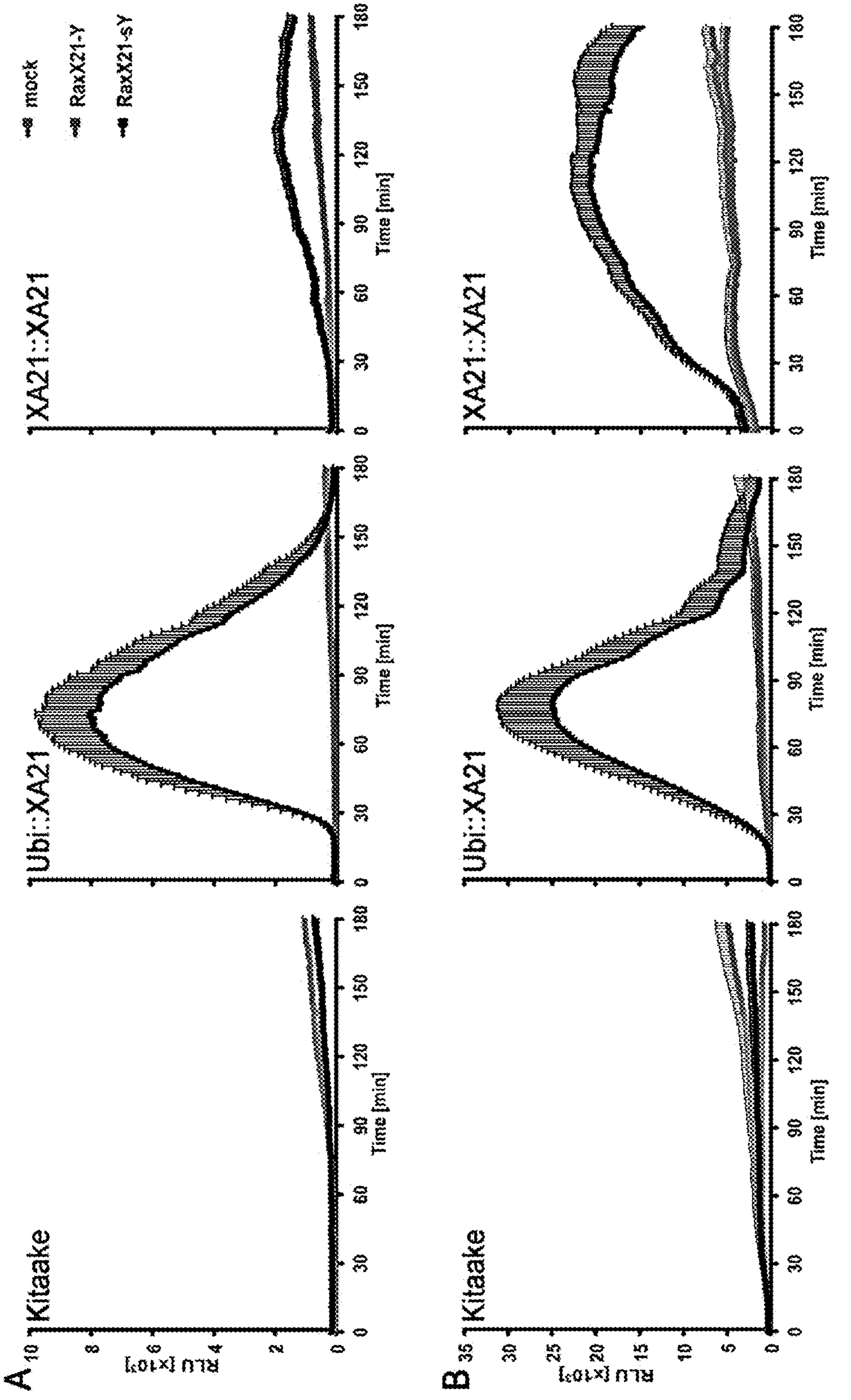

FIGS. 33A and 33B. Chemically synthesized RaxX21-sY activates the production of ROS in Kitaake lines expressing XA21 from its native promoter (XA21:XA21). ROS production in five-week (FIG. 33A) and six-week (FIG. 33B) old leaves of Kitaake, Ubi::XA21 and XA21::XA21 rice plants treated with $H_2O$ (mock), RaxX21-Y or RaxX21-sY (250 nM). Data points depict mean ROS production±SE (n=6). This experiment was repeated 3 times with similar results.

Figure 34A:
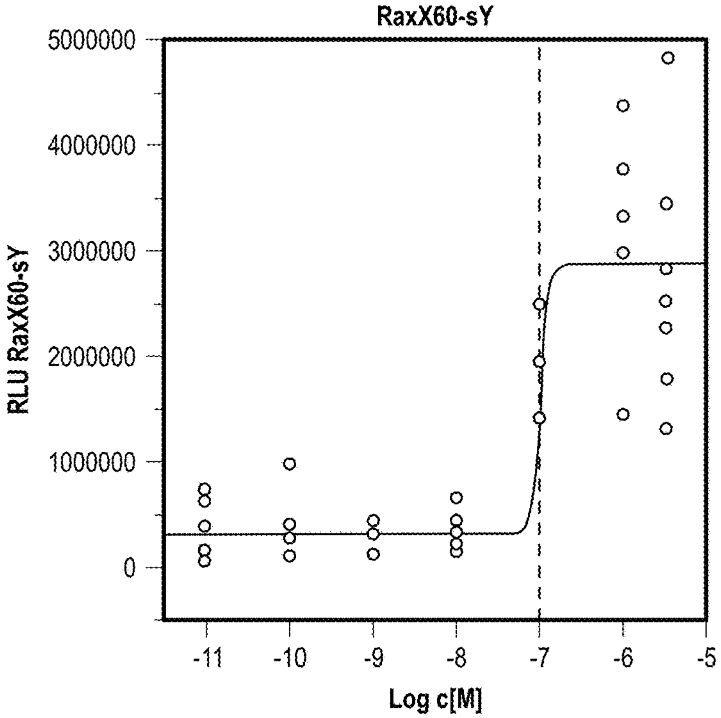
Figure 34B:
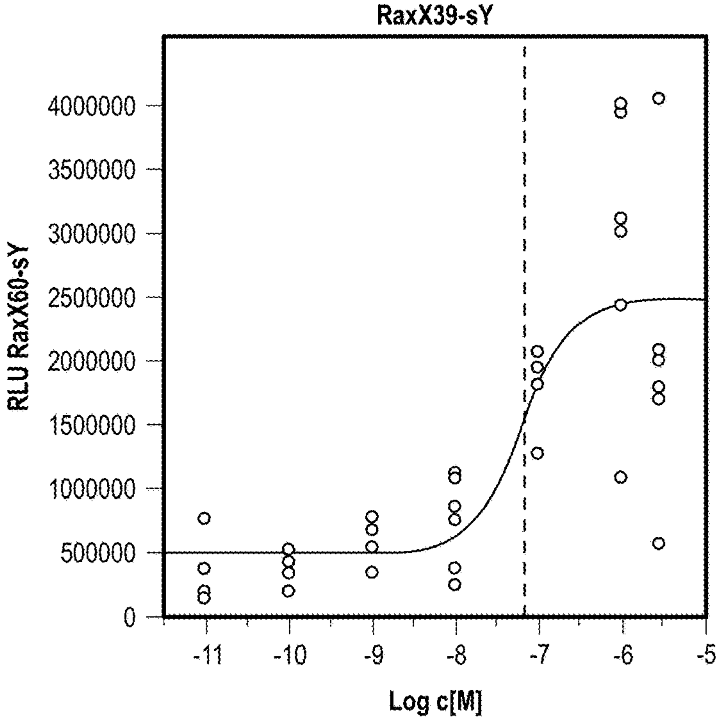
Figure 34C:
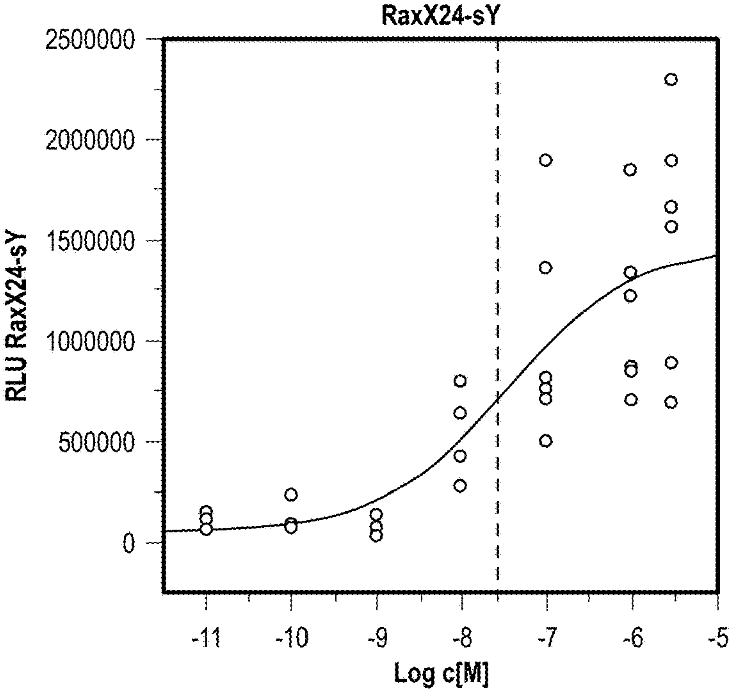
Figure 34D:
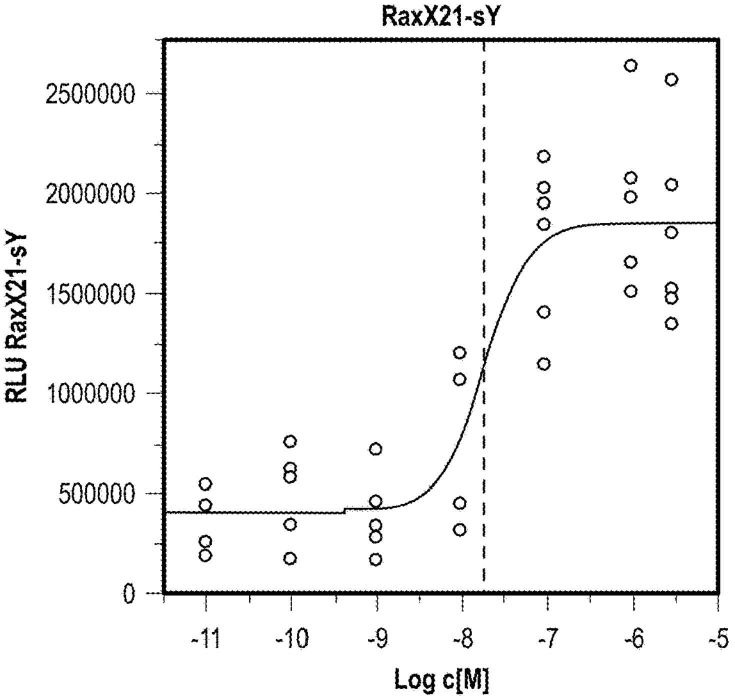
Figure 34E:
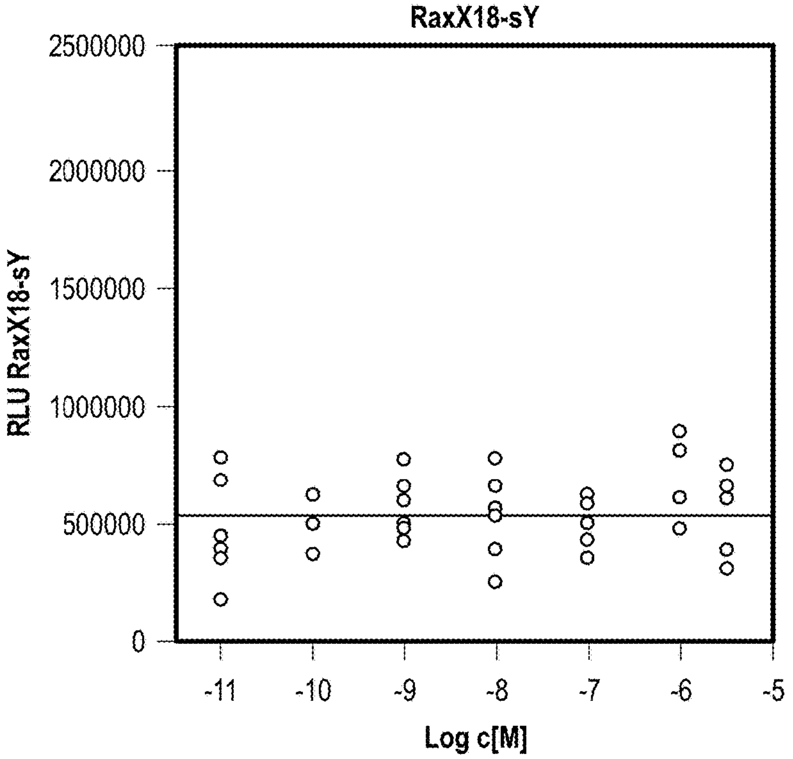

FIGS. 34A-34E. ROS production dose response curves in Ubi::XA21 leaves treated with chemically synthesized RaxX sulfated peptides. Individual data points depict single measurements of total ROS production over 3 h in leaves of five-week old Ubi::XA21 rice plants treated with the indicated peptides (10 pmol to 3 The fitted curve depicts the best-fitted model to the non-linear logistic 4p formula using the JMP software package. The vertical line indicates the inferred EC50 value. These experiments were repeated at least twice with similar results. RaxX60-sY (FIG. 34A), RaxX39-sY (FIG. 34B), RaxX24-sY (FIG. 34C), RaxX21-sY (FIG. 34D), and RaxX18-sY (FIG. 34E)

FIGS. 35A and 35B. The tyrosine sulfated peptide axY(S)22, derived from Ax21, does not trigger XA21-mediated immune responses in rice. Defense gene induction (Os06g37224) (FIG. 35A) and ROS production (FIG. 35B) in five-week old leaves of Kitaake and Ubi::XA21 rice plants treated with $H_2O$ (mock), axY(S)22 (1 μM), RaxX21-Y or RaxX21-sY (250 nM). Data points depict mean expression level±SD (n=2) or mean ROS production±SE (n=6). These experiments were repeated at least 3 times with similar results.

FIG. 36. Expression and purification of different RaxX alleles when heterogously expressed in *E. coli*. RaxX60-sY and the indicated variants (2 μg) were expressed and purified as described in the material and methods. The purified proteins were analyzed using a Tris-tricine gel (16.5%) and stained with SimplyBlue SafeStain.

Figure 37:
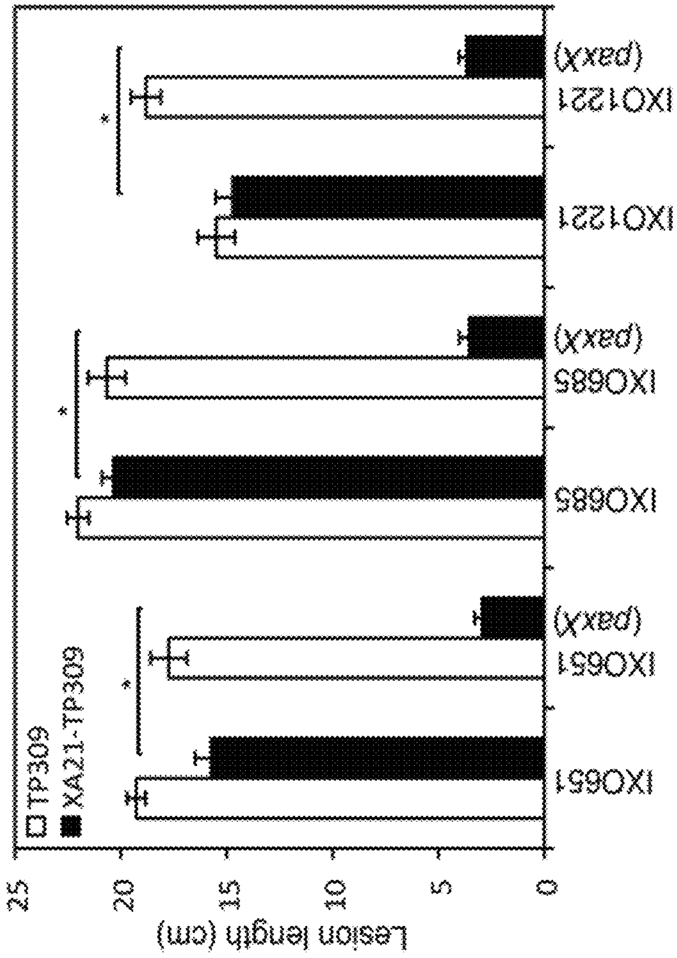

FIG. 37. Complementation of Xoo isolates IXO651, IXO685, and IXO1221 with praxX confers upon these strains the ability to activate XA21-mediated immunity. TP309 (open bars) or XA21-TP309 (black bars) were inoculated by clipping with scissors dipped in Xoo suspensions ($10^8$ CFU/mL). Bars indicate the mean lesion length±1 standard error (SE) 14 days after inoculation (n≥4). The '*' indicates statistically significant difference using Dunnett's test (α=0.01).

Figures 38A, 38B:
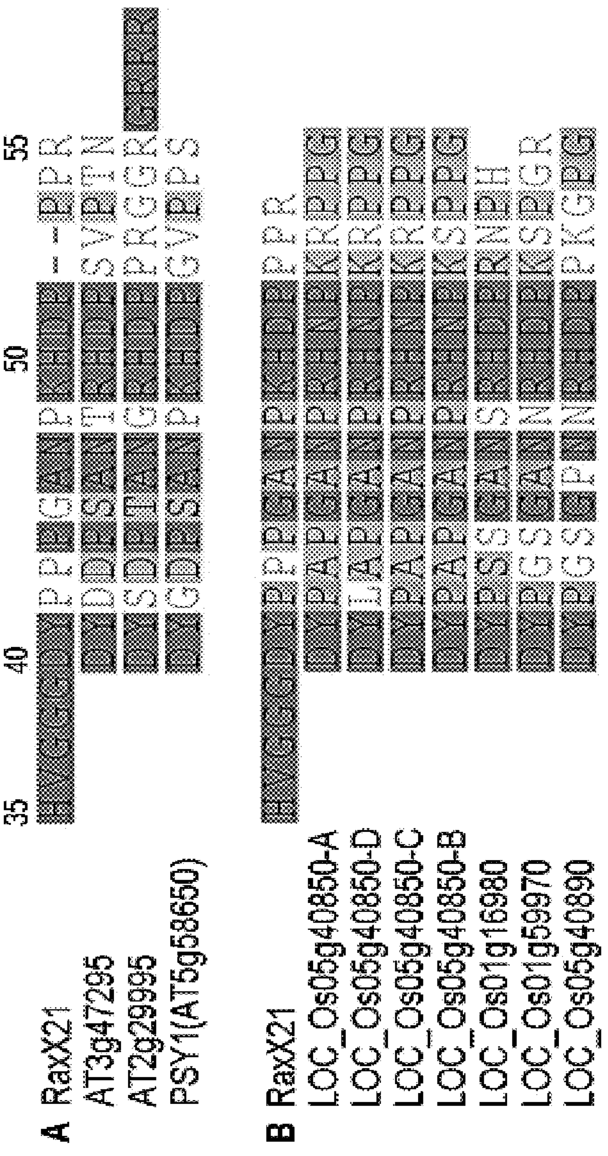

FIGS. 38A and 38B. RaxX is similar to the *Arabidopsis thaliana* peptide signaling factors PSY1 and to rice PSY1 homologs. (FIG. 38A) Alignment of RaxX21 from PXO99 (SEQ ID NO:59) with the 18 amino acid *Arabidopsis* plant peptide containing sulfated tyrosine 1, PSY1 (AT5g58650) (SEQ ID NO:62), and two homologs from *Arabidopsis* (Amano Y et al. (2007)*Proc Natl Acad Sci USA* 104(46): 18333-18338) (AT3G47295=SEQ ID NO:60, AT2g29995=SEQ ID NO:61). The numbering corresponds to the full length RaxX sequence. (FIG. 38B) Alignment of RaxX21 with 4 rice PSY1 homologs. These PSY1 rice homologs were identified by BLAST analysis using the 18 amino acid sequence of processed PSY1. Four rice genes encoding PSY1 like sequences were identified: Os01g16980 (SEQ ID NO:67), Os01g59970 (SEQ ID NO:68), Os05g40890 (SEQ ID NO:69), and Os05g40850. Os05g40850 carries four tandem repeats containing highly similar PSY1-like sequences, labeled Os05g40850-A-D (Os05g40850-A=SEQ ID NOS: 63, Os05g40850-B=SEQ ID NO: 64, Os05g40850-C=SEQ ID NO: 65, Os05g40850-D=SEQ ID NO:66). Alignments of the amino acid sequences corresponding to the processed PSY1 peptide with RaxX21 were generated using Geneious software (Kearse M, et al. (2012) *Bioinformatics* 28(12):1647-1649).

Figures 39A, 39B:
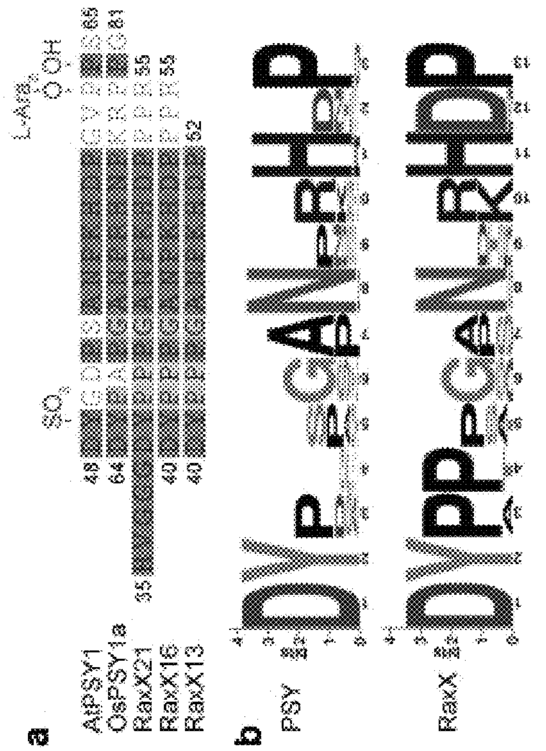

FIG. 39*a-b*. Sequence similarity of RaxX and plant PSYs.a) The sequence of RaxX21 (SEQ ID NO:59) from Xoostrain PX099 was alignedwith the 18 amino acid AtPSY1 (SEQ ID NO:62) and a PSY-like repeat of OsPSY1 (SEQ ID NO:63). Endogenous AtPSY1 has 3 postranslationally modified residues (as shown): a sulfotyrosine and two hydroxyprolines. The first hydroxyproline is further modified by chain of three L-arabinose residues(L-Ara3). The synthetic RaxX peptides RaxX16 (SEQ ID NO:70) and RaxX13 (SEQ ID NO:46) are truncated relative to RaxX21 as depicted. b) Sequence logos depicting the amino acid composition in the conserved 13-amino acid region of RaxX and PSY proteins. The logos were generated from 34 PSY sequences (FIG. 45) and 17 non-redundant RaxX13 sequences (SEQ ID NO:231) (Table 51).

FIG. 40*a-f*. Sulfated RaxX21 promotes root growth in *Arabidopsis* and rice. Root lengths of *Arabidopsis* a) Col-0 or c) tpst-1 seedlings were grown on 0.5×MS vertical plates with or without 100 nMof the indicated peptides. Bars indicate the average seedling root length measured after 8 days (n≥18). b and d) 8-day old Col-0 and test-1 seedlings grown as in 40a and c, respectively. e) Growth rate of six day old tpst-1 seedlings following transfer to 0.5×MS plates containing 250 nMRaxX21-sY, 250 nM AtPSY1, or lacking peptide (Mock) (n≥7). Growth was monitored by continual imaging over 20 h. f) Root lengths of 6-day old rice seedlings (Tapei 309) grown on 0.5×MS with or without 100 nM of the indicated peptides (n≥37). Statistical analysis was performed using the Tukey-Kramer honestly significant difference test for mean comparison using the JMP software. Different letters represent significant differences within each plant genotype (p≤0.05).

FIG. 41. The Arabidopsisgene At1g72300 is not required for RaxX- and PSY-induced root growth. a) *Arabidopsis* At1g72300 or b) AtPSKR1/AtPSKR2/At1g72300 triple receptor mutant seeds were grown on 0.5×MS plates with or without 100 nM of the indicated peptides. Root lengths were measured 8 days after placing seeds on plates. Error bars indicate standard error (n≥10). Statistical analysis was performed using the Tukey-Kramer honestly significant difference test for mean comparison using the JMP software. Different letters represent significant differences within each plant genotype (p≤0.05). The experiment was performed at least three times with similar results.

FIG. 42*a-d*. Differential activities of PSY and RaxX peptides ingrowth promotion and activation of XA21-mediated immunity. ROS production in leaves of a) XA21 rice (XA21-Kitaake) and b) wild type rice (Kitaake) treated with $H_2O$ (Mock) or 500 nM of the indicated peptide. Bars represent average ROS production over 90 min following addition of peptide (n=6). RLU stands for relative light units. c) TP309 seeds were grown on 0.5×MS media for with or without 100 nM of the indicated peptides. Root lengths were measured 5 daysafter placing seeds on plates (n≥25). d) Arabidopsistpst-1 seeds were grown on 0.5×MS vertical plates with or without 100 nM of the indicated peptides. Root lengths were measured 8 daysafter placing seeds on plates (n≥16). Error bars indicate standard error. Statistical analysis was performed using the Tukey-Kramer honestly significant difference test for mean comparison using the IMP software. Different letters represent significant differences within each plant genotype (p≤0.05). Experiments were performed at least two times with similar results.

Figure 43:
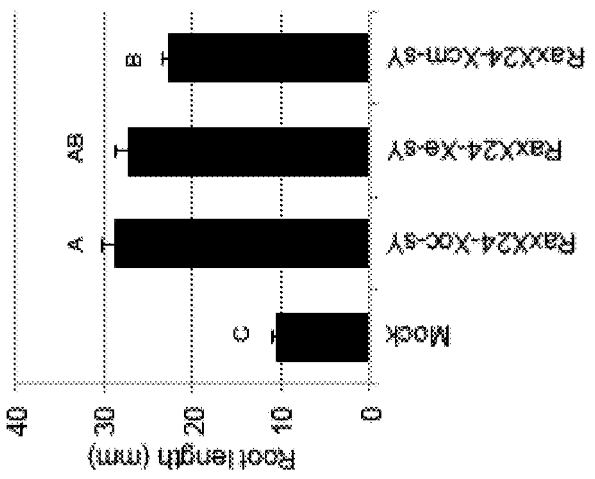

FIG. 43. RaxX peptides derived from RaxX encoded by Xoc, Xe, and Xcm promote root growth in *Arabidopsis* seedlings. tpst-1 seedlings were grown on 0.5×MS vertical plates with or without 100 nM of the indicated peptides. Bars indicate the average seedling root length measured after 8 days (n≥18). Error bars indicate error. Statistical analysis was performed using the Tukey-Kramer honestly significant difference test for mean comparison using the IMP software. Different letters represent significant differences within each plant genotype (p≤0.05). Experiments were performed at least two times with similar results.

Figure 44:
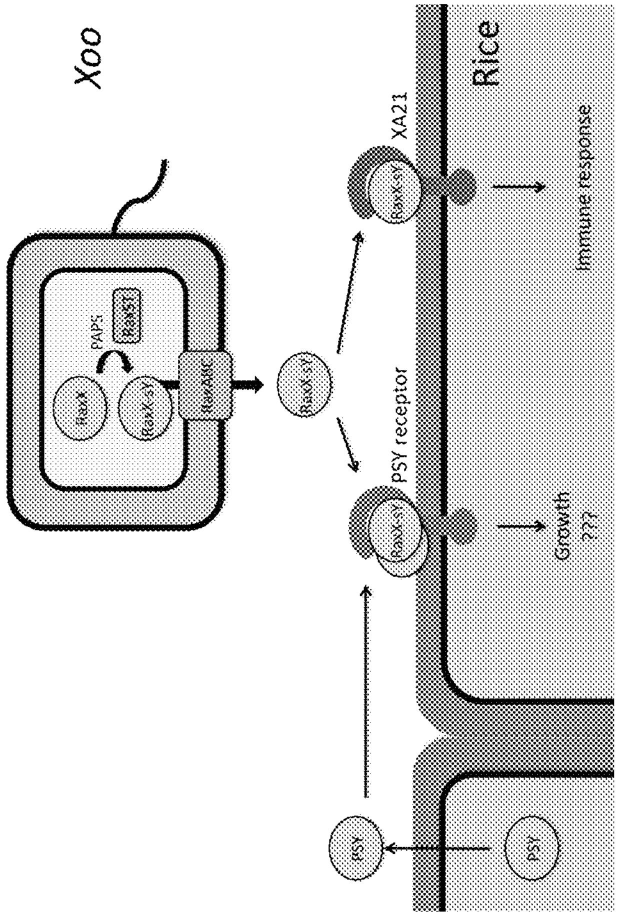

FIG. 44. Proposed model of RaxX production and activation of PSY and XA21 signaling. PSY is produced and detected by plant cells to regulate growth. RaxX is produced in Xoo, sulfated by RaxSt, and secreted by a type I secretion system composed of RaxA, RaxB, and RaxC. Secreted sulfated RaxX binds to the endogenous PSY receptor(s) and activates PSY signaling. The wild rice *O. longistaminata* subsequently evolved the immune receptor XA21 which selectively recognizes RaxX, but not endogenous PSY peptides.

Figure 45B:
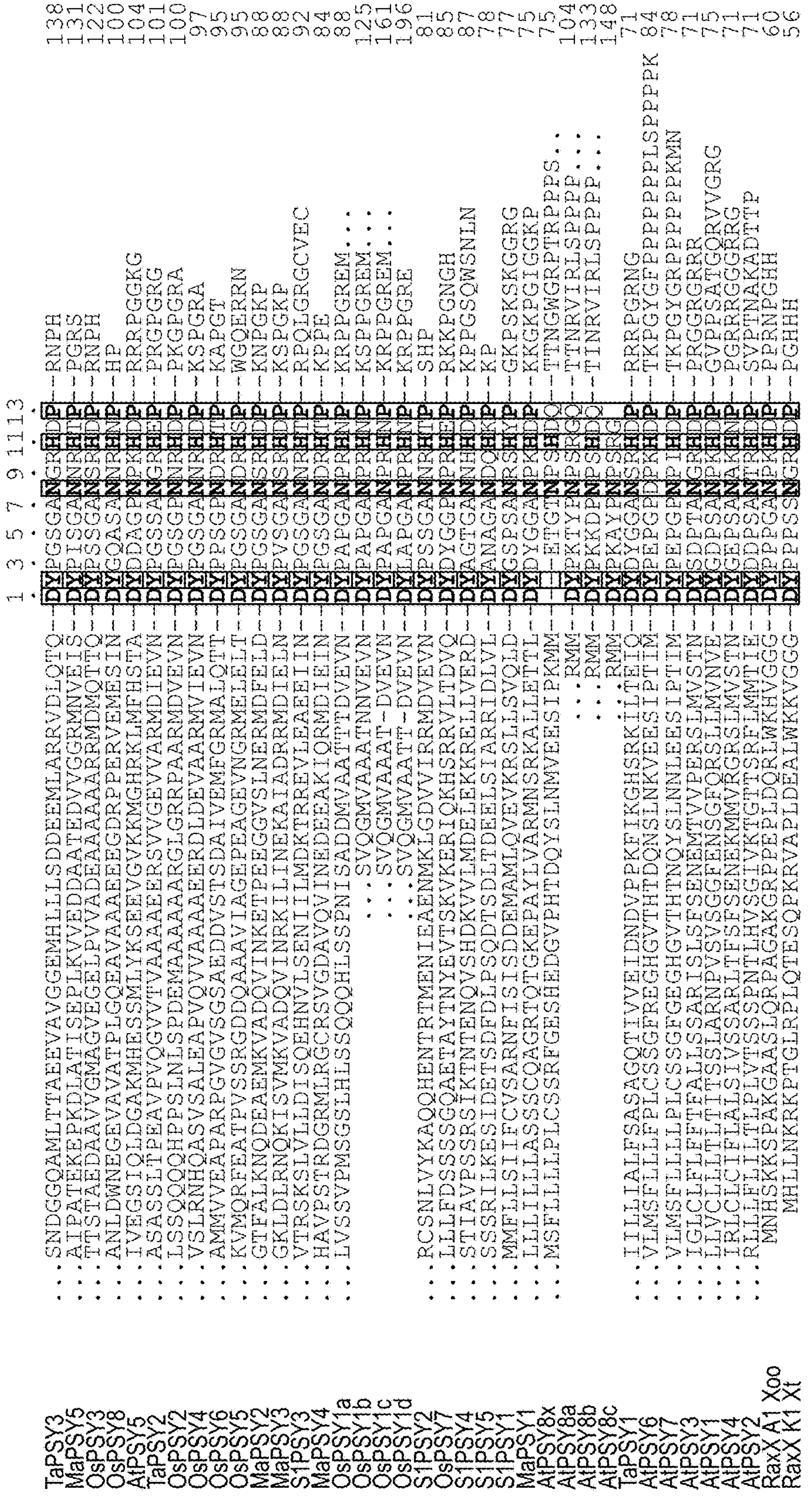

FIG. 45. Putative PSY-like proteins from *Arabidopsis* (At), rice (Os), banana (Ma), tomato (Sl), and wheat (Ta). PSY-like proteins were identified as described in the Material and Methods. The sequences (SEQ ID NOS: 71-106 and 23, respectively) are aligned based on the highly conserved 13-amino acid region. The conserved tyrosine, which is sulfated in AtPSY1, is highlighted in yellow. OsPSY1 and AtPSY8 have multiple repeats of the PSY-like motif within the full-length protein labeled with an appended letter. AtPSY8 has one pseudo-repeat lacking the tyrosine (AtPSY8x). The individual repeats are noted with an appended lowercase letter. For comparison, the RaxX sequences from *X. oryzae* pv. *oryzae* strain PXO99 and *X. translucens* strain 4699 are also included in the alignment. The residues of the conserved 13-amino acid region are numbered at the top of the FIG., with positions 5, 7, and 9 in red. These three residues are important for recognition of RaxX by XA21.

Figure 46:
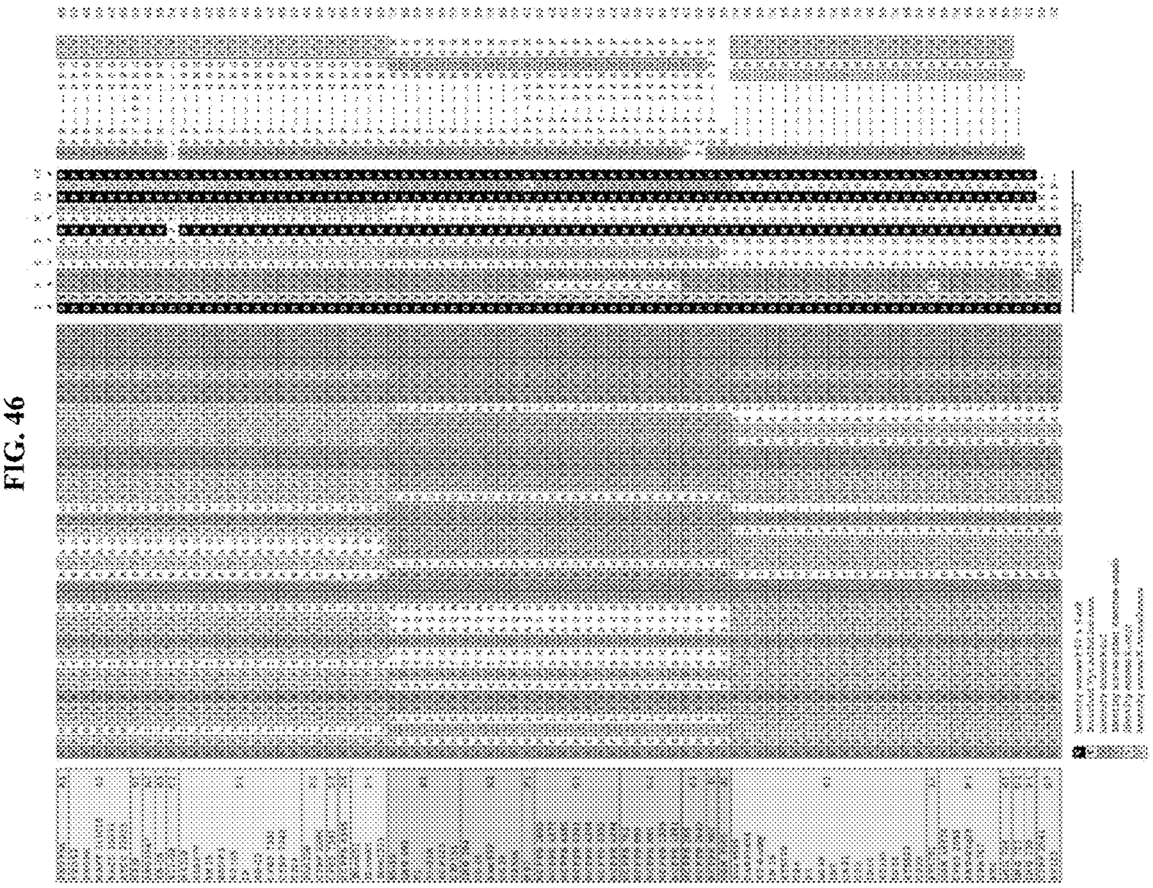

FIG. 46. Comparison of the RaxX sequences from diverse bacterial strains.RaxX sequences (SEQ ID NOS:107-188, respectively) from *X. oryzae* (SEQ ID NOS:107-133), *X. translucens* (SEQ ID NOS:162-188), and other *Xanthomonas* strains (SEQ ID NOS:134-161). Amino acids are colored according to conservation among *Xanthomonas* strains and among all PSY-like proteins. The invariant tyrosine is shown. The residues of the conserved 13-amino acid PSY-like motif are numbered at the top of the FIG., with amino acids in positions 5, 7, and 9 of particular note. These three residues are important for recognition of RaxX by XA21.

Figure 47:
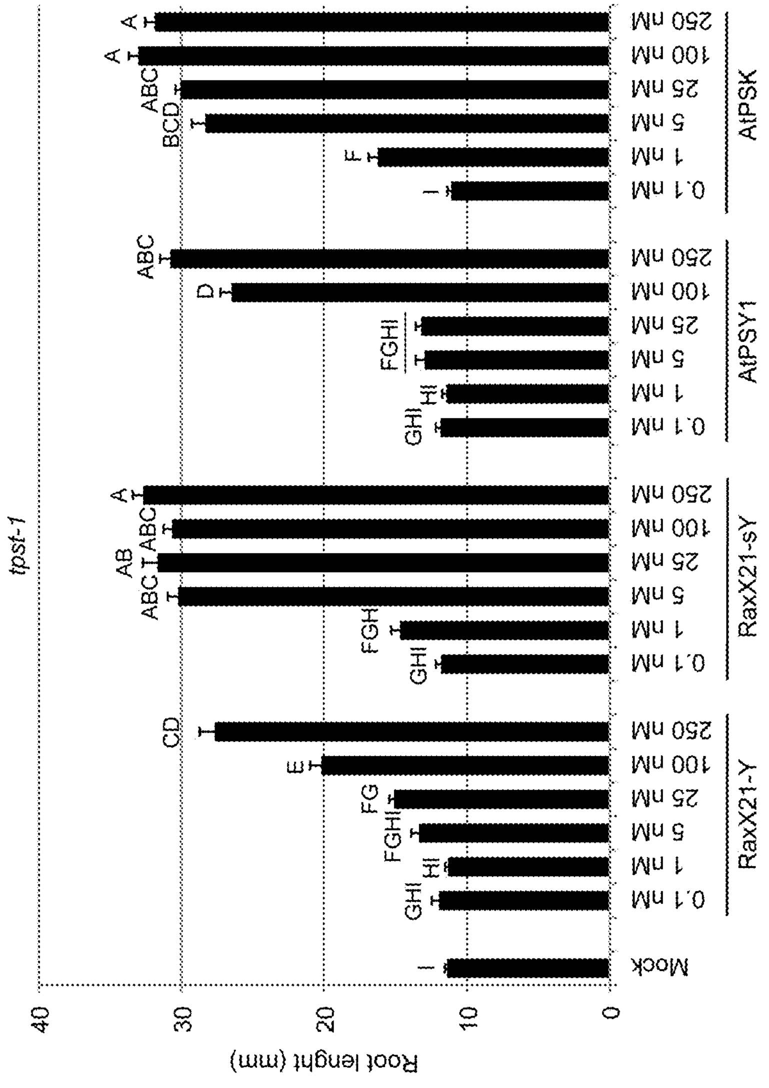

FIG. 47. Dose dependent activity of RaxX21-Y, RaxX21-sY, AtPSY1, and PSK on root growth of *Arabidopsis* tpst-1 seedlings. *Arabidopsis* tpst-1 seeds were grown on 0.5×MS plates with or without the indicated peptides as described in the materials and methods. Root lengths were measured 8 days after plating seeds. Error bars indicate standard error (n≥16). Statistical analysis was performed using the Tukey-Kramer honestly significant difference test for mean comparison using the IMP software. Different letters represent significant differences within each plant genotype (p≤0.05).

Figure 48:
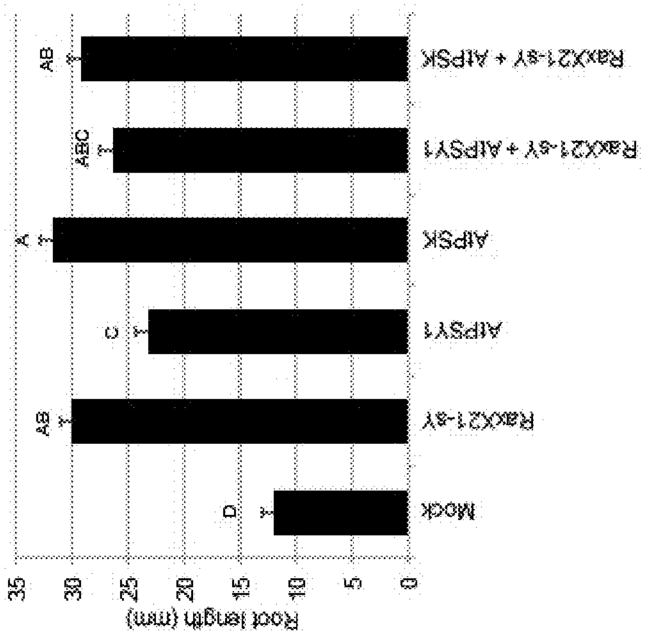

FIG. 48. RaxX, AtPSY1, and PSK do not have additive effects on root growth. tpst-1 seedlings were grown on 0.5×MS vertical plates with or without 100 nM of each of the indicated peptides. Bars indicate the average seedling root length measured 8 days after plating seeds (n≥18). Error bars indicate error. Statistical analysis was performed using the Tukey-Kramer honestly significant difference test for mean comparison using the JMP software. Different letters represent significant differences within each plant genotype ($p \leq 0.05$). Experiments were performed at least two times with similar results.

Figure 49:
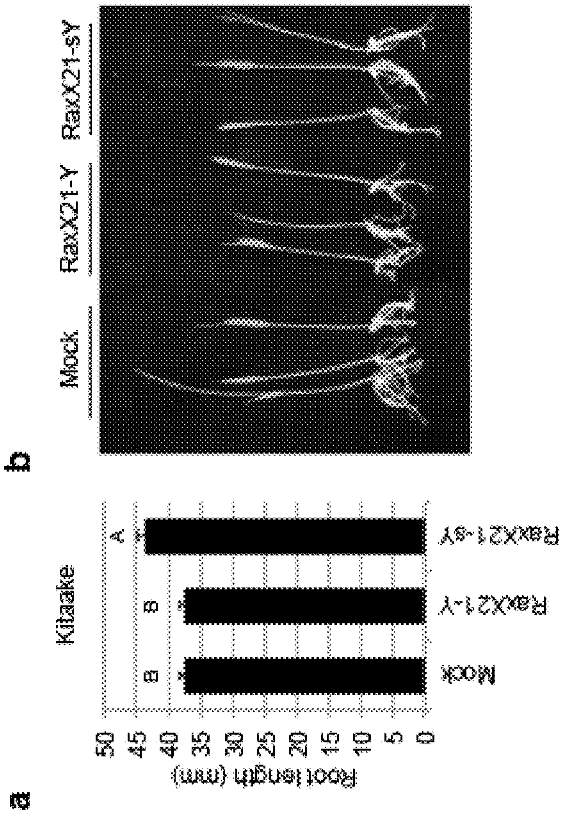

FIG. 49. Sulfated RaxX21 promotes root growth in Kitaake rice. a) Root lengths of 4-day old rice seedlings (Kitaake cultivar) grown on 0.5×MS with or without 100 nM of the indicated peptides ($n \geq 35$). b) Rice seedling grown as in a) were photographed. Error bars indicate error. Statistical analysis was performed using the Tukey-Kramer honestly significant difference test for mean comparison using the IMP software. Different letters represent significant differences within each plant genotype ($p \leq 0.05$). Experiments were performed at least two times with similar results.

Figure 50:
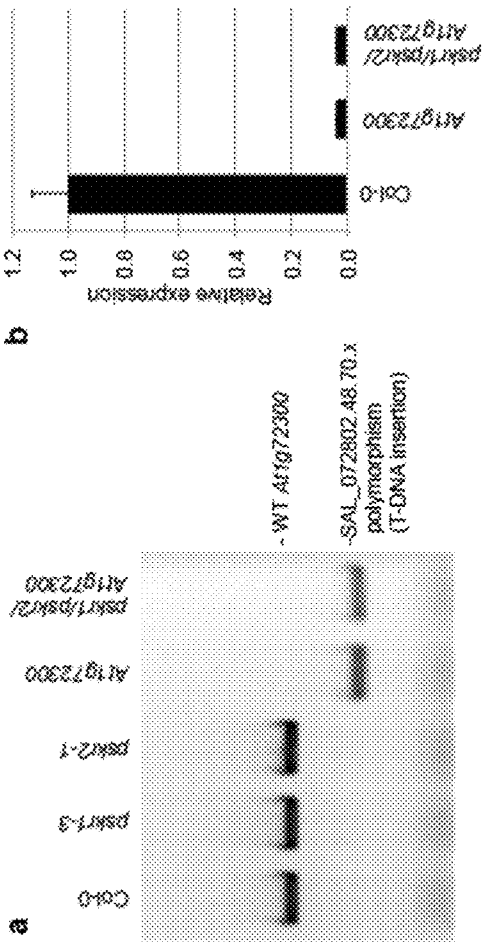

FIG. 50. Validation of the At1g72300 mutants. a) The At1g72300 mutants were confirmed by PCR using the SIGnAL T-DNA Primer Design protocol (http://signal.salk.edu/tdnaprimers.2.html). Wild typeAt1g72300 or the SAL_072802.48.70.x polymorphism (T-DNA insertion in At1g72300) were detected by PCR with the following primers: LBb1.3, 5'-ATTTTGCCGATTTCGGAAC-3' (SEQ ID NO:189); LP, 5'-GAGAACCTTTAGCTGCCCAAC-3' (SEQ ID NO:190); RP, 5'-ACAATGATTTCAGCGGTGATC-3.' (SEQ ID NO:191) b) At1g72300 transcript levels were assessed by qRT-PCR. 8-day old Col-0 or At1g72300 (SALK 072802C). RNA was treated with DNAseI, and cDNA was synthesized using MultiScribe (Applied Biosystems). qPCR reactions were performed with iTaq (BioRad) with annealing and amplification at 55° C. for 5 s and denaturation at 95° C. for 10 srun for 40 cycles. The following primers were used for qPCR: At1g72300:5'-GAGAACCTTTAGCTGCCCAAC-3' (SEQ ID NO:189), 5'-GCAATACAATCAGCTTTCCAGCC-3' (SEQ ID NO:192), Actin: 5'-GGTAACATTGTGCTCAGTGGTGG-3' (SEQ ID NO:193), 5'-GGTGCAACGACCTTAATCTTCAT-3' (SEQ ID NO:194)) Transcript levels are normalized to actin, and relative to wild-type.

Figure 51:
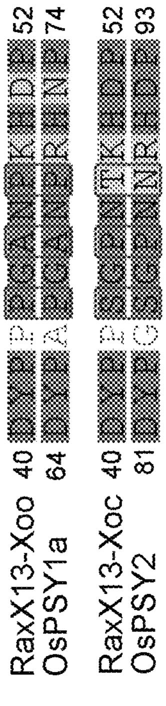

FIG. 51. Sequence similarity of RaxX from Xoo and Xoc with selected rice PSYs. 13 amino acid RaxX sequences from Xoo (strain PXO99) (SEQ ID NO:195) and Xoc (strain BSL256) (SEQ ID NO:197) were aligned with the corresponding 13 amino acid fragments of OsPSY1a (SEQ ID NO:196) and OsPSY2 (SEQ ID NO:198), respectively. RaxX residues 44, 46, and 48 (marked in red boxes) are important for activation of XA21-mediated immunity.

DETAILED DESCRIPTION OF THE INVENTION

I. Introduction

Provided herein is a newly characterized peptide, RaxX, that activates pathogen responses and root growth in plants.

Gram negative bacterial infections pose an increasing problem due in part to appearance of antibiotic resistant strains. These bacteria are particularly persistent, at least in part because they can grow within biofilms that protect them from adverse environmental factors.

*Xanthomonas oryzae* pv. *oryzae* (Xoo) is both a serious disease of rice, an important US crop, and is a predictive model organism for studies of other *Xanthomonas* species, which infect virtually all plant species. Sequence analysis of the raxX-raxSTAB genomic region reveals that orthologs are present in the agronomically important pathogens *X. oryzae* pv. *oryzicola* (Xoc) (98% identity), *X. campestris* pv. vesicatoria (Xcv) (88% identity), *X. axonopodis* pv. *citrumelo* (Xac) (88% identity) and *X. campestris* pv. *musacearum* (Xcm) (>85% identity). The present results are thus relevant for essentially all agronomically important plant hosts, and of fundamental biological relevance to agriculture.

The present results show isolation and characterization of RaxX (Required for Activation of XA21-mediated immunity), a small protein conserved in many species of the Gram-negative bacterial genus *Xanthomonas* and in species of related genera. RaxX-mediated biological processes are mediated by a Type I secretion system, a tyrosine sulfotransferase, and a response regulator (e.g., RaxR). In *Xanthomonas*, RaxA, RaxB, CvaA, and CvaB are predicted to process and secrete RaxX.

Small molecules play a key role in bacterial infection of plants and animals. The present results demonstrate for the first time the small protein RaxX, its tyrosine sulfation by RaxST, and processing and secretion by RaxAB and CvaAB in Gram-negative bacteria. Sulfated RaxX is shown to trigger robust resistance in plants expressing XA21. Thus, the characterization of RaxX, RaxST, and the other Rax and Cva genes radically alters the conceptual framework underlying the understanding of Gram-negative bacterial infection.

The present findings have important implications for development of novel approaches to disrupt Gram-negative bacterial infection. For example, RaxX (potentially in combination with other Rax and Cva genes involved in XA21-mediated immunity in plants) can be used to develop antagonists to disrupt small protein-mediated processes in Gram-negative bacterial infection.

II. Definitions

"Enhanced disease resistance" refers to an increase in the ability of a plant to prevent pathogen infection or pathogen-induced symptoms. Enhanced resistance can be increased resistance relative to a particular pathogen species or genus or can be increased resistance to all pathogens (e.g., systemic acquired resistance). The terms "pathogen response," "disease resistance," "immune response," and like terms are used interchangeably unless otherwise indicated. While plants do not have an adaptive immune system per se, one of skill in the art will understand immunity terms as commonly used with relation to plants. Disease resistance can take the form of a hypersensitive response, in which cells of the plant that detect pathogen undergo programmed cell death (see, e.g., Watanabe and Lam (2006) *Multigenic and Induced Systemic Resistance in Plants* p. 83). Disease resistance can also be manifested by release of antimicrobial chemicals and hormones, e.g., reactive oxygen species (H2O2, peroxynitrite, phytoalexins), defensins, thionins, chitinase, peroxidase, etc. Disease resistance can also be detected by detecting pathogen-induced or defense gene expression, e.g., as shown in FIGS. 6 and 7.

The term "exogenous application" taken in its broadest context includes contacting or administering cells, tissues, organs or organisms with a suitable compound or element. The compound may be applied to a plant in a suitable form for uptake (such as through application to the soil for uptake via the roots, or by applying directly to the leaves, for example by spraying).

The term "sulfated tyrosine" is used to include tyrosine-O-sulfate residues comprising a sulfate group covalently bound via the hydroxyl group of the tyrosine side chain. Sulfate may be added to a tyrosine by post-translational modification of a peptide or protein (e.g., by RaxST), by chemical synthesis (e.g., incorporating a sulfonated tyrosine into a synthetically produced polypeptide), or by chemical alteration. As used herein, "Y" indicates a tyrosine residue, while "Y*" indicates a sulfated tyrosine.

"Pathogens" include, but are not limited to, viruses, bacteria, nematodes, fungi or insects (see, e.g., Agrios, *Plant Pathology* (Academic Press, San Diego, Calif. (1988)).

The term "homolog" refers to both interspecies orthologs and intraspecies paralogs. Unless indicated otherwise, a homolog will share at least some activity (e.g., at least 25, 30, 40, 50, 60, 75, 80, 90% or higher level of activity) with the named gene or gene product (e.g., polypeptide), and thus be a "functional" homolog. Orthologs are genes in different species that typically retain the same function and evolved from a common ancestral gene prior to speciation. Paralogs are similar or related genes within a species genome. Paralogs typically arise from duplication, and often have overlapping functions.

The term "promoter" refers to regions or sequence located upstream and/or downstream from the start of transcription and which are involved in recognition and binding of RNA polymerase and other proteins to initiate transcription. The term includes constitutive, inducible, and tissue specific promoters, any of which can be used as described herein. A "plant promoter" is a promoter capable of initiating transcription in plant cells. A plant promoter can be, but does not have to be, a nucleic acid sequence originally isolated from a plant.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide sequence is "heterologous to" an organism or a second polynucleotide sequence if it originates from a different strain or species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or *Current Protocols in Molecular Biology* Volumes 1-3, John Wiley & Sons, Inc. (1994-1998)). In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

The term "nucleic acid" or "polynucleotide" as used herein refers to a deoxyribonucleotide or ribonucleotide in either single- or double-stranded form. The term encompasses nucleic acids containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see *Oligonucleotides and Analogues, a Practical Approach*, edited by F. Eckstein, IRL Press at Oxford University Press (1991); *Antisense Strategies*, Annals of the New York Academy of Sciences, Volume 600, Eds. Baserga and Denhardt (NYAS 1992); Milligan (1993) J. Med. Chem. 36:1923-1937; *Antisense Research and Applications* (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189-197. Other synthetic backbones encompassed by the term include methyl-phosphonate linkages or alternating methylphosphonate and phosphodiester linkages (Strauss-Soukup (1997) *Biochemistry* 36: 8692-8698), and benzylphosphonate linkages (Samstag (1996) *Antisense Nucleic Acid Drug Dev* 6: 153-156).

The phrase "host cell" refers to a cell from any organism. Preferred host cells are derived from plants, bacteria, yeast, fungi, insects or other animals. Methods for introducing polynucleotide sequences into various types of host cells are well known in the art.

An "expression cassette" refers to a nucleic acid construct, which when introduced into a host cell (e.g., a plant cell), results in transcription and/or translation of a RNA or polypeptide, respectively.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

One example of algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%, e.g., at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters, as described below. One of skill will recognize that the percent identity values above can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, e.g., any integer from 40% to 100%. Exemplary embodiments include at least 40%, 45%, 50%, 55%, 60%, 65%, 70%, 75%, 80%, 85%, 90%, 95%, or 99%. In some embodiments, polypeptides that are "substantially similar" share sequences as noted above except that residue positions which are not identical may differ by conservative amino acid changes. Conservative amino acid substitutions refer to the interchangeability of residues having similar side chains. Provided herein are polynucleotides encoding a polypeptide comprising an amino acid sequence substantially identical to raxX (e.g., the polypeptide sequence of SEQ ID NO:1, allelic variants, and homologs thereof). The present invention also provides for a polypeptide comprising an amino acid sequence substantially identical to raxX.

The following eight groups each contain amino acids that are conservative substitutions for one another:

1) Alanine (A), *Glycine* (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

III. Polypeptides Involved in Pathogen Resistance and Root Growth and Uses Thereof Provided herein are small peptide molecules that are conserved across species that can be used as targets for inhibiting Gram negative and nosocomial bacterial infection. Such polypeptides include raxX and raxX-like polypeptides.

RaxX (and variants and homologs thereof) can be used to activate immunity in plants expressing XA21, and to develop antagonists that disrupt raxX function in bacteria. Such antagonists can then be used as antibiotics to combat infection in plants, animals, etc.

The polypeptides described herein have a number of uses. Notably, contacting a plant with a polypeptide as described herein can induce or enhance disease resistance in a plant. Moreover, the inventors have found that contacting a plant with a polypeptide as described herein enhances root growth. The contacting can occur by applying exogenous (not expressed in the plant) polypeptide to the plant, or by expressing the polypeptide in the plant.

In some embodiments, the plants express XA21 or a functional equivalent, i.e., a disease resistance gene product that enables recognition of a polypeptide as described herein, and subsequently induces disease resistance in the plant. The XA21 gene was first isolated from rice. See, e.g., Song, W. et al., *Science* 270:1804 (1995); and U.S. Pat. No. 5,977,434. The plant can express XA21 endogenously (e.g., not by recombinant expression) or the plant can be transgenic or otherwise recombinantly manipulated to express XA21 (e.g., heterologous XA21 from a different plant strain or species). Thus, while XA21 was originally identified in rice, XA21 can be expressed in plants other than rice. Plants other than rice have XA21 activity, and can be identified, e.g., by enhanced disease resistance in response to contact with a polypeptide as described herein.

Provided herein are methods of identifying a plant having XA21 activity by contacting a non-rice plant with a polypeptide as described herein (either recombinantly produced, purified, or expressed from a bacterial or fungal pathogen) and identifying a contacted plant that has enhanced disease resistance or other manifestation of disease resistance (e.g., a hypersensitive response) as a result the presence of the polypeptide in the contacting step.

Small proteins such as raxX are an attractive therapeutic target because of the important role that they play in the global regulation of multiple bacterial factors and in the virulence of an organism at multiple different infection stages. Quorum sensing (QS) is often mediated by small proteins, so disruption of the small protein interactions can prevent pathogenic bacteria from initiating the gene expression cascade required for successful establishment in the host. Bacterial mutants impaired in QS are attenuated in virulence (Jayaraman et al. (2008) *Annu Rev Biomed Eng* 10:145).

A common problem associated with antibiotic control of infection is that the chemical reduces the growth of the bacteria. This strategy increases selection pressure on the bacteria to evolve mechanisms to resist the chemical. In contrast, it is more difficult for the bacteria to evolve or change its QS system because in order for the bacteria to no longer bind to the antagonist it would need to mutate the binding domain of the QS receptor. In this case, however, the receptor would no longer be able to bind the endogenous QS factor and would therefore be crippled in virulence. Even if a bacterium successfully mutated the receptor to no longer bind the antagonist but was able to retain binding with the endogenous QS molecule, other bacteria in the population would still be susceptible to the antagonist. Consequently, a bacterium with resistance to a chemical antagonist has no growth advantage compared with neighboring bacteria and is not able to outgrow other bacteria in subsequent generations. Anti-QS strategies thus offer the attractive possibility that any mutations to resist the chemical would also reduce bacterial fitness, giving these chemicals a long functional lifetime.

Provided herein are methods of screening for compounds that antagonize RaxST or RaxX density dependent expression in Gram negative bacteria (e.g. *Xanthomonas*). Test compounds can be obtained from libraries of characterized natural compounds and synthetic derivatives (e.g. NCI, Spectrum, and Enzo libraries). In some embodiments, highly antagonistic compounds from the first screen (e.g., at least 2 or 3 standard deviations from negative control values) are further screened for inhibition of raxX-mediated and/or raxST-mediated virulence of pathogens in plant cells.

This screen identifies molecules that have the potential to affect several different stages of the raxX-mediated signaling pathway (e.g. raxX sulfation, secretion, uptake, transmission of signal from the sensor to kinase domain, transfer of signal to the response regulators, etc), not just small molecules that disrupt protein-protein interactions. Established assays can then be used to determine the effect of candidate compounds on RaxX secretion, processing and sulfation (e.g., Han and Lee (2012) *Nature Comm*). Similar screening methods can be carried out for raxX variants and raxX species homologs to investigate and screen for inhibitors in other pathogen-host systems, including infections of Gram negative bacteria (and antibiotic resistant strains) in humans.

Bacteria, including bacterial causal agents of animal and human disease, rely on various processes for virulence. Administration of a therapeutically effective amount of a polypeptide as described herein (e.g., raxX and raxX-like peptides), dominant-negative variants, and/or inhibitors obtained from the above screening methods, can disrupt virulence functions of bacterial animal or human pathogens in animals (e.g., bovines, poultry animals, pigs, sheep, dogs, cats, horses, rats, mice, etc.) or humans, thereby treating or ameliorating disease caused by such bacterial agents. Variants and inhibitors of the presently disclosed peptides that block endogenous bacterial processes required for virulence are of particular interest. Such treatment is expected to be effective against any bacterial animal or human pathogen that uses a polypeptide substantially identical to a RaxX polypeptide of the invention as a QS agent. Exemplary bacterial species include, but are not limited to, *Staphylococcus aureus, Bordetella pertussis, Stenotrophomonas maltophilia, Lactobacillus plantarum* and *Lactobacillus* sake.

Administration of a polypeptide or inhibitory molecule as described herein can be by any of the routes normally used for introducing pharmaceuticals. The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences,* $17^{th}$ ed. 1985)).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intrathecally or into the eye (e.g., by eye drop or injection). The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient should be sufficient to induce a beneficial response in the subject over time, i.e., reduce pathogen infection and effects. The optimal dose level for any patient will depend on a variety of factors including the efficacy of the specific modulator employed, the age, body weight, physical activity, and diet of the patient, and on a possible combination with other drug. The size of the dose also will be determined by the existence, nature, and extent of any adverse side-effects that accompany the administration of a particular compound or vector in a particular subject. Administration can be accomplished via single or divided doses.

IV. Agricultural Applications

Provided herein are agricultural formulations formulated for contacting to plants, wherein the formulation comprises a polypeptide (e.g., a sulfated polypeptide as described herein). The formulations can be suitable for treating plants or plant propagation material, such as seeds, in accordance with the present invention, e.g., in a carrier. Suitable additives include buffering agents, wetting agents, coating agents, polysaccharides, and abrading agents. Exemplary carriers include water, aqueous solutions, slurries, solids and dry powders (e.g., peat, wheat, bran, vermiculite, clay, pasteurized soil, many forms of calcium carbonate, dolomite, various grades of gypsum, bentonite and other clay minerals, rock phosphates and other phosphorous compounds, titanium dioxide, humus, talc, alginate and activated charcoal). Any agriculturally suitable carrier known to one skilled in the art would be acceptable and is contemplated for use in the present invention. The formulations can also include at least one surfactant, herbicide, fungicide, pesticide, or fertilizer.

Treatment can be performed using a variety of known methods, e.g., by spraying, atomizing, dusting or scattering the compositions over the propagation material or brushing or pouring or otherwise contacting the compositions over the plant or, in the event of seed, by coating, encapsulating, or otherwise treating the seed. The formulations described herein can also or alternatively be introduced into the soil or other media into which the seed is to be planted. In some embodiments, a solid or liquid carrier is used. In some embodiments, peat is suspended in water as a carrier of the desired polypeptide, and this mixture is sprayed into the soil or planting media and/or over the seed as it is planted.

V. Recombinant Techniques and Compositions

To use isolated sequences in the above techniques, recombinant DNA vectors suitable for transformation of plant cells are prepared. Techniques for transforming a wide variety of higher plant species are well known and described in the technical and scientific literature, e.g., Weising et al. *Ann. Rev. Genet.* 22:421-477 (1988). A polynucleotide sequence encoding a desired polypeptide (e.g., a polypeptide as described herein, e.g., including but not limited to XA21, raxB, raxST, raxX, and functional fragments, allelic variants, and homologs thereof), will be combined with transcriptional and translational initiation regulatory sequences which will direct the transcription of the sequence from the polynucleotid in the intended tissues of the transformed plant.

For example, a plant promoter can be employed which will direct expression of the polynucleotide in all tissues of a transgenic plant, in a specific tissue (tissue-specific promoters), organ (organ-specific promoters), or under certain conditions (inducible promoters). Examples of tissue-specific promoters under developmental control include promoters that initiate transcription only in certain tissues, such as fruit, seeds, flowers, pistils, or anthers. Suitable promoters include those from genes encoding storage proteins or the lipid body membrane protein, oleosin.

A polyadenylation region at the 3'-end of the coding region can also be included. The polyadenylation region can be derived from the natural gene, from a variety of other plant genes, or from T-DNA.

The vector comprising the sequences (e.g., promoters or coding regions) from coding sequences described herein will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Constitutive Promoters

A promoter, or an active fragment thereof, can be employed which will direct expression of a nucleic acid encoding a fusion protein of the invention, in all transformed cells or tissues, e.g., as those of a regenerated plant. Such promoters are referred to herein as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless *Arch. Virol.* 142:183-191 (1997)); the 1'- or 2'-promoter derived from T-DNA of *Agrobacterium tumefaciens* (see, e.g., Mengiste supra (1997); O'Grady *Plant Mol. Biol.* 29:99-108) (1995)); the promoter of the tobacco mosaic virus; the promoter of Figwort mosaic virus (see, e.g., Maiti *Transgenic Res.* 6:143-156) (1997)); actin promoters, such as the *Arabidopsis* actin gene promoter (see, e.g., Huang *Plant Mol. Biol.* 33:125-139 (1997)); alcohol dehydrogenase (Adh) gene promoters (see, e.g., Millar *Plant Mol. Biol.* 31:897-904 (1996)); ACT11 from *Arabidopsis* (Huang et al. *Plant Mol. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Biol* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf (1995) "Comparison of different constitutive and inducible promoters for the overexpression of transgenes in *Arabidopsis thaliana*," *Plant Mol. Biol.* 29:637-646.

Inducible Promoters

Alternatively, a plant promoter may direct expression of the nucleic acids under the influence of changing environmental conditions or developmental conditions. Examples of environmental conditions that may affect transcription by inducible promoters include anaerobic conditions, elevated temperature, drought, or the presence of light. Examples of developmental conditions that may affect transcription by inducible promoters include senescence and embryogenesis. Such promoters are referred to herein as "inducible" promoters.

Exemplary inducible promoters include those promoters that are specifically induced upon infection by a virulent pathogen. Useful promoters include PR10b, Os06g13390, Os04g10010, Os02g36190.1, Os04g09920.1, Os06g28050, Os06g37224.1, Os10g28299, Os11g31550.1, Os12g36830.1, those discussed in PCT application WO 99/43824, and promoters from:

a. pathogen response genes (e.g., Lee et al. (2011) *PNAS* 108:18548);

b. lipoxygenases (e.g., Peng et al, *J. Biol. Chem.* 269:3755-3761 (1994)), c. peroxidases (e.g., Chittoor et al. *Molec. Plant-Microbe Interact.* 10:861-871 (1997)), d. hydroxymethylglutaryl-CoA reductase, e. phenylalanine ammonia lyase, f. glutathione-S-transferase, g. chitinases (e.g., Zhu et al. *Mol. Gen. Genet.* 226:289-296 (1991)), h. genes involved in the plant respiratory burst (e.g., Groom et al. *Plant J.* 10:515-522 (1996)); and i. pathogenesis-related (PR) protein promoters.

Other examples of developmental conditions include cell aging, and embryogenesis. For example, the invention incorporates the senescence inducible promoter of *Arabidopsis, SAG* 12, (Gan and Amasino, *Science,* 270:1986-1988 (1995)) and the embryogenesis related promoters of LEC1 (Lotan et al., *Cell,* 93:1195-205 (1998)), LEC2 (Stone et al., *Proc. Natl. Acad. of Sci.,* 98:11806-11811 (2001)), FUS3 (Luerssen, *Plant J.* 15:755-764 (1998)), AtSERK1 (Hecht et al. *Plant Physiol* 127:803-816 (2001)), AGL15 (Heck et al. *Plant Cell* 7:1271-1282 (1995)), and BBM (BABYBOOM). Other inducible promoters include, e.g., the drought-inducible promoter of maize (Busk supra (1997)) and the cold, drought, and high salt inducible promoter from potato (Kirch *Plant Mol. Biol.* 33:897-909 (1997)).

Plant promoters which are inducible upon exposure to plant hormones, such as auxins or cytokinins, can be used to express the nucleic acids of the invention. For example, the invention can use the auxin-response elements E1 promoter fragment (AuxREs) in the soybean (*Glycine max* L.) (Liu *Plant Physiol.* 115:397-407 (1997)); the auxin-responsive *Arabidopsis* GST6 promoter (also responsive to salicylic acid and hydrogen peroxide) (Chen *Plant J.* 10:955-966 (1996)); the auxin-inducible parC promoter from tobacco (Sakai 37:906-913 (1996)); a plant biotin response element (Streit *Mol. Plant Microbe Interact.* 10:933-937 (1997)); and, the promoter responsive to the stress hormone abscisic acid (Sheen *Science* 274:1900-1902 (1996)). The invention can also use the cytokinin inducible promoters of ARR5 (Brandstatter and Kieber, *Plant Cell,* 10:1009-1019 (1998)), ARR6 (Brandstatter and Kieber, *Plant Cell,* 10:1009-1019 (1998)), ARR2 (Hwang and Sheen, *Nature,* 413:383-389 (2001)), the ethylene responsive promoter of ERF1 (Solano et al., *Genes Dev.* 12:3703-3714 (1998)), and the β-estradiol inducible promoter of XVE (Zuo et al., *Plant J,* 24:265-273 (2000)).

Plant promoters which are inducible upon exposure to chemicals reagents which can be applied to the plant, such as herbicides or antibiotics, are also used to express the nucleic acids of the invention. For example, the maize In2-2 promoter, activated by benzenesulfonamide herbicide safeners, can be used (De Veylder *Plant Cell Physiol.* 38:568-577 (1997)) as well as the promoter of the glucocorticoid receptor protein fusion inducible by dexamethasone application (Aoyama, Plant J., 11:605-612 (1997)); application of different herbicide safeners induces distinct gene expression patterns, including expression in the root, hydathodes, and the shoot apical meristem. The coding sequence of the described nucleic acids can also be under the control of, e.g., a tetracycline-inducible promoter, e.g., as described with transgenic tobacco plants containing the *Avena sativa* L. (oat) arginine decarboxylase gene (Masgrau *Plant* 11:465-473 (1997)); or, a salicylic acid-responsive element (Stange *Plant J.* 11:1315-1324 (1997)).

Tissue-Specific Promoters

Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, or any embryonic tissue.

A variety of promoters specifically active in vegetative tissues, such as leaves, stems, roots and tubers, can also be used to express the nucleic acids used in the methods of the invention. For example, promoters controlling patatin, the major storage protein of the potato tuber, can be used, e.g., Kim *Plant Mol. Biol.* 26:603-615 (1994); Martin *Plant J.* 11:53-62 (1997). The ORF13 promoter from *Agrobacterium rhizogenes* which exhibits high activity in roots can also be used (Hansen *Mol. Gen. Genet.* 254:337-343 (1997)). Other useful vegetative tissue-specific promoters include: the tarin promoter of the gene encoding a globulin from a major taro (*Colocasia esculenta* L. Schott) corm protein family, tarin (Bezerra *Plant Mol. Biol.* 28:137-144 (1995)); the curculin promoter active during taro corm development (de Castro *Plant Cell* 4:1549-1559 (1992)) and the promoter for the tobacco root-specific gene TobRB7, whose expression is localized to root meristem and immature central cylinder regions (Yamamoto *Plant Cell* 3:371-382 (1991)).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier *FEBS Lett.* 415:91-95 (1997)). A ribulose bisphosphate carboxylase promoters expressed almost exclusively in mesophyll cells in leaf blades and leaf sheaths at high levels, described by Matsuoka *Plant J.* 6:311-319 (1994), can be used. Another leaf-specific promoter is the light harvesting chlorophyll a/b binding protein gene promoter, see, e.g., Shiina *Plant Physiol.* 115:477-483 (1997); Casal *Plant Physiol.* 116:1533-1538 (1998). The *Arabidopsis thaliana* myb-related gene promoter (Atmyb5) (Li *FEBS Lett.* 379:117-121 (1996)) is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16-cell stage of embryo development and persists beyond the heart stage. A leaf promoter identified in maize by Busk *Plant J.* 11:1285-1295 (1997) can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio *Cell* 86:423-433 (1996) and Long *Nature* 379:66-69 (1996), can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto *Plant Cell.* 7:517-527 (1995)). Also useful are kn1-related genes from maize and other species which show meristem-specific expression, see, e.g., Granger *Plant Mol. Biol.* 31:373-378 (1996); Kerstetter *Plant Cell* 6:1877-1887 (1994); Hake Philos. *Trans. R. Soc. Lond. B. Biol. Sci.* 350:45-51 (1995). For example, the *Arabidopsis thaliana* KNAT1 or KNAT2 promoters. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln *Plant Cell* 6:1859-1876 (1994)).

In some embodiments, the promoter is a root-specific promoter. This can be useful, for example, in enhancing root growth.

One of skill will recognize that a tissue-specific promoter may drive some expression of operably linked sequences in tissues other than the target tissue. Thus, as used herein, a tissue-specific promoter is one that drives higher expression in the target tissue than in other tissues.

In some embodiments, a nucleic acid described herein can be expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai (1995) *Proc. Natl. Acad. Sci. USA* 92:1679-1683) the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer *Plant Mol. Biol.* 31:1129-1139 (1996)).

VI. Transgenic Plants

Provided herein are transgenic plants. In some embodiments, the transgenic plant comprises:

a first heterologous expression cassette comprising a first promoter operably linked to a polynucleotide encoding a ligand of XA21 (e.g., comprising a sequence encoding a polypeptide substantially identical to raxX, or an active fragment thereof, e.g., with the Tyr corresponding to Tyr10 of SEQ ID NO:1 sulfonated). In some embodiments, such plants endogenously express XA21.

Optionally (e.g., when the plant does not endogenously express XA21 or have endogenous XA21-recognition activity), the plant can also comprise:

a second heterologous expression cassette comprising a second promoter operably linked to a polynucleotide encoding an XA21 polypeptide (e.g., a polypeptide substantially identical to the XA21 polypeptide described in U.S. Pat. No. 5,977,434); and/or a third heterologous expression cassette comprising a third promoter operably linked to a polynucleotide encoding a sulfur transferase (e.g., raxST gene, or an ortholog or other active variant thereof) capable of sulfating the tyrosine Y* of the polypeptide product of the first expression cassette.

Provided herein are transgenic plants comprising the first and second expression cassettes, comprising the first and third expression cassettes, comprising the second and third expression cassettes, or all three expression cassettes.

In some embodiments, the invention provides for a transgenic plant comprising the second expression cassette contacted with an exogenous XA21 ligand (e.g., comprising a polypeptide sequence substantially identical to raxX, or an active fragment thereof, wherein the).

DNA constructs of the invention may be introduced into the genome of the desired plant host by a variety of conventional techniques. For example, the DNA constructs may be introduced directly into the genomic DNA of the plant cell using techniques such as electroporation and microinjection of plant cell protoplasts. The DNA constructs can be introduced directly to plant tissue using biolistic methods, such as DNA particle bombardment. The DNA constructs can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. (1984) *Embo J.* 3:2717. Electroporation techniques are described in Fromm et al. (1985) *Proc. Natl. Acad. Sci. USA* 82:5824. Biolistic transformation techniques are described in Klein et al. (1987) *Nature* 327:70-73.

*Agrobacterium tumefaciens*-mediated transformation techniques, including disarming and use of binary vectors, are well described in the scientific literature. See, for example Horsch et al. (1984) *Science* 233:496 and Fraley et al. (1983) *Proc. Natl. Acad. Sci. USA* 80:4803.

Transformed plant cells which are derived by any of the above transformation techniques can be cultured to regenerate a whole plant which possesses the transformed genotype and thus the desired phenotype such as increased disease resistance compared to a control plant that was not transformed or transformed with an empty vector. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and *Binding, Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al. (1987) *Ann. Rev. of Plant Phys.* 38:467.

The nucleic acids and encoded polypeptides of the invention can be used to confer enhanced disease resistance on essentially any plant. Thus, the invention has use over a broad range of plants, including but not limited to species of *Asparagus, Atropa, Avena, Brassica, Citrus, Citrullus, Capsicum, Cucumis, Cucurbita, Daucus, eucalyptus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Setaria, Miscanthus, Nicotiana, Oryza, Panicum, Pennisetum, Persea, Pisum, Populus, Pyrus, Prunus, Raphanus, Secale, Senecio, Sinapis, Solanum, Sorghum, Trigonella, Triticum, Vitis, Vigna*, and, *Zea*.

VII. Selecting Plants with Enhanced Resistance

Plants with enhanced resistance can be selected or identified in many ways, including but not limited to the following. Plants with enhanced resistance can be identified by determining resistance of a plant to a specific plant pathogen. Possible pathogens include, but are not limited to, viruses, bacteria, nematodes, fungi or insects (see, e.g., Agrios, *Plant Pathology* (Academic Press, San Diego, Calif.) (1988)). One of skill in the art will recognize that resistance responses of plants vary depending on many factors, including what pathogen or plant is used. Generally, enhanced resistance is measured by the reduction or elimination of disease symptoms (e.g., lesion formation) when compared to a control plant (e.g., a plant not contacted with a pathogen, a plant expressing or contacted with an immune polypeptide as described herein, and/or a plant not expressing XA21 or a protein with XA21 activity). In some cases, however, enhanced resistance can also be measured by the production of the hypersensitive response (FIR) of the plant (see, e.g., Staskawicz et al. (1995) *Science* 268:661). Plants with enhanced resistance can produce an enhanced hypersensitive response relative to control plants.

Disease resistance can also be determined by detecting release of antimicrobial chemicals or hormones by a plant, e.g., reactive oxygen species (H2O2, peroxynitrite, phytoalexins), defensins, thionins, chitinase, peroxidase, etc.

Disease resistance can also be determined by detecting gene expression of genes that are upregulated or downregulated during pathogen response. For example, expression of the following genes is upregulated in plants fending off pathogen attack: PR10b, Os04g10010, 0506g37224, Os06g13390, Os11g02100, Os10g28299, Os06g35700, Os12g36830, Os11g31550, Os04g09920, Os02g36190, and homologs thereof. Enhanced resistance can thus also be determined by measuring the increased expression of a gene operably linked to a promoter of a defense-related gene including but not limited to those listed above. Measurement of such expression can be measured by quantifying the accumulation of RNA or protein expression product (e.g., using northern or western blot techniques, respectively).

Defense gene promoter expression can also be determined by operably linking a reporter gene to the promoter. Reporter gene constructs allow for ease of measurement of expression from the promoter of interest. Examples of reporter genes include: β-gal, GUS (see, e.g., Jefferson et al. (1987) EMBO J6:3901), green fluorescent protein (GFP), luciferase, and others.

VIII. Examples

Introduction

The rice PRR, XA21, confers resistance to strains of the Gram-negative bacteria *Xanthomonas oryzae* pv. *oryzae* (Xoo). Xa21 codes for a predicted cell-surface localized receptor-like kinase consisting of an extracellular LRR domain, a transmembrane domain, and a non-RD cytoplasmic kinase domain (Tunkel et al., Mol. Microbiol. 58:289 (2005); Song et al., *Science* 270:1804 (1995)). Because identification of the PAMP that XA21 recognizes could have significant impact toward understanding this large class of receptors, we have directed a major effort towards isolation of this molecule. The present results show that raxX is a PAMP recognized by XA21.

Figure 1:
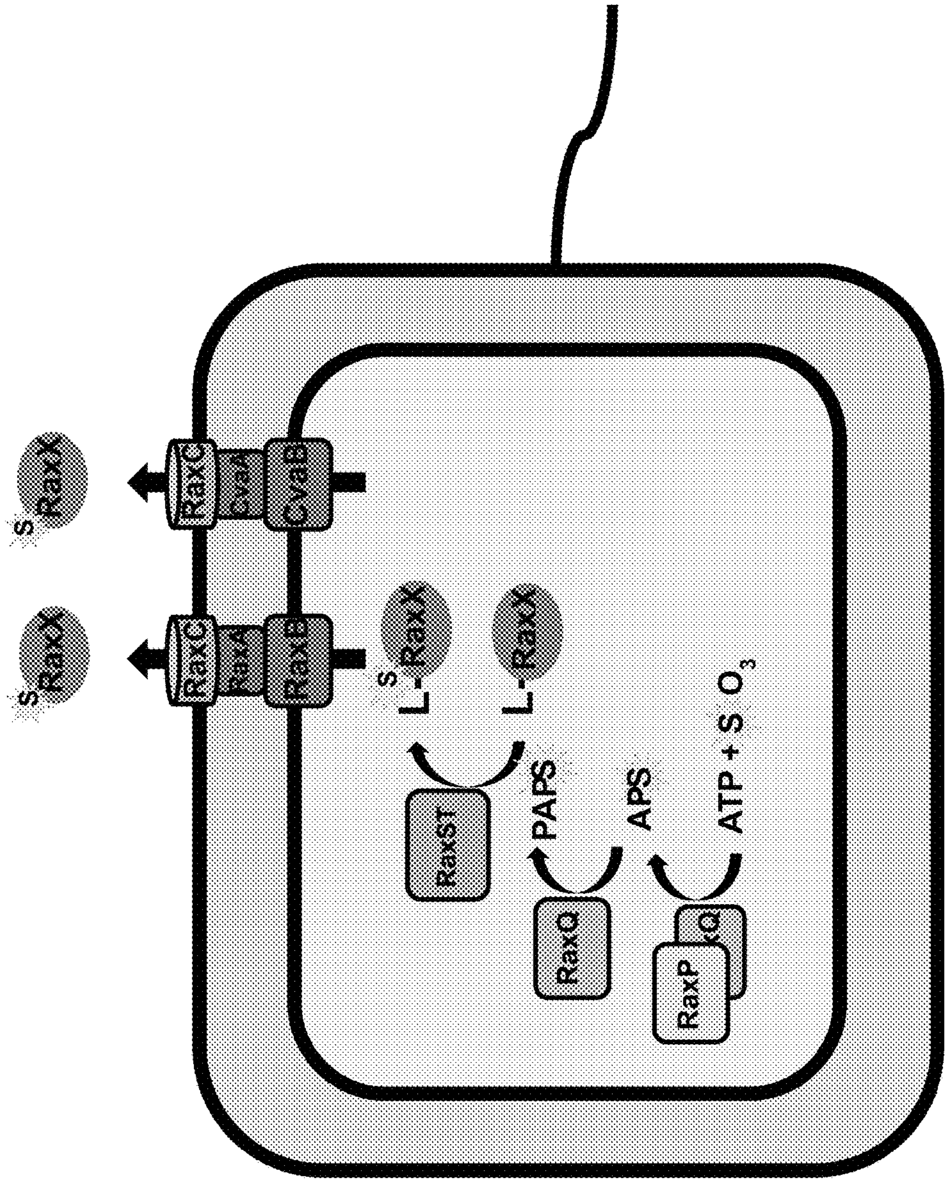
FIG. 1. Model for the synthesis and secretion of proteins required for activation of XA21-mediated immunity (encoded by rax genes). In this model, the adenosine-5'-triphosphate (ATP) sulfurylase RaxP and the adenosine-5'-phosphosulfate (APS) kinase RaxQ catalyze the production of the universal sulfuryl group donor 3'-phosphoadenosine-5'-phosphosulfate (PAPS). The RaxST sulfotransferase utilizes PAPS as a substrate to sulfate RaxX. RaxX contains a leader sequence (L), which we hypothesize is cleaved by the peptidase domain of RaxB and secreted outside the bacterial cell by the RaxABC T1SS. CvaA and CvaB, which are predicted orthologs of RaxA and RaxB, respectively, are hypothesized to serve as an alternate T1SS to process and secrete sulfated RaxX.

Previous studies, using genetic approaches, led to the identification of six Xoo genes falling into two functional classes, which are required for activation of XA21-mediated immunity (rax) (see FIG. 1). Genes in the first class, raxA, raxB, and raxC, encode a predicted membrane fusion protein (MFP), an adenosine triphosphate (ATP) binding cassette (ABC) transporter protein, and an outer membrane protein (OMP), respectively. Together these three proteins are predicted to comprise a type I secretion system (T1SS), a structure known to be involved in secretion of molecules outside of the bacterial cell (da Silva et al. (2004) *Mol Plant Microbe Interact* 17:593; Holland et al. (2005) *Mol Membr Biol* 22:29). RaxB falls into a clade of ABC-transporters that carry a proteolytic peptidase domain in their N-termini, termed C39, which cleaves a characteristic double glycine (GG) motif-containing signal peptide from substrates before secretion (Holland et al. (2005) *Mol Membr Biol* 22:29; Dirix et al. (2004) *Peptides* 25:1425). RaxABC T1SS appears to be involved in the secretion of peptides/proteins and that these substrates are processed before or during secretion. We show herein that cvaB shares overlapping function with raxB.

The second class of rax genes is involved in sulfation. raxP and raxQ, encode an ATP sulfurylase and an adenosine-5'-phosphosulfate (APS) kinase. These proteins function in concert to produce 3'-phosphoadenosine 5'-phosphosulfate (PAPS), the universal sulfuryl group donor. This class also includes the raxST-encoded sulfotransferase. raxST resides in the same operon with raxA and raxB (raxSTAB), indicating that this group of proteins targets similar substrates and/or control a similar biological process. Strains carrying mutations in these rax genes compromise the ability of Xoo to activate XA21-mediated immunity. In support of a role for these genes in a shared biological process, raxST and other rax genes are transcriptionally regulated by cell density, where high cell density induces, and low cell density represses, gene expression (Lee et al. (2006) *PNAS* 103: 18395).

Xoo is both a serious disease of rice, an important US crop, and is a model organism for studies of other Xanthomonads, which infects virtually all plant species. Amino acid sequence identity examination of the raxX-raxSTAB genomic region reveals that orthologs are present in the agronomically important pathogens *X. oryzae* pv. *oryzicola* (Xoc) (98% identity), *X. campestris* pv. vesicatoria (Xcv) (88% identity), *X. axonopodis* pv. *citrumelo* (Xac) (88% identity) and *X. campestris* pv. *musacearum* (Xcm) (>85% identity). In addition, the XA21 pattern recognition receptor (PRR) class of receptors is widespread in plants and critical for plant health. The present results can thus be applied to other pathogen-host systems.

Example 1: RaxST is a Functional Tyrosine Sulfotransferase

Tyrosine sulfation was previously thought to be a process restricted to eukaryotes. Xoo RaxST is, however, capable of in vitro tyrosine sulfotransferase activity (Han et al. (2012) *Nature Comm* 3:1153). A raxST insertion mutant strain can overcome XA21-mediated resistance and form long lesions on XA21 carrying plants, compared with the short lesions observed with its wild type parent strain (PXO99A) (da Silva et al. (2004) *Mol Plant Microbe Interact* 16:593). We have recently generated a new RaxST mutant, which has the entire raxST gene deleted (PXO99AΔraxST). PXO99AΔraxST has the same phenotype as the original raxST insertion mutant (FIG. 2), further confirming that raxST is required for activation of XA21-mediated immunity.

We complemented the PXO99AΔraxST mutant phenotype by insertion of the full-length raxST driven by its putative native promoter in to the bacterial chromosome. To create this strain, we isolated the raxST gene plus a 500 bp upstream sequence and ligated it into the suicide vector pJP5603, which contains a kanamycin resistance marker. The vector also carries a 500 bp sequence that is homologous to a region of the Xoo genome located 2 Mbp upstream of the raxSTAB operon.

Figure 2:
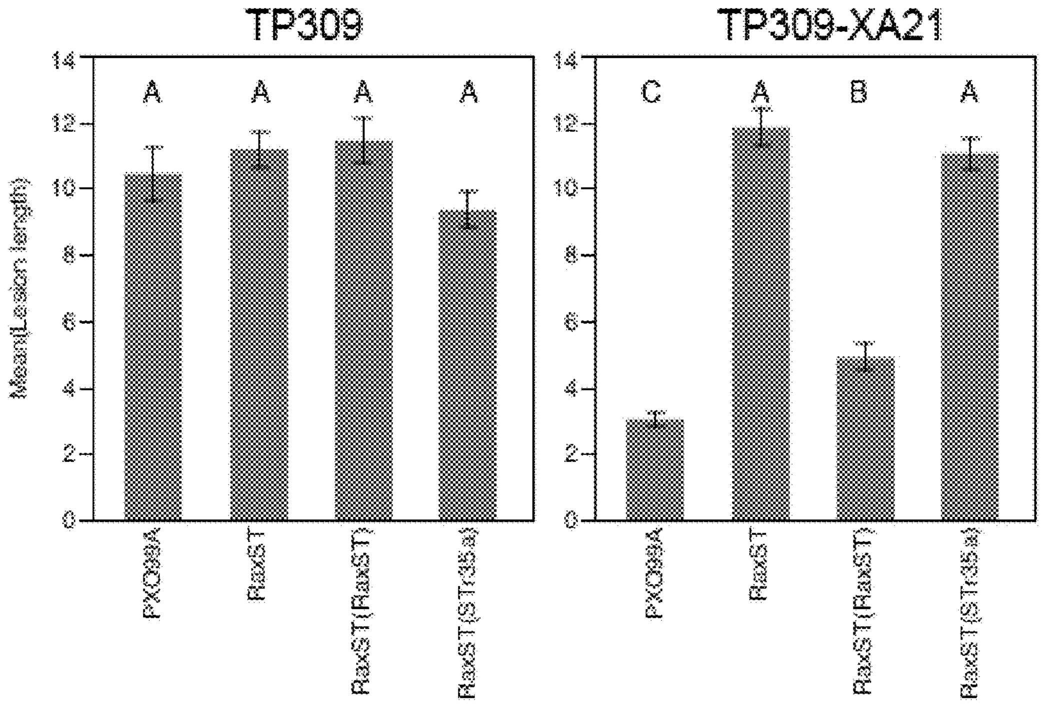
FIG. 2. raxST is required for activation of XA21-mediated immunity. The standard leaf clipping method (Jiang et al. (2013) *Plant J.* 73:814) was used to inoculate rice plants (TP309 and TP309-XA21) with a $10^8$ CFU/mL bacterial suspension. Lesion lengths were measured 14 days post inoculation. Bars represent the mean of at least 10 leaves±SE.

PXO99A, PXO99AΔraxST, and the complemented raxST deletion mutant (PXO99AΔraxST(RaxST)) were tested for their ability to form lesions on susceptible rice cultivar Tapei 309 (TP309) using an established leaf clipping method, and the resistant line expressing the XA21 receptor driven by the native promoter (TP309-XA21). FIG. 2 shows that raxST restores XA21-mediated immune activation to the PXO99AΔraxST strain. A similarly constructed mutant carrying a raxST variant with the conserved residue Arg35, part of the predicted PAPS binding motif, mutated to alanine, cannot complement the activation phenotype. In other words, Arg35 is critical for activation of XA21-mediated immunity, suggesting that PAPS binding is required for activation. All strains grow to high levels in control TP309 plants, lacking XA21.

Example 2: raxB/cvaB Double Insertion Mutant Overcomes XA21 Mediated Immunity The presence of predicted components of a T1SS together with RaxST in the same operon led us to hypothesize that the targets of RaxST-mediated sulfation are secreted through this system. However, PXO99AΔraxST forms longer disease lesions on TP309-XA21 plants than raxA or raxB insertion mutants, indicating different effects. We recently identified a RaxB homolog, named CvaB, with 50% identity to RaxB, and created an insertion mutant in the gene encoding this protein. We found that while a mutation in cvaB alone did not alter Xoo virulence on XA21 plants, a strain carrying mutations in both raxB and cvaB resulted in significantly longer lesions than those of the raxB single insertion mutant (FIG. 3). Because CvaB is the only predicted ortholog for RaxB, we hypothesize that the raxB/ cvaB double mutant is incapable of secreting proteins that activate XA21-mediated immunity.

Example 3: Identification of a Small Peptide (RaxX) that is a Candidate for RaxST-Mediated Sulfation We hypothesized that the coding sequence for the substrate of the raxSTAB operon may be localized in the same genomic region. To identify candidates that may be substrates of RaxA/B and serve to activate XA21-mediated immunity, we created three strains carrying various deletions in the regions upstream and downstream of the raxSTAB operon. One mutant strain, carrying a 1 kb deletion upstream of RaxSTAB (PXO99AΔUps), could overcome XA21-mediated immunity, similar to strains carrying a deletion in raxST (FIG. 4).

We next examined whether this 1 kb region contained ORFs encoding potential targets of RaxST sulfation. We identified one small ORF, encoding a 60 amino acid polypeptide within this region called raxX, which is expressed in Xoo. All Xoo strains that carry raxX activate XA21-mediated immunity.

To test the role of raxX in XA21-mediated immunity, we complemented the PXO99AΔUps mutant with the raxX ORF plus its native promoter using the broad host range vector pVSP61. FIG. 4 shows that introduction of raxX in the PXO99AΔUps (PXO99AΔUps(raxX)) mutant partially complemented the mutant phenotype (i.e. complementation partially restored the ability of Xoo to activate XA21-mediated immunity). To confirm that raxX is responsible for the complementation, we mutated the start codon in the complementation construct (PXO99AΔUps(raxXatg-ccc)). This mutant still caused long lesions on TP309-XA21 indicating that raxX encodes a factor required for activation of XA21-mediated immunity.

Example 4: The Conserved Tyrosine of RaxX is Required for Activation of XA21-Mediated Immunity We hypothesized that RaxX is a target of RaxST sulfation and that sulfation of RaxX is required for activation of XA21-mediated immunity. RaxX contains a tyrosine that is conserved among all of the sequenced *Xanthomonas* species that contain the RaxSTAB operon. Although this tyrosine is not predicted to be sulfated by three common sulfation prediction software programs, which all have been trained with eukaryotic protein sulfation sites, it does have an acidic residue in the −1 position, which is observed in some tyrosine sulfation sites. To test if this tyrosine is the target of sulfation, we generated a complementation construct encoding RaxX with the tyrosine mutated to phenylalanine (PXO99AΔUps(raxXY41F)). The construct was introduced into PXO99AΔups, and tested for its ability to induce resistance on TP309-XA21 plants. PXO99AΔUps (raxXY41F) formed long lesions on TP309-XA21 plants similar to the PXO99AΔUps (FIG. 4). The data thus show that RaxX is a RaxST target and suggests that sulfated RaxX is detected by XA21.

Example 5: The RaxX Deletion Mutant Overcomes XA21-Mediated Immunity

The 1 kb deletion analysis and complementation results suggest that the peptide RaxX, encoded upstream from raxST is required for activation of XA21-mediated immunity. To confirm these results, we made a more precise deletion mutant deleting only the raxX gene using a marker free approach and the suicide vector pUFR80. We complemented the marker free raxX deletion mutant with our raxX complementation construct. The mutant and complemented strain were tested for their ability to form lesions on TP309 and TP309-XA21 plants. The PXO99AΔraxX formed long lesions on TP309-XA21 (21.8 cm), whereas the complemented strain PXO99AΔraxX(raxX) caused short lesions (6.8 cm) similar to PXO99A (6.6 cm).

Example 6: Construction of a pRaxST-GFP Reporter Strain

To further investigate the role of RaxST in XA21-mediated immunity, we established a promoter-reporter system to perform a genetic screen to identify regulators of raxST. The reporter construct (pRaxST-GFP) has the raxST promoter region (defined to be −135 to −151 bp) fused to GFP (green fluorescent protein). Using qPCR, we found that expression levels of the pRaxST-GFP transcript in the PXO99A (pRaxST-GFP) strain at high cell densities is similar to levels of raxST expression in the PXO99A wild type strain. Because raxST is expressed in a cell density dependent manner in the wild-type strain, mutants that no longer express pRaxST-GFP at high cell density are likely to be impaired in the function of genes that serve as regulators of raxSTAB. Mutants in the PXO99 (pRaxST-GFP) strain can thus be used to identify such regulators.

Example 7: Generation of High Purity Non-Sulfated and Sulfated RaxX-his in *E. coli*

To further test whether raxX is the target of RaxST-mediated sulfation and RaxAB-mediated processing and secretion, we designed a novel and efficient method to synthesize selectively sulfated proteins in *E. coli*. To carry out these experiments we created a RaxX fusion protein with an N-terminal MBP-tag followed by a 3C protease cleavage site and a C-terminal 6×His tag (MBP-3C-RaxX-His). MBP-3C-RaxX-His was expressed at high levels in *E. coli* at 20° C. overnight. MBP-3C-RaxX-His was purified on a Ni-NTA column and the N-terminal MBP-tag removed by overnight 3C protease treatment. We further purified RaxX-His by size-exclusion chromatography to homogeneity. Following this two-step purification method we are able to obtain approximately 3 mg of pure RaxX-His per liter of culture.

In order to produce sulfated RaxX-His we used a recombinant expression system for sulfated proteins where the codon for the desired sulfotyrosine residue is mutated to the TAG amber codon, which typically leads to translation termination. In this system, however, a specifically engineered orthogonal aminoacyl-tRNA synthetase/tRNA (aaRS/tRNA) pair is co-expressed from the pULTRA SYP29 plasmid. This tRNA recognizes the amber codon and incorporates sulfotyrosine, which is supplied in the media, at the desired position (Liu and Schultz (2006) *Nature Biotech.* 24:1436; Liu et al. (2009) *Nature Protocols* 4:1784). Using this system and our previously established expression and purification conditions described above for MBP-3C-RaxX-His we obtain approximately 1 mg of pure sufated RaxX (sY)-His per liter of culture. We confirmed tyrosine sulfation of RaxX(sY)-His by band shift assays on Tris-Tricine gels and selective reaction monitoring mass-spectrometry on trypsin digested peptides (FIGS. 5A and 5B).

Example 8: Purified, Sulfated RaxX Activates XA21-Mediated Immunity

Using the RaxX-His peptides purified as described above, we tested for RaxX-His and RaxX(sY)-His ability to induced defense gene expression in wild type plants or plants expressing XA21. As shown in FIG. 6, RaxX-His induced defense gene expression, e.g., PR10b, in a tyrosine sulfation and XA21-dependent manner.

Example 9: Characterization of Fragment of raxX that Activates XA21-Mediated Immunity Five different proteases were used individually to digest 50 ug RaxX-sY (amino acids 21-60 of the full length RaxX). The digests were incubated overnight with 1 μg protease: GluC, Trypsin, ArgC, LysC, or AspN. Digest of RaxX-sY was complete for all digests when assessed by SDS-PAGE.

Detached leaf assays (Kitaake) were performed with a 500 nM (FIG. 7A) or 1 μM (FIG. 7B) peptide and gene expression was measured by qPCR after 24 hours of treatment. Controls included undigested RaxX-sY, RaxX (unsulfated), and untreated. Expression of Os06g13390 is shown as an indication of XA21-mediated gene expression.

The central ArgC peptide (amino acids 32-55) was active in these assays, indicating this fragment binds XA21 and activates pathogen resistance response. The digestion sites for each of the indicated proteases is shown in FIG. 7C.

Example 10: Establishment of Characterization Models

The raxB/cvaB double insertion mutant can be used to identify proteins that are no longer secreted in this strain. We therefore established methods to extract Xoo supernatants and characterize proteins present in this fraction using LC-MS/MS-based shotgun proteomics. To generate the supernatants, we grew Xoo cells overnight in two types of rich nutrient media (PSB and YEB) and one type of minimal nutrient media (M9) to an $OD_{600}$ of 0.5. We used three types of media to obtain a representative profile of secreted Xoo proteins that are not biased by specific growing conditions. Proteins were precipitated using 80% acetone precipitation or 0.1% TCA; trypsin and/or lysyl endopeptidase digested (to obtain maximum peptide coverage), and purified/desalted over a C18 column prior to mass spectrometry analysis. Samples were then analyzed by LC-MS/MS and data interpreted.

Essentially, protease digested samples (~5 μg) were analyzed by ESI-Q-TOF (Agilent 6550 iFunnel Q-TOF LC/MS). Data acquired and exported using MassHunter (Agilent Technologies) and the resultant MS/MS data was analyzed using Mascot (Matrix Sciences) against a custom database comprising the RefSeq PXO99A proteins (ca. 5000 proteins) and all Viridiplantae proteins (ca. 565,000 proteins) available through NCBI. Thresholds were also set to reduce the false discovery rate ($p \leq 0.05$) and ensure significant peptide and protein matching. This led to the identification of over 100 secreted proteins from the three conditions in two independent experiments.

In addition, we successfully identified native RaxX protein in lysed cell samples of the wild type PXO99A Xoo strain. Briefly, total protein was extracted from PXO99A grown on solid YEB agar using Tris:Urea and treated similar to the methods described above. Digested peptide samples were then tested in the Orbitrap Fusion (Thermo Fisher), leading to the detection of native RaxX protein.

We have also established methods to isolate proteins from Xoo apoplastic fluids. Four week-old rice plants were infected with PXO99A using established methods (Kauffman et al. (1973) *Plant Dis Rep* 57:537). Approximately 100 leaves were inoculated with each strain. Six days post inoculation, 5 cm leaf sections closest to the infection site were harvested, shredded into 2 mm pieces, submerged in water and vacuum infiltrated at 22 psi four times for 15 min each. Infiltrated leaves were then surface dried and placed in a 35 ml syringe fitted into a 50 ml Falcon tube. The fitted tubes were centrifuged for 10 min at 5000 rpm twice. Approximately 7 ml of apoplastic fluid was collected from the 100 leaf samples. This strategy can be used to identify Xoo proteins that are secreted only in the presence of the host using LC-MS/MS based proteomics.

Summary

The present results demonstrate the role of the sulfotransferase RaxST in activation of the rice XA21 receptor. The results also allow us to identify genes that regulate raxSTAB expression and further characterize raxX, RaxST, RaxB, the interaction with the rice XA21 PRR, and the implications for homologous interactions. While the present results show that raxX activates XA21-mediated immunity, we cannot rule out that there are other raxST targets and that these may also activate XA21-mediated immunity.

We found a number of RaxX homologs in other Gram negative bacteria. Exemplary coding sequences are shown below in the informal sequence listing. The percent identity is shown for the amino acid sequences in FIG. 8, and the nucleotide coding sequences in FIG. 9. An alignment of raxX amino acid sequences is shown in FIGS. 10A and 10B.

Example 11

Plasma membrane localized receptors are critical components of the innate immune responses of animals and plants (Jones J D & Dangl J L (2006) *Nature* 444(7117):323-329; Ronald P C & Beutler B (2010) *Science* 330(6007):1061-1064; Kawai T & Akira S (2010) *Nature immunology* 11(5):373-384; Schwessinger B & Ronald P C (2012) *Annual review of plant biology* 63:451-482). Many of these receptors recognize and respond to the presence of conserved microbial molecules and are often referred to as pattern recognition receptors (PRRs). In animals, this recognition is carried out, in part, by toll-like receptors (TLRs) (Kawai T & Akira S (2010) *Nature immunology* 11(5):373-384). Humans have 10 characterized TLRs that recognize conserved microbial molecules such as lipopolysaccharide or flagellin (Poltorak A, et al. (1998) *Science* 282(5396):2085-2088; Hayashi F, et al. (2001) *Nature* 410(6832):1099-1103).

In plants, cell surface receptor kinases (RKs) and receptor-like proteins (RLPs) recognize (conserved) microbial molecules in the apoplast (Song W Y, et al. (1995) *Science* 270(5243):1804-1806; Chen X, et al. (2006) *Plant J* 46(5):794-804; Sun X, et al. (2004) *Plant J* 37(4):517-527; Gomez-Gomez L & Boller T (2000) *Mol Cell* 5(6):1003-1011; Macho A P & Zipfel C (2014) *Mol Cell* 54(2):263-272; Cao Y, et al. (2014) *eLife* 3; Hayafune M, et al. (2014) *Proc Natl Acad Sci USA* 111(3):E404-413). Well-characterized LRR-RKs include *Arabidopsis* FLS2 that detects flagellin, or its peptide epitope flg22, and the elongation factor Tu receptor (EFR) that detects the bacterial elongation factor Tu, or its peptide epitope elf18 (Gomez-Gomez L & Boller T (2000) *Mol Cell* 5(6):1003-1011; Zipfel C, et al. (2006) *Cell* 125(4):749-760). Lacking an adaptive immune system, plants have an extended array of innate immune receptors encoded in their genome. Rice, for example, has over 300 RKs predicted to serve as innate immune receptors based on the presence of a "non-RD" kinase domain which lack the arginine-aspartate motif (Dardick C & Ronald P (2006) *PLoS pathogens* 2(1):e2; Dardick C, Schwessinger B, & Ronald P (2012) *Current opinion in plant biology* 15(4): 358-366). Of the few non-RD RKs characterized to date, all have a role in innate immunity or symbiosis (Schwessinger B & Ronald P C (2012) *Annual review of plant biology* 63:451-482; Berrabah F, et al. (2014) *The New phytologist* 203(4):1305-1314).

The rice XA21 RK, one of the first innate immune receptors isolated, mediates recognition of the Gram-negative bacterium *Xanthomonas oryzae* pv. *oryzae* (Xoo), the causal agent of a serious disease of rice (Song W Y, et al. (1995) *Science* 270(5243):1804-1806; Khush G S, Bacalangco E, & Ogawa T (1990) *Rice Genetics Newsl.* 7:121-122). Previous efforts to identify the microbial molecule that activates the XA21-mediated immune response led to the identification of a number of Xoo genes that are required for activation of XA21 (rax genes). These genes encode a tyrosine sulfotransferase, RaxST, and three components of a predicted type 1 secretion system (T1SS): a membrane fusion protein, RaxA; an ATP-binding cassette transporter, RaxB; and an outer membrane protein, RaxC (da Silva F G, et al. (2004) *Mol Plant Microbe Interact* 17(6):593-601). raxST, raxA, and raxB are located in a single operon (raxSTAB) (da Silva F G, et al. (2004) *Mol Plant Microbe Interact* 17(6):593-601). Based on these findings, we hypothesized that the activator of XA21-mediated immunity is a tyrosine sulfated, type 1-secreted protein (da Silva F G, et al. (2004) *Mol Plant Microbe Interact* 17(6):593-601). However, the identity of this molecule has remained elusive (Lee S W, et al. (2013) *Science* 342(6155):191; Ronald P (2013) *Scientific American*; Bahar O, et al. (2014) *Peer J* 2: e242). Here we report the identification of the tyrosine sulfated protein RaxX, as the activator of XA21-mediated immunity.

Results

RaxX is Required for Activation of XA21-Mediated Immunity

Figures 11A, 11B, 11C, 11D:
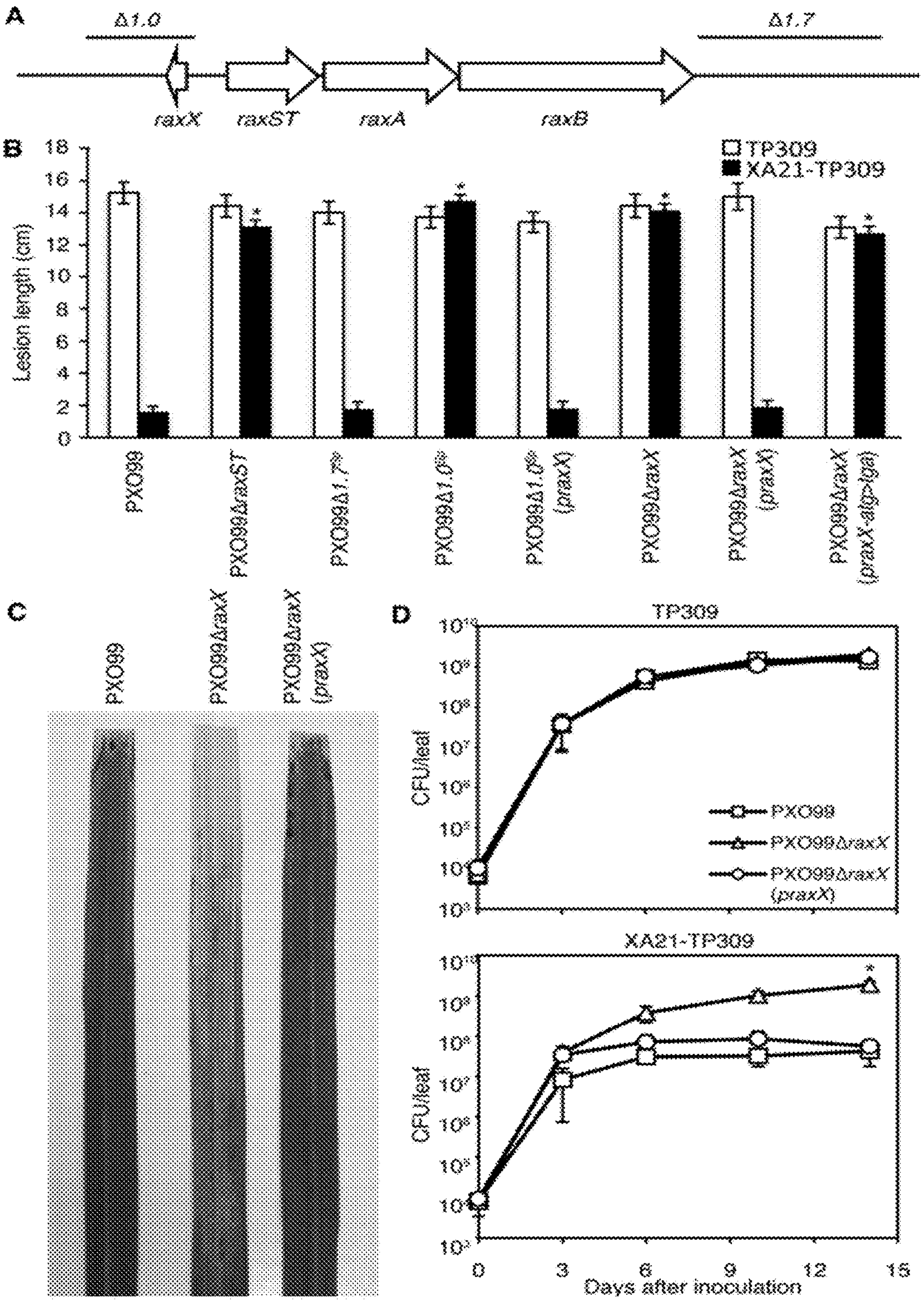

RaxB belongs to a subgroup of T1SS ABC transporters that contain a C39 peptidase domain (da Silva F G, et al. (2004) *Mol Plant Microbe Interact* 17(6):593-601). In other bacterial species, substrates for this class of secretion systems are often encoded in or near the T1SS operon (Michiels J et al., (2001) *Trends Microbiol* 9(4):164-168). We therefore hypothesized that the RaxST/A/B substrate may be genetically linked to the raxSTAB operon. To test this hypothesis, we generated mutants in the Xoo strain PXO99 (Salzberg S L, et al. (2008) *BMC genomics* 9:204) with either a 1 kb deletion ~0.4 kb upstream from raxST (PXO99Δ1.0$^{Sp}$) or a 1.7 kb deletion immediately after raxB (PXO99Δ1.7$^{Sp}$) (FIG. 11A). The mutants were used to inoculate Taipei 309 (TP309), a rice variety lacking XA21, and XA21-TP309, a transgenic derivative expressing XA21 under control of its native promoter (Song W Y, et al. (1995) *Science* 270(5243): 1804-1806). On TP309, all strains formed long, water-soaked lesions typical of the disease (FIG. 11B). PXO99Δ1.7$^{Sp}$ formed short lesions on XA21-TP309 similar to the control strain PXO99. In contrast, PXO99Δ1.0$^{Sp}$, formed long lesions on XA21-TP309. These results suggested that the region upstream to the raxSTAB operon contains an element that is required for activation of XA21-mediated immunity.

Sequence analysis of this 1 kb region revealed the presence of a 183 nucleotide ORF (covering the PXO99 genomic region 1, 282, 744-1, 282, 926). The ORF, which we named raxX (FIG. 11A), is not annotated in the PXO99 genome. We found that raxX is conserved among all sequenced *Xanthomonas* strains that encode the raxSTAB operon (FIGS. 15A-15B), but that it is not present in *Xanthomonas* species that lack the raxSTAB operon. RaxX shares no homology with other microbial proteins of known function.

To further investigate the role of RaxX, we transformed PXO99Δ1.0$^{Sp}$ with a broad-range host vector expressing raxX under control of its native promoter (praxX). PXO99Δ1.0$^{Sp}$ (praxX) regained the ability to activate XA21-mediated immunity and formed short lesions on XA21-TP309 (FIG. 11B). To confirm the importance of raxX in activation of XA21-mediated immunity, we generated a marker-free PXO99 mutant with the raxX open reading frame deleted (PXO99ΔraxX). As observed for PXO99Δ1.0$^{Sp}$, PXO99ΔraxX evades the XA21-mediated immune response, forming long lesions on XA21-TP309 (FIGS. 11B, C). PXO99ΔraxX(praxX) also regained the ability to activate XA21-mediated immunity (FIGS. 11B, C). Similar results were obtained when these strains were inoculated on rice plants overexpressing XA21 in the Kitaake genetic background (Ubi::Xa21) (Park C J, et al. (2010) *Plant science: an international journal of experimental plant biology* 179(5):466-471) (FIGS. 12A-12D). A variant of praxX carrying a mutation in the predicted start codon (praxX-atg>tga) failed to complement PXO99ΔraxX (FIG. 1B). PXO99ΔraxX bacterial populations accumulated to more than 30-fold higher levels in inoculated XA21-TP309 rice leaves than those of strains PXO99 and PXO99ΔraxX(praxX) (FIG. 11D). These results indicate that RaxX is required for activation of XA21-mediated immunity.

RaxX is Sulfated on its Central Tyrosine by RaxST

In addition to RaxST, we have previously identified two other rax genes involved in microbial sulfation. These genes, raxP and raxQ, encode an ATP sulfurylase and an adenosine-5'-phosphosulfate kinase, and work in concert to produce the universal sulfuryl group donor 3'-phosphoadenosine 5'-phosphosulfate (PAPS) (Shen Y et al. (2002) *Mol Microbiol* 44(1):37-48). The requirement of these three genes for activation of XA21-mediated immunity by Xoo suggests that tyrosine sulfation plays a key functional role in this process.

To further investigate this possibility, we transformed a raxST mutant strain (PXO99ΔraxST$^{Sp}$), which forms long lesions on XA21-TP309, with a plasmid expressing raxST under control of its native promoter (praxST). PXO99ΔraxST$^{Sp}$(praxST) regained the ability to activate XA21-mediated immunity. RaxST carries a predicted PAPS binding motif conserved in mammalian sulfotransferases including the human tyrosine sulfotransferases TPST1 and TPST2 (FIGS. 13A-13D) (da Silva F G, et al. (2004) *Mol Plant Microbe Interact* 17(6):593-601). In TPST2, mutation of the conserved arginine in the PAPS binding motif impairs enzymatic activity (Teramoto T, et al. (2013) *Nat Commun* 4:1572). We generated a similar mutation in raxST and tested if the expression of this mutant variant on a plasmid (praxST-R35A) could complement the PXO99ΔraxST$^{Sp}$ infection phenotype on XA21 expressing rice plants. The strain PXO99ΔraxST$^{Sp}$ (praxST-R35A) failed to activate XA21-mediated immunity (FIG. 12A) suggesting that sulfotransferase activity of RaxST is critical for its function.

Based on the genetic association of raxXwith the raxSTAB operon, the importance of tyrosine sulfation for activation of the XA21-mediated immune response, and the presence of a single tyrosine residue in PXO99 RaxX (Y41) that is conserved between all available RaxX sequences (FIGS. 15A-15B), we hypothesized that RaxX Y41 is sulfated by RaxST and that this sulfation is required for RaxX function. To test this hypothesis, we transformed PXO99ΔraxXwith a plasmid carrying a derivative of RaxX with tyrosine 41 mutated to phenylalanine (PXO99ΔraxX (praxX-Y41F)). PXO99ΔraxX(praxX-Y41F) failed to activate XA21-mediated immunity in XA21-TP309 (FIG. 12A and FIGS. 18A-18B). We also demonstrated that sulfated RaxX peptides, but not peptides carrying an Y41 to F substitution, are immunogenic on XA21 expressing rice plants (FIG. 19). These results support the hypothesis that sulfation of RaxX Y41 is required for its activation of XA21-mediated immunity.

To determine if RaxX Y41 is sulfated by RaxST in vitro, we incubated a chemically synthesized peptide covering the C-terminal region of RaxX (RaxX39, amino acids 22-60) with purified His-RaxST (FIG. 20) in the presence of PAPS. Trypsin-digested peptides were analyzed by liquid chromatography tandem mass spectrometry (LC-MS/MS) in both negative and positive nanoelectrospray modes with ultraviolet photodissociation (UVPD) to generate informative a, b, c, x, y, and z product ions from cleavage of the peptide backbone. This method has previously been shown to facilitate the characterization of sulfated tyrosine residues within peptides by tandem mass spectrometry (MS/MS). The lability of the sulfation modification proves problematic for other MS/MS methods (Han S W, et al. (2012) *Nat Commun* 3:1153; Robinson M R, Moore K L, & Brodbelt J S (2014) *Journal of the American Society for Mass Spectrometry* 25(8):1461-1471). In negative ion mode, the sulfate group is retained on all product ions, thus allowing the sulfate modification to be unequivocally localized to Y41 of RaxX. MS/MS data showed fragment ions that account for 93% sequence coverage of peptide HVGGGDsYPPPGANPK (SEQ ID NO:4; FIG. 12B). The high-resolution verification of the peptide mass in the negative mode MS1 (HVGGGDsYPPPGANPK; SEQ ID NO:4) is displayed in FIG. 21. The extracted ion chromatograms of the peptides of interest and positive mode UVPD mass spectrum are shown in FIG. 22 and FIG. 23, respectively.

Figure 12C:
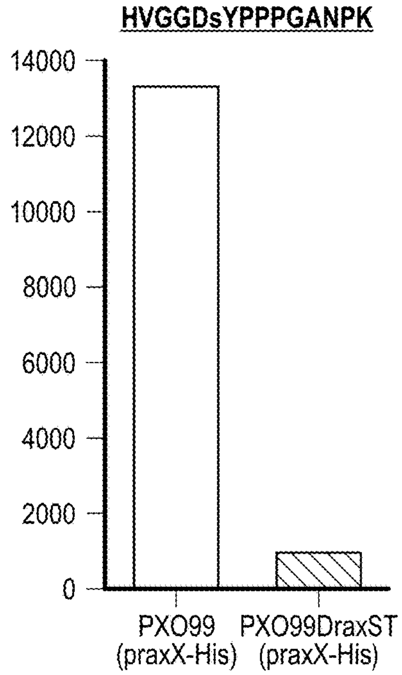
Figure 12D:
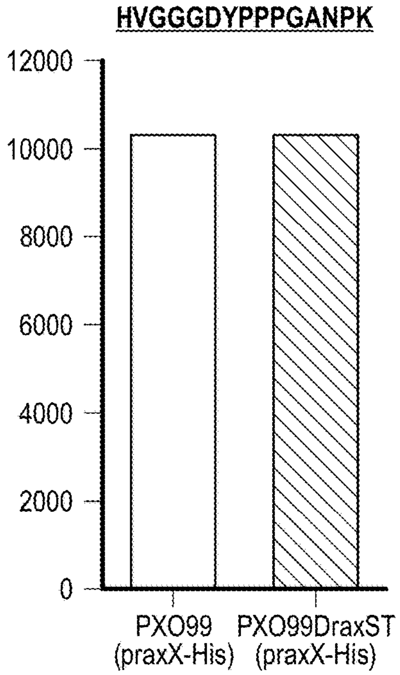

We next tested if RaxX is sulfated in vivo. Using selected reaction monitoring mass-spectrometry (SRM-MS) we observed sulfation on tryptic peptides covering Y41 derived from RaxX-His purified from PXO99(praxX-His) (FIG. 12C, FIGS. 24 and 26A-26B). The sulfated version of the tryptic peptide covering Y41 of RaxX-His purified from PXO99ΔraxST(praxX-His) was not detectable with multiple SRM transitions above the background noise level (~50-100 cps) (FIG. 12C, FIGS. 26A-26B). In contrast, we did detect the corresponding nonsulfated peptide covering Y41 at high levels and with high confidence for RaxX-His isolated from both PXO99 (praxX-His) and PXO99ΔraxST(praxX-His) (FIG. 12D, FIGS. 25A-25D). In combination these results demonstrate that RaxST sulfates RaxX on Y41 in vivo and that sulfation of RaxX is required for its immunogenic activity on XA21 expressing rice plants.

RaxX is Sufficient for Activation of XA21-Mediated Immunity

Infection assays using bacterial mutants clearly demonstrate that RaxX is required for activation of XA21-mediated immunity. We next sought to determine if sulfated RaxX can trigger XA21-mediated defense responses in the absence of Xoo. For this purpose, we produced full-length sulfated recombinant RaxX (RaxX60, 1-60 aa) using an expanded genetic code approach (Liu C C & Schultz P G (2006) *Nature biotechnology* 24(11):1436-1440; Lajoie M J, et al. (2013) *Science* 342(6156):357-360). We heterologously expressed RaxX in *E. coli* together with an engineered aminoacyl-tRNA synthetase specific for sulfotyrosine, a cognate engineered amber suppressor tRNA and the non-standard amino acid sulfotyrosine (sY) (Liu C C et al., (2009) *Nature protocols* 4(12):1784-1789). Nonsulfated RaxX was also expressed in *E. coli* without sulfotyrosine. We confirmed purity and tyrosine sulfation status of RaxX60 by gel-based assays and SRM-MS analysis (FIG. 25A-25D). We tested if the resulting highly purified, full-length, sulfated RaxX60-sY and nonsulfated RaxX60-Y proteins could trigger defense gene expression in leaves of rice plants overexpressing XA21 (Ubi::XA21). As shown in FIGS. 27A-27B, sulfated RaxX60-sY, but not the nonsulfated form RaxX60-Y, triggered strong up-regulation of defense marker genes (Table 3) in detached leaves of Ubi::XA21. Leaves from Kitaake rice plants, which lack the XA21 immune receptor, are insensitive to RaxX60-Y and RaxX60-sY. These results demonstrate that sulfated RaxX60-sY is sufficient to activate XA21-mediated defense gene expression in rice.

Figures 13A, 13B, 13C:
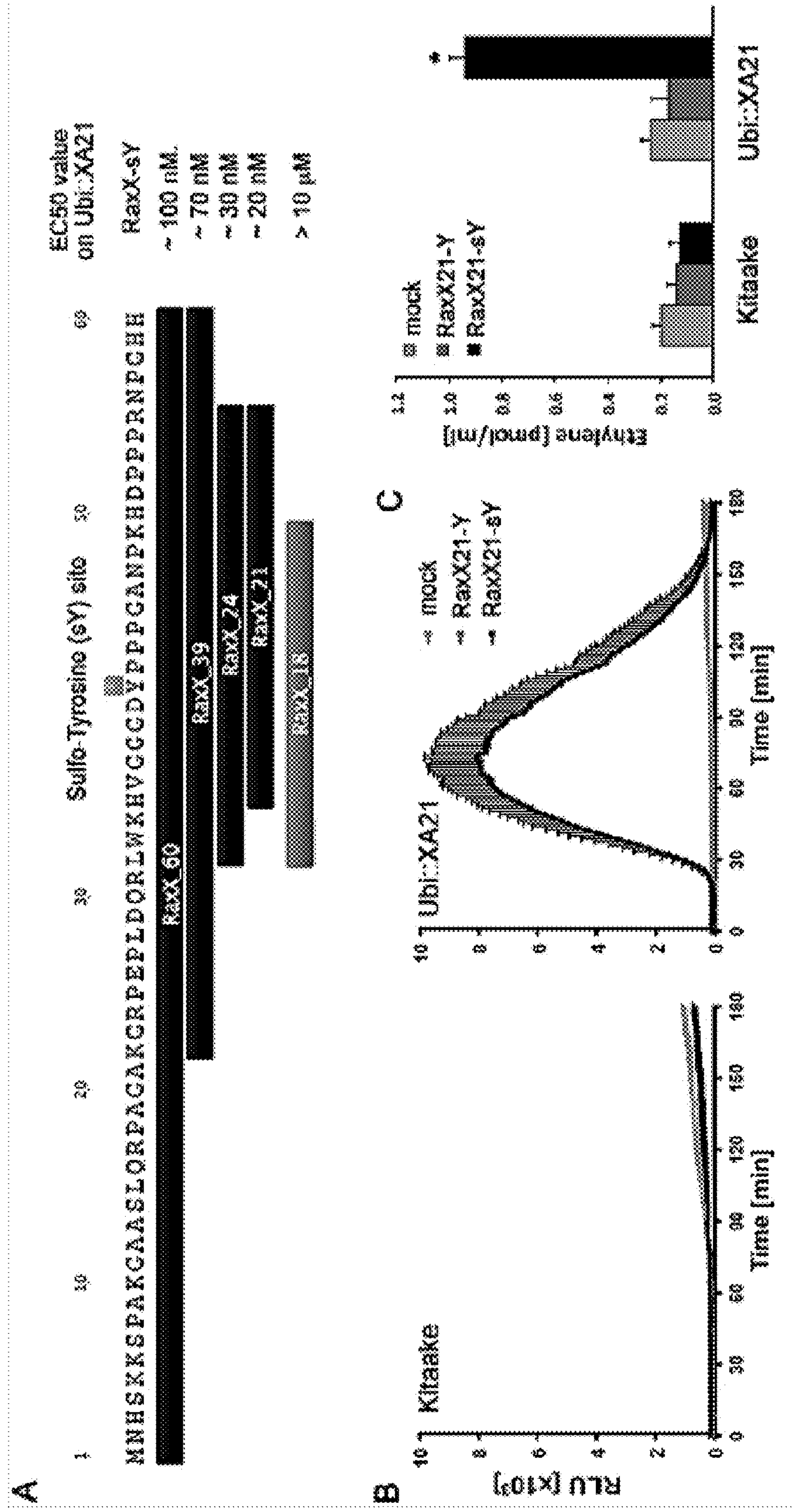

To identify a 'minimal' epitope of RaxX that is sufficient to trigger these responses, we took biochemical and rational design approaches. We first tested whether chemically synthesized RaxX39 is sufficient to trigger XA21-dependent defense gene expression (FIG. 13A, FIGS. 28A-28B). We found that sulfated RaxX39-sY triggers defense gene expression in an XA21-dependent manner, whereas nonsulfated RaxX39 does not (FIGS. 28A-28B). To further narrow down the active region, we subjected RaxX39 to digestion with four site-specific proteases (GluC, ArgC, AspN, and trypsin). The predicted digestion patterns were confirmed by gel-based assays and by SRM-MS analysis for ArgC, AspN and trypsin digests (FIGS. 29A-29D). We tested the resulting RaxX fragments for their ability to activate XA21-dependent signaling (FIG. 30A). Only RaxX39-sY digestion products resulting from GluC and ArgC treatments retained activity on Ubi::XA21 plants. The ability of the ArgC fragment (32-55 aa) to activate XA21-mediated immunity was confirmed with chemically synthesized RaxX24-sY (32-55 aa) peptides (FIG. 13A, FIG. 30B). Next, we tested N- and C-terminal truncated versions of RaxX24-sY peptides. Chemically synthesized RaxX21-sY (35-55 aa) retained the ability to induce XA21-dependent signaling whereas RaxX18-sY (32-49 aa) was compromised in this activity (FIG. 13A, FIG. 30B). These results indicate that a chemically synthesized tyrosine sulfated 21 amino acid derivative of RaxX, named RaxX21-sY, is sufficient to activate XA21-mediated defense responses.

Figure 13D:
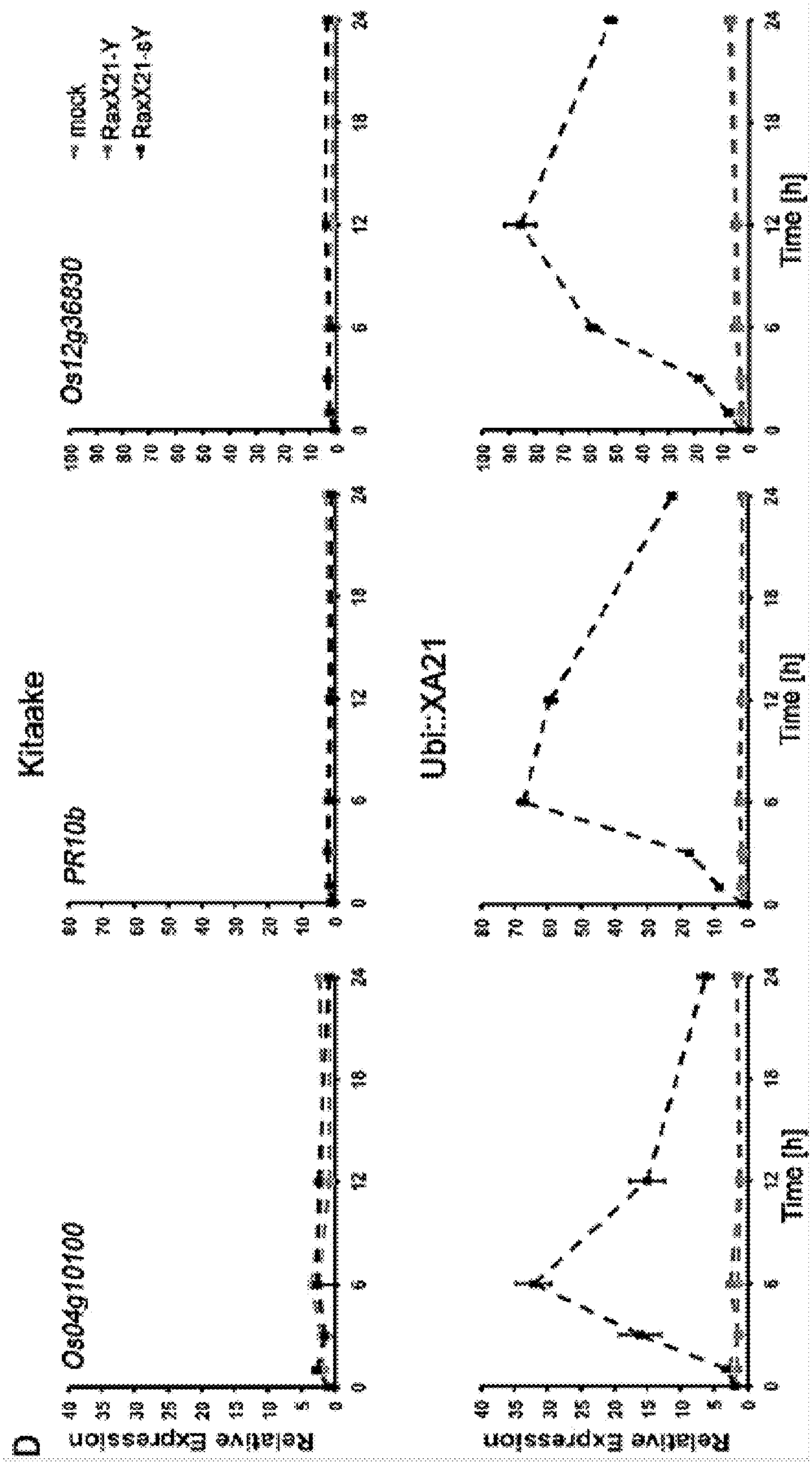

In addition to activation of defense marker gene expression, the activation of PRR-triggered immunity in plants often involves the production of ethylene and reactive oxygen species (ROS) (Macho A P & Zipfel C (2014) *Mol Cell* 54(2):263-272; Boller T & Felix G (2009) *Annual review of plant biology* 60:379-406). These responses are known to contribute to the final disease outcome in many plant pathogen interactions (Macho A P & Zipfel C (2014) *Mol Cell* 54(2):263-272; Boller T & Felix G (2009) *Annual review of plant biology* 60:379-406). We therefore tested if RaxX21-sY is able to trigger these hallmarks of plant innate immune signaling in XA21-expressing rice leaves (FIGS. 13B-13D, FIGS. 31A through 33B). As shown in FIGS. 13B-13D, only sulfated RaxX21-sY, but not RaxX21-Y, was able to activate defense marker gene expression and the production of ROS and ethylene in an XA21-dependent manner. These responses were most pronounced in rice plants overexpressing XA21 (Ubi::XA21). Nonetheless, we also observed significant RaxX21-sY-mediated upregulation of defense gene expression and ROS production in Kitaake lines expressing XA21 from its native promoter (XA21::XA21) (FIGS. 32 through 33B) with the highest levels of ROS production observed in rice leaves harvested at later stages of development (FIGS. 33A-33B).

To assess the sensitivity of XA21-expressing rice plants towards the different RaxX epitopes, we established the RaxX concentration needed to trigger the half maximal response (often referred to as the EC50 value) using the fast and quantitative ROS assay. The EC50 value in Ubi::XA21-expressing rice plants ranges from ~100 nM for RaxX60-sY, ~70 nM for RaxX39-sY to ~30 nM for RaxX24-sY and ~20 nM for RaxX21-sY (FIG. 13A and FIGS. 34A-34E). In contrast, the further truncated peptide RaxX18-sY was completely inactive, even at high peptide concentrations (FIGS. 34A-34E). As an additional control, we tested an unrelated tyrosine sulfated peptide called axY(S)22, derived from a PXO99 outer membrane protein (ACD57244), for its ability to activate XA21-mediated immunity (Lee S W, et al. (2013) *Science* 342(6155):191; Bahar O, et al. (2014) *Peer J* 2:e242). Rice leaves overexpressing XA21 were insensitive to axY(S)22 at high peptide concentrations (1 μM) under conditions in which RaxX21-sY induced ROS production and defense gene expression changes (FIGS. 35A-35B). In summary, our data demonstrates that XA21-mediated immune signaling in rice is specifically induced by RaxX60-sY, and sulfated epitopes derived from the full RaxX60 protein, at low nanomolar concentrations.

Identification of a RaxX Variant that Evades XA21-Mediated Immunity

Figures 14A, 14B, 14C, 14D, 14E:
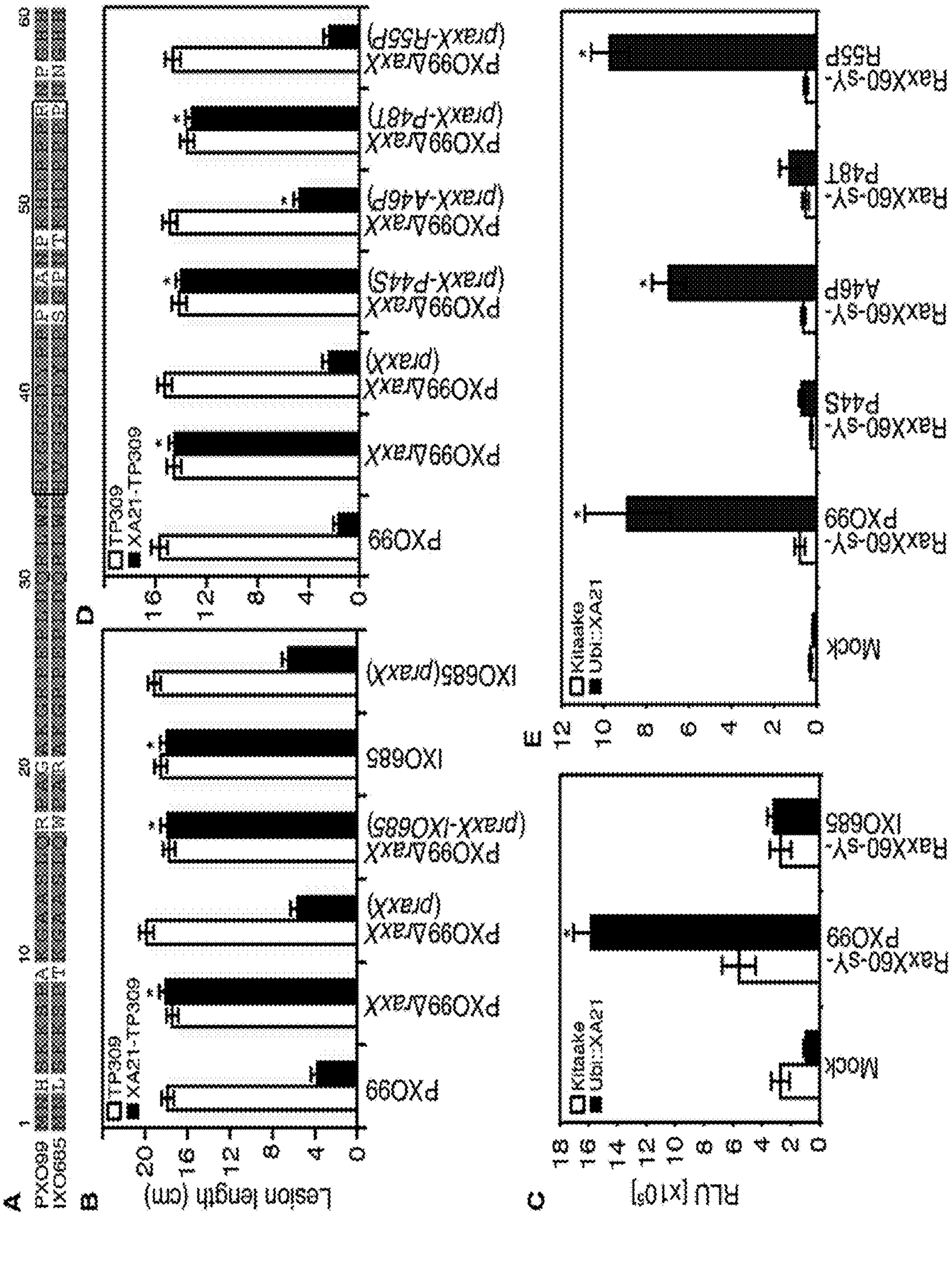

When XA21 was first discovered, it was demonstrated to confer resistance to most tested strains of Xoo (Khush G S, Bacalangco E, & Ogawa T (1990) *Rice Genetics Newsl.* 7:121-122; Wang G L et al. (1996) *Mol Plant Microbe Interact* 9(9):850-855). Since that time, several field strains that evade XA21-mediated immunity have been identified (Mishra D, et al. (2013) *PLoS One* 8(11):e81996; Wang C L, et al. (2014) *Mol Plant Pathol* 15(4):333-341). For most of these strains, the molecular basis of immune evasion is unknown. However, we previously demonstrated that two of these Xoo strains, DY89031 and CK89021, carry mutations in raxA and raxST, respectively (da Silva F G, et al. (2004) *Mol Plant Microbe Interact* 17(6):593-601). We hypothesized that other strains may evade XA21-mediated immunity because they encode variant raxX alleles. Indeed, we found that RaxX from the Indian field isolate IXO685, which evades XA21 mediated immunity (Mishra D, et al. (2013) *PLoS One* 8(11):e81996), differs in 9 amino acids as compared with RaxX from PXO99 (FIG. 14A). Four amino acid changes are located in the RaxX21 sequence.

We tested if raxX from IXO685 expressed under control of the native promoter of PXO99 raxX was able to complement the PXO99ΔraxX mutant phenotype on XA21 expressing rice plants. We found that PXO99ΔraxX(praxX-IXO685) was unable to activate XA21-mediated immunity (FIG. 14B). Likewise, recombinant, highly purified RaxX60-sY-IXO685 produced using our expanded genetic code system was not able to trigger XA21-mediated ROS production (FIG. 14C, FIG. 36). Expression of the PXO99 raxX allele in the IXO685 strain conferred the strain with the ability to activate XA21-mediated immunity (FIG. 14B). These results indicate that IXO685 is able to overcome XA21-mediated immunity because it has acquired several non-synonymous substitutions in the raxX ORF. Two other Indian field isolates, (IXO651 and IXO1221), which are also able to evade XA21-mediated immunity (Mishra D, et al. (2013) *PLoS One* 8(11):e81996) and share the identical raxX sequence with IXO685 can also be complemented withprax (FIG. 37).

To determine if the four identified residues within the RaxX21 minimal epitope that differ with the XA21-evading strains are essential for XA21 activation, we carried out mutational analyses. The four residues were mutated in praxX and the mutated alleles were tested for functional complementation of the PXO99ΔraxX mutant by inoculation of XA21-expressing rice plants (FIG. 14D). PXO99ΔraxX(praxX-P44S) and PXO99ΔraxX(praxX-P481) formed long lesions on XA21-TP309; PXO99ΔraxX (praxX-A46P) displayed an intermediate phenotype; and PXO99ΔraxX(praxX-R55P) formed short lesions. Consistent with this result, highly purified recombinant RaxX60-sY-P44S and RaxX60-sY-P48T proteins, produced using our expanded genetic code system, are unable to induce ROS production in Kitaake Ubi::XA21 (FIG. 14E, FIG. 36). Thus, P44 and P48 are required for activation of XA21-mediated immunity. In other words, the alterations of these specific amino acids in RaxX of IXO685, IXO651, and IXO1221 enable these strains to evade XA21-mediated immunity.

Discussion

Our results indicate that the presence or absence of sulfation and the residues near Y41 are decisive for the ability of RaxX to trigger XA21-mediated immunity and that Y1 is a substrate for RaxST-mediated sulfation. We have identified RaxX in at least 8 *Xanthomonas* species that infect maize, cassava, sugar cane, tomatoes, peppers, wheat, alfalfa, onions, banana, and citrus (FIGS. 11A-11D). In all of these strains, raxX is encoded upstream of raxST, raxA, and raxB. The colocalization of the rax genes suggest that they function in a common biological process and that the RaxX proteins in these species are also substrates for RaxST-mediated sulfation.

While tyrosine sulfation has not been demonstrated in other prokaryotic species, it is a common posttranslational modification of eukaryotic proteins and plays important roles in regulating plant development and in mediating the interactions of plants and animals with microbes. For example, in humans, sulfation of the C—C chemokine receptor type 5 (CCR5) is critical for binding of the envelope glycoprotein gp120 by the human immunodeficiency virus (HIV) (Farzan M, et al. (1999) *Cell* 96(5):667-676). In plants, the sulfated peptide signaling factors PSK (phytosulfokine) and PSY1 (plant peptide containing sulfated tyrosine 1) have been implicated in xylem trachea development, root growth, suppression of plant defense and promotion of plant health (Matsubayashi Y (2014) *Annual review of plant biology* 65:385-413; Mosher S, et al. (2013) *Plant J* 73(3):469-482).

Although RaxX shares no homology with microbial proteins of known function, we have noted a remarkable similarity between the sulfated, secreted *Arabidopsis* 18 amino acid peptide signaling factor PSY1, four predicted rice PSY1 orthologs and RaxX residues 40-55 (FIGS. 38A-38B). These similarities suggest the exciting possibility that in the absence of XA21, Xoo and other Xanthomonads utilize sulfated RaxX to mimic PSY-like peptides in order to suppress host defense responses, facilitate infection or enhance plant health, maintenance of which is critically important for propagation and survival of biotrophic pathogens (Mosher S, et al. (2013) *Plant J* 73(3):469-482; Amano Y et al. (2007) *Proc Natl Acad Sci USA* 104(46):18333-18338; Mosher S & Kemmerling B (2013) *Plant Signal Behav* 8(5):e24119).

The robust immunity conferred by XA21 to most Xoo strains is a highly valued agronomic trait and therefore XA21 has been introgressed into diverse rice varieties grown by rice farmers (Sundaram M, et al. (2008) Marker assisted introgression of bacterial blight resistance in Samba Mahsuri, an elite indica rice variety. 160 3(411-422); Huang B et al. (2012) *Euphytica* 187:449-459; Chen S et al. (2000) *Crop Science* 40(1):239-244; Toenniessen G H, O'Toole J C, & DeVries J (2003) *Current opinion in plant biology* 6(2): 191-198; Gopalakrishnan S, et al. (2008) *Plant Breeding* 127(2):131-139; Win K M, et al. (2012) *Field Crops Research* 137:186-194). The discovery of raxX and allelic variants that can evade XA21-mediated recognition can be used to screen Xoo field populations for the presence of potentially virulent variants. Such an anticipatory breeding approach would alert farmers of the need to plant different varieties or mixtures prior to the breakdown of XA21-mediated immunity.

The knowledge gained from these studies can also be used to expand the spectrum of XA21-mediated immunity to additional strains of Xoo. For example, new synthetic receptors of XA21 with novel engineered recognition specificities such as those that can recognize RaxX from IXO685 would be of great interest. Because *Xanthomonas* species affect virtually all crop plants, it is expected that future studies will lead to new strategies for engineering resistance to non-rice pathogens. For example, *X. axonopodis* pv. *citrumelo, X. euvesicatoria* and *X. oryzae* pv. *oryzicola*, which cause serious diseases on citrus, tomato, and rice, carry alternate raxX alleles (FIGS. 15A-15B). This knowledge provides an opportunity to engineer new XA21 variants that recognize these alleles and use the novel variants for engineering plants resistant to *Xanthomonas* infections that cannot be controlled by more conventional genetic methods.

The sulfated RaxX/Xa21 interaction represents a new biological system for studies of the interaction of sulfated epitopes and their receptors. A recent report of the generation of a potent new anti-viral drug (Gardner M R, et al. (2015) *Nature* 519(7541):87-91), which was based on more than 10 years of work on a single family of sulfated peptides, indicates the clinical relevance of studies of sulfopeptides. Thus the studies reported here are applicable to generation of therapeutic reagents with the potential to block microbial infection of both plants and animals.

Materials and Methods

Bacterial Culture and Growth Conditions

Lists of plasmids and bacterial strains used in this study are provided in Table 1 and S2. Xoo was cultured on peptone sucrose agar (PSA) plates at 28° C. with the appropriate antibiotic(s). YEB medium (5 g/L yeast extract, 10 g/L tryptone, 5 g/L NaCl, 5 g/L sucrose, 0.5 g/L $MgSO_4$, pH 7.3) was used for liquid culture at 28° C. with shaking at 230 rpm. *E. coli* was cultured at 37° C. and 230 rpm in lysogenic broth (LB) for cloning or M9T (per 1 liter: M9 plus 10 g tryptone, 5 g NaCl; after autoclaving add 1 mL of 1M MgSO4 and 1 mL of 0.02% biotin for expression). Kanamycin was used at 50 µg/mL, carbenicillin at 50 µg/mL, spectinomycin at 50 µg/mL, and cephalexin at 20 µg/mL.

Xoo Mutation and Complementation

Xoo mutants were generated in Philippine race 6 strain PXO99Az, a derivative of strain PXO99 (referred to simply as PXO99 in this manuscript) (Salzberg S L, et al. (2008) *BMC genomics* 9:204; Hopkins C M et al., (1992) *Mol Plant Microbe Interact* 5(6):451-459). PXO99ΔraxST$^{Sp}$, PXO99Δ1.0$^{Sp}$, and PXO99Δ1.7$^{Sp}$ were generated by marker exchange mutagenesis using the suicide vector pJP5603 (Penfold R J & Pemberton J M (1992) *Gene* 118(1):145-146). ~500 bp sequences flanking both sides of the region to be deleted were sequentially cloned into the multiple cloning site using the restriction enzyme sites KpnI/BamHI and BamHI/SalI. A spectinomycin resistance cassette was ligated between the two flanking sequences using the BamHI site. PXO99 competent cells were transformed with the suicide plasmids by electroporation and plated to PSA with 50 µg/mL spectinomycin. Colonies with the expected antibiotic resistance phenotype for double crossover (spectinomycin resistant, kanamycin sensitive) were validated by PCR.

Marker free raxX (PXO99 ΔraxX) and raxST (PXO99ΔraxSI) mutants were generated using the vector pUFR80 (Castañeda A et al., (2005) *Mol Plant Microbe Interact* 18:1306-1317). ~500 bp sequences flanking were sequentially cloned into the multiple cloning site of pUFR80 using the sites EcoRI/BamHI and BamHI/HindIII. praxX-KO-MF and praxST-KO-MF were transformed into PXO99 competent cells by electroporation, and the cells were plated to nutrient agar (NA) (CM0001, OXOID) with 50 µg/mL kanamycin. Transformants were grown in nutrient broth without kanamycin and plated to NA with 5% sucrose to select for a second crossover event. Colonies were analyzed by PCR to identify deletion mutants.

Strains were transformed using derivatives of the broad host range vector pVSP61 (Loper J E & Lindow S E (1994) *Applied and environmental microbiology* 60(6):1934-1941). The raxX and raxST sequences along with their predicted promoter region (300 bp upstream of the predicted start codons) were cloned into pVSP61 using the EcoRI/HindIII sites. Point mutations were generated by QuikChange mutagenesis. For praxX-IXO685, the raxX promoter from PXO99 was first introduced into pVSP61 using the sites EcoRI/BamHI to generate praxXprom. The raxX sequence from IXO685 was amplified from genomic DNA and cloned into praxXprom behind the PXO99 raxX promoter using the restriction sites BamHI/HindIII.

Rice and Rice Growth Conditions for Inoculations

*Oryza sativa* ssp. *japonica* rice varieties Taipei 309 (TP309), a 106-17-derived transgenic line of TP309 carrying XA21 driven by its own promoter (XA21-TP309) (Song W Y, et al. (1995) *Science* 270(5243):1804-1806), Kitaake, and Ubi::Myc::XA21-Kitaake line 7-A-8 (Ubi::XA21) (Park C J, et al. (2010) *Plant science: an international journal of experimental plant biology* 179(5):466-471) were used for rice inoculations. Native Tapei 309 and Kitaake do not contain XA21. Seeds were germinated in distilled water at 28° C. for one week, and then transplanted into sandy soil (80% sand, 20% peat from Redi-Gro, Sacramento, Calif.) in 5.5 inch square pots (2 seedlings/pot). Plants were grown in tubs in a greenhouse. The plants were top watered daily with fertilizer water (N, 58 ppm; P, 15 ppm; K, 55 pm; Ca, 20 ppm; Mg, 13 ppm; S, 49 ppm; Fe, 1 ppm; Cu, 0.06 ppm; Mn, 0.4 ppm; Mo, 0.02 ppm; Zn, 0.1 ppm; B, 0.4 ppm) for 4 weeks, followed by water for 2 weeks. Six weeks after planting, the rice was transferred to a growth chamber set to 28° C./24° C., 80%/85% humidity, and 14/10 h lighting for the day/night cycle.

Plants were inoculated 2-3 days after transfer using the scissors clipping method (Kauffman H et al. (1973) *Plant Disease Reporter* 57:537-541). Bacteria for inoculation were taken from PSA plates and resuspended in water at a density of $10^8$ colony forming units per mL. Water soaked lesions were measured 14 days after inoculation. In planta bacterial growth analysis was carried out as described (Bahar O, et al. (2014) *Peer J* 2:e242.). Four biological replicates were measured for each data point. Each biological replicate was the mean number of colonies from four technical replicates.

Generation of RaxX Peptides

Sulfated (sY) and nonsulfated (Y) versions of RaxX39 (KGRPEPLDQRLWKHVGGGDYPPPGANPKHDPP-PRNPGHH; SEQ ID NO:3), RaxX24 (LWKHVGGGDYP-PPGANPKHDPPPR (SEQ ID NO:1)), RaxX21 (HVGGGDYPPPGANPKHDPPPR (SEQ ID NO:199)), RaxX18 (LWKHVGGGDYPPPGANPK (SEQ ID NO:200)) and ax22(S)Y (Lee S W, et al. (2013) *Science* 342(6155): 191) were ordered from Pacific Immunology. The peptides were checked for purity by HPLC and MS analysis by the company. All peptides were resuspended in $ddH_2O$. No other solvents were required to dissolve the peptide.

For the expanded genetic code approach, full length RaxX (RaxX60) from PXO99 was expressed as an MBP-3C-RaxX-His fusion protein in *E. coli* C321.ΔA.exp (Lajoie M J, et al. (2013) *Science* 342(6156):357-360). *E. coli* C321.ΔA.exp was cotransformed with SYP29_pULTRA_SY, made by cloning the sY-specific aminoacyl-tRNA synthetase from (Liu C C et al., (2009) *Nature protocols* 4(12):1784-1789) into the pULTRA system (Chatterjee A et al. (2013) *Biochemistry* 52(10):1828-1837) and pBAD/MBP-3C-RaxX-His (Amber) to generate sulfated RaxX or pBAD/MBP-3C-RaxX-His to generate nonsulfated RaxX. Transformed bacteria were grown in 0.5 L of M9T media. For expression of sulfated RaxX, sulfotyrosine (sY), synthesized as described in (Liu C C et al., (2009) *Nature protocols* 4(12):1784-1789), was added to a final concentration of 3 mM. Cultures were grown at 37° C. with shaking at 230 rpm. Expression was induced at an O.D. of 0.6-0.7 by addition of 1 mM IPTG and 0.25% (w/vol) arabinose for 5 h. MBP-3C-RaxX-His was purified from intracellular total protein extracts over a 5 mL Ni-NTA column on an FPLC (Akta, GE Healthcare). The MBP-tag was removed by overnight digestion with 3C protease at a concentration of 1:200 (w/w) at 4° C. The MBP was separated from full length RaxX-His over a 1 mL SP-XL column, a strong cation exchanger, on an FPLC (Akta, GE Healthcare). Nonsulfated RaxX was expressed and purified in the same way, except pBAD/MBP-3C-RaxX-His plasmids without Amber mutations were used, and no sulfotyrosine was added to the cultures. The yield for sulfated and nonsulfated highly purified RaxX-His was about 1 mg protein per 1 L of culture. All RaxX allelic variants were prepared according to the same protocol.

In Vitro Sulfation of RaxX by his-RaxST

RaxST was expressed as a full length fusion protein with an N-terminal His-tag in BL21(DE3) cells and purified using Ni-NTA agarose beads (QIAGEN). His-RaxST expression was confirmed by SDS-PAGE with Coomassie-blue staining and western blot analysis with Penta-HiS™ antibody (QIAGEN) (FIGS. 18A-18B). The in vitro sulfation reaction was carried out as described in Han et al (Han S W, et al. (2012) *Nat Commun* 3:1153). 20 μg of the purified RaxST was incubated with 170 μg of RaxX39 in the presence of sulfation buffer (25 mM Tris pH 7.5, 150 mM NaCl, 20 mM $MgCl_2$, 480 μM PAPS) for 4 h at 30° C.

nanoLC-UVPD Mass Spectrometry

Proteins from in vitro sulfation reactions were buffer exchanged into 50 mM Tris HCl (pH 8.5), 1 M urea using a 3 KDa molecular weight cut-off (MWCO) filter and digested with trypsin overnight at 37° C. using a 1:25 enzyme to substrate ratio. Following digestion, samples were passed through a 10 K MWCO filter to separate RaxX39 peptides from trypsin.

Tryptic peptides of RaxX39 were separated by reversed phase liquid chromatography at 300 nL/min using a Dionex Ultimate 3000 NSLC system configured for preconcentration. Mobile phases A and B were water and acetonitrile, respectively, both containing 0.1% formic acid. A solution of 2% acetonitrile and 0.1% formic acid was used for sample loading onto a New Objective IntegraFrit 100 μm×3 cm trap column (Woburn, Mass.) packed in-house with 5 μm, 100 Å Michrom Magic C18 AQ (Auburn, Calif.). After 5 min of preconcentration at 7 μL/min, the trap column was switched in-line with a with a New Objective PicoFrit analytical column (Woburn, Mass.) (75 μm×15 cm) packed with Waters 3.5 μm, 130 Å X Bridge BEH C18 (Milford, Ma). A 23 min linear gradient starting at 2% B and ending at 40% B was used for separation.

LC-MS/MS analysis was performed on a Thermo Scientific Velos Pro mass spectrometer (Thermo Fisher Scientific, Bremen, Germany) equipped with a Coherent (Santa Clara, Calif.) Excistar XS excimer laser operated at 193 nm with a pulse frequency of 500 Hz (Madsen J A, et al. (2013) *Molecular & cellular proteomics*: MCP 12(9):2604-2614). Data acquisition was carried out by first performing a full MS1 scan from m/z 300-2000 followed by 3 MS/MS UVPD events to activate the doubly charged sulfopeptide of interest, HVGGGDsYPPPGANPK (SEQ ID NO:4), at m/z 769.8 in negative mode and m/z 771.8 in positive mode. A single laser pulse was used for ion activation in negative mode during a 2.0 ms activation period. Two laser pulses were used for ion activation in the positive mode. In both polarities the isolation width was 3 Da and the activation q value was 0.10. MS/MS fragmentation patterns were manually interpreted. For the UVPD mass spectrum shown in FIG. 12B, the neutral loss of $SO_3$ and $CO_2$ from the precursor ion and/or charge reduced precursor ion are denoted as "—$SO_3$" and "—$CO_2$", respectively in the spectrum. Product ions a+1 and x+1 correspond to homolytic cleavage of the Ca-carbonyl bond of the peptide backbone without subsequent transfer of hydrogen radicals to produce even electron a and x ions which are the diagnostic N-terminal and C-terminal ions used to identify the peptide.

High resolution mass measurement of the diagnostic tryptic peptide corresponding to HVGGGDsYPPPGANPK (SEQ ID NO:4) from the RaxX39 sample sulfated by RaxST in vitro was undertaken on a ThermoFisher Scientific Instruments Orbitrap Elite mass spectrometer operated at an FT resolution of 120,000 at m/z 400.

Isolation of RaxXfrom PXO99 for Selected Reaction Monitoring Mass Spectrometry

Briefly, RaxX-His proteins were purified from Xoo strains and their sulfation was analyzed by SRM-MS. PXO99 (praxX-His) and PXO99 ΔraxST(praxX-His) were cultured in 1 L XVM2 (Wengelnik K & Bonas U (1996) *J Bacteriol* 178(12):3462-3469) liquid media for 40 h at 28° C. The cells were harvested by centrifugation at 10,000 rpm for 20 min at 4° C. RaxX-His was purified from intracellular total protein extract over a 5 mL Ni-NTA column on an FPLC (Akta, GE Healthcare). Isolation of Rax-His was confirmed by Coomassie-blue staining and western blot analysis with Penta-His™ antibody (QIAGEN) (FIG. 20).

Selected Reaction Monitoring Mass Spectrometry (SRM-MS)

Purified RaxX-His was digested with 1 μg of trypsin in the presence of 5 mM DTT. Peptide digests were analyzed using an Agilent 1260 liquid chromatography system (Agilent, Santa Clara, Calif.) operating in normal flow mode at 400

μL/min coupled to an Agilent 6460QQQ Mass Spectrometer (Agilent). Peptides were separated on an Ascentis Express Peptide C18 column (2.7 μm particle size, 160 Å pore size, 5 cm length×2.1 mm i.d., coupled to a 5 mm×2.1 mm i.d. guard column with similar particle and pore size, operating at 60° C.; Sigma-Aldrich, St. Louis, Mo.) using a 43-minute method with the following gradient: initial conditions were 98% Buffer A (0.1% formic acid), 2% Buffer B (99.9% acetonitrile, 0.1% formic acid) after which B was increased to 35% over 35.70 min, followed by an increase to 90% B in 18 s, where it was held for 2 min. Buffer B was then decreased to 5% in 30 s where it was held for 2.5 min, then further decreased to 2% and held for 2 min to re-equilibrate the column.

The eluted peptides were ionized via an Agilent Jet Stream ESI source operating in positive-ion mode with the following source parameters: Gas temperature=250° C., Gas flow=13 L/min, Nebulizer pressure=35 psi, Sheath Gas temperature=250° C., Sheath Gas flow=11 L/min, Capillary voltage=3500 V, Nozzle voltage=0 V. The data were acquired using Agilent MassHunter, version B.06.00. Data were acquired in MRM mode with transitions generated via Skyline (MacLean B, et al. (2010) *Bioinformatics* 26(7): 966-968) software (version 2.6). In silico SRM transitions were selected with 2+ and 3+ charge states, no missed tryptic cleavages, sulfated and non-sulfated tyrosine modifications, and singly-charged fragment ions from both the y- and b-series. The Skyline generated method was refined to three transitions per peptide and set to Agilent 6460QQQ for instrument-specific collision energies. The final method consists of 36 transitions, with a 25-ms dwell time per transition and MS1 and MS2 resolution set to unit. Acquired SRM data were imported into Skyline where confident peptide quantification was based on multiple concurrent SRM transitions above background signal and peak areas were refined with the mProphet algorithm (Reiter L, et al. (2011) *Nat Methods* 8(5):430-435).

Rice and Rice Growth Conditions for Plant Defense Assays

Kitaake, Ubi::Myc::XA21-Kitaake line 7-A-8 (Ubi::XA21) (Park C J, et al. (2010) *Plant science: an international journal of experimental plant biology* 179(5):466-471) and XA21::XA21-Kitaake (Park C J, et al. (2010) *Plant science: an international journal of experimental plant biology* 179(5):466-471) were grown in growth chambers at 24° C. or 28° C. with a 14 h/10 h light-dark cycle at 80% humidity. Rice plants were grown in hydroponic system using A-OK Starter Plugs (Gordan) and watered with Hoaglands solution twice a week.

Assays for Reactive Oxygen Species

Leaves of 4- to 6-week-old hydroponically grown rice plants were cut longitudinally along the mid vein and then transversely into 1 to 1.5 mm thick leaf pieces. These leaf pieces were floated on autoclaved $ddH_2O$ overnight. The next morning two leaf pieces were transferred into one well of a 96-well white plate containing 100 μL excitation solution (5-20 mM L-012 [Wako, Japan], 0.5-2 mg/mL HRP [Sigma]). Leaf pieces were treated with the indicated concentration of peptides or mock treated ($ddH_2O$ or a peptide buffer solution). Chemiluminescence was measured for 3 h with 0.5 s per reading with a high sensitivity plate reader (TriStar, Berthold, Germany).

Gene Expression Assays

Rice leaf tissue was treated with peptides as described previously with slight adaptations (Chen X, et al. (2014) *Molecular plant* 7(5):874-892). Leaves of 4-week-old hydroponically grown rice plants were cut into 2 cm long strips and incubated for at least 12 h in $ddH_2O$ to reduce residual wound signal. Leaf strips were treated with the indicated peptides and for the indicated time. Leaf tissue was snap-frozen in liquid nitrogen and processed appropriately. PR10b and Os04g10100 were previously described as defense marker genes in rice (Chen X, et al. (2014) *Molecular plant* 7(5):874-892). Other defense marker genes, Os12g36830 and Os06g37224, were identified in RNAseq experiments as upregulated genes after elf18 treatment of rice leaves expressing EFR::XA21::GFP (Schwes singer B, et al. (2015) *PLoS pathogens* 11(3):e1004809), (internet site genome.jgi.doe.gov/pages/dynamicOrganismDownload.jsf?organism=OrysatspilotREDO). For qRT-PCR reactions, the Bio-Rad SsoFast EvaGreen Supermix was used. The genes and qRT-PCR primer pairs are listed in Table 3. qRT-PCR reactions were run for 40 cycles with annealing and amplification at 62° C. for 5 s and denaturation at 95° C. for 5 s. The expression levels of all defense marker genes were normalized to the actin gene expression level and to the respective mock treated control at 0 or 1 h.

Ethylene Production

Leaves of 3-4 weeks old hydroponically grown rice plants were cut in small horizontal strips (~0.3-0.5 mm) and floated on water in Petri dishes overnight at room temperature. Ethylene biosynthesis was assayed by placing leaf samples in 6-mL tubes with 500 μL of water or the indicated peptide at a concentration of 1 μM as indicated. Tubes were sealed with rubber caps, and ethylene accumulating in the head-space within 4 h of incubation was determined by gas chromatography as described (Felix G et al. (1999) *Plant J* 18(3):265-276).

RaxX39 Peptide Digestion

10 μg of RaxX39-Y or RaxX39-sY were digested in buffer D (50 mM Tris HCl, 1 mM DTT) with 1 μg of one of the following site-specific proteases: GluC, ArgC, AspN, or trypsin. Digestions or mock reactions were performed at 25° C. for 16 h.

Statistical Analysis

Statistical analyses were performed using IMP software (ASAS Institute Inc., Cary, N.C., USA).

TABLE 1

Plasmids used in this study.

| Strain | Relevant characteristics | Source |
|---|---|---|
| | $X_{OO}$ suicide plasmids for mutant generation | |
| pJP5603 | Suicide vector, requires pir+ strain for replication, $Km^R$ | Penfold RJ & Pemberton JM (1992) *Gene* 118(1): 145-146 |

TABLE 1-continued

Plasmids used in this study.

| Strain | Relevant characteristics | Source |
|---|---|---|
| pUFR80 | Suicide vector with sacB, for double crossover selection on sucrose, $Km^R$ | Castañeda A et al., (2005) *Mol Plant Microbe Interact* 18: 1306-1317 |
| praxST-KO-Sp | pJP5603-based vector for deletion of raxST, contains flanking regions 1,282,801-1,283,300* and 1,284,171-1,284,648, $Km^RSp^R$ | This study |
| pΔ1.7-KO-Sp | pJP5603-based vector for deletion of PXO99 genomic region 1,287,700-1,289,400, contains flanking regions 1,287,199-1,287,699 and 1,289,401-1,289,900, $Km^RSp^R$ | This study |
| pΔ1.0-KO-Sp | pJP5603-based vector for deletion of PXO99 genomic region 1,282,000-1,283,000, contains flanking regions 1,281,498-1,281,999 and 1,283,001-1,283,501, $Km^RSp^R$ | This study |
| praxX-KO-MF | pUFR80-based vector for marker free (MF) deletion of PXO99 raxX (1,282,744-1,282,926), contains flanking regions 1,282,254-1,282,743 and 1,1,282,927-1,283,416, $Km^R$, $sacB^+$ | This study |
| praxST-KO-MF | pUFR80-based vector for marker free (MF) deletion of PXO99 raxST, contains flanking regions 1,282,801-1,283,300 and 1,284,171-1,284,648, $Km^R$, $sacB^+$ | This study |
| | $X_{OO}$ complementation plasmids | |
| pVSP61 | Broad host range vector used for complementation, $Km^R$ | Loper JE & Lindow SE (1994) *Applied and environmental microbiology* 60(6): 1934-1941 |
| praxST | raxST with native promoter (300 bp) from PXO99 in pVSP61, $Km^R$ | This study |
| praxST-R35A | praxST, arginine 35 mutated to alanine, $Km^R$ | This study |
| praxX | raxX with native promoter (300 bp) from PXO99 (c1,282,744-1,283,226) in pVSP61, $Km^R$ | This study |
| praxX-atg>tga | praxX, raxX start codon mutated to stop codon TGA, $Km^R$ | This study |
| praxX-Y41F | praxX, tyrosine 41 mutated to phenylalanine, $Km^R$ | This study |
| praxX-P44S | praxX, proline 44 mutated to serine, $Km^R$ | This study |
| praxX-A46P | praxX, alanine 46 mutated to proline, $Km^R$ | This study |
| praxX-P48T | praxX, proline 48 mutated to threonine, $Km^R$ | This study |
| praxX-R55P | praxX, arginine 55 mutated to proline, $Km^R$ | This study |
| praxX-His | praxX with a 6xHis tag at the end of raxX | This study |
| praxXprom | raxX promoter (300 bp) from PXO99 - (c1,282,927-1,283,226) in pVSP61, $Km^R$ | This study |
| praxX-IXO685 | raxX from Xoo strain IXO685 cloned behind the PXO99 raxX promoter (300 bp) in pVSP61, $Km^R$ | This study |
| | *E. coli* expression plasmids | |
| SYP29_pULTRA_SY | The sY-specific aminoacyl-tRNA synthetase from (Liu CC *et at.*, (2009) *Nature protocols* 4(12): 1784-1789) cloned into the pULTRA system (Chatterjee A *et al.* (2013) *Biochemistry* 52(10): 1828-1837), SpR | This study |
| pBAD/Myc-His A | $Cb^R$ | Invitrogen |
| pET28a(+) | $Km^R$ | Novagen |
| pET28a(+):raxST | Full length of PXO99 raxST cloned into pET28a(+) between EcoRI and XhoI restriction enzyme sites, $Km^R$ | This study |

TABLE 1-continued

Plasmids used in this study.

| Strain | Relevant characteristics | Source |
|---|---|---|
| pMAL/MBP-3C-RaxX-His | raxX from PXO99 (c1,282,926-1,283,226) cloned into pMAL-c4X by addition of a 3C coding sequence at the 5'-end and a 6-His coding sequence followed by a stop codon at the 3'-end, $Cb^R$ | This study |
| pBAD/MBP-3C-RaxX-His | MBP-3C-RaxX-His coding for raxX from PXO99 (c1,282,926-1,283,226) cloned into pBAD/Myc-His A by PCR amplification, restriction ligation using NcoI/HindIII, $Cb^R$ | This study |
| pBAD/MBP-3C-RaxX-Y41F-His | pBAD/MBP-3C-RaxX-His, tyrosine 41 mutated to phenylalanine, $Cb^R$ | This study |
| pBAD/MBP-3C-RaxX-P44S-His | pBAD/MBP-3C-RaxX-His, proline 44 mutated to serine, $Cb^R$ | This study |
| pBAD/MBP-3C-RaxX-A46P-His | pBAD/MBP-3C-RaxX-His, alanine 46 mutated to proline, $Cb^R$ | This study |
| pBAD/MBP-3C-RaxX-P48T-His | pBAD/MBP-3C-RaxX-His, proline 48 mutated to threonine, $Cb^R$ | This study |
| pBAD/MBP-3C-RaxX-R55P-His | pBAD/MBP-3C-RaxX-His, arginine 55 mutated to proline, $Cb^R$ | This study |
| pBAD/MBP-3C-RaxX-His (Amber) | MBP-3C-RaxX-His coding for raxX from PXO99 (c1,282,926-1,283,226) cloned into pBAD/Myc-His A with a change of the Y41 codon from TAT to TAG for incorporation of the non-standard amino acid sulfotyrosine, $Cb^R$ | This study |
| pBAD/MBP-3C-RaxX-Y41F-His (Amber) | pBAD/MBP-3C-RaxX-His (Amber), tyrosine 41 mutated to phenylalanine, $Cb^R$ | This study |
| pBAD/MBP-3C-RaxX-P44S-His (Amber) | pBAD/MBP-3C-RaxX-His (Amber), proline 44 mutated to serine, $Cb^R$ | This study |
| pBAD/MBP-3C-RaxX-A46P-His (Amber) | pBAD/MBP-3C-RaxX-His (Amber), alanine 46 mutated to proline, $Cb^R$ | This study |
| pBAD/MBP-3C-RaxX-P48T-His (Amber) | pBAD/MBP-3C-RaxX-His (Amber), proline 48 mutated to threonine, $Cb^R$ | This study |
| pBAD/MBP-3C-RaxX-R55P-His (Amber) | pBAD/MBP-3C-RaxX-His (Amber), arginine 55 mutated to proline, $Cb^R$ | This study |
| pBAD/MBP-3C-RaxX-His (IXO685, Amber) | 3C-RaxX-His coding for raxX from IXO685 cloned into pBAD/MBP-Myc-His A with a change of the Y41 codon from TAT to TAG for incorporation of the non-standard amino acid sulfotyrosine, $Cb^R$ | This study |

$Cp^R$—cephalexin resistance,
$Km^R$—kanamycin resistance,
$Sp^R$—spectinomycin resistance,
$Cb^R$—carbenicillin resistance
*Numbers indicate the sequence as annotated in the PXO99 genome. c before the number indicates the reverse complement.

TABLE 2

Bacterial strains used in this study.

| Strain | Relevant characteristics | Source |
|---|---|---|
| | Xoo strains | |
| PXO99 | Philippine race 6 strain PXO99Az, $Cp^R$ | Hopkins CM et al., (1992) *Mol Plant Microbe Interact* 5(6): 451-459 |
| PXO99ΔraxST$^{Sp}$ | PXO99ΔraxST::Sp, $Sp^R$ | This study |
| PXO99Δ1.7$^{Sp}$ | PXO99Δ1,287,700-1,289,400::Sp, $Cp^RSp^R$ | This study |
| PXO99Δ1.0$^{Sp}$ | PXO99Δ1,282,000-1,283,000::Sp, $Cp^RSp^R$ | This study |
| PXO99ΔraxX | PXO99ΔraxX(marker free), $Cp^R$ | This study |
| PXO99ΔraxST | PXO99ΔraxST(marker free), $Cp^R$ | This study |
| IXO685 | Field isolate of Xoo taken from diseased rice in Kerala, India, $Cp^R$ | Mishra D, *et al.* (2013) *PLoS One* |

TABLE 2-continued

Bacterial strains used in this study.

| Strain | Relevant characteristics | Source |
|---|---|---|
| | | 8(11): e81996 |
| | *E. coli* strains | |
| C321.ΔA.exp | All UAG codons mutated to UAA and RF1 removed | Lajoie MJ, *et al.* (2013) *Science* 342(6156): 357-360 |
| DH5α | Used for general cloning | |
| EC100D | Used for pJP5603-based cloning, $pir^+$ | |
| BL21(DE3) | F ompT gal dcm lon hsdSB(rB− mB−) λ(DE3 [lacI lacUV5-17 gene 1 ind1 sam7 nin5]), used for expressing raxST in pET28a(+) | |

$Cp^R$—cephalexin resistance,
$Km^R$—kanamycin resistance,
$Sp^R$—spectinomycin resistance

TABLE 3

Marker genes and Primers used for qPCR.

| Gene | Annotated function | Primer name | Primer Sequence (5'-3') |
|---|---|---|---|
| PR10b | pathogenesis-related Bet v I family protein, putative ribonuclease, induced by SA and during fungal infection (McGee JD, Hamer JE, & Hodges TK (2001) *Mol Plant Microbe Interact* 14(7): 877-886) | PR10b-Q1<br>PR10b-Q2 | GTCGCGGTGTCGGTGGAGAG (SEQ ID NO: 201)<br>ACGGCGTCGATGAATCCGGC (SEQ ID NO: 202) |
| Os04g10100 | Momilactone A synthase, required for phytoalexin production, induced by elicitors and UV radiation (Shimura K, et al. (2007) *J Biol Chem* 282(47): 34013-34018; Atawong A, Hasegawa M, & Kodama O (2002) *Bioscience, biotechnology, and biochemistry* 66(3): 566-570) | Os04g10100-Q1<br>Os04g10100-Q2 | AAATGATTTGGGACCAGTCG (SEQ ID NO: 203)<br>GATGGAATGTCCTCGCAAAC (SEQ ID NO: 204) |
| Os12g36830 or RSOsPR10 | pathogenesis-related Bet v I family protein, induced by abiotic stress, JA and fungal infection (Hashimoto M, et al. (2004) *Plant & cell physiology* 45(5): 550-559) | Os12g36830-Q1<br>Os12g36830-Q2 | GAGAAGCTCATCCTCGACGG (SEQ ID NO: 205)<br>GCATACTCGGTAGGGTGAGC (SEQ ID NO: 206) |
| Os06g37224 or OsKOL5 | ent-kaurene oxidase, phytoalexin production, induced by elicitors (Itoh H, et al. (2004) *Plant molecular biology* 54(4): 533-547) | Os06g37224-Q1<br>Os06g37224-Q2 | GAGAAGCTCATCCTCGACGG (SEQ ID NO: 205)<br>GCATACTCGGTAGGGTGAGC (SEQ ID NO: 206) |
| Actin | | Actin-Q1<br>Actin-Q2 | TCGGCTCTGAATGTACCTCCTA (SEQ ID NO: 207)<br>CACTTGAGTAAAGACTGTCACTTG (SEQ ID NO: 208) |

Example 12: Enhancement of Root Growth

This example shows, e.g., that sulfated raxX actively promotes root growth in rice, a model cereal crop and also a model for bioenergy feedstocks.

Sulfated RaxX induces root growth in rice. Both Kittake and TP309 rice seeds were germinated on MS agar media containing 100 nM sulfated RaxX21 (RaxX21-sY) or 100 nM nonsulfated RaxX21 (RaxX21-Y). RaxX21 is a 21 amino acid peptide of RaxX, which can activate XA21- mediated immunity on rice. Root length of the seedling was measured after 5 days. The RaxX21-sY treated rice seeds had significantly longer roots than Mock (water) treated or RaxX21-Y treated seeds (t-test, P<0.01 (n>35)).

Sulfated RaxX21 (RaxX21-sY) promotes growth of *Arabidopsis thaliana* seedling roots. *Arabidopsis thaliana* Col0 seedlings were sterilized with 30% bleach, washed 5 times with water, and placed in the dark at 4° C. for 4 days. The seeds were placed on plates containing ½ Murashige and Skoog media with vitamins (Caisson) plus 1% sucrose, pH 5.7, solidified with 0.5% Phytagel (Sigma). Plates were treated with water, 100 nM RaxX21-Y, or 100 nM RaxX21-sY. The plates were incubated vertically under continuous light for 6 days. RaxX21-sY (i.e., sulfated) had statistically longer root lengths after 6 days compared to RaxX21-Y (i.e., unsulfated) or mock treated controls at a statistical significance at $\alpha$=0.05 based on the Tukey Kramer honestly significant difference test.

Example 13

We have recently shown that the rice receptor XA21 recognizes a sulfated protein, called RaxX, produced by the bacterial pathogen *Xanthomonas oryzae* pv. *oryzae* (Xoo). This recognition triggers a robust and effective immune response (Song W Y et al., 1995, *Science,* 270(5243): 1804-1806; Pruitt R N et al., 2015, *Science Advances*). A synthetic 21-amino acid sulfated derivative of RaxX (RaxX21-sY) from Xoo strain PXO99 (FIG. 39A) is sufficient to activate XA21-mediated immune responses (Pruitt R N et al., 2015, *Science Advances*).

Sequence analysis revealed that RaxX21 is similar to the peptide hormone PSY (plant peptide containing sulfated tyrosine), which promotes cellular proliferation and expansion in *Arabidopsis* (Amano Y et al., 2007, *Proc Natl Acad Sci USA,* 104(46): 18333-18338) (Pruitt R N et al., 2015, *Science Advances*). *Arabidopsis* PSY1 (AtPSY1) is the best-characterized member of the plant PSY peptide family. AtPSY1 is an 18-amino acid glycopeptide with a single sulfotyrosine residue (FIG. 39A) (Amano Y et al., 2007, *Proc Natl Acad Sci USA,* 104(46): 18333-18338) that is secreted, processed and promotes root elongation primarily through regulation of cell size. AtPSY1 is widely expressed in *Arabidopsis* tissues (Amano Y et al., 2007, *Proc Natl Acad Sci USA,* 104(46): 18333-18338). AtPSY1 promotes acidification of the apoplastic space through activation of membrane proton pumps (Fuglsang A T et al., 2014, *Plant J.,* 80(6): 951-964). This acidification is thought to activate pH-dependent expansins and cell wall remodeling enzymes that loosen the cellulose network (Cosgrove D J, 2000, *Plant Physiol Biochem.,* 38(1-2): 109-124; Hager A., 2003, *J Plant Res.,* 116(6): 483-505). Concomitant water uptake by the cell leads to cellular expansion. In addition to PSY, plants produce two other classes of tyrosine sulfated peptides: phytosulfokine (PSK) (Matsubayashi Y, Sakagami Y, 1996, *Proc Natl Acad Sci USA,* 93(15): 7623-7627) and root meristem growth factor (RGF) (Matsuzaki Y et al., 2010, *Science,* 329(5995): 1065-1067), PSK and RGF are also processed, secreted, and play a role in regulation of growth.

Here we demonstrate that RaxX peptides derived from diverse *Xanthomonas* species promote root growth, mimicking the growth promoting activities of PSY peptides. We also show that, unlike RaxX, PSY peptides do not activate XA21-mediated immunity. Thus, XA21 is a highly selective immune receptor capable of specifically recognizing the bacterial mimic. Based on these findings we propose a model whereby Xoo and other *Xanthomonas* strains produce RaxX to reprogram the host environment by hijacking PSY signaling. XA21 later evolved to recognize and respond to specifically to RaxX.

Materials and Methods

Identification of Putative RaxX Proteins

Putative PSY-like proteins were identified by NCBI Protein BLAST analysis using the default settings for short sequences (Altschul S F et al., 1990, *J Mol Biol.,* 215(3): 403-410). For *S. lycopersicum* BLAST was performed using the Sol Genomics Network with the BLOSUM 62 algorithm (https://solgenomics.net/tools/blast/). Proteins were identified from a single source for each plant: *A. thaliana* Col-0 (refseq_protein, taxid: 3702), *O. sativa* Nipponbare (refseq_protein, taxid: 39947), *Triticum aestivum* Chinese Spring (taxid:4565), *Musa acuminata* subsp. *Malaccensis* (refseq_protein, taxid 214687), *S. lycopersicum* cv. Heinz 1706 (ITAG release 2.40). BLAST was initially performed with the 18 amino acid sequence of AtPSY1 (DYGDPSANPKHDPGVPPS (SEQ ID NO:62)). Criteria for selection were as follows: (1) Candidates must match the query with an expect-value≤20 for NCBI Protein BLAST analysis (PAM 30 algorithm), (2) Candidates must have an invariant Asp-Tyr at the beginning of the query, (3) The full length protein must be between 60 and 200 amino acids with the PSY like motif in the second half, (4) The protein must be predicted to have a secretion signal by SignalP 4.0 (Petersen T N et al., 2011, *Nat Methods,* 8(10): 785-786). Additional candidates were identified by subsequent iterative BLAST with the 18 amino acid RaxX sequences from candidate RaxX proteins identified in the initial BLAST. The final list is shown in FIG. 45. If multiple splicing variants were identified in the searching, only one is listed.

Sequence Analysis and Visualization

Sequence alignments in FIG. 39*a* was generated with Geneious software using default parameters (Kearse M et al., 2012, *Bioinformatics,* 28(12): 1647-1649). Sequence logos were constructed using WebLogo (Schneider T D, Stephens R M, 1990, *Nucleic Acids Res.,* 18(20): 6097-6100; Crooks G E et al., 2004, *Genome Res.,* 14(6): 1188-1190) with the 13-amino acid PSY-like sequences from the RaxX sequences shown in Table 51 and the PSY sequences in FIG. 45. The bit score for a given residue indicates the conservation at that position, while the size of the individual letters within the stack indicate relative frequency of that amino acid at the position.

*Arabidopsis* Growth Conditions

All *Arabidopsis thaliana* used this study were in the Col-0 background. The AtTPST mutant, tpst-1, (SALK_009847) and homozygous At1g72300 mutant (SALK_072802C) were obtained from the *Arabidopsis* Biological Resource Center (ARBC). A homozygous tpst-1 line was isolated from progeny of the SALK_009847 seeds. The AtPSKR1/AtPSKR2/At1g72300 triple receptor mutant (Mosher S, Kemmerling B, 2013, *Plant Signal Behav.,* 8(5): e24119) was obtained from Birgit Kemmerling's laboratory. Plants were grown on the indicated media or on Sungro professional growing mix under continuous light.

RaxX and PSY1 Peptides

The peptides used in this study are listed in Table S2. All peptides other than RaxX21-Y are tyrosine sulfated as indicated ($Y^S$). The synthetic AtPSY1 peptide used in these experiments lacks the hydroxy- and L-$Ara_3$-modifications at the C-terminus. The natural processed, modified state of OsPSY1a is not known. The 18-amino OsPSY1a acid peptide was synthesized based on alignment with AtPSY1.

RaxX13-sY was obtained from Peptide 2.0. All other peptides were obtained from Pacific Immunology. The peptides were resuspended in ddH$_2$O.

*Arabidopsis* Root Growth Assays

*Arabidopsis* seeds were treated with 30% bleach for 12 minutes and then washed 4-5 times with autoclaved water. Sterilized seeds were incubated in the dark at 4° C. for 3-4 days. Plates were prepared with 0.5× Murashige and Skoog (MS) medium with vitamins (Caisson, MSP09), 1% sucrose, pH 5.7, 0.5% Phytagel (Sigma, P8169). Peptide (or water for mock treatments) was added to the indicated concentration (from a 1 mM stock) just before pouring into a plate. Seeds were placed on the plate (20 seeds per plate), and the lids were secured with Micropore surgical tape (1530-0). Plates were incubated vertically under continuous light (55 µmol m$^{-2}$ s$^{-1}$) at 24° C. Seedlings with delayed germination were marked after 3 days, and were not included in the analysis. Root lengths were measured after 8 days.

*Arabidopsis* Live Imaging of Root Growth

Live imaging of roots was performed as described previously with modifications to the media (Duan L et al., 2013, *Plant Cell*, 25(1): 324-341; Geng Y et al., 2013, *Plant Cell*, 25(6): 2132-2154). Sterilized tpst-1 seeds were grown on 1% agar media containing 1×MS nutrients (Caisson, MSP01), 1% sucrose, and 0.5 g l$^{-1}$ MES, adjusted to pH 5.7 with KOH. After 6 days, seeds were transferred to 0.5% Phytagel (Sigma, P8169) media containing 0.5×MS (Caisson, MSP09, 1% sucrose, and 0.5 g l$^{-1}$ MES, adjusted to pH 5.7 with KOH. Imaging and semiautomated image analysis were performed as described previously (Geng Y et al., 2013, *Plant Cell*, 25(6): 2132-2154).

Rice Root Growth Assays

Seeds of *Oryza sativa* sp. *japonica* cultivars Kitaake or Taipei 309 (TP309) were dehusked and sterilized with 30% bleach for 30 min. The seeds were washed 4-5 times with water and plated to cups with 50 mL 0.5×MS (Caisson MSP09), 1% sucrose (pH 5.7 with KOH/NaOH) containing 0.25% Phytagel. Peptides were added to 100 nM just before pouring into the cups. 20 seedlings were added per cup. The seedling roots were measured after 4-6 day incubation in a 28° C. chamber with 13 h/11 h light/dark cycle and a light intensity of 15 µmol m$^{-2}$ s$^{-1}$.

ROS Assays

Kitaake and a transgenic derivative expressing XA21 under the ubiquitin promoter (XA21-Kitaake) were greenhouse grown. ROS assays were carried out using leaves of 6-week-old rice plants as described previously (Pruitt R N et al., 2015, *Science Advances*). Briefly, leaves of were cut longitudinally along the mid vein and then transversely into 1- to 1.5-mm-thick leaf pieces. After overnight incubation on sterile water, leaf pieces were transferred into a 96-well white plate (2 pieces per well). Each well contained 100 µl of excitation solution [0.2 mM L-012 (Wako) and 50 µg ml$^{-1}$ horseradish peroxidase (Sigma)]. The indicated concentration of peptides was added (or water for mock control), and chemiluminescence was measured for 90 minutes with a TriStar (Berthold) plate reader.

Supplemental Information

Table S1. RaxX13 sequences from diverse *Xanthomonas* sources.

The RaxX sequences were grouped into three categories *X. oryzae* (blue), *X. translucens* (green) and other *Xanthomonas* strains (orange). The full length sequences of the strains are shown in FIG. 46. A short-hand letter/number code was given to each RaxX13 sequence. RaxX proteins that are identical over the 13 amino acid PSY-like region have the same letter. Proteins that are identical over the entire RaxX sequence have the same letter and number.

Table S1

RaxX13 sequences from diverse *Xanthomonas* sources.

| # | RaxX13 | Species | Pathovar | Strain | Host | PMID/BioSample |
|---|---|---|---|---|---|---|
| A1 | DYPPPGANPKHDP (SEQ ID NO: 195) | *X. oryzae* | pv. *oryzae* | PXO99A | Rice | 1353345 |
| A2 | DYPPPGANPKHDP (SEQ ID NO: 195) | *X. oryzae* | pv. *oryzae* | KACC 10331 | Rice | |
| | | *X. oryzae* | pv. *oryzae* | PXO83 | Rice | 1353345 |
| | | *X. oryzae* | pv. *oryzae* | PXO86 | Rice | 1353345 |
| | | *X. oryzae* | pv. *oryzae* | MAFF 311016 | Rice | |
| | | *X. oryzae* | — | ATCC 35933† | Rice | |
| B1 | DYPPSGPNPKHDP (SEQ ID NO: 209) | *X. oryzae* | pv. *oryzae* | NAI8 | Rice | 21515727 |
| B2 | DYPPSGPNPKHDP (SEQ ID NO: 209) | *X. oryzae* | pv. *oryzae* | AXO1947 | Rice | |
| B3 | DYPPSGPNPKHDP (SEQ ID NO: 209) | *X. oryzae* | — | X8-1A | Rice | 21515727 |
| C1 | DYPPAGPSTKHDP (SEQ ID NO: 210) | *X. oryzae* | — | X11-5A | Rice | 21515727 |
| D1 | DYPPSGPNTKHDP (SEQ ID NO: 197) | *X. oryzae* | pv. *oryzicola* | BLS279 | Rice | 26257749 |
| | | *X. oryzae* | pv. *oryzicola* | R5115 | Rice | 26257749 |
| | | *X. oryzae* | pv. *oryzicola* | BX0R1 | Rice | 26257749 |
| | | *X. oryzae* | pv. *oryzicola* | MAI10 | Rice | 26257749 |
| | | *X. oryzae* | pv. *oryzicola* | LB | Rice | 26257749 |
| | | *X. oryzae* | pv. *oryzicola* | B8-12 | Rice | 26257749 |
| | | *X. oryzae* | pv. *oryzicola* | CFBP 7331 | Rice | |
| | | *X. oryzae* | pv. *oryzicola* | CFBP 7342 | Rice | |
| | | *X. oryzae* | pv. *oryzicola* | CIX4 | Rice | |
| | | *X. oryzae* | pv. *oryzicola* | YM15 | Rice | |

Table S1-continued

RaxX13 sequences from diverse *Xanthomonas* sources.

| # | RaxX13 | Species | Pathovar | Strain | Host | PMID/ BioSample |
|---|---|---|---|---|---|---|
| D2 | DYPPSGPNTKHDP | *X. oryzae* | pv. *oryzicola* | BLS256 | Rice | 26257749 |
| | (SEQ ID NO: 197) | *X. oryzae* | pv. *oryzicola* | CFBP 2286 | Rice | 26257749 |
| D3 | DYPPSGPNTKHDP (SEQ ID NO: 211) | *X. oryzae* | pv. *oryzicola* | BAI5 = CFBP 7341 | Rice | 26257749 |
| D4 | | *X. campestris* | pv. *leersiae* | NCPPB 4346 | Southern Cutgrass | 21515727 |
| D5 | | *X. oryzae* | | IXoo651 | Rice | |
| | | *X. oryzae* | | IXoo685 | Rice | |
| | | *X. oryzae* | | IXoo1221 | Rice | |
| E1 | DYPPPGANTKHDP (SEQ ID NO: 212) | *X. euvesicatoria* | 85-10 | 85-10 | Pepper | 16237009 |
| | | *X. axonopodis* | pv. *dieffenbachiae* | LMG 695 | Anthurium | SAMN02903992 |
| | | *X. alfalfae* | sb. *citrumelonis* | F1 | Citrus | 21908674 |
| | | *X. perforans* | | 91-118 | Pepper & Tomato | 26089818 |
| | | *X. axonopodis* | pv. *phaseoll* | XCP123 | Lima Bean | 26500625 |
| | | *X. axonopodis* | pv. *manihotis* | CIO151 | Cassava | 22699502 |
| E2 | DYPPPGANTKHDP | *X. axonopodis* | pv. *manihotis* | LMG 784 | Cassava | 25085494 |
| | (SEQ ID NO: 213) | *X. axonopodis* | pv. *manihotis* | UG28 | Cassava | 22699502 |
| | | *X. axonopodis* | pv. *manihotis* | Xam672 | | 25085494 |
| | | *X. axonopodis* | pv. *manihotis* | UG39 | Cassava | 22699502 |
| | | *X. axonopodis* | pv. *manihotis* | UA536 | Cassava | 22699502 |
| F1 | DYPPPGANDRHNP (SEQ ID NO: 214) | *X. maliensis* | — | M97† | Rice | 25586569 |
| G1 | DYAPPGSNDRHDP (SEQ ID NO: 215) | *X. campestris* | pv. *musacearum* | NCPPB 2005 | Ensete ventricosum | 24704974 |
| | | *X. campestris* | pv. *musacearum* | NCPPB 4379 | Banana | 24704974 |
| | | *X. campestris* | pv. *musacearum* | NCPPB 4380 | Banana | 24704974 |
| | | *X. campestris* | pv. *musacearum* | NCPPB 4381 | Banana | 24704974 |
| | | *X. campestris* | pv. *musacearum* | NCPPB 4384 | Banana | 24704974 |
| | | *X. campestris* | pv. *musacearum* | NCPPB 4392 | Banana | 24704974 |
| | | *X. campestris* | pv. *musacearum* | NCPPB 4394 | Banana | 24704974 |
| G2 | DYAPPGSNDRHDP | *X. vasicola* | pv. *vasculorum* | NCPPB 702 | Sugarcane | 24704974 |
| | (SEQ ID NO: 216) | *X. vasicola* | pv. *vasculorum* | NCPPB 890 | | |
| | | *X. vasicola* | pv. *vasculorum* | NCPPB 895 | | |
| | | *X. vasicola* | pv. *vasculorum* | NCPPB 1326 | Sugarcane | 24704974 |
| | | *X. vasicola* | pv. *vasculorum* | NCPPB 1381 | Sugarcane | 24704974 |
| H1 | DYPPPGSNNRHDP | *X. vasicola* | pv. *vasculorum* | NCPPB 206 | Maize | 24704974 |
| | (SEQ ID NO: 217) | *X. vasicola* | pv. *vasculorum* | NCPPB 2649 | | |
| I1 | DYPPTGPNTRHDP (SEQ ID NO: 218) | *X. axonopodis* | pv. *vasculorum* | NCPPB 900 | Sugarcane | 25263632 |
| J1 | DYPPSAANDRHDP (SEQ ID NO: 219) | *X. axonopodis* | pv. *axonopodis* | DSM 3585 † | Imperial Grass | SAMN02646552 |
| K1 | DYPPPSSNGRHDP (SEQ ID NO: 220) | *X. translucens* | pv. *undulosa* | Xtu 4699 | Wheat & Barley | 26729225 |
| | | *X. translucens* | — | CR31 | Wheat & Barley | 26729225 |
| | | *X. translucens* | — | CS2 | Wheat & Barley | 26729225 |
| | | *X. translucens* | — | C522 | Wheat & Barley | 26729225 |
| | | *X. translucens* | — | CS4 | Wheat & Barley | 26729225 |
| | | *X. translucens* | — | DAR61454 | Wheat & Barley | 24416331 |
| | | *X. translucens* | — | LB10 | Wheat & Barley | 26729225 |
| | | *X. translucens* | — | LB5 | Wheat & Barley | 26729225 |
| | | *X. translucens* | — | LG48 | Wheat & Barley | 26729225 |
| | | *X. translucens* | — | LG54 | Wheat & Barley | 26729225 |

Table S1-continued

RaxX13 sequences from diverse *Xanthomonas* sources.

| # | RaxX13 | Species | Pathovar | Strain | Host | PMID/ BioSample |
|---|---|---|---|---|---|---|
| | | *X. translucens* | — | LW16 | Wheat & Barley | 26729225 |
| | | *X. translucens* | — | P3 | Wheat & Barley | 26/29225 |
| | | *X. translucens* | — | XT-Rocky | Wheat & Barley | 26729225 |
| | | *X. translucens* | — | XT130 | Wheat & Barley | 26729225 |
| | | *X. translucens* | — | XT5523t | Wheat & Barley | 26729225 |
| | | *X. translucens* | — | XT5770 | Wheat & Barley | 26729225 |
| L1 | DYAPPSSNGRHDP (SEQ ID NO: 221) | *X. translucens* | — | XT5791 | Wheat & Barley | 26729225 |
| M1 | DYPPPHSNDRHDP (SEQ ID NO: 222) | *X. translucens* | pv. *translucens* | DSM 18974† | Barley | — |
| | | *X. translucens* | pv. *graminls* | CFBP 2053 | — | 26450740 |
| | | *X. translucens* | pv. *graminis* | ART-Xtg29 | Forage grass | 23578314 |
| | | *X. translucens* | pv. *translucens* | UPB787 | — | — |
| | | *X. translucens* | — | XT8 | Barley | 26729225 |
| N1 | DYPPTGANDKHDP (SEQ ID NO: 223) | *X. translucens* | pv. *poae* | LMG 728 | Poa trivialls | SAMEA3486272 |
| O1 | DYPPSGPNTRHDP (SEQ ID NO: 224) | *X. translucens* | pv. *arrhenatheri* | LMG 727 | Arrhenatherum elatius | SAMEA3486180 |
| P1 | DYPTAGANRKHDP (SEQ ID NO: 225) | *X. translucens* | pv. *phlei* | LMG 730 | Phleum pratense | SAMEA3486273 |
| Q1 | DYPTAGANRKHDP (SEQ ID NO: 225) | *X. translucens* | pv. *cerealis* | CFBP 2541† | Wheat & Barley | 25676771 |
| | | *X. translucens* | — | XT123 | Wheat & Barley | 26729225 |

TABLE S2

Synthetic peptides used in this study

| Peptide | Sequence | Sequence Source |
|---|---|---|
| RaxX21-Y | HVGGGDYPPPGANPKHDPPPR (SEQ ID NO: 59) | Xoo PXO99 |
| RaxX21-sY | HVGGGDY$^S$PPPGANPKHDPPPR* (SEQ ID NO: 59) | Xoo PXO99 |
| RaxX16-sY | DY$^S$PPPGANPKHDPPPR (SEQ ID NO: 226) | Xoo PXO99 |
| RaxX13-sY | DY$^S$PPPGANPKHDP (SEQ ID NO: 195) | Xoo PXO99 |
| AtPSY1 | DY$^S$GDPSANPKHDPGVPPS (SEQ ID NO: 62) | *A. thaliana* Col-0 |
| OsPSY1a | DY$^S$PAPGANPRHNPKRPPG (SEQ ID NO: 63) | *O. sativa* Nipponbare |
| PSK | Y$^S$IY$^S$TQ (SEQ ID NO: 227) | *A. thaliana* Col-0 |
| RaxX24-Xoc-sY | LWKHVGGGDY$^S$PPSGPNTKHDPPPP (SEQ ID NO: 228) | *X. oryzae* pv. *oryzicola* BSL256 |

TABLE S2-continued

| Synthetic peptides used in this study | | |
|---|---|---|
| Peptide | Sequence | Sequence Source |
| RaxX24-Xe-sY | LWKHVGGGDY$^S$PPPGANTKHDPPPK (SEQ ID NO: 229) | *X. euvesicatoria* 85-10 |
| RaxX24-Xcm-sY | LWKHVGGGDY$^S$APPGSNDRHDPPKP (SEQ ID NO: 230) | *X. campestris* pv. *musacearum* NCPPB4394 |

*Y$^S$ indicates sulfated tyrosine.

Results

RaxX is Similar in Sequence to PSY Peptides

The region of similarity between RaxX from Xoo and AtPSY1 corresponds to amino acids 40-52 of RaxX. RaxX and AtPSY1 share 10 identical residues over this region (FIG. 39*a*). RaxX is sulfated by the bacterial sulfotransferase RaxST on Y41, which corresponds to the sulfated residue of AtPSY1 (Amano Y et al., 2007, *Proc Natl Acad Sci USA,* 104(46): 18333-18338; Pruitt R N et al., 2015, *Science Advances*). An aspartate precedes the sulfated tyrosine in both RaxX and AtPSY1. The presence of a nearby acidic residue is a common hallmark of tyrosine sulfation sites (Moore K L, 2009, *Proc Natl Acad Sci USA,* 106(35): 14741-14742).

We extended our analysis to include PSY and RaxX peptides from diverse species (FIG. 45-46, Table S1). BLAST search using the 18 amino acid AtPSY1 as a query identified 8 PSY-like proteins in rice (FIG. 45). One of the rice PSY proteins, OsPSY1 (Os05g40850), has four nearly identical PSY-like repeats, the first of which (OsPSY1a) is shown in FIG. 1. Analysis of *Arabidopsis* using the same criteria also revealed a total of eight PSY like proteins including the three that had been previously identified (FIG. 45) (Amano Y et al., 2007, *Proc Natl Acad Sci USA,* 104(46): 18333-18338; Matsubayashi Y., 2014, *Annu Rev Plant Biol.,* 65: 385-413). We also identified PSY-like proteins in tomato, banana and wheat, three diverse and economically important crops (FIG. 45). Alignment of PSY peptides from these different species revealed a highly conserved 13-amino acid region beginning with the aspartate-tyrosine residue pair (FIG. 45). This 13-amino acid sequence corresponds precisely to the region of sequence similarity between RaxX and AtPSY1 (FIG. 39*a*).

Alignment of the RaxX sequences from diverse strains reveals a region of high conservation immediately around the tyrosine, which is sulfated in Xoo strain PXO99 (FIG. 46). Sequence logos were constructed for the PSY-like motif using the identified RaxX and PSY sequences (FIG. 39*b*). These logos further highlight the similarity of 13-amino acid region of RaxX and PSY sequences. Residues that are highly variable in RaxX are also highly variable in PSY. Based on the similarity of RaxX and PSY peptides and the finding that RaxX is also tyrosine sulfated (Pruitt R N et al., 2015, *Science Advances*), we hypothesized that RaxX serves as a functional mimic of PSY peptides and that RaxX may have PSY-like activity.

RaxX Promotes Root Growth Similar to PSY Peptides

To test our hypothesis that RaxX can mimic the growth stimulating activity of PSY-like peptides, we evaluated the effect of RaxX21 treatment on root growth of *Arabidopsis* seedlings. RaxX21-sY promoted root growth in a similar manner to that observed for AtPSY1 in *Arabidopsis* (FIG. 40*a, b*). After 8 days on media containing 100 nM RaxX21-sY, the average root length of Col-0 seedlings was 61 mm whereas seedlings grown on plates without peptide had an average root length of 54 mm. Similar root growth-promoting effects were observed in experiments using AtPSY1 and OsPSY1a peptides (FIG. 40*a, b*).

We also performed root growth experiments on an *Arabidopsis* line lacking AtTPST, the tyrosine sulfotransferase responsible for modification of PSY, PSK and RGF peptides (Komori R et al., 2009, *Proc Natl Acad Sci USA,* 106(35): 15067-15072; Matsuzaki Y et al., 2010, *Science,* 329(5995): 1065-1067). tpst-1 mutant plants are dwarf and have stunted roots (Komori R et al., 2009, *Proc Natl Acad Sci USA,* 106(35): 15067-15072). Because this mutant lacks endogenous PSY, PSK and RGF signaling, effects of exogenous application of sulfated peptides can be better quantified (Igarashi D, Tsuda K, Katagiri F, 2012, *Plant J.,* 71(2): 194-204; Mosher S, Kemmerling B, 2013, *Plant Signal Behav.,* 8(5): e24119). Consistent with earlier reports, we observed that mock treated tpst-1 mutant seedlings have much shorter roots than Col-0 (FIGS. 40C and D). Treatment of tpst-1 plants with RaxX21-sY or AtPSY1 increases root growth 1.5-2 fold relative to mock treatment (FIG. 40*c, d*).

We determined the minimum concentration of RaxX21-sY needed to induce root growth in *Arabidopsis*. tpst-1 seeds were grown on plates containing 0.1-250 nM peptide. RaxX21-sY was effective at inducing root growth at concentrations in the low nanomolar range (FIG. 47). This activity is comparable to PSK (FIG. 47). Nonsulfated RaxX21 (RaxX21-Y) also promoted root growth, but was less active than the sulfated version (FIG. 40*a-d*, 47). AtPSY1 was less active than RaxX21-sY and PSK. We hypothesize that the reduced potency of the synthetic AtPSY1 used in this study was due to the lack of glycosylation (See materials and methods). Glycosylation of AtPSY1 was previously shown to be important for full activity (Amano Y et al., 2007, *Proc Natl Acad Sci USA,* 104(46): 18333-18338).

We next used a live root imaging system (Duan L et al., 2013, *Plant Cell,* 25(1): 324-341; Geng Y et al., 2013, *Plant Cell,* 25(6): 2132-2154) to assess changes in root growth rate upon exposure to RaxX21-sY. Root growth of tpst-1 seedlings on plates containing 250 nM RaxX21-sY, AtPSY1 or no peptide (Mock) was monitored over 24 h. Within 4-5 hours, seedlings grown on RaxX21-sY- or AtPSY1-containing plates had an increased root growth rate compared to seedlings on mock plates (FIG. 40*e*).

To determine if RaxX induces root growth using the same signaling pathway as AtPSY1, we grew *Arabidopsis* seedlings on plates containing both RaxX and AtPSY1 peptides. Roots of *Arabidopsis* seedlings grown on plates containing 100 nM RaxX21-sY and 100 nM AtPSY1 were similar in length to those grown on plates with 100 nM RaxX21-sY alone (FIG. 48). Similar results were observed when seedlings were co-treated with 100 nM RaxX21-sY and 100 nM PSK (FIG. 48). The observation that RaxX, AtPSY1, and PSK do not have additive effects on root growth suggests that these peptides induce root growth via the same pathway. Alternatively it may be that the 100 nM RaxX21-sY treatment already reached the maximum growth potential (Matsuzaki Y et al., 2010, *Science,* 329(5995): 1065-1067).

Because RaxX21-sY comes from the rice pathogen Xoo, we tested whether this peptide also has growth promoting activity in rice seedlings. AtPSY1 and RaxX21-sY treatment significantly enhanced root growth on rice varieties Tapei 309 (FIG. 40*f*) and Kitaake (FIG. 49). Collectively, these results indicate that RaxX21-sY promotes root growth in a similar manner to PSY and PSK peptides in both *Arabidopsis* and rice.

At1g72300 is not Required for Induction of Root Growth by RaxX or AtPSY1

The leucine-rich repeat receptor kinase encoded by At1g72300 has been proposed to serve as the AtPSY1 receptor (Amano Y et al., 2007, *Proc Natl Acad Sci USA,* 104(46): 18333-18338). We therefore tested if At1g72300 is required for perception of RaxX21-sY. For these assays we used the At1g72300 mutant line SALK_072802C. This is the same line used in all published studies of PSY1/At1g72300, (Amano Y et al., 2007, *Proc Natl Acad Sci USA,* 104(46): 18333-18338; Mosher S, Kemmerling B, 2013, *Plant Signal Behav.,* 8(5): e24119; Mosher S et al., 2013, *Plant J,* 73(3): 469-482; Fuglsang A T et al., 2014, *Plant J.,* 80(6): 951-964; Mahmood K et al., 2014, *BMC Genomics,* 15: 441), and was shown to have the lowest transcript level of available mutants (Fuglsang A T et al., 2014, *Plant* 1, 80(6): 951-964). We independently validated the mutant genotype (FIG. 50). We found that treatment of the At1g72300 mutant line with either RaxX21-sY or AtPSY1 increased root growth in a similar manner to that observed for treatment of wild type Col-0 seedlings (FIG. 40*a, b,* 41a). We also found that a mutant lacking At1g72300 and the homologous PSK receptors, AtPSKR1 and AtPSKR2, also responds to RaxX and AtPSY1 treatment (FIG. 41*b*). These results indicate that At1g72300 is not required for perception of RaxX21-sY or AtPSY1.

RaxX21-sY and PSY do not Attenuate Elf18-Induced Growth Inhibition

Exogenous addition of PSK has previously been shown to attenuate the *Arabidopsis* immune response to biotrophic pathogens (Igarashi D, Tsuda K, Katagiri F, 2012, *Plant J.,* 71(2): 194-204; Mosher S, Kemmerling B, 2013, *Plant Signal Behav.,* 8(5): e24119; Mosher S et al., 2013, *Plant J,* 73(3): 469-482). Although PSK and AtPSY1 share no sequence similarity, they have nevertheless been hypothesized to serve similar roles (Mosher S, Kemmerling B, 2013, *Plant Signal Behav.,* 8(5): e24119; Mosher S et al., 2013, *Plant J.* 73(3): 469-482); Matsubayashi Y., 2014, *Annu Rev Plant Biol.,* 65: 385-413). Thus, we hypothesized that induction of PSY signaling by PSY or RaxX21-sY may also attenuate plant immune responses. To test this hypothesis, we employed a seedling growth inhibition assay. *Arabidopsis* seedlings were grown in the presence of the bacterial elicitor elf18, which causes activation of immune response and impairs growth. We demonstrated that co-incubation of seedlings with PSK attenuates elf18-mediated growth inhibition as previously reported (Igarashi D, Tsuda K, Katagiri F, 2012, *Plant J.,* 71(2): 194-204) (FIG. 51). However, RaxX21-sY and AtPSY1 do not prevent elf18-triggered growth inhibition in *Arabidopsis* under the conditions tested (FIG. 51). These results indicate that RaxX21-sY and PSY1 do not have the same effects on immune modulation as PSK in *Arabidopsis* seedlings in response to elf18 treatment.

RaxX and PSY Peptides Differentially Activate PSY-Like Growth Promotion and XA21-Immune Responses Activation of XA21-mediated immunity by RaxX21-sY triggers a number of immune responses including production of reactive oxygen species (ROS), induction of marker gene expression, and production of ethylene (Pruitt R N et al., 2015, *Science Advances*). These immune responses are tightly regulated, because aberrant activation of immunity can have negative effects on plant growth and health (Spoel S H, *Dong X,* 2012, *Nat Rev Immunol.,* 12(2): 89-100; Rodriguez E et al., 2015, *FEBS J.*). We therefore hypothesized XA21 would specifically recognize RaxX but not the homologous PSY peptides, because unregulated recognition of endogenous PSY1 would have deleterious effects.

We have previously shown that RaxX21-sY treatment induces robust ROS production in rice leaves expressing XA21 (Pruitt R N et al., 2015, *Science Advances*). Therefore, to assess XA21-mediated recognition of the sulfated peptides, we measured ROS production XA21 rice leaves upon treatment with water, RaxX21-sY, AtPSY1, or OsPSY1a (FIG. 42A). Unlike RaxX21-sY, AtPSY1 and OsPSY1a failed to induce ROS production in XA21 rice leaves. Robust ROS production was not observed in rice leaves lacking XA21 (FIG. 42*b*). PSK also failed to activate XA21-mediated immune response (FIG. 42*a, b*). These results suggest that the XA21 and PSY receptor(s) have different specificities. PSY signaling is activated by both PSY and RaxX (FIG. 40), whereas the XA21-mediated immune response is only activated by RaxX.

To further delineate the region of RaxX required for PSY-like activity and activation of XA21, we synthesized two smaller RaxX peptides based on similarity to AtPSY1. RaxX16-sY begins with the aspartate (D40) at the beginning of the PSY-like motif (FIG. 39*a*). RaxX13-sY also begins with D40 but is C-terminally truncated relative to RaxX21-sY and RaxX16-sY (FIG. 39*a*). RaxX13-sY contains the region of highest similarity shared between the RaxX and PSY peptides (FIG. 39, 45). Both the RaxX13-sY and RaxX16-sY peptides are still capable of promoting root growth in *Arabidopsis* and rice (FIG. 442*c, d*). We next tested whether these peptides could activate XA21-mediated immunity in the same manner as RaxX21-sY (Pruitt R N et al., 2015, *Science Advances*). For this purpose, ROS production was measured in detached XA21 rice leaves treated with water, RaxX13-sY, RaxX16-sY, or RaxX21-sY. RaxX16-sY and RaxX21-sY triggered a ROS response characteristic of the XA21-mediated immune response. In contrast, treatment with RaxX13-sY did not induce ROS production in XA21 rice leaves (FIG. 42*a*). Thus, RaxX13-sY is able to induce AtPSY1 like growth effects, but fails to activate an XA21-mediated immune response. These experiments reveal that RaxX residues 53-55, which are present in RaxX16 but not RaxX13, are important for activation of XA21 but are not required for root growth promoting activity.

RaxX from Diverse *Xanthomonas* Species have PSY Activity

We next asked whether RaxX from other *Xanthomonas* strains also have PSY-like activity. To address this question, we synthesized 24-amino acid peptides covering the PSY-like region for three different RaxX sequences from *X. oryzae* pv. *oryzicola* strain BSL256 (RaxX24-Xoc-sY), *X. campestris* pv *musacearum* strain NCPPB4394 (RaxX24-Xcm-sY), and *X. euvesicatoria* strain 85-10 (RaxX24-XesY) (Table S2). Xoc, Xcm, and Xe are pathogens of rice, banana, and tomato/pepper, respectively (Table S1). Xoc colonizes the mesophyll of rice, whereas Xoo colonizes the xylem. All three RaxX sulfated peptides promoted root growth on *Arabidopsis* seedlings in a manner similar to that of RaxX21-sY derived from Xoo strain PXO99 (FIG. 43). In other words, the proteins encoded by diverse allelic variants of raxX retain PSY like activity. These results demonstrate that the use of RaxX as a mimic of plant PSYs is employed by many *Xanthomonas* species that infect diverse plant species.

Discussion

In a classical evolutionary arms race, both the pathogen and host develop and deploy an arsenal of strategies to infect or resist their partner. For example, many pathogens secrete an array of molecular factors designed to manipulate host biology and suppress the immune response. In turn, plants have developed a set of immune receptors that recognize these molecules or their activities and launch mechanisms to destroy the pathogen, which the pathogen then tries to counter.

The findings reported here and in previous studies, suggest a model where Xoo produces, sulfates, and secretes a peptide that mimics PSY peptides (da Silva F G et al., 2004, *Mol Plant Microbe Interact,* 17(6): 593-601; Pruitt R N et al., 2015, *Science Advances*) (FIG. 44). Plants evolved the receptor XA21 to specifically recognize the bacterial mimic, allowing it to launch a defense response in the presence of the pathogen but not in the presence of the highly conserved PSY peptide hormones, which are predicted to be necessary for normal growth and development.

The hypothesis that RaxX is a mimic of PSY is well supported by the high level of sequence similarity (FIG. 39), the tyrosine sulfation status of RaxX and PSY peptides (Amano Y et al., 2007, *Proc Natl Acad Sci USA,* 104(46): 18333-18338; Pruitt R N et al., 2015, *Science Advances*), and the similar growth promoting activities of both peptides (FIG. 40, 47-49). Significantly, both RaxX and PSY1 require a tyrosine sulfation for full activity. Tyrosine sulfation is an important posttranslational modification that mediates protein-protein interactions. Plants and animals employ tyrosine-sulfated proteins, to regulate growth, development, immunity and other biological processes. Tyrosine sulfated proteins in animal cells have roles in coagulation, leukocyte adhesion, HIV entry, and chemokine signaling (Farzan M et al., 1999, *Cell,* 96(5): 667-676; Moore K L, 2009, *Proc Natl Acad Sci USA,* 106(35): 14741-14742; Stone M J et al., 2009, *N Biotechnol.,* 25(5): 299-317).

Due to the similar sequence and functional mimicry in root growth promotion we hypothesize that PSY1 and RaxX target a common cognate plant receptor. The leucine-rich repeat receptor kinase At1g72300 was originally hypothesized to serve as the receptor for AtPSY1 based on the observation that the root length was not increased by endogenous AtPSY1 treatment in an At1g72300 mutant (Amano Y et al., 2007, *Proc Natl Acad Sci USA,* 104(46): 18333-18338). However, the At1g72300 mutant line still partially responds to AtPSY1 treatment in proton efflux experiments (Fuglsang A T et al., 2014, *Plant* 1, 80(6): 951-964), and transcriptomics analysis reveals that many AtPSY1-regulated genes are regulated independently of At1g72300 (Mahmood K et al., 2014, *BMC Genomics,* 15: 441). We found that RaxX and AtPSY1 still promote root growth in the absence of At1g72300. Collectively, these findings indicate that At1g72300 is not the receptor for PSY peptides or that it is not the only receptor. Additional work is required to understand how PSY and RaxX are perceived in plants.

The precise role of RaxX in Xoo biology is not known. Because bacteria have been demonstrated to employ biomimics to hijack the plants' endogenous systems and reprogram the host environment to facilitate pathogen infection (Weiler E W et al., 1994, *FEBS Lett.,* 345(1): 9-13; Melotto M et al., 2006, *Cell,* 126(5): 969-980; Mitchum M G et al., 2012, *Annu Rev Phytopathol,* 50: 175-195; Chen S et al., 2015, *Physiol.,* 167(1): 262-272), we hypothesize that Xoo may use RaxX in a similar manner. Xoo is a biotrophic pathogen and thus requires living host tissues, which ensures prolonged supply of the carbon and other nutrients necessary for bacterial survival. The ability of Xoo to promote the host growth would thus benefit a biotroph (Nino-Liu D O, Ronald P C, Bogdanove A J, 2006, *Mol Plant Pathol.,* 7(5): 303-324; Fatima U, Senthil-Kumar M, 2015, *Front Plant Sci.,* 6: 750).

Xanthomonads enters through hydathodes, natural openings in the leaf, or wounds and multiplies in the xylem or mesophyll tissues. To date, growth promoting activities for RaxX or PSY1 have only been demonstrated on roots. We used induction of root growth as an indicator of PSY-like activity in this study because this is a robust well-characterized effect of AtPSY1. It is known, however, that AtPSY1 is widely expressed in various plant tissues (Amano Y et al., 2007, *Proc Natl Acad Sci USA,* 104(46): 18333-18338). *Arabidopsis* seedlings overexpressing AtPSY1 not only have longer roots, but also larger cotyledons (Amano Y et al., 2007, *Proc Natl Acad Sci USA,* 104(46): 18333-18338). Recently, a PSY-like peptide in soybean was shown to be translocated from the roots to the xylem (Okamoto S et al., 2015, *Plant J.,* 84(3): 611-620). These findings suggest that PSY peptides likely have important unidentified roles outside of the roots.

The growth promoting properties of RaxX are reminiscent of the hypertrophy in tomato and pepper leaves induced by the Xe effector AvrBs3. AvrBS3 enhances transcription of host genes including auxin-induced and expansin-like genes that contribute to host cell enlargement (Marois E et al., 2002, *Mol Plant Microbe Interact,* 15(7): 637-646). This phenotype is thought to facilitate dissemination because the bacteria are able to multiply in the enlarged cells and escape from the infected site to other plants (Marois E et al., 2002, *Mol Plant Microbe Interact,* 15(7): 637-646; Kay S et al., 2007, *Science,* 318(5850): 648-651). Although we have not observed an effect of RaxX on disease lesion development on rice leaves (da Silva F G et al., 2004, *Mol Plant Microbe Interact,* 17(6): 593-601; Pruitt R N et al., 2015, *Science Advances*), the AvrBs3 example suggests a possible role for RaxX in bacterial maintenance, persistence or transmission.

In this paper we demonstrate that XA21 is able to recognize RaxX16, but not RaxX13 indicating that the C-terminal end of the RaxX16 sequence (RaxX amino acids 53-55) is required for XA21 recognition. Residues within the RaxX13 region are also important for recognition by XA21. In a previous study, we identified three residues (44, 46, and 48) of RaxX from Xoo that are involved in XA21 activation (Pruitt R N et al., 2015, *Science Advances*). Mutation of RaxX P44 and P48 completely abolished the immunogenic activity of RaxX on XA21-rice. Mutation of A46 had a partial effect. Interestingly, these residues are not required for root growth promoting activity. For example, RaxX24-Xoc contains amino acid differences at positions 44, 46 and 48, but is still capable of inducing root growth in *Arabidopsis* (FIG. 43, 46, Table 1).

Comparison of the RaxX Xoo and RaxX-Xoc sequences with rice PSY sequences suggests the possibility that RaxX from the *Xanthomonas* strains have evolved to mimic different PSY peptides. The three residues from RaxX-Xoo (strain PXO99) which are required for recognition by XA21 are identical to those in OsPSY1a. In contrast, the amino acids of RaxX-Xoc (strain BSL256) are similar to those in OsPSY2. If these two peptides have evolved to mimic different PSY peptides, it would indicate that there are multiple PSY receptors in rice, which differentially recognize diverse PSY peptides. Multiple receptors have been reported for RGF peptides. It is not yet clear if the RGF receptors have different affinities for specific RGF peptides (Shinohara H et al., 2016, *Proc Natl Acad Sci USA*). Using multiple receptors and multiple ligands with different affinities would allow for a more complex and tunable signaling network.

To further investigate the possibility that RaxX may have evolved to mimic specific host PSY peptides, we compared the sequences of RaxX13 and PSY from various species (FIG. 39B). We did not observe a correlation between the sequences of RaxX from the pathogen and PSYs from a compatible host. However, alignment of the 13-amnio acid region did highlight variation at positions 5, 7, and 9. These residues correspond to RaxX amino acids 44, 46, and 48, which are important for XA21 recognition. Notably, the variation is not random. For example, the most common amino acids in position 5 of the sequences analyzed are serine and proline in both RaxX and PSY (FIG. 39B). The amino acids in this position could affect the ability of the peptides to activate specific PSY receptor(s), as they do for XA21. Alternatively, the PSY receptor(s) may simply be able to accommodate serine or proline at this position. Further research, including the characterization of the PSY receptor(s), will help address questions of specificity and lead to a greater understanding of PSY signaling.

The study of microbial mimicry of host molecules provides insight into both host and pathogen biology, and can lead to novel strategies for disease prevention (Gardner M R et al., 2015, *Nature,* 519(7541): 87-91). Recent studies of the JA receptor have provided new insight into selective recognition of endogenous hormones. The endogenous JA receptor is sensitive to both JA-Ile and the mimic coronatine. By making a structure-guided point mutation of a single amino acid, Zhang, et al generated a modified JA receptor which has strongly reduced sensitivity to coronatine while retaining endogenous JA-Ile recognition (Zhang L et al., 2015, *Proc Natl Acad Sci USA,* 112(46): 14354-14359. *Arabidopsis* with the modified JA receptor displayed enhanced resistance to coronatine producing *Pseudomonas* strains, and have a normal phenotype in the absence of infection (Zhang L et al., 2015, *Proc Natl Acad Sci USA,* 112(46): 14354-14359). The Zhang et al. study demonstrates how understanding of bacterial mimicry of host factors can be used to engineer plants with enhanced resistance to bacterial pathogens. The findings presented in this work provide another striking example of co-evolution between the host and pathogen and provide a framework for future work directed at understanding how XA21 and the PSY receptor(s) differentially recognize RaxX and endogenous PSY peptides.

In the claims appended hereto, the term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety.

IX. Exemplary Sequences Discussed Herein

Exemplary Xoo raxX polypeptide: LWKHVGGGDYPPPGANPKHDPPPR (SEQ ID NO:1).

Exemplary Xoo raxX polypeptide:

(SEQ ID NO: 2)
PLDQRLWKHVGGGDYPPPGANPKHDPPPRNPGHH

Exemplary Xoo raxX polypeptide:

(SEQ ID NO: 3)
KGRPEPLDQRLWKHVGGGDYPPPGANPKHDPPPRNPGHH.

Exemplary Xoo raxX polypeptide: HVGGGDYPPPGANPK (SEQ ID NO:4).

Consensus raxX polypeptide:

(SEQ ID NO: 22)
MNLSKKSPTKGAASLQRPAGAKGRPEPLDQRLWKHVGGGDYPPPGXNTKH

DPPPNNGHH.

Nonredundant raxX alleles. raxX is present in other species (e.g., *Xanthomonas perforans, Xanthomonas axonopodis manihotis, Xanthomonas axonopodis citrumelo*) that are not included on this list because they are identical in sequence to one of those listed below.

>RaxX_Xac_F1 *Xanthomonas axonopodis* pv. *citrumelo* F1 chromosome, complete genome

SEQ ID NO: 5

ATGAATCTGTCGAAAAAATCGCCAACCAATGGTGCGCAAGCGCTGCAGCG

GCCCGCCGGGGCCAAGGGCCAGCTGGAGCCCCTGGACCAGCGGCTGTGGA

AGCATGTCGGCGGTGGGGACTATCCCCCGCCGGGCGCCAATACCAAGCAC

GATCCGCCGCCCAAGAACGGGCACCACTGA

>RaxX_Xam_UA303 *Xanthomonas axonopodis* pv. *manihotis* str. UA303 UA303_contig73, whole genome shotgun sequence
>gi|390589119|gb|AKEM01000102.1|*Xanthomonas axonopodis* pv. *manihotis* str. UA303 UA303_contig73, whole genome shotgun sequence

SEQ ID NO: 6

ATGAACCTGTCGAAAAAATCGCCAACCAATGGTGCGCAAGCGCTGCAGCG

GCCCGCCGGGGCCAAGGGCCAGCTGGAGCCCCTGGACCAGCGTATGTGGA

AGCATGTCGGCGGTGGGGACTATCCCCCGCCGGGCGCCAATACCAAGCAC

GATCCGCCGCCCAAGAACGGGCACCACTGA

>RaxX_Xcm_NCPPB4394 A new nucleotide sequence entered manually

SEQ ID NO: 7

ATGAAACTATTGAAAAAATCGCCATCCAATGGCGCGGGATCGCTCCAGCG

GTCGGCCGGCGCCAAGGGCCGGCTAGAGCCGCTGGACCAGCGTCTGTGGA

AGCATGTCGGGGGTGGGGACTATGCCCCGCCGGGCTCGAATGACCGCCAC

GACCCACCAAAGCCGCCGCCCAAAAAAGGGAACCCTTGA

>RaxX_Xcv_NCPPB702 A new nucleotide sequence entered manually

SEQ ID NO: 8

ATGGAACTATTGAAAAAATCGCCATCCAATGGCGTGGGATCGCTCCAGCG

GTCGGCCGGCGCCAAGGGCCGGCTAGAGCCGCTGGACCAGCGTCTGTGGA

AGCATGTCGGGGGTGGGGACTATGCCCCGCCGGGCTCGAATGACCGCCAC

GACCCACCAAAGCCGCCGCCCAAAAAAGGGAACCCTTGA

>RaxX_Xe_85-10 A new nucleotide sequence entered
manually
SEQ ID NO: 9
ATGAATCTGTCGAAAAAATCGCCAACCAATGGTGCGCAAGCGCTGCAGCG

GCCCGCCGGGGCCAAGGGCCAGCTGGAGCCCCTGGACCAGCGTCTGTGGA

AGCATGTCGGCGGTGGGGACTATCCCCCGCCGGGCGCCAATACCAAGCAC

GATCCGCCGCCCAAGAACGGGCACCACTGA

>RaxX_Xo_ATCC35933 Xanthomonas oryzae ATCC 35933
K396DRAFT_scaffold00007.7_C, whole genome shotgun sequence

SEQ ID NO: 10

ATGAACCACTCGAAAAAATCGCCCACCAAGGGTGCGGCATCGCTGCAGCG

GCCCGCCGGGGCCAAGGGCCGACCGGAGCCGCTCGACCAGCGTCTGTGGA

AGCATGTCGGCGGTGGGGACTATCCCCCGCCGGGCGCGAATCCCAAGCAC

GATCCGCCGCCGCGCAACCCCGGGCACCATTGA

>RaxX_Xo_X8-1A *Xanthomonas oryzae* X8-1A Xo_X8-1A_contig_259, whole genome shotgun sequence >gi|332357675|gb|AFHL01000259.1|*Xanthomonas oryzae* X8-1A Xo_X8-1A_contig_259, whole genome shotgun sequence

SEQ ID NO: 11

ATGAACCTGTCGAAAAAATCGCCAACCAAGGGTGCGGCATCGCTGCAGCG

GCCCGCCGGGGCCAAGGGCCGACCGGAGCCGCTGGACCAGCGTCTGTGGA

AGCATGTCGGCGGTGGGGACTATCCCCCGTCGGGCCCGAATCCCAAGCAC

GATCCACCGGGCAACAACGGGCACCATTGA

>RaxX_Xo_X11-5A *Xanthomonas oryzae* X11-5A Xo_X11-5A_contig_110, whole genome shotgun sequence >gi|332357382|gb|AFHK01000110.1|*Xanthomonas* oryzae X11-5A Xo_X11-5A_contig_110, whole genome shotgun sequence

SEQ ID NO: 12

ATGAACCTGTCGAAAAAATCGCCAACCAAGGGTGCGGCATCGCTGCAGCG

GTCCGCCGGGGCCAAGGGCCGACCGGAGCCGCTGGACCAGCGTCTGTGGA

AGCATGTCGGCGGTGGGGACTATCCCCCGGCGGGCCCGAGTACCAAGCAC

GATCCGCACCATTGA

>RaxX_Xoc_BSL256 A new nucleotide sequence entered manually

SEQ ID NO: 13

ATGAACCTCTTGAAAAAATCGCCAACCAAGGGGGCGGCATCGCTGCAGCG

GCCCGCCGGGGCCAAGGGCCGACCGGAGCCGCTCGACCAGCGTCTGTGGA

AACATGTCGGCGGTGGGGACTACCCCCCGTCGGGCCCGAATACCAAGCAC

GATCCGCCGCCGCCCAACAACGGGCACCATTGA

>RaxX_Xoc_MAI10 *Xanthomonas oryzae* pv. *oryzicola* MAI10 172, whole genome shotgun sequence

SEQ ID NO: 14

ATGAACCTCTCGAAAAAATCGCCAACCAAGGGGGCGGCATCGCTGCAGCG

GCCCGCCGGGGCCAAGGGCCGACCGGAGCCGCTCGACCAGCGTCTGTGGA

AACATGTCGGCGGTGGGGACTACCCCCCGTCGGGCCCGAATACCAAGCAC

GATCCGCCGCCGCCCAACAACGGGCACCATTGA

>RaxX_Xoo_AXO947 A new nucleotide sequence entered manually

SEQ ID NO: 15

ATGAACCTCTCGAAAAAATCGCCAACCAAGGGTGCGGCATCGCTGCAGCG

GCCCGCCGGGGCCAAGGTCCGACCGGAGCCGCTCGACCAGCGTCTGTGGA

AGCATGTCGGCGGTGGGGACTACCCCCCGTCGGGCCCGAATCCCAAGCAC

GATCCGCCGCCGCGCAACAACGGGCACCATTGA

>RaxX_Xoo_IXoo685 A new nucleotide sequence entered manually

SEQ ID NO: 16

ATGAACCTCTCGAAAAAATCGCCAACCAAGGGTGCGGCATCGCTGCAGTG

GCCCGCCAGGGCCAAGGGCCGACCGGAGCCGCTCGACCAGCGCCTGTGGA

AGCATGTCGGCGGTGGGGACTACCCCCCGTCGGGCCCGAATACCAAGCAC

GATCCGCCGCCGCCCAACAACGGGCACCATTGA

>RaxX_Xoo_IXoo884 A new nucleotide sequence entered manually

SEQ ID NO: 17

ATGAACCACTCGAAAAAATCGCCCACCAAGGGTGCGGCATCGCTGCAGCG

GCCCGCCGGGGCCAAGGGCCGACCGGAGCAGCTCGACCAGCGTCTGTGGA

AGCATGTCGGCGGTGGGGACTATCCCCCGCCGGGCGCGAATCCCAAGCAC

GATCCGCCGCCGCGCAACCCCGGGCACCATTGA

>RaxX_Xoo_NAI8 *Xanthomonas oryzae* pv. *oryzae* NAI8 478, whole genome shotgun sequence

SEQ ID NO: 18

ATGAACCTCTCGAAAAAATCGCCAACCAAGGGTGCGGCATCGCTGCAGCC

GCCCGCCGGGGCCAAGGGCCGACCGGAGCCGCTCGACCAGCGTCTGTGGA

AGCATGTCGGCGGTGGGGACTACCCCCCGTCGGGCCCGAATCCCAAGCAC

GATCCGCCGCATCCGCCGCCGCGCAACAACGGGCACCATTGA

>RaxX_Xoo_PXO99 *Xanthomonas oryzae* pv. *oryzae* PXO99A chromosome, complete genome

SEQ ID NO: 19

ATGAACCACTCGAAAAAATCGCCCGCCAAGGGTGCGGCATCGCTGCAGCG

GCCCGCCGGGGCCAAGGGCCGACCGGAGCCGCTCGACCAGCGTCTGTGGA

AGCATGTCGGCGGTGGGGACTATCCCCCGCCGGGCGCGAATCCCAAGCAC

GATCCGCCGCCGCGCAACCCCGGGCACCATTGA

>RaxX_Xsp._M97 *Xanthomonas* sp. M97 strain 97M contig_1212, whole genome shotgun sequence >gi|507136377|gb|AQPR01001212.1|*Xanthomonas* sp. M97 contig_1212, whole genome shotgun sequence

SEQ ID NO: 20

ATGAACCTGTCGAAGAAATCGCCAACCTATGGCGCGCAATCGCTGCAGCG

GCCCGCCGGGGCCAAGGGCCGGCTGGAGCCCCTGGACCAGCGTCTGTGGA

AGCATGTCGGCGGTGGGGACTATCCCCCGCCGGGCGCGAACGACCGCCAC

AACCCGCCACCGCCGCCGTCCAACGGCGGACACCACTGA

>RaxX_Xvv_NCPPB206 A new nucleotide sequence entered manually

SEQ ID NO: 21

ATGGAACTATTGAAAAAATCGCCATCCAATGGCGTGGGATCGCTCCAGCG

GTCGGCCGGCGCCAAGGGCCGGCTAGAGCCGCTGGACCAGCGTCTGTGGA

AGCATGTCGGGGGTGGGGACTATCCCCCACCGGGCTCGAATAACCGCCAC

GATCCAACACAGCCGCCGCCCAAAAAAGGGAAACCTTGA 13 mer RaxX peptide

SEQ ID NO: 46

DYPPPGANPKHDP

What is claimed is:

1. A method of enhancing disease resistance in a plant, the method comprising contacting the plant with a composition comprising a sufficient amount of a polypeptide comprising:

SEQ ID NO:1; or

SEQ ID NO:48, to enhance the disease resistance of the plant compared to a plant that is not contacted by the polypeptide, wherein the contacting comprises spraying, atomizing, dusting or scattering the polypeptide onto the plant or applying the polypeptide to soil such that roots of the plant uptake the polypeptide.

2. The method of claim 1, wherein the plant expresses XA21 or a homolog thereof.

3. The method of claim 1, wherein the Tyr is sulfated.

4. The method of claim 1, wherein the polypeptide is encoded by a polynucleotide selected from the group of sequences consisting of SEQ ID NOs:5-21.

5. The method of claim 1, wherein the polypeptide is 13-30 amino acid long.

6. The method of claim 1, wherein the composition further comprises a surfactant, herbicide, fungicide, pesticide, or fertilizer.

7. The method of claim 1, wherein the polypeptide is a purified polypeptide.

8. The method of claim 1, wherein the contacting comprising comprises contacting the plant with a bacteria comprising a heterologous polynucleotide that expresses the polypeptide.

9. The method of claim 1, wherein the polypeptide comprises SEQ ID NO:1.

10. The method of claim 1, wherein the polypeptide comprises SEQ ID NO:48.

11. The method of claim 1, wherein the polypeptide comprises SEQ ID NO:46.

* * * * *